US012698321B2

(12) United States Patent
Bjorkman et al.

(10) Patent No.: US 12,698,321 B2
(45) Date of Patent: Aug. 4, 2026

(54) ANTIBODIES WHICH HAVE SPECIFICITY TO A SARBECOVIRUS SPIKE PROTEIN RECEPTOR-BINDING DOMAIN AND METHODS OF USE THEREOF FOR TREATING A CORONAVIRUS INFECTION

(71) Applicants: California Institute of Technology, Pasadena, CA (US); City of Hope, Duarte, CA (US)

(72) Inventors: Pamela J. Bjorkman, Pasadena, CA (US); Alexander A. Cohen, Pasadena, CA (US); Chengcheng Fan, Pasadena, CA (US); John C. Williams, Duarte, CA (US); Miso Park, Duarte, CA (US)

(73) Assignee: California Institute of Technology, Pasadena, CA (US)

( * ) Notice: Subject to any disclaimer, the term of this patent is extended or adjusted under 35 U.S.C. 154(b) by 804 days.

(21) Appl. No.: 18/060,814

(22) Filed: Dec. 1, 2022

(65) Prior Publication Data

US 2023/0250157 A1 Aug. 10, 2023

Related U.S. Application Data

(60) Provisional application No. 63/375,618, filed on Sep. 14, 2022, provisional application No. 63/341,314, filed on May 12, 2022, provisional application No. 63/285,441, filed on Dec. 2, 2021.

(51) Int. Cl.
*C07K 16/104* (2026.01)
*A61P 31/14* (2006.01)

(52) U.S. Cl.
CPC ............ *C07K 16/104* (2026.01); *A61P 31/14* (2018.01); *C07K 2317/76* (2013.01); *C07K 2317/92* (2013.01)

(58) Field of Classification Search
CPC . A61P 31/14; C07K 16/1003; C07K 2317/76; C07K 2317/92; C07K 2317/33; C07K 2317/34; G01N 33/56983; G01N 2333/165; G01N 2469/10
See application file for complete search history.

(56) References Cited

U.S. PATENT DOCUMENTS

| | | |
|---|---|---|
| 4,444,887 A | 4/1984 | Hoffmann |
| 4,676,980 A | 6/1987 | Segal et al. |
| 4,694,778 A | 9/1987 | Learn |
| 4,716,111 A | 12/1987 | Osband |
| 4,816,397 A | 3/1989 | Boss |
| 4,816,567 A | 3/1989 | Cabilly |
| 4,946,778 A | 8/1990 | Ladner |
| 4,980,286 A | 12/1990 | Morgan |
| 5,225,539 A | 7/1993 | Winter |
| 5,258,498 A | 11/1993 | Huston |
| 5,413,923 A | 5/1995 | Kucherlapati |

| | | |
|---|---|---|
| 5,530,101 A | 6/1996 | Queen |
| 5,545,806 A | 8/1996 | Lonberg |
| 5,545,807 A | 8/1996 | Surani |
| 5,565,332 A | 10/1996 | Hoogenboom |
| 5,569,825 A | 10/1996 | Lonberg |
| 5,585,089 A | 12/1996 | Queen |
| 5,625,126 A | 4/1997 | Lonberg |
| 5,633,425 A | 5/1997 | Lonberg |
| 5,658,570 A | 8/1997 | Newman |
| 5,661,016 A | 8/1997 | Lonberg |
| 5,693,761 A | 12/1997 | Queen |
| 5,693,762 A | 12/1997 | Queen |
| 5,693,780 A | 12/1997 | Newman |
| 5,756,096 A | 5/1998 | Newman |
| 5,777,085 A | 7/1998 | Co |
| 5,807,715 A | 9/1998 | Morrison |
| 5,814,318 A | 9/1998 | Lonberg |
| 5,859,205 A | 1/1999 | Adair |
| 5,892,019 A | 4/1999 | Schlom |
| 5,939,598 A | 8/1999 | Kucherlapati |
| 6,150,584 A | 11/2000 | Kucherlapati |
| 6,180,370 B1 | 1/2001 | Queen |
| 6,190,370 B1 | 2/2001 | Tsui |
| 6,210,671 B1 | 4/2001 | Co |
| 6,329,511 B1 | 12/2001 | Vasquez |
| 6,420,140 B1 | 7/2002 | Hori |
| 6,458,592 B1 | 10/2002 | Jakobovits |
| 2022/0168414 A1 | 6/2022 | Cohen et al. |

FOREIGN PATENT DOCUMENTS

| | | |
|---|---|---|
| EP | 0173494 | 3/1986 |
| EP | 0203089 | 4/1986 |
| EP | 0239400 | 9/1987 |
| EP | 0519596 | 12/1992 |
| EP | 0592106 | 4/1994 |

(Continued)

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig. M. M. (1995) Methods: A Companion to Methods in Enzymology, 8:83-93.*
MacCallum et al. (Oct. 11, 1996) J. Mol. Biol., 262(5):732-745. (doi: 10.1006/jmbi.1996.0548).*
Casset et al (2003) Biochemical and Biophysical Research Communications, 307:198-205. (doi:10.1016/S0006-291X(03)01131-8).*

(Continued)

*Primary Examiner* — Robert S Landsman
(74) *Attorney, Agent, or Firm* — Dickinson Wright PLLC

(57) ABSTRACT

Disclosed herein include antibodies or fragments thereof having specificity to a sarbecovirus spike protein receptor binding domain. Also provided are compositions, methods, and kits for isolating and using said antibodies or fragments thereof for preventing or treating, for example a coronavirus infection.

20 Claims, 98 Drawing Sheets

Specification includes a Sequence Listing.

(56) References Cited

FOREIGN PATENT DOCUMENTS

| | | |
|---|---|---|
| WO | WO1987002671 | 7/1987 |
| WO | WO1991000360 | 1/1991 |
| WO | WO1991010741 | 7/1991 |
| WO | WO1991009967 | 11/1991 |
| WO | WO1993008829 | 5/1993 |
| WO | WO1996033735 | 10/1996 |
| WO | WO1996034096 | 10/1996 |
| WO | WO1998016654 | 4/1998 |
| WO | WO1998046645 | 10/1998 |
| WO | WO1998024893 | 11/1998 |
| WO | WO1998052976 A1 | 11/1998 |
| WO | WO1998050433 | 12/1998 |
| WO | WO2000034317 | 6/2000 |
| WO | WO2012092376 A2 | 7/2012 |
| WO | WO2021211775 | 4/2021 |
| WO | WO2021203053 | 10/2021 |

OTHER PUBLICATIONS

Chen et al. (1995) EMBO J., 14(12):2784-2794. (doi: 10.1002/j. 1460-2075.1995.tb07278.x).*

Al-Lazikani, Bissan, Arthur M. Lesk, and Cyrus Chothia. "Standard conformations for the canonical structures of immunoglobulins." Journal of molecular biology 273.4 (1997): 927-948.

Altschul, Stephen F., et al. "Basic local alignment search tool." Journal of molecular biology 215.3 (1990): 403-410.

Altschul, Stephen F., et al. "Gapped BLAST and PSI-BLAST: a new generation of protein database search programs." Nucleic acids research 25.17 (1997): 3389-3402.

Baker, T. S., et al. "Structures of bovine and human papillomaviruses. Analysis by cryoelectron microscopy and three-dimensional image reconstruction." Biophysical journal 60.6 (1991): 1445-1456.

Barnes, Christopher O., et al. "SARS-CoV-2 neutralizing antibody structures inform therapeutic strategies." Nature 588.7839 (2020): 682-687.

Barnes, Christopher O., et al. "Structures of human antibodies bound to SARS-CoV-2 spike reveal common epitopes and recurrent features of antibodies." Cell 182.4 (2020): 828-842.

Berkeley Lights, "Rapid High-Resolution Screening of Plasma B Cells to Identify Antibody Lead Candidates" (2020).

Bird, Robert E., et al. "Single-chain antigen-binding proteins." Science 242.4877 (1988): 423-426.

Bowen, John E., et al. "SARS-CoV-2 spike conformation determines plasma neutralizing activity." BioRxiv (2021).

Brouwer, Philip JM, et al. "Potent neutralizing antibodies from COVID-19 patients define multiple targets of vulnerability." Science 369.6504 (2020): 643-650.

Brune, Karl D., et al. "Plug-and-Display: decoration of Virus-Like Particles via isopeptide bonds for modular immunization." Scientific reports 6.1 (2016): 19234.

Buchwald, Henry, et al. "Long-term, continuous intravenous heparin administration by an implantable infusion pump in ambulatory patients with recurrent venous thrombosis." Surgery 88.4 (1980): 507-516.

Burki, Talha Khan. "Omicron variant and booster COVID-19 vaccines." The Lancet Respiratory Medicine 10.2 (2022): e17.

Cao, Yunlong, et al. "Potent neutralizing antibodies against SARS-CoV-2 identified by high-throughput single-cell sequencing of convalescent patients' B cells." Cell 182.1 (2020): 73-84.

Chothia, Cyrus, and Arthur M. Lesk. "Canonical structures for the hypervariable regions of immunoglobulins." Journal of molecular biology 196.4 (1987): 901-917.

Chothia, Cyrus, et al. "Conformations of immunoglobulin hypervariable regions." Nature 342.6252 (1989): 877-883.

Chothia, Cyrus, Israel Gelfand, and Alexander Kister. "Structural determinants in the sequences of immunoglobulin variable domain." Journal of molecular biology 278.2 (1998): 457-479.

Cohen, Alexander A., et al. "Construction, characterization, and immunization of nanoparticles that display a diverse array of influenza HA trimers." PLoS One 16.3 (2021): e0247963.

Cohen, Alexander A., et al. "Mosaic nanoparticles elicit cross-reactive immune responses to zoonotic coronaviruses in mice." Science 371.6530 (2021): 735-741.

Cohen, Alexander A., et al. "Mosaic RBD nanoparticles protect against multiple sarbecovirus challenges in animal models." bioRxiv (2022).

Crawford, Katharine HD, et al. "Protocol and reagents for pseudotyping lentiviral particles with SARS-CoV-2 spike protein for neutralization assays." Viruses 12.5 (2020): 513.

Davies, David R., and Henry Metzger. "Structural basis of antibody function." Annual review of immunology 1.1 (1983): 87-115.

Dunbar, James, et al. "SAbPred: a structure-based antibody prediction server." Nucleic acids research 44.W1 (2016): W474-W478.

During, Matthew J., et al. "Controlled release of dopamine from a polymeric brain implant: in vivo characterization." Annals of Neurology: Official Journal of the American Neurological Association and the Child Neurology Society 25.4 (1989): 351-356.

Emsley, Paul, et al. "Features and development of Coot." Acta Crystallographica Section D: Biological Crystallography 66.4 (2010): 486-501.

Escolano, Amelia, et al. "Sequential immunization of macaques elicits heterologous neutralizing antibodies targeting the V3-glycan patch of HIV-1 Env." Science translational medicine 13.621 (2021): eabk1533.

Fishwild, Dianne M., et al. "High-avidity human IgGκ monoclonal antibodies from a novel strain of minilocus transgenic mice." Nature biotechnology 14.7 (1996): 845-851.

Fan, Chengcheng, et al. "Neutralizing monoclonal antibodies elicited by mosaic RBD nanoparticles bind conserved sarbecovirus epitopes." Immunity 55.12 (2022): 2419-2435.

Food and Drug Administration. "Fact sheet for health care providers emergency use authorization (EUA) of regen-cov (casirivimab and imdevimab)." (2021) Available at: www.fda.gov/media/145611/download in 54 pages.

Food and Drug Administration. "Fact sheet for health care providers emergency use authorization (eua) of bamlanivimab and etesevimab." (2022) Available at: www.fda.gov/media/145802/download in 45 pages.

Food and Drug Administration. "Fact sheet for healthcare providers: emergency use authorization (EUA) of sotrovimab." (2022). Available at: https://www.fda.gov/media/149534/download in 21 pages.

Food and Drug Administration. "Fact sheet for healthcare providers: emergency use authorization for evusheld™ (tixagevimab co-packaged with cilgavimab)." (2022). Available at: https://www.fda.gov/media/154701/download in 30 pages.

GenBank AAV98001.1, "spike glycoprotein [SARS coronavirus C028]." Available at: www.ncbi.nlm.nih.gov/protein/AAV98001.1 National Library of Medicine 2023 in 3 pages.

GenBank AHX37569.1, "spike protein [Rhinolophus affinis coronavirus]." Available at: www.ncbi.nlm.nih.gov/protein/ AHX37569.1 National Library of Medicine 2023 in 3 pages.

GenBank DQ412042, "Bat SARS coronavirus Rf1, complete genome." Available at: www.ncbi.nlm.nih.gov/protein/ DQ412042.1 National Library of Medicine 2023 in 11 pages.

GenBank KY352407, "Severe acute respiratory syndrome-related coronavirus strain BtKY72, complete genome." Available at: www. ncbi.nlm.nih.gov/protein/KY352407 National Library of Medicine 2023 in 11 pages.

GenBank NC014470 "Bat coronavirus BM48-31/BGR/2008, complete genome." Available at: www.ncbi.nlm.nih.gov/protein/ NC014470 National Library of Medicine 2023 in 13 pages.

GenBank QHR63300, "spike glycoprotein [Bat coronavirus RaTG13]." Available at: www.ncbi.nlm.nih.gov/protein/QHR63300 National Library of Medicine 2023 in 3 pages.

GenBank QIA48632, "spike protein [Pangolin coronavirus]." Available at: www.ncbi.nlm.nih.gov/protein/QIA48632 National Library of Medicine 2023 in 2 pages.

GenBank QVN46569.1, "spike glycoprotein [Bat SARS-like coronavirus Khosta-2]." Available at: www.ncbi.nlm.nih.gov/protein/ QVN46569.1 National Library of Medicine 2023 in 2 pages.

(56)  References Cited

OTHER PUBLICATIONS

GenBank: AAP13441, "S protein [SARS coronavirus Urbani]." Available at: www.ncbi.nlm.nih.gov/protein/AAP13441.1. National Library of Medicine 2023 in 3 pages.

GenBank: JX993988, "Bat coronavirus Cp/Yunnan2011, complete genome." Available at: www.ncbi.nlm.nih.gov/nuccore/JX993988 National Library of Medicine 2023 in 3 pages.

GenBank: KC881005, "Bat SARS-like coronavirus RsSHC014, complete genome." Available at: www.ncbi.nlm.nih.gov/nuccore/KC881005 National Library of Medicine 2023 in 12 pages.

GenBank: KF367457, "Bat SARS-like coronavirus WIV1, complete genome." Available at: www.ncbi.nlm.nih.gov/nuccore/KF367457 National Library of Medicine 2023 in 12 pages.

GenBank: KY417143, "Bat SARS-like coronavirus isolate Rs4081, complete genome." Available at: www.ncbi.nlm.nih.gov/nuccore/KY417143National Library of Medicine 2023 in 12 pages.

GenBank: MT246667, "Severe acute respiratory syndrome coronavirus 2 strain FDAARGOS_983 isolate SARS-CoV-2/human/USA/USA-WA1/2020, complete genome." Available at: www.ncbi.nlm.nih.gov/nuccore/MT246667.1 National Library of Medicine 2023 in 3 Pages.

Gibson, Daniel G., et al. "Creation of a bacterial cell controlled by a chemically synthesized genome." science 329.5987 (2010): 52-56.

Gibson, Daniel G., et al. "Enzymatic assembly of DNA molecules up to several hundred kilobases." Nature methods 6.5 (2009): 343-345.

Gillies, Stephen D., Kin-Ming Lo, and John Wesolowski. "High-level expression of chimeric antibodies using adapted cDNA variable region cassettes." Journal of immunological methods 125.1-2 (1989): 191-202.

Gisaid: EPI_ISL_412977 "hCoV-19/bat/Yunnan/RmYN02/2019." (2019) Available at: https://gisaid.org/. in 3 pages.

Gisaid: EPI_ISL_852605 "hCoV-19/bat/Cambodia/RShSTT200/2010." (2010) Available at: https://gisaid.org/. in 3 pages.

Goddard, Thomas D., et al. "UCSF ChimeraX: Meeting modern challenges in visualization and analysis." Protein Science 27.1 (2018): 14-25.

Greaney, Allison J., et al. "Comprehensive mapping of mutations in the SARS-CoV-2 receptor-binding domain that affect recognition by polyclonal human plasma antibodies." Cell host & microbe 29.3 (2021): 463-476.

Greaney, Allison J., et al. "Mapping mutations to the SARS-CoV-2 RBD that escape binding by different classes of antibodies." Nature communications 12.1 (2021): 4196.

Hagensee, M. E., et al. "Three-dimensional structure of vaccinia virus-produced human papillomavirus type 1 capsids." Journal of virology 68.7 (1994): 4503-4505.

Hamers-Casterman, C., T. Atarhouch, and G. Muyldermans. "Bajyama songa, E., Bendahman, N. & Hamers, R.(1993)." Nature (London) 363: 446-448.

Henikoff, Steven, and Jorja G. Henikoff. "Amino acid substitution matrices from protein blocks." Proceedings of the National Academy of Sciences 89.22 (1992): 10915-10919.

Holmes, Kathryn V.. "Coronaviruses (Coronaviridae)." Encyclopedia of Virology (1999): 291-298.

Howard, Matthew A., et al. "Intracerebral drug delivery in rats with lesion-induced memory deficits." Journal of Neurosurgery 71.1 (1989): 105-112.

Hsieh, Ching-Lin, et al. "Structure-based design of prefusion-stabilized SARS-CoV-2 spikes." Science 369.6510 (2020): 1501-1505.

Hu, Ben, et al. "Discovery of a rich gene pool of bat SARS-related coronaviruses provides new insights into the origin of SARS coronavirus." PLoS pathogens 13.11 (2017): e1006698.

Huo, Jiandong, et al. "Neutralization of SARS-CoV-2 by destruction of the prefusion spike." Cell host & microbe 28.3 (2020): 445-454.

Huston, James S., et al. "[3] Protein engineering of single-chain Fv analogs and fusion proteins." Methods in enzymology. vol. 203. Academic Press, 1991. 46-88.

Huston, James S., et al. "Protein engineering of antibody binding sites: recovery of specific activity in an anti-digoxin single-chain Fv analogue produced in Escherichia coli." Proceedings of the National Academy of Sciences 85.16 (1988): 5879-5883.

International Search Report and Written Opinion dated Mar. 21, 2023 in PCT Patent Application No. PCT/US2022/080745.

Jespers, Laurent S., et al. "Guiding the selection of human antibodies from phage display repertoires to a single epitope of an antigen." Bio/technology 12.9 (1994): 899-903.

Jette, Claudia A., et al. "Broad cross-reactivity across sarbecoviruses exhibited by a subset of COVID-19 donor-derived neutralizing antibodies." Cell reports 36.13 (2021).

Jette, Claudia A., et al. "Cryo-EM structures of HIV-1 trimer bound to CD4-mimetics BNM-III-170 and M48U1 adopt a CD4-bound open conformation." Nature Communications 12.1 (2021): 1950.

Joliot, Alain, et al. "Antennapedia homeobox peptide regulates neural morphogenesis." Proceedings of the National Academy of Sciences 88.5 (1991): 1864-1868.

Jones, Peter T., et al. "Replacing the complementarity-determining regions in a human antibody with those from a mouse." Nature 321.6069 (1986): 522-525.

Junghans, R. P., et al. "Anti-Tac-H, a humanized antibody to the interleukin 2 receptor with new features for immunotherapy in malignant and immune disorders." Cancer Research 50.5 (1990): 1495-1502.

Kabat, Elvin Abraham. Sequences of proteins of immunological interest. No. 91. US Department of Health and Human Services, Public Health Service, National Institutes of Health, 1991.

Kabsch, Wolfgang. "xds." Acta Crystallographica Section D: Biological Crystallography 66.2 (2010): 125-132.

Karlin and Altschul. "Applications and statistics for multiple high-scoring segments in molecular sequences." Proceedings of the National Academy of Sciences 90.12 (1993): 5873-5877.

Keeble, Anthony H., et al. "Approaching infinite affinity through engineering of peptide-protein interaction." Proceedings of the National Academy of Sciences 116.52 (2019): 26523-26533.

Kim, Young-Il, et al. "Development of spike receptor-binding domain nanoparticles as a vaccine candidate against SARS-CoV-2 infection in ferrets." MBio 12.2 (2021): 10-1128.

Köhler, Georges, and Cesar Milstein. "Continuous cultures of fused cells secreting antibody of predefined specificity." nature 256.5517 (1975): 495-497.

Kozbor, Danuta, and John C. Roder. "The production of monoclonal antibodies from human lymphocytes." Immunology Today 4.3 (1983): 72-79.

Kreer, Christoph et al. "Longitudinal Isolation of Potent Near-Germline SARS-CoV-2-Neutralizing Antibodies from COVID-19 Patients." Cell vol. 182,6 (2020): 1663-1673. doi:10.1016/j.cell.2020.08.046.

Krissinel, Evgeny, and Kim Henrick. "Inference of macromolecular assemblies from crystalline state." Journal of molecular biology 372.3 (2007): 774-797.

Lan, Jun, et al. "Structure of the SARS-CoV-2 spike receptor-binding domain bound to the ACE2 receptor." nature 581.7807 (2020): 215-220.

Landau, Meytal, et al. "ConSurf 2005: the projection of evolutionary conservation scores of residues on protein structures." Nucleic acids research 33.suppl_2 (2005): W299-W302.

Langer, Robert, and Nikolaos Peppas. "Chemical and physical structure of polymers as carriers for controlled release of bioactive agents: a review." Journal of Macromolecular Science—Reviews in Macromolecular Chemistry and Physics 23.1 (1983): 61-126.

Langer, Robert. "New methods of drug delivery." Science 249.4976 (1990): 1527-1533.

Lefranc, Marie-Paule, et al. "IMGT®, the international ImMunoGeneTics information system® 25 years on." Nucleic acids research 43.D1 (2015): D413-D422.

Levy, Robert J., et al. "Inhibition of calcification of bioprosthetic heart valves by local controlled-release diphosphonate." Science 228.4696 (1985): 190-192.

(56)                    References Cited

OTHER PUBLICATIONS

Liebschner, Dorothee, et al. "Macromolecular structure determination using X-rays, neutrons and electrons: recent developments in Phenix." Acta Crystallographica Section D: Structural Biology 75.10 (2019): 861-877.

Liu, Hejun, et al. "Cross-neutralization of a SARS-CoV-2 antibody to a functionally conserved site is mediated by avidity." Immunity 53.6 (2020): 1272-1280.

Liu, Lihong, et al. "Potent neutralizing antibodies against multiple epitopes on SARS-CoV-2 spike." Nature 584.7821 (2020): 450-456.

Liu, Lihong, et al. "Striking antibody evasion manifested by the Omicron variant of SARS-CoV-2." Nature 602.7898 (2022): 676-681.

Lonberg, Nils, and Dennis Huszar. "Human antibodies from transgenic mice." International reviews of immunology 13.1 (1995): 65-93.

Lonberg, Nils, et al. "Antigen-specific human antibodies from mice comprising four distinct genetic modifications." Nature 368.6474 (1994): 856-859.

Marks, James D., et al. "By-passing immunization: building high affinity human antibodies by chain shuffling." Bio/technology 10.7 (1992): 779-783.

Mastronarde, David N. "Automated electron microscope tomography using robust prediction of specimen movements." Journal of structural biology 152.1 (2005): 36-51.

Mccafferty, John, et al. "Phage antibodies: filamentous phage displaying antibody variable domains." nature 348.6301 (1990): 552-554.

Mcphillips, Timothy M., et al. "Blu-Ice and the Distributed Control System: software for data acquisition and instrument control at macromolecular crystallography beamlines." Journal of synchrotron radiation 9.6 (2002): 401-406.

Menachery, Vineet D., et al. "A SARS-like cluster of circulating bat coronaviruses shows potential for human emergence." *Nature medicine* 21.12 (2015): 1508-1513.

Menachery, Vineet D., et al. "SARS-like WIV1-CoV poised for human emergence." Proceedings of the National Academy of Sciences 113.11 (2016): 3048-3053.

Morrison, Sherie L. "Success in specification." Nature 368.6474 (1994): 812-813.

Morrison, Sherie L. "Transfectomas provide novel chimeric antibodies." Science 229.4719 (1985): 1202-1207.

Morrison, Sherie L., and Vernon T. Oi. "Genetically engineered antibody molecules." Advances in immunology 44 (1989): 65-92.

Morrison, Sherie L., et al. "Chimeric human antibody molecules: mouse antigen-binding domains with human constant region domains." Proceedings of the National Academy of Sciences 81.21 (1984): 6851-6855.

Needleman, Saul B., and Christian D. Wunsch. "A general method applicable to the search for similarities in the amino acid sequence of two proteins." Journal of molecular biology 48.3 (1970): 443-453.

Neuberger, Michael S., Gareth T. Williams, and Robert O. Fox. "Recombinant antibodies possessing novel effector functions." Nature 312.5995 (1984): 604-608.

Neuberger, Michael. "Generating high-avidity human Mabs in mice." Nature biotechnology 14.7 (1996): 826-826.

Newman, Roland, et al. ""Primatization" of recombinant antibodies for immunotherapy of human diseases: a macaque/human chimeric antibody against human CD4." Bio/Technology 10.11 (1992): 1455-1460.

Niu, Ling, et al. "A structural landscape of neutralizing antibodies against SARS-CoV-2 receptor binding domain." Frontiers in Immunology 12 (2021): 647934.

Padlan, Eduardo A. "A possible procedure for reducing the immunogenicity of antibody variable domains while preserving their ligand-binding properties." Molecular immunology 28.4-5 (1991): 489-498.

Padlan, Eduardo A. "Anatomy of the antibody molecule." Molecular immunology 31.3 (1994): 169-217.

Pearson, William R., and David J. Lipman. "Improved tools for biological sequence comparison." Proceedings of the National Academy of Sciences 85.8 (1988): 2444-2448.

Pettersen, Eric F., et al. "UCSF Chimera—a visualization system for exploratory research and analysis." Journal of computational chemistry 25.13 (2004): 1605-1612.

Pettersen, Eric F., et al. "UCSF ChimeraX: Structure visualization for researchers, educators, and developers." Protein Science 30.1 (2021): 70-82.

Piccoli, Luca, et al. "Mapping neutralizing and immunodominant sites on the SARS-CoV-2 spike receptor-binding domain by structure-guided high-resolution serology." Cell 183.4 (2020): 1024-1042.

Pinto, Dora, et al. "Cross-neutralization of SARS-CoV-2 by a human monoclonal SARS-CoV antibody." Nature 583.7815 (2020): 290-295.

Planas, Delphine, et al. "Sensitivity of infectious SARS-CoV-2 B.1.1.7 and B.1.351 variants to neutralizing antibodies." Nature medicine 27.5 (2021): 917-924.

Presta, Leonard G. "Antibody engineering." Current Opinion in Structural Biology 2.4 (1992): 593-596.

Punjani, Ali, et al. "cryoSPARC: algorithms for rapid unsupervised cryo-EM structure determination." Nature methods 14.3 (2017): 290-296.

Rahikainen, Rolle, et al. Overcoming symmetry mismatch iRahikainen, Rolle, et al. "Overcoming symmetry mismatch in vaccine nanoassembly through spontaneous amidation." Angewandte Chemie International Edition 60.1 (2021): 321-330.

Rettig, Trisha A., et al. "Characterization of the naive murine antibody repertoire using unamplified high-throughput sequencing." PloS one 13.1 (2018): e0190982.

Riechmann et al., "Reshaping human antibodies for therapy," Nature. 1988, 332(6162):323-7.

Robbiani, Davide F., et al. "Convergent antibody responses to SARS-CoV-2 in convalescent individuals." Nature 584.7821 (2020): 437-442.

Rogers, Thomas F., et al. "Isolation of potent SARS-CoV-2 neutralizing antibodies and protection from disease in a small animal model." *Science* 369.6506 (2020): 956-963.

Roguska, Michael A., et al. "Humanization of murine monoclonal antibodies through variable domain resurfacing." Proceedings of the National Academy of Sciences 91.3 (1994): 969-973.

Roux et al., "Comparisons of the Ability of Human IgG3 Hinge Mutants, IgM, IgE, and IgA2, to Form Small Immune Complexes: A Role for Flexibility and Geometry," J Immunol 1998, 161 (8), 4083-4090.

Saudek, C D et al. "A preliminary trial of the programmable implantable medication system for insulin delivery." The New England journal of medicine vol. 321,9 (1989): 574-9.

Schrodinger, L., and Warren DeLano. "PyMOL." (2020) Available at: pymol.org/2/. in 9 Pages.

Sefton, M V. "Implantable pumps." Critical reviews in biomedical engineering vol. 14,3 (1987): 201-40.

Seydoux, Emilie, et al. "Analysis of a SARS-CoV-2-infected individual reveals development of potent neutralizing antibodies with limited somatic mutation." Immunity 53.1 (2020): 98-105.

Shu, Liming, et al. "Secretion of a single-gene-encoded immunoglobulin from myeloma cells." Proceedings of the National Academy of Sciences 90.17 (1993): 7995-7999.

Skerra, Arne, and Andreas Plückthun. "Assembly of a functional immunoglobulin Fv fragment in *Escherichia coli*." Science 240. 4855 (1988): 1038-1041.

Smith, H. G. "Using antibodies. A laboratory manual. E. Harlow and D. Lane." Plant Growth Regulation 30.1 (2000): 95-95.

Smith, Temple F., and Michael S. Waterman. "Comparison of biosequences." Advances in applied mathematics 2.4 (1981): 482-489.

Starr, Tyler N., et al. "SARS-CoV-2 RBD antibodies that maximize breadth and resistance to escape." Nature 597.7874 (2021): 97-102.

Studnicka, Gary M., et al. "Human-engineered monoclonal antibodies retain full specific binding activity by preserving non-CDR complementarity-modulating residues." Protein Engineering, Design and Selection 7.6 (1994): 805-814.

(56)  References Cited

OTHER PUBLICATIONS

Suresh, M. R., A. C. Cuello, and C. Milstein. "[17] Bispecific monoclonal antibodies from hybrid hybridomas." Methods in enzymology. vol. 121. Academic Press, 1986. 210-228.

Starr, Tyler N., et al. "ACE2 binding is an ancestral and evolvable trait of sarbecoviruses." Nature 603.7903 (2022): 913-918.

Takeda, Shun-ichi, et al. "Construction of chimaeric processed immunoglobulin genes containing mouse variable and human constant region sequences." Nature 314.6010 (1985): 452-454.

Tan, Tiong Kit, et al. "A COVID-19 vaccine candidate using SpyCatcher multimerization of the SARS-CoV-2 spike protein receptor-binding domain induces potent neutralising antibody responses." Nature communications 12.1 (2021): 542.

Thermo Fisher Scientific-US, "Crosslinking and Photoactivatable Reagents—Chapter 5" in Molecular Probes™ Handbook a Guide to Fluorescent Probes and Labeling Technologies, 11th edition (2010).

Tortorici, M. Alejandra, et al. "Broad sarbecovirus neutralization by a human monoclonal antibody." Nature 597.7874 (2021): 103-108.

Traunecker, André, Antonio Lanzavecchia, and Klaus Karjalainen. "Bispecific single chain molecules (Janusins) target cytotoxic lymphocytes on HIV infected cells." The EMBO Journal 10.12 (1991): 3655-3659.

Verhoeyen, Martine, Cesar Milstein, and Greg Winter. "Reshaping human antibodies: grafting an antilysozyme activity." Science 239. 4847 (1988): 1534-1536.

Viralzone, "Sars-CoV-2 circulating variants", https://viralzone.expasy.org/9556, in 5 pages, 2023.

Ward, E. Sally, et al. "Binding activities of a repertoire of single immunoglobulin variable domains secreted from *Escherichia coli*." Nature 341.6242 (1989): 544-546.

Washington, Nicole L., et al. "Emergence and rapid transmission of SARS-CoV-2 B.1.1.7 in the United States." Cell 184.10 (2021): 2587-2594.

Wec, Anna Z., et al. "Broad neutralization of SARS-related viruses by human monoclonal antibodies." Science 369.6504 (2020): 731-736.

Winn, Martyn D., et al. "Overview of the CCP4 suite and current developments." Acta Crystallographica Section D: Biological Crystallography 67.4 (2011): 235-242.

Winter, Greg, and Cesar Milstein. "Man-made antibodies." Nature 349.6307 (1991): 293-299.

Winters et al., "Rapid single B cell antibody discovery using nanopens and structured light," MABS, 11(6): 1025-1035 (2019).

Wu, George Y., and Catherine H. Wu. "Receptor-mediated in vitro gene transformation by a soluble DNA carrier system." Journal of Biological Chemistry 262.10 (1987): 4429-4432.

Yoon, Hyejin, et al. "CATNAP: a tool to compile, analyze and tally neutralizing antibody panels." Nucleic acids research 43.W1 (2015): W213-W219.

Zakeri, Bijan, et al. "Peptide tag forming a rapid covalent bond to a protein, through engineering a bacterial adhesin." Proceedings of the National Academy of Sciences 109.12 (2012): E690-E697.

Zhang, Baoshan, et al. "A platform incorporating trimeric antigens into self-assembling nanoparticles reveals SARS-CoV-2-spike nanoparticles to elicit substantially higher neutralizing responses than spike alone." Scientific reports 10.1 (2020): 18149.

Zhou, Daming, et al. "Structural basis for the neutralization of SARS-CoV-2 by an antibody from a convalescent patient." Nature structural & molecular biology 27.10 (2020): 950-958.

Zhou, Hong, et al. "Identification of novel bat coronaviruses sheds light on the evolutionary origins of SARS-CoV-2 and related viruses." Cell 184.17 (2021): 4380-4391.

Zhou, Tongqing, et al. "Structural basis for potent antibody neutralization of SARS-CoV-2 variants including B. 1.1. 529." Science 376.6591 (2022): eabn8897.

Zost, Seth J., et al. "Potently neutralizing and protective human antibodies against SARS-CoV-2." Nature 584.7821 (2020): 443-449.

Zost, Seth J., et al. "Rapid isolation and profiling of a diverse panel of human monoclonal antibodies targeting the SARS-CoV-2 spike protein." Nature medicine 26.9 (2020): 1422-1427.

* cited by examiner

| IC50 (μg/mL) | Mosaic-8 | | | | | | Homotypic | |
|---|---|---|---|---|---|---|---|---|
| | M8a-3 | M8a-6 | M8a-28 | M8a-31 | M8a-34 | | HSW-1 | HSW-2 |
| SARS-CoV-2 WA1 D614G | 0.18 | >100 | 0.001 | 5.5 | 1.5 | | 28 | 34 |
| SARS-CoV-2 Beta | 0.25 | >100 | 0.067 | 6.3 | 1.9 | | 31 | >50 |
| SARS-CoV-2 Delta | 0.13 | 33 | 0.051 | 5.7 | 0.71 | | 11 | 37 |
| SARS-CoV-2 Omicron BA.1 | 1.3 | >100 | 0.011 | 18 | >100 | | 17 | >100 |
| SARS-CoV-2 Omicron BA.2 | 3.8 | >100 | 0.020 | 6.0 | 21 | | 17 | >100 |
| SARS-CoV | 0.029 | 29 | 7.4 | 0.99 | 0.052 | | >50 | >50 |
| WIV1 | 0.014 | 21 | 13 | 0.79 | 0.58 | | 8.0 | >50 |
| SHC014 | 0.005 | 17 | >100 | 0.30 | 0.002 | | >50 | >50 |
| BtKY72 | 0.005 | 8.2 | 7.8 | 0.020 | 0.006 | | 0.20 | 10 |
| Khosta2/SARS-CoV Chimera | 9.1 | 64.5 | >100 | 0.33 | 0.12 | | >100 | >100 |
| LyRa3/SARS-CoV Chimera | 0.076 | >100 | 69 | 35 | 0.17 | | 15.4 | >100 |

IC50 (μg/mL)

| < 0.01 | 0.01 - 0.1 | 0.1 - 1 | 1 - 10 | 10 - 100 |
|---|---|---|---|---|

FIG. 2B

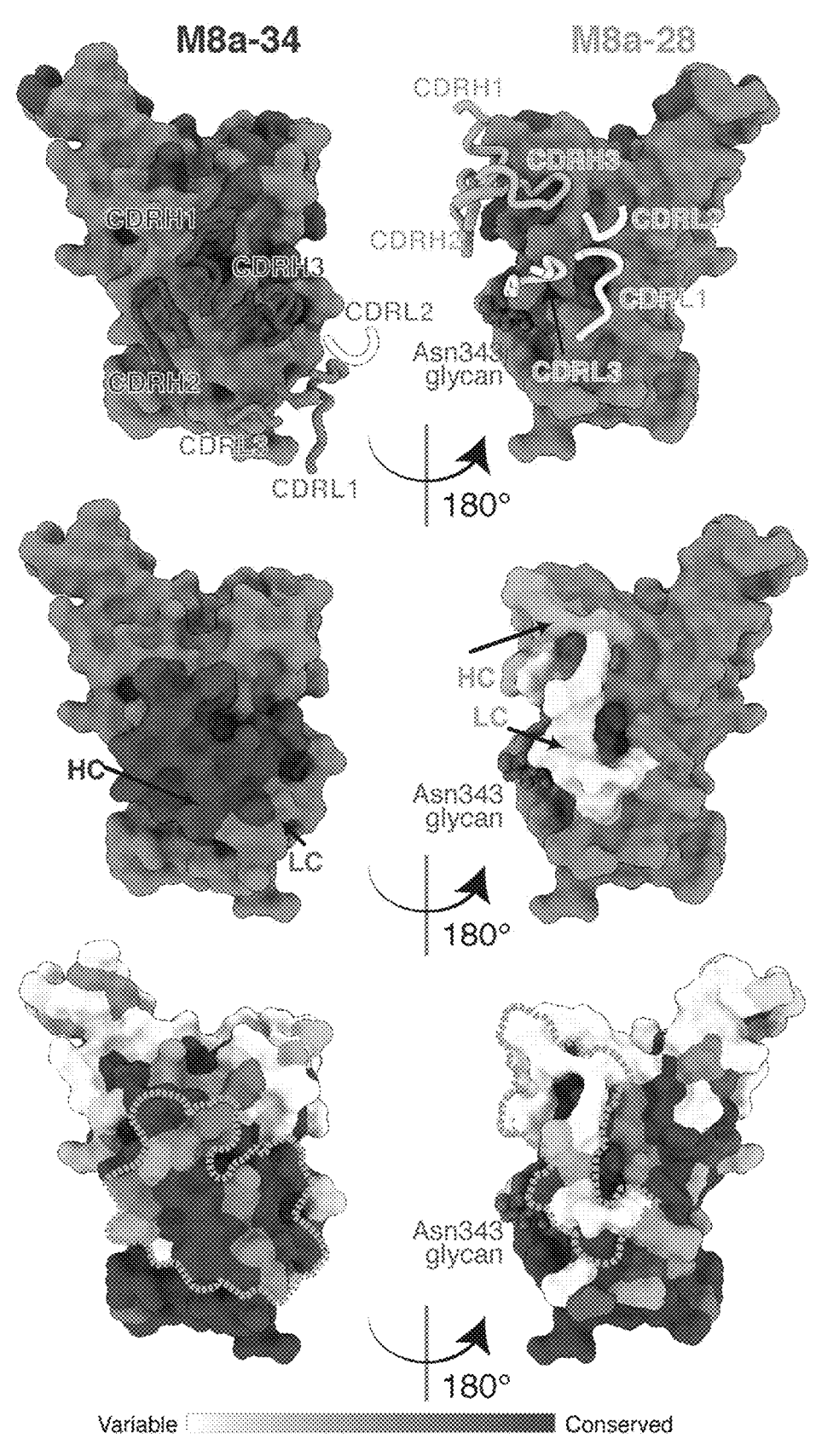
*FIG. 4E*             *FIG. 4F*

HSW-1

Variable ▭▭▭▭▭▭▭▭▭▭ Conserved

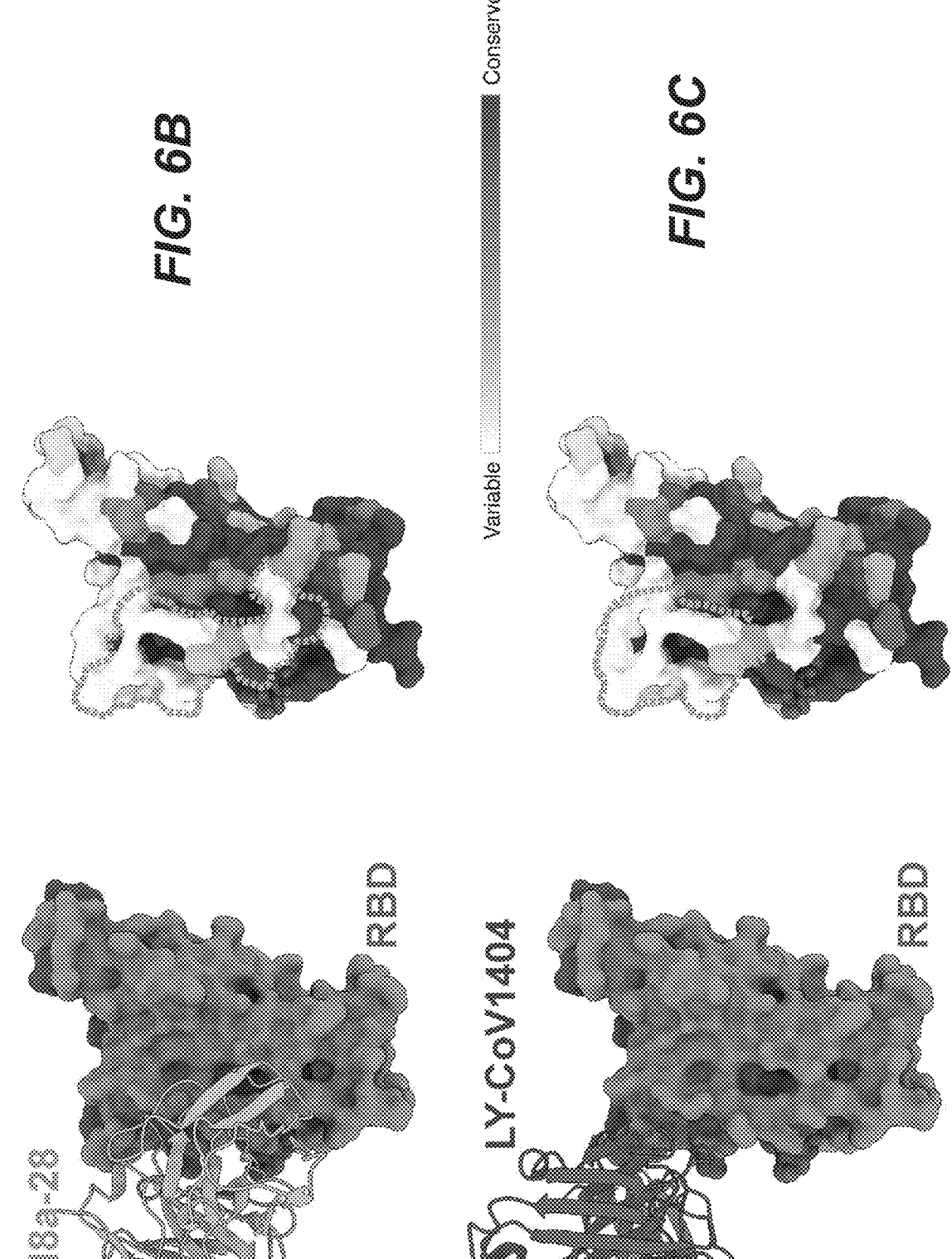

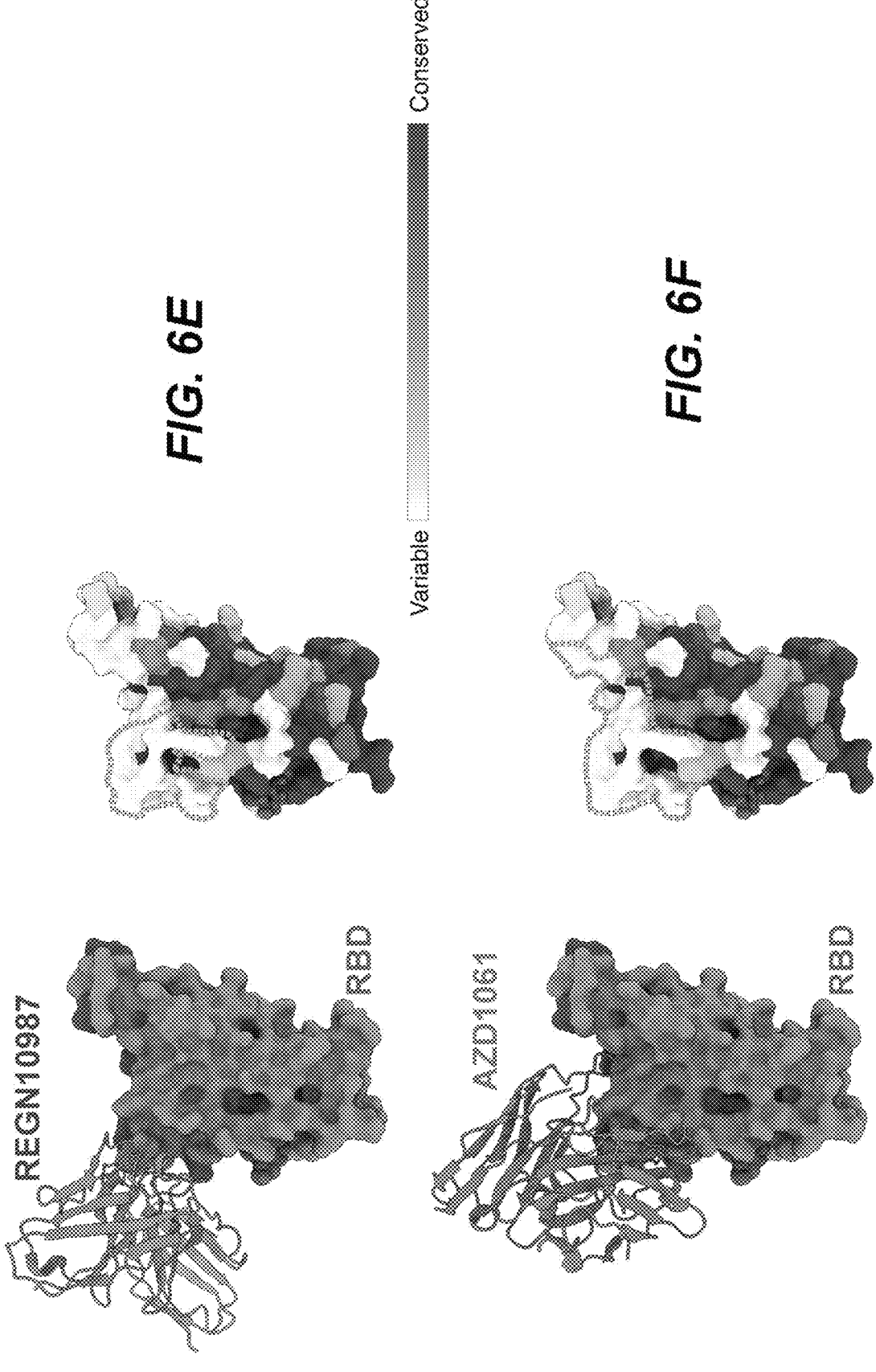

| Name | SEQ ID NO |
|---|---|
| Consensus | |
| SARS-CoV-2 | SEQ ID NO: 88 |
| RShSTT200 | SEQ ID NO: 89 |
| Pang17 | SEQ ID NO: 90 |
| RaTG13 | SEQ ID NO: 91 |
| SARS-CoV | SEQ ID NO: 92 |
| WIV1 | SEQ ID NO: 93 |
| SHC014 | SEQ ID NO: 94 |
| LYRa3 | SEQ ID NO: 95 |
| C028 | SEQ ID NO: 96 |
| Rs4081 | SEQ ID NO: 97 |
| RmYN02 | SEQ ID NO: 98 |
| RF1 | SEQ ID NO: 99 |
| Yun11 | SEQ ID NO: 100 |
| BM4831 | SEQ ID NO: 101 |
| BtKY72 | SEQ ID NO: 102 |
| Khosta2 | SEQ ID NO: 103 |
| | SEQ ID NO: 104 |

*FIG. 7A*

| Loading outcome | Homotypic SARS-CoV-2 RBD-mi3 immunized mice | percent of chip | Mosaic-8 RBD-mi3 immunized mice | percent of chip |
|---|---|---|---|---|
| Pens with single cell | 7699 | 70.0 | 7747 | 70.4 |
| Pens with >1 cell | 1431 | 13.0 | 1948 | 17.7 |
| Total Pens with cells | 9130 | 83.0 | 9695 | 88.1 |

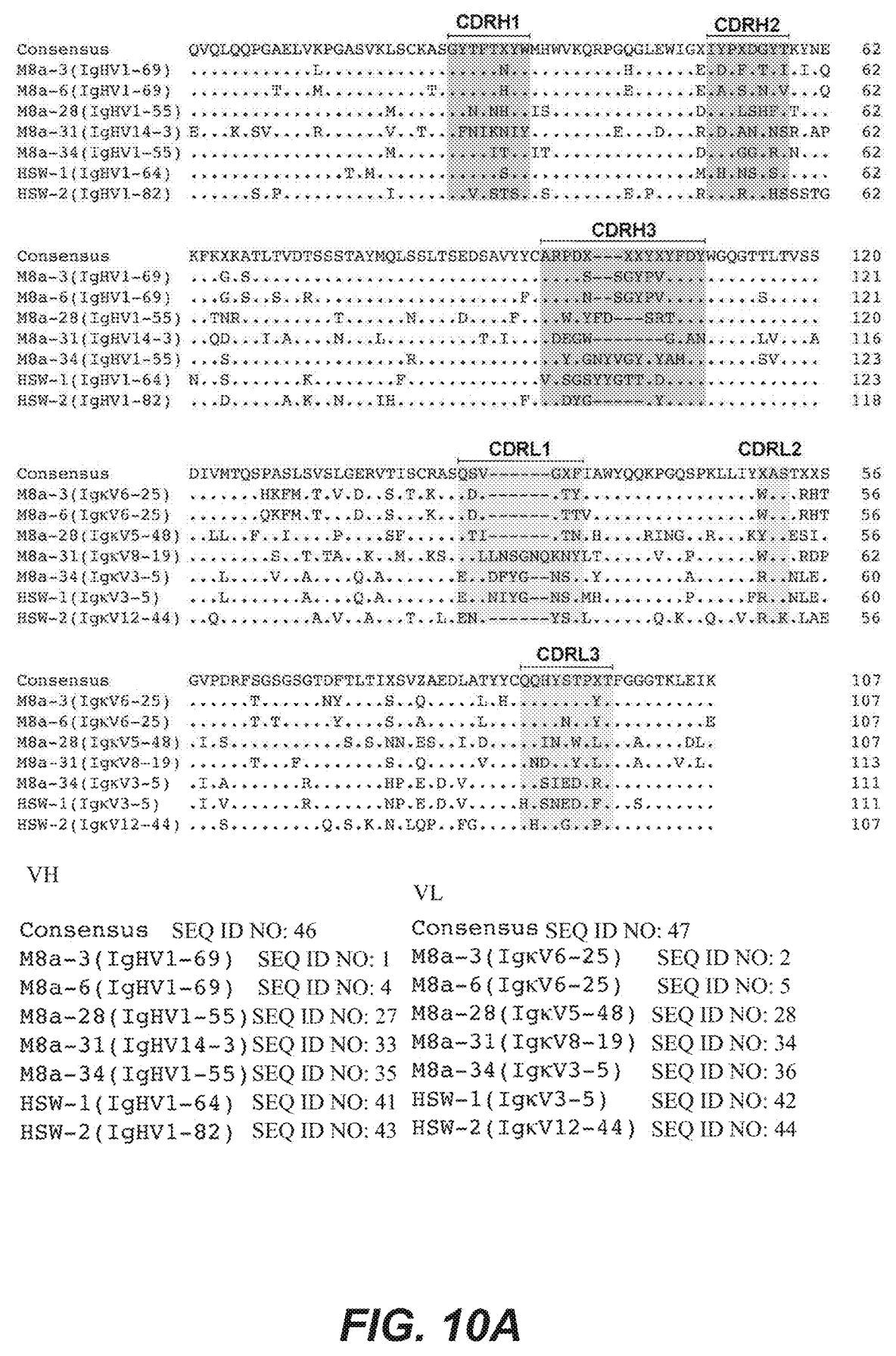

|  |  | CDRH1 | | CDRH2 | | |
|---|---|---|---|---|---|---|
| Consensus | QVQLQQPGAELVKPGASVKLSCKASGYTFTXYWMHWVKQRPGQGLEWIGXIYPXDGYTKYNE | | | | | 62 |
| M8a-3(IgHV1-69) | ..........L............N.................H..........E.D.T.I.I.Q | | | | | 62 |
| M8a-6(IgHV1-69) | .......T...M.........T....H..............E...........E.A.S.N.V...Q | | | | | 62 |
| M8a-28(IgHV1-55) | .................M.....N.NH..IS..............D.....LSHT.T.... | | | | | 62 |
| M8a-31(IgHV14-3) | E...K.SV....R......V..T...PNIKNIY.........E....D...R.D.AN.NSR.AP | | | | | 62 |
| M8a-34(IgHV1-55) | .................M.......IT...IT..............D....GG.R.N.... | | | | | 62 |
| HSW-1(IgHV1-64) | .............T.M........S................M.H.NS.S..... | | | | | 62 |
| HSW-2(IgHV1-82) | ......S.P.........I......V.STS..S........E.P....R...R..HSSSTG | | | | | 62 |

|  |  | CDRH3 | | | |
|---|---|---|---|---|---|
| Consensus | KPKXKATLTVDTSSSTAYMQLSSLTSEDSAVYYCARPDX----XXYXYFDYWGQGTTLTVSS | | | 120 |
| M8a-3(IgHV1-69) | ...G.S.........................S--SGYPV..........L | | | 121 |
| M8a-6(IgHV1-69) | ...G.S..S..R.................F.....N--SGYPV.......S..... | | | 121 |
| M8a-28(IgHV1-55) | ..TNR........T......N....D....F....W.YFD---SRT........ | | | 120 |
| M8a-31(IgHV14-3) | ..QD...I.A.....N...L.........T.I....DRGW--------G.AN.....LV...A | | | 116 |
| M8a-34(IgHV1-55) | ...S..................R..............Y.GNYVGY.YAN......SV.... | | | 123 |
| HSW-1(IgHV1-64) | N..S.......K.........F...........V.SGSYYGTT.D........ | | | 123 |
| HSW-2(IgHV1-82) | ...D.....A.K..N...IH...........F....DYG------Y......... | | | 118 |

|  |  | CDRL1 | | CDRL2 | |
|---|---|---|---|---|---|
| Consensus | DIVMTQSPASLSVSLGERVTISCRASQSV--------GXFIAWYQQKPGQSPKLLIYXASTXXS | | | | 56 |
| M8a-3(IgKV6-25) | ......HKFM.T.V.D...S.T.K...D.--------.TY...............W...RHT | | | | 56 |
| M8a-6(IgKV6-25) | ......QKFM.T...D..S...K...D.--------.TTV...............W...RHT | | | | 56 |
| M8a-28(IgKV5-48) | ..LL..F..I.....P.....SF......TI--------.TN.H....RING..R...KY..ESI. | | | | 56 |
| M8a-31(IgKV8-19) | ........S..T.TA..K..M..KS...LLNSGNQKNYLT.....V..P......W...RDP | | | | 62 |
| M8a-34(IgKV3-5) | ...L.....V..A....Q.A.......E..DFYG--NS..Y.........A......R..NLE. | | | | 60 |
| HSW-1(IgKV3-5) | ...L........A....Q.A.......E..NIYG--NS.MH..........P.....FR..NLE. | | | | 60 |
| HSW-2(IgKV12-44) | ..Q.........A.V..A...T..L.EN.--------YS.L.......Q.K..Q..V.R.K.LAE | | | | 56 |

|  |  | CDRL3 | |
|---|---|---|---|
| Consensus | GVPDRFSGSGSGTDFTLTIXSVZAEDLATYYCQQHYSTPXTFGGGTKLEIK | | 107 |
| M8a-3(IgKV6-25) | ......T......NY....S..Q.....L.H............Y........ | | 107 |
| M8a-6(IgKV6-25) | ......T.T.....Y....S..A.....L......N..Y.........E | | 107 |
| M8a-28(IgKV5-48) | .I.S...........S.S.NN.ES..I.D.....IN.W.L...A....DL. | | 107 |
| M8a-31(IgKV8-19) | ......T...F.........S..Q.....V....ND..Y.L...A...V.L. | | 113 |
| M8a-34(IgKV3-5) | .I.A.......R........HP.E.D.V......SIED.R......... | | 111 |
| HSW-1(IgKV3-5) | .I.V.......R........NP.E.D.V.....H.SNED.F...S....... | | 111 |
| HSW-2(IgKV12-44) | ...S.........Q.S.K.N.LQP..FG....H..G..P........... | | 107 |

VH

Consensus    SEQ ID NO: 46
M8a-3(IgHV1-69)    SEQ ID NO: 1
M8a-6(IgHV1-69)    SEQ ID NO: 4
M8a-28(IgHV1-55) SEQ ID NO: 27
M8a-31(IgHV14-3) SEQ ID NO: 33
M8a-34(IgHV1-55) SEQ ID NO: 35
HSW-1(IgHV1-64)    SEQ ID NO: 41
HSW-2(IgHV1-82)    SEQ ID NO: 43

VL

Consensus SEQ ID NO: 47
M8a-3(IgKV6-25)    SEQ ID NO: 2
M8a-6(IgKV6-25)    SEQ ID NO: 5
M8a-28(IgKV5-48)    SEQ ID NO: 28
M8a-31(IgKV8-19)    SEQ ID NO: 34
M8a-34(IgKV3-5)    SEQ ID NO: 36
HSW-1(IgKV3-5)    SEQ ID NO: 42
HSW-2(IgKV12-44)    SEQ ID NO: 44

*FIG. 10A*

|  | M8a-6 VH | M8a-28 VH | M8a-31 VH | M8a-34 VH | HSW-1 VH | HSW-2 VH |
|---|---|---|---|---|---|---|
| M8a-3 VH | 87.6 | 70.7 | 58.7 | 74.8 | 76.4 | 69.4 |
| M8a-6 VH |  | 67.5 | 53.7 | 72.4 | 72.4 | 68.6 |
| M8a-28 VH |  |  | 55.8 | 76.4 | 70.7 | 66.7 |
| M8a-31 VH |  |  |  | 56.9 | 55.3 | 60.2 |
| M8a-34 VH |  |  |  |  | 75.6 | 69.1 |
| HSW-1 VH |  |  |  |  |  | 67.5 |

|  | M8a-6 VL | M8a-28 VL | M8a-31 VL | M8a-34 VL | HSW-1 VL | HSW-2 VL |
|---|---|---|---|---|---|---|
| M8a-3 VL | 89.7 | 54.2 | 62.8 | 57.7 | 54.1 | 60.7 |
| M8a-6 VL |  | 53.3 | 61.1 | 58.6 | 55.9 | 57.0 |
| M8a-28 VL |  |  | 50.4 | 55.0 | 56.8 | 52.3 |
| M8a-31 VL |  |  |  | 55.8 | 54.9 | 52.2 |
| M8a-34 VL |  |  |  |  | 88.3 | 56.8 |
| HSW-1 VL |  |  |  |  |  | 55.9 |

*FIG. 10B*

SARS-CoV-2 Spike 6P + M8a-6 Fab

Unliganded WA1 spike

WA1 spike
+ C118 Fab

WA1 spike
+ M8a-31 Fab

Omicron BA.1 spike
+ M8a-31 Fab

WA1 spike
+ M8a-34 Fab

WA1 spike
+ HSW-1 Fab

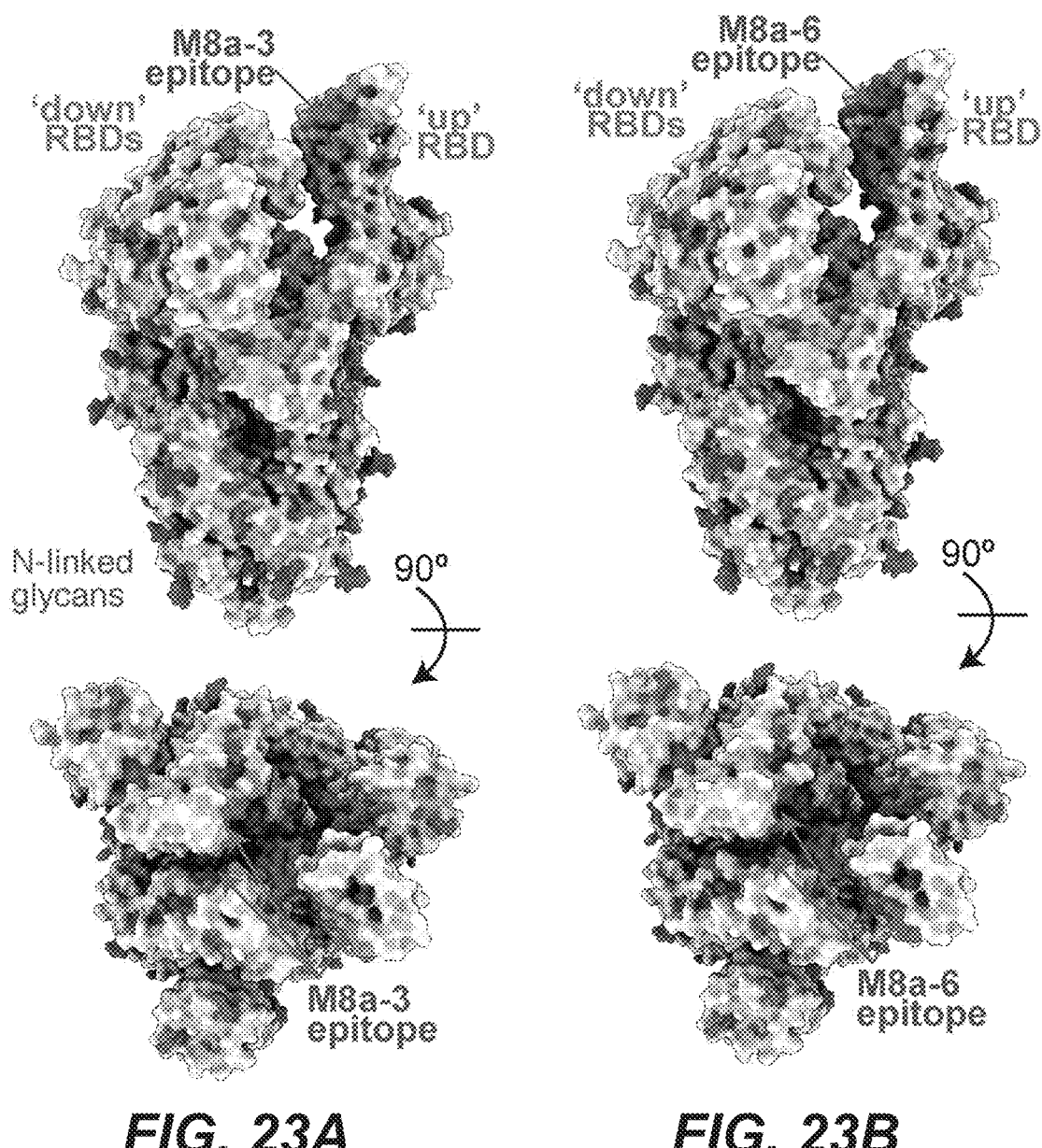
*FIG. 23A*    *FIG. 23B*

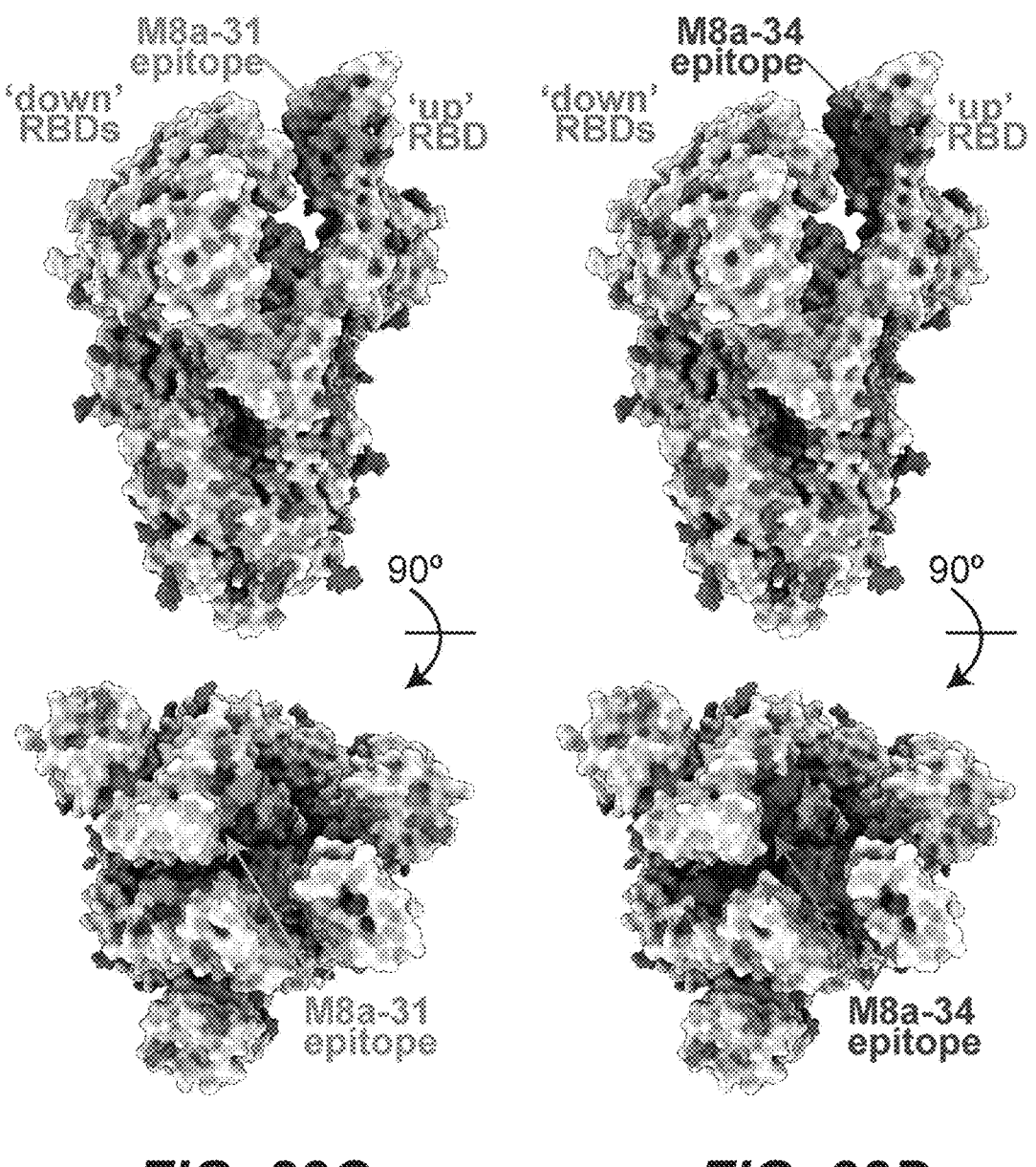
FIG. 23C          FIG. 23D

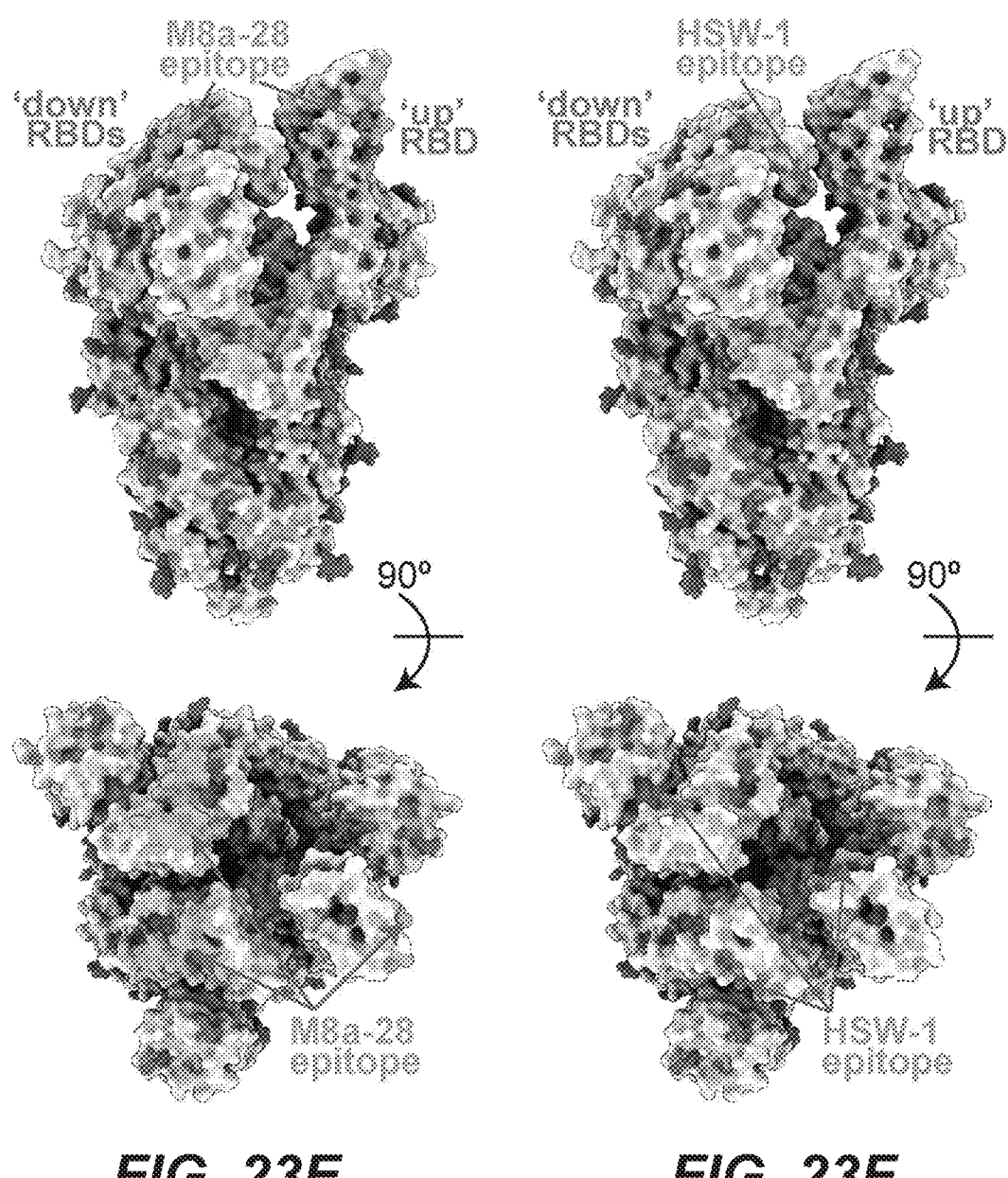
FIG. 23E            FIG. 23F

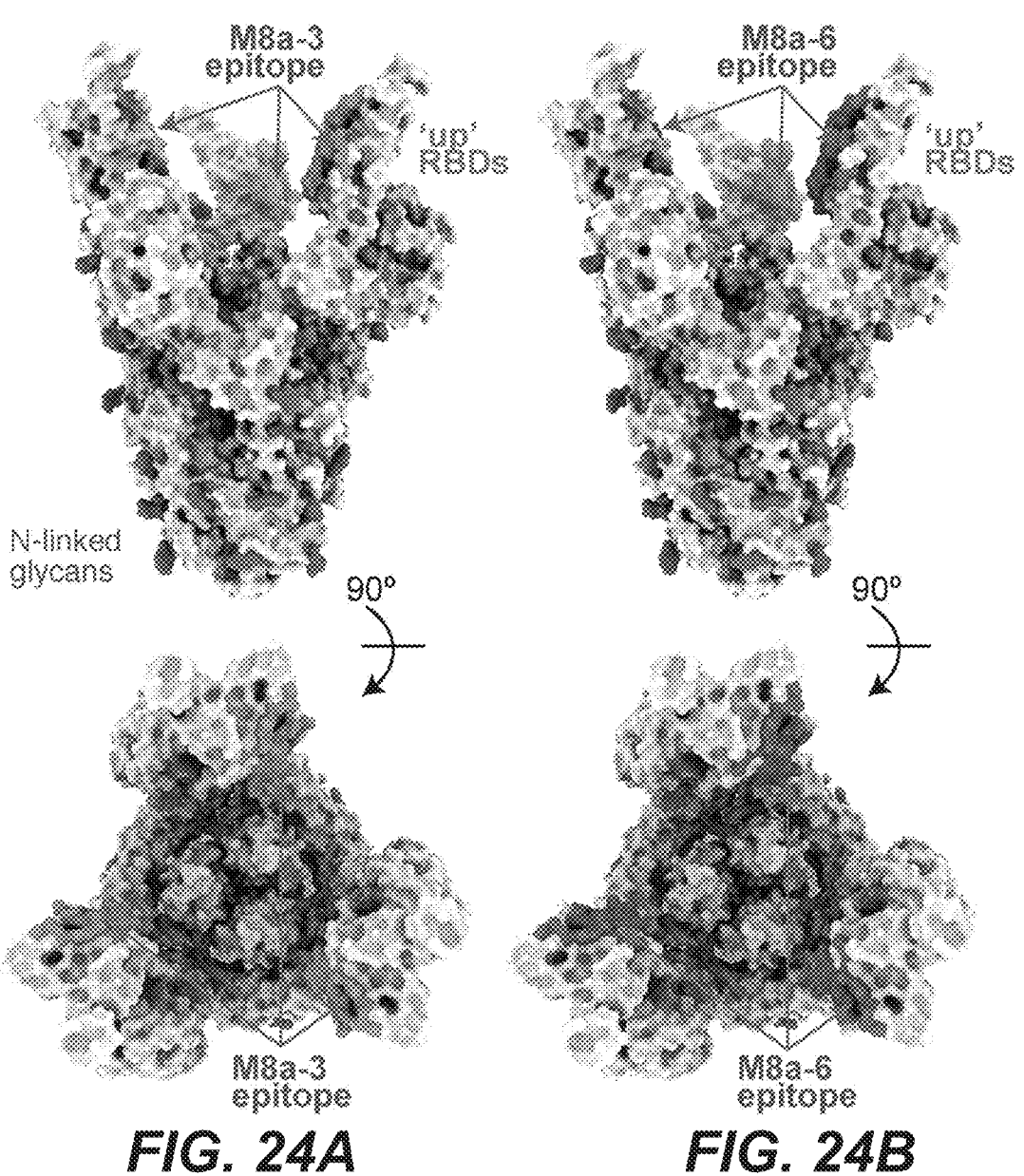
FIG. 24A          FIG. 24B

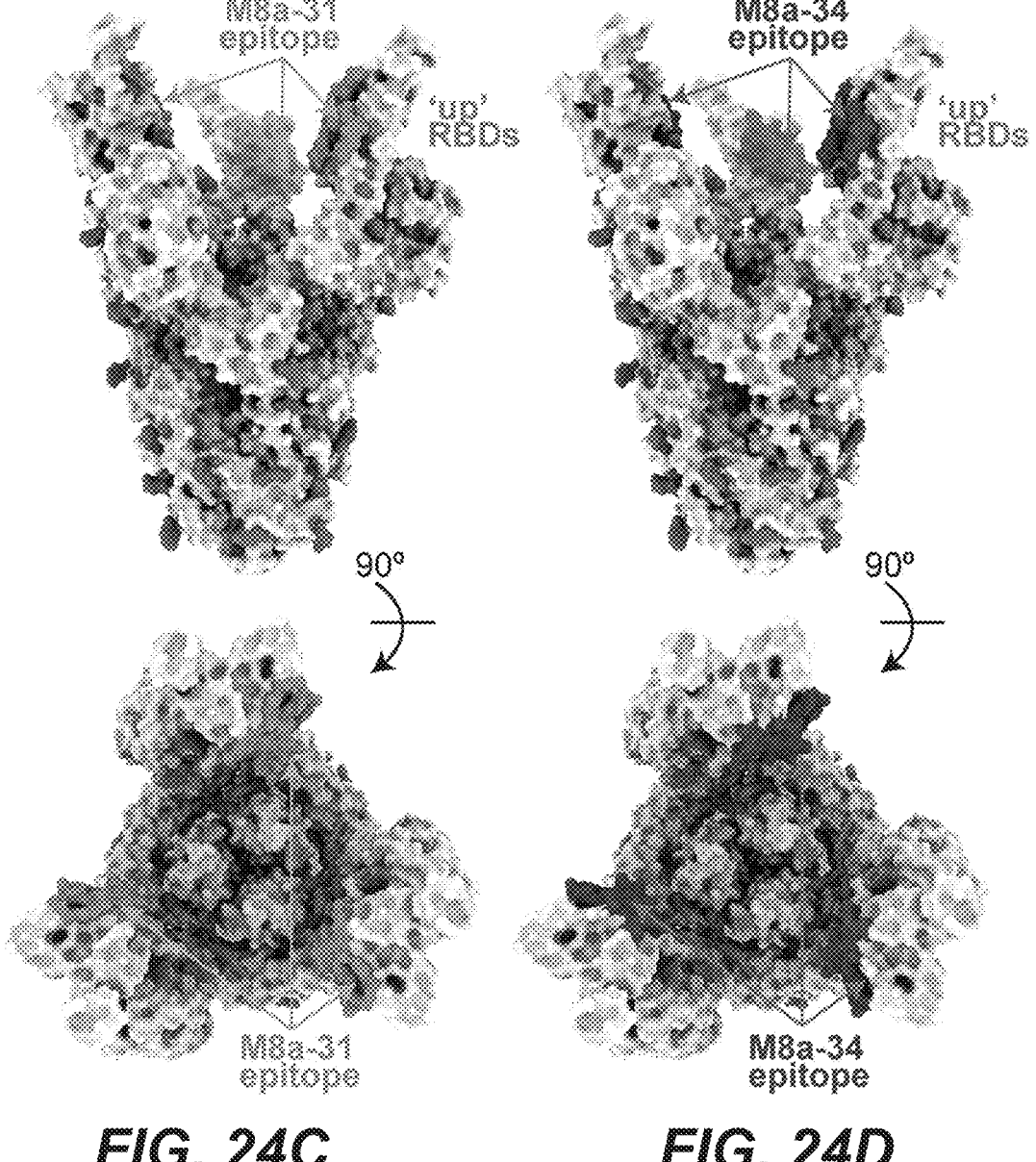
FIG. 24C    FIG. 24D

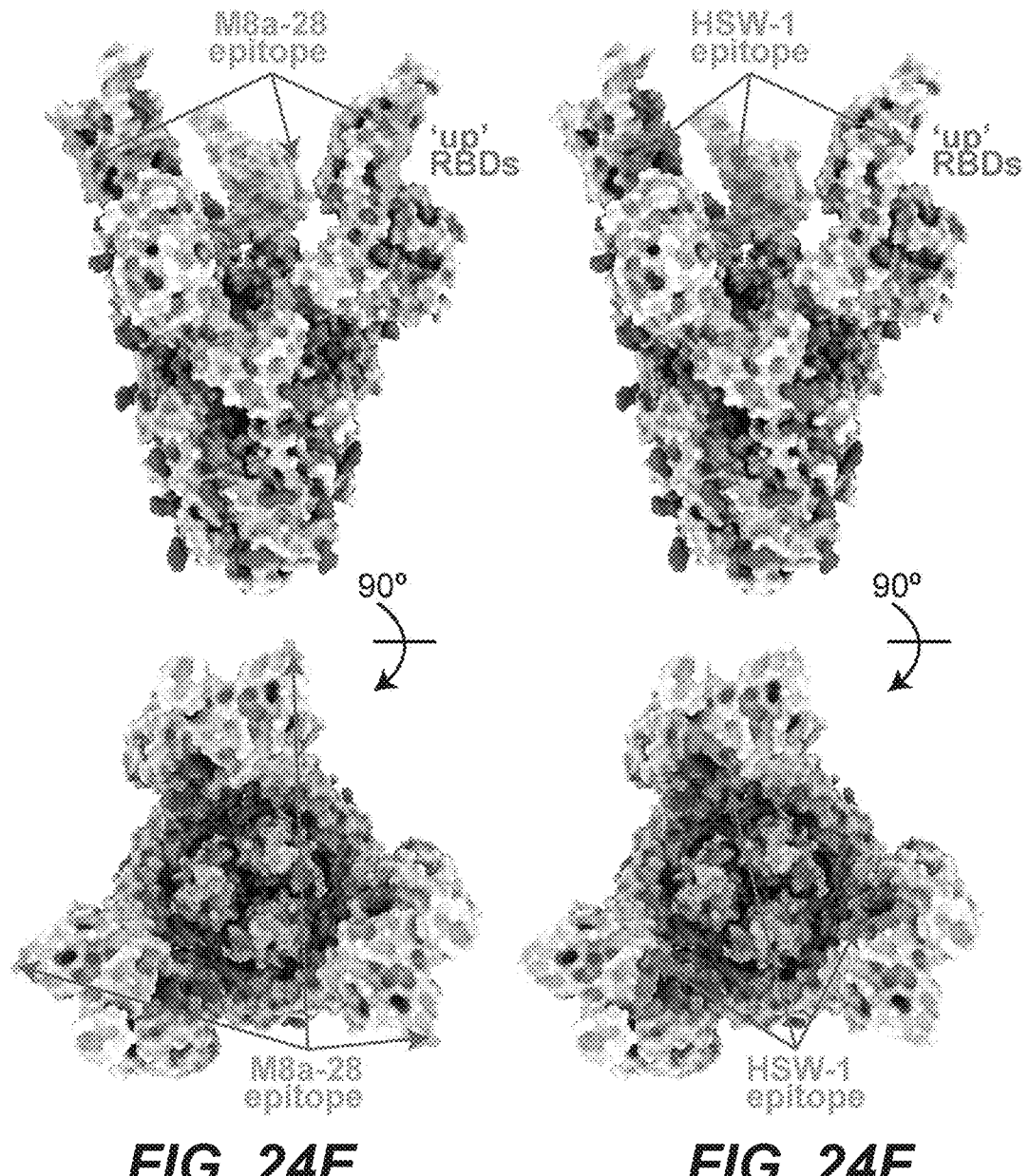
*FIG. 24E*                 *FIG. 24F*

SEQUENCE LISTING

```
Sequence total quantity: 105
SEQ ID NO: 1              moltype = AA  length = 121
FEATURE                   Location/Qualifiers
source                    1..121
                          mol_type = protein
                          organism = synthetic construct
SEQUENCE: 1
QVQLQQPGAE LVLPGASVKL SCKASGYTFT NYWMHWVKQR PGHGLEWIGE IDPFDTYIKI  60
NQKFKGKSTL TVDTSSSTAY MQLSSLTSED SAVYYCARPD SSGYPVYFDY WGQGTTLTVS  120
S                                                                  121

SEQ ID NO: 2              moltype = AA  length = 107
FEATURE                   Location/Qualifiers
source                    1..107
                          mol_type = protein
                          organism = synthetic construct
SEQUENCE: 2
DIVMTQSHKF MSTSVGDRVS ITCKASQDVG TYIAWYQQKP GQSPKLLIYW ASTRHTGVPD  60
RFTGSGSGTN YTLTISSVQA EDLALYHCQQ HYSTPYTFGG GTKLEIK               107

SEQ ID NO: 3              moltype = AA  length = 118
FEATURE                   Location/Qualifiers
source                    1..118
                          mol_type = protein
                          organism = synthetic construct
SEQUENCE: 3
DVQLQESGPG LVKPSQSLSL TCSVTGYSIT SGYYWNWIRQ FPGNKLEWMG YISYDGSNNY  60
NPSLKNRISI TRDTSKNQFF LKLNSVTTED TATYYCAREA RGAWFAYWGQ GTLVTVSA    118

SEQ ID NO: 4              moltype = AA  length = 121
FEATURE                   Location/Qualifiers
source                    1..121
                          mol_type = protein
                          organism = synthetic construct
SEQUENCE: 4
QVQLQQPGTE LVMPGASVKL SCKTSGYTFT HYWMHWVKQR PGEGLEWIGE IAPSDNYVKY  60
NQKFKGKSTL SVDRSSSTAY MQLSSLTSED SAVYFCARPD NSGYPVYFDY WGQGTSLTVS  120
S                                                                  121

SEQ ID NO: 5              moltype = AA  length = 107
FEATURE                   Location/Qualifiers
source                    1..107
                          mol_type = protein
                          organism = synthetic construct
SEQUENCE: 5
DIVMTQSQKF MSTSLGDRVS ISCKASQDVG TTVAWYQQKP GQSPKLLIYW ASTRHTGVPD  60
RFTGTGSGTD YTLTISSVAA EDLALYYCQQ HYNTPYTFGG GTKLEIE               107
```

-continued

```
SEQ ID NO: 6               moltype = AA   length = 119
FEATURE                    Location/Qualifiers
source                     1..119
                           mol_type = protein
                           organism = synthetic construct
SEQUENCE: 6
QAYLQQSGAE MVRPGASVKM SCKASGYTFN NYNMHWVKQT PSQGLEWIGG FYPGNDDTAY  60
SQKFKGKATL TVDKSSSTAF MHLSSLTSED SAVYFCARSL GRYYAMDYWG QGTSVTVSS   119

SEQ ID NO: 7               moltype = AA   length = 111
FEATURE                    Location/Qualifiers
source                     1..111
                           mol_type = protein
                           organism = synthetic construct
SEQUENCE: 7
DIVLTQSPAS LAVSLGQRAT ISCRASESVD DFGISYMNWF QQKPGQTPKL LIYGASNQGS  60
GVPARFSGSG SGTDFSLNIH PMEEDDPAMY FCQQSKEVPY TFGGGTKLEI K           111

SEQ ID NO: 8               moltype = AA   length = 121
FEATURE                    Location/Qualifiers
source                     1..121
                           mol_type = protein
                           organism = synthetic construct
SEQUENCE: 8
QVQLQQPGAE LVRPGSSVKL SCKASGYTFT SYWIHWVRQR PIEGPEWIGM IDPSDSGNHF  60
NQNFKDKATW TVDKSSNTAY MQLSSLTTED SAVYYCARGS GSTYRGYFDY WGHGTTLTVS  120
S                                                                  121

SEQ ID NO: 9               moltype = AA   length = 107
FEATURE                    Location/Qualifiers
source                     1..107
                           mol_type = protein
                           organism = synthetic construct
SEQUENCE: 9
DIQMTQSSSY LSVSLGGRVT ITCKASDHIN NWLAWYQQKP GNTPRLLISG ATNLETGVPS  60
RFSGSGSGKD YTLSITSLQT EDVATYYCQQ YWSSPLTFGA GTKLELK               107

SEQ ID NO: 10              moltype = AA   length = 112
FEATURE                    Location/Qualifiers
source                     1..112
                           mol_type = protein
                           organism = synthetic construct
SEQUENCE: 10
DVLMTQTPLS LPVSLGDQVS ISCRSSQSIV HSNGNTYLEW FLQKPGQSPK VLIYKVSTRF  60
SGVPDRFSGS GSGTDFILKI RRVEAEDLGV YYCFQGSHVP FTFGSGTKLE IK          112

SEQ ID NO: 11              moltype = AA   length = 123
FEATURE                    Location/Qualifiers
source                     1..123
                           mol_type = protein
                           organism = synthetic construct
SEQUENCE: 11
EVQLQQSGPE LVKPGASVKI PCKASGYTFT DYNMDWVKQS HEKSLEWIGE IDPNNGDTIY  60
NQKFKGKASL TVDKSSSTAY MELRSLTSED TAVYYCAKRG YYGSSLWWYF DVWGTGTTVT  120
VSS                                                                123

SEQ ID NO: 12              moltype = AA   length = 107
FEATURE                    Location/Qualifiers
source                     1..107
                           mol_type = protein
                           organism = synthetic construct
SEQUENCE: 12
DIQMTQSSSS FSVSLGDRVT ITCKASEDIY IRLAWYQQRP GNAPRLLISN AISLETGVPS  60
RFSGSGSGKD YTLSITSLQT EDVATYYCQQ YWSTPWTFGG GTKLEIK               107

SEQ ID NO: 13              moltype = AA   length = 118
FEATURE                    Location/Qualifiers
source                     1..118
                           mol_type = protein
                           organism = synthetic construct
SEQUENCE: 13
EVHLQQSGPE LVKPGDSVKI SCKAFGYSFT GYFLNWVMQS HGKSLEWIGR INPYSGDSLY  60
NQKFKDKATL TVDKSSSTAH MELRSLTSED SAVYYCARDG GNYGFDYWGQ GTTLTVSS    118

SEQ ID NO: 14              moltype = AA   length = 115
FEATURE                    Location/Qualifiers
source                     1..115
                           mol_type = protein
```

-continued

```
                          organism = synthetic construct
SEQUENCE: 14
QVQLQQSGPE LARPGASVKL SCRASGYTVT SFGLSWMKQR TGQGLEWIGE IYPTSKNTYY   60
NDKFRTKATL TADKSSSTAY MELRSLTSED SAVYFCVLYD YFDYWGQGTT LTVSS        115

SEQ ID NO: 15            moltype = AA   length = 106
FEATURE                  Location/Qualifiers
source                   1..106
                         mol_type = protein
                         organism = synthetic construct
SEQUENCE: 15
QIVLTQSPAI MSASPGEKVT ISCSASSSVS YMYWYQQKTG SSPKPWIYRT SNLASGVPVR   60
FSGSGSGTSY SLTISSMEAE DAATYYCQQY QSYPRTFGGG TKLEIK                 106

SEQ ID NO: 16            moltype = AA   length = 120
FEATURE                  Location/Qualifiers
source                   1..120
                         mol_type = protein
                         organism = synthetic construct
SEQUENCE: 16
QIQLVQSGPE LKKPGETVKI SCKASGYIFT TYGMSWVKQA PGKGLKWMGW INTYSGVPTY   60
ADDFKGRFAF SLETSANTAS LWINNLKNED TATYLCARRI RDFDGPFDYW GQGTTLTVSS   120

SEQ ID NO: 17            moltype = AA   length = 123
FEATURE                  Location/Qualifiers
source                   1..123
                         mol_type = protein
                         organism = synthetic construct
SEQUENCE: 17
EVQLQQSGPE LVKPGASVKI PCKASGYTFT DYNMDWVKQS HEKSLEWIGE IDPNNGDTIY   60
NQKFKGKASL TVDKSSSTAY MELRSLTSED TAVYYCAKRG YYGSSLWWYF DVWGTGTTVT   120
VSS                                                               123

SEQ ID NO: 18            moltype = AA   length = 121
FEATURE                  Location/Qualifiers
source                   1..121
                         mol_type = protein
                         organism = synthetic construct
SEQUENCE: 18
QVQLQQPGAE LVRPGFSVKL SCKASGYTFT SYWIHWVRQR PIEGPEWIGM IDPFDSGNHF   60
NQNFKDKATW TVDKSSNTAY MQLSSLTTED FAVYYCARGS GSTYRGYFDY WGHGTTLTVS   120
S                                                                 121

SEQ ID NO: 19            moltype = AA   length = 111
FEATURE                  Location/Qualifiers
source                   1..111
                         mol_type = protein
                         organism = synthetic construct
SEQUENCE: 19
YTTLFRSETV KISCKASGYT FTTYGMSWVK QAPGKGLKWM GWINTYSGVP TYGDDFKGRF   60
AFSLETSAST AYLQINNLKN EDTATYFCAR GDYYGGYFDV WGTGTTVTVS S           111

SEQ ID NO: 20            moltype = AA   length = 112
FEATURE                  Location/Qualifiers
source                   1..112
                         mol_type = protein
                         organism = synthetic construct
SEQUENCE: 20
DIVMTQAAFS NPVTLGTSAS ISCRSSKSLL HSNGITYLYW YLQKPGQSPQ LLIYQMSNLA   60
SGVPDRFSSS GSGTDFTLRI SRVEAEDVGV YYCAQNLELP YTFGGGTKLE IK          112

SEQ ID NO: 21            moltype = AA   length = 123
FEATURE                  Location/Qualifiers
source                   1..123
                         mol_type = protein
                         organism = synthetic construct
SEQUENCE: 21
EVQLQQSGPE LVKPGASVKI PCKASGYTFT DYNMDWVKQS HEKSLEWIGE IDPNNGDTIY   60
NQKFKGKASL TVDKSSSTAY MELRSLTSED TAVYYCAKRG YYGSSLWWYF DVWGTGTTVT   120
VSS                                                               123

SEQ ID NO: 22            moltype = AA   length = 113
FEATURE                  Location/Qualifiers
source                   1..113
                         mol_type = protein
                         organism = synthetic construct
SEQUENCE: 22
DIVMTQSPSS LTVTAGEKVT MSCKSSQSLL NSGNQKNYLT WYQQKPGQPP KLLIYWASTR   60
ESGVPDRFTG SGSGTDFTLT ISSVQAEDLA VYYCQNDYSY PLTFGAGTKL ELK         113
```

-continued

```
SEQ ID NO: 23            moltype = AA  length = 107
FEATURE                  Location/Qualifiers
source                   1..107
                         mol_type = protein
                         organism = synthetic construct
SEQUENCE: 23
DIVMTQSHKF MSTSVGDRVS ITCKASQDVG TAIAWYQQKP GQSPKLLIYW ASTRHTGVPD   60
RFTGSGSGTN YTLTISSVQA EDLALYHCQQ HYSTPYTFGG GTKLEIK                 107

SEQ ID NO: 24            moltype = AA  length = 123
FEATURE                  Location/Qualifiers
source                   1..123
                         mol_type = protein
                         organism = synthetic construct
SEQUENCE: 24
EVQLQQSVAE LVRPGASVKL SCTASGFNIK NTYMHWVKQR PEQGLEWIGR IDPSIDHTRY   60
APKFQGKAVI TAFTSSNTAY LQLSSLTSED TAIYYCAREG GGNYPYYYAI DYWGQGTSVT   120
VSS                                                                123

SEQ ID NO: 25            moltype = AA  length = 107
FEATURE                  Location/Qualifiers
source                   1..107
                         mol_type = protein
                         organism = synthetic construct
SEQUENCE: 25
DIQMTQSSSS FSVSLGDRVT ITCKASEDIY IRLAWYQQRP GNAPRLLISN AISLETGVPS   60
RFSGSGFGKD HTLSITSLQT EDVATYYCQQ YWSTPWTFGG GTKLEIK                 107

SEQ ID NO: 26            moltype = AA  length = 113
FEATURE                  Location/Qualifiers
source                   1..113
                         mol_type = protein
                         organism = synthetic construct
SEQUENCE: 26
DIVMSQSPSS LAVSVGEKVT MSCKSSQSLL YSSNQKNYLA WYQQKPGQSP KLLIYWASTR   60
ESGVPDRFTG SGSGTDFTLT ISSVKAEDLA VYYCQQYYSY PWTFGGGTKL EIK          113

SEQ ID NO: 27            moltype = AA  length = 120
FEATURE                  Location/Qualifiers
source                   1..120
                         mol_type = protein
                         organism = synthetic construct
SEQUENCE: 27
QVQLQQPGAE LVKPGASVKM SCKASGYNFN HYWISWVKQR PGQGLEWIGD IYPLSHFTTY   60
NEKFTNRATL TVDTSSTTAY MQLNSLTSDD SAVFYCARWD YFDSRTFDYW GQGTTLTVSS   120

SEQ ID NO: 28            moltype = AA  length = 107
FEATURE                  Location/Qualifiers
source                   1..107
                         mol_type = protein
                         organism = synthetic construct
SEQUENCE: 28
DILLTQFPAI LSVSPGERVS FSCRASQTIG TNIHWYQQRI NGSPRLLIKY ASESISGIPS   60
RFSGSGSGTD FSLSINNVES EDIADYYCQQ INSWPLTFGA GTKLDLK                 107

SEQ ID NO: 29            moltype = AA  length = 123
FEATURE                  Location/Qualifiers
source                   1..123
                         mol_type = protein
                         organism = synthetic construct
SEQUENCE: 29
EVQLQQSVAE LVRPGASVKL SCTASGFNIK NTYMHWVKQR PEQGLEWIGR IDPSIDHTRY   60
APKFQGKAVI TAFTSSNTAY LQLSSLTSED TAIYYCAREG GGNYPYYYAI DYWGQGTSVT   120
VSS                                                                123

SEQ ID NO: 30            moltype = AA  length = 112
FEATURE                  Location/Qualifiers
source                   1..112
                         mol_type = protein
                         organism = synthetic construct
SEQUENCE: 30
DIVMTQAAFS NPVTLGTSAS ISCRSTKSLL HSNGITYLYW YLQKPGQSPQ LLIYQMSNLA   60
SGVPDRFSSS GSGTDFTLRI SRVEAEDVGV YYCAQNLELP YTFGGGTKLE IK           112

SEQ ID NO: 31            moltype = AA  length = 117
FEATURE                  Location/Qualifiers
source                   1..117
                         mol_type = protein
```

-continued

```
                            organism = synthetic construct
SEQUENCE: 31
QVHLQQSGPE LVKPGASVKI SCKASGYGFS SSWMNWVKQR PGKGLEWIGR IYPGDGDTNY    60
NDKFQGKATL TADRSSSTAY MHLTSLTSAD SAVYFCARSL LYSFDYWGQG TTLTVSS      117

SEQ ID NO: 32            moltype = AA  length = 112
FEATURE                  Location/Qualifiers
source                   1..112
                         mol_type = protein
                         organism = synthetic construct
SEQUENCE: 32
DVVVTQTPLS LPVSFGDQVS ISCRSSQSLA GSYGHTYLSW YLHKSGQSPQ LLIYGISNRF    60
SGVPDRFSGS GSGTDFTLKI STIKPEDLGM YYCLQGTHQP LTFGAGTKLE LK          112

SEQ ID NO: 33            moltype = AA  length = 116
FEATURE                  Location/Qualifiers
source                   1..116
                         mol_type = protein
                         organism = synthetic construct
SEQUENCE: 33
EVQLKQSVAE LVRPGASVKV SCTASGFNIK NIYMHWVKQR PEQGLDWIGR IDPANGNSRY    60
APKFQDKATI TADTSSNTAY LQLSSLTSED TAIYYCADEG WGFANWGQGT LVTVSA      116

SEQ ID NO: 34            moltype = AA  length = 113
FEATURE                  Location/Qualifiers
source                   1..113
                         mol_type = protein
                         organism = synthetic construct
SEQUENCE: 34
DIVMTQSPSS LTVTAGEKVT MSCKSSQSLL NSGNQKNYLT WYQQKVGQPP KLLIYWASTR    60
DPGVPDRFTG SGFGTDFTLT ISSVQAEDLA VYYCQNDYSY PLTFGAGTKV ELK         113

SEQ ID NO: 35            moltype = AA  length = 123
FEATURE                  Location/Qualifiers
source                   1..123
                         mol_type = protein
                         organism = synthetic construct
SEQUENCE: 35
QVQLQQPGAE LVKPGASVKM SCKASGYTFI TYWITWVKQR PGQGLEWIGD IYPGGGRTNY    60
NEKFKSKATL TVDTSSSTAY MQLRSLTSED SAVYYCARYD GNYVGYYYAM DYWGQGTSVT   120
VSS                                                               123

SEQ ID NO: 36            moltype = AA  length = 111
FEATURE                  Location/Qualifiers
source                   1..111
                         mol_type = protein
                         organism = synthetic construct
SEQUENCE: 36
DIVLTQSPVS LAVSLGQRAT ISCRASESVD FYGNSFIYWY QQKPGQAPKL LIYRASNLES    60
GIPARFSGSG SRTDFTLTIH PVEADDVATY YCQQSIEDPR TFGGGTKLEI K           111

SEQ ID NO: 37            moltype = AA  length = 115
FEATURE                  Location/Qualifiers
source                   1..115
                         mol_type = protein
                         organism = synthetic construct
SEQUENCE: 37
QVQLQQSGPE LARPGASVKL SCRASGYTVT SFGLSWMKQR TGQGLEWIGE IYPTSKNTYY    60
NDKFRTKATL TADKSSSTAY MELRSLTSED SAVYFCVLYD YFDYWGQGTT LTVSS       115

SEQ ID NO: 38            moltype = AA  length = 118
FEATURE                  Location/Qualifiers
source                   1..118
                         mol_type = protein
                         organism = synthetic construct
SEQUENCE: 38
QVQLQQTGAE LVKPGASVKM SCKASGYTFT SYWIIWVKKR PGQGLEWIGD IYPGSGSTNY    60
NEKFKSKATL TVDTSSSTAY MQLSSLTSED SAVYYCTRGG SRFAMDYWGQ GTSVTVSS    118

SEQ ID NO: 39            moltype = AA  length = 112
FEATURE                  Location/Qualifiers
source                   1..112
                         mol_type = protein
                         organism = synthetic construct
SEQUENCE: 39
DIVMTQAAPS VPVTPGESVS ISCRSSKSLL HSNGNTYLYW FLQRPGQSPQ LLIYRMSNLA    60
SGVPDRFSGS GSGTAFTLRI SRVEAEDVGV YYCMQHLEYP YTFGGGTKLE IK          112

SEQ ID NO: 40            moltype = AA  length = 107
```

-continued

```
FEATURE              Location/Qualifiers
source               1..107
                     mol_type = protein
                     organism = synthetic construct
SEQUENCE: 40
NIVMTQSPKS MSMSVGERVT LSCKASENVG TYVSWYQQKP EQSPKLLIYG ASNRYTGVPD   60
RFTGSGSATD FTLTISSVQA EDLADYHCGQ SYSYPFTFGS GTKLEIK               107

SEQ ID NO: 41        moltype = AA  length = 123
FEATURE              Location/Qualifiers
source               1..123
                     mol_type = protein
                     organism = synthetic construct
SEQUENCE: 41
QVQLQQPGAE LVKPGTSMKL SCKASGYTFT SYWMHWVKQR PGQGLEWIGM IHPNSGSTKY   60
NENFKSKATL TVDKSSSTAY MQFSSLTSED SAVYYCVRSG SYYGTTYDYF DYWGQGTTLT  120
VSS                                                              123

SEQ ID NO: 42        moltype = AA  length = 111
FEATURE              Location/Qualifiers
source               1..111
                     mol_type = protein
                     organism = synthetic construct
SEQUENCE: 42
DIVLTQSPAS LAVSLGQRAT ISCRASESVN IYGNSFMHWY QQKPGQPPKL LIFRASNLES   60
GIPVRFSGSG SRTDFTLTIN PVEADDVATY YCHQSNEDPF TFGSGTKLEI K          111

SEQ ID NO: 43        moltype = AA  length = 118
FEATURE              Location/Qualifiers
source               1..118
                     mol_type = protein
                     organism = synthetic construct
SEQUENCE: 43
QVQLQQSGPE LVKPGASVKI SCKASGYVFS TSWMSWVKQR PGEGPEWIGR IYPRDGHSSS   60
TGKFKDKATL TADKSSNTAY IHLSSLTSED SAVYFCARDY GYYYFDYWGQ GTTLTVSS    118

SEQ ID NO: 44        moltype = AA  length = 107
FEATURE              Location/Qualifiers
source               1..107
                     mol_type = protein
                     organism = synthetic construct
SEQUENCE: 44
DIQMTQSPAS LSASVGEAVT ITCRLSENVY SFLAWYQQKQ GKSPQLLVYR AKTLAEGVPS   60
RFSGSGSGTQ FSLKINSLQP EDFGTYYCQH HYGTPPTFGG GTKLEIK               107

SEQ ID NO: 45        moltype = AA  length = 107
FEATURE              Location/Qualifiers
source               1..107
                     mol_type = protein
                     organism = synthetic construct
SEQUENCE: 45
DIQMTQSPAS LSASVGETVT ITCRASENIY SYLAWYQQKQ GKSPQLLVYN AKTLAEGVPS   60
RFSGSGSGTQ FSLKINSLQP EDFGSYYCQH HYGTPPTFGG GTKLEIK               107

SEQ ID NO: 46        moltype = AA  length = 120
FEATURE              Location/Qualifiers
source               1..120
                     mol_type = protein
                     organism = synthetic construct
VARIANT              31
                     note = X can be "N", "H", "T", or "S"
VARIANT              50
                     note = X can be "E", "D", "R", or "M"
VARIANT              54
                     note = X can be "F", "S", "L", "A", "G", "N", or "R"
VARIANT              101..103
                     note = X can be "S", "N", "Y", "W", "G", "T", or absent
VARIANT              105
                     note = X can be "V", "R", "Y", "D", or absent
VARIANT              66
                     note = X can be "G", "N", "D", or "S"
SEQUENCE: 46
QVQLQQPGAE LVKPGASVKL SCKASGYTFT XYWMHWVKQR PGQGLEWIGX IYPXDGYTKY   60
NEKFKXKATL TVDTSSSTAY MQLSSLTSED SAVYYCARPD XXXYXYFDYW GQGTTLTVSS  120

SEQ ID NO: 47        moltype = AA  length = 107
FEATURE              Location/Qualifiers
source               1..107
                     mol_type = protein
```

```
                          organism = synthetic construct
VARIANT                   31
                          note = X can be "T", "N", or "S"
VARIANT                   50
                          note = X can be "W", "Y", or "R"
VARIANT                   54..55
                          note = X can be "R", "H", "S", "I", "D", "L", "E", or "A"
VARIANT                   76
                          note = X can be "S", "N", or "H"
VARIANT                   96
                          note = X can be "Y", "L", "R", "F", or "P"
SEQUENCE: 47
DIVMTQSPAS LSVSLGERVT ISCRASQSVG XFIAWYQQKP GQSPKLLIYX ASTXXSGVPD   60
RFSGSGSGTD FTLTIXSVZA EDLATYYCQQ HYSTPXTFGG GTKLEIK                107

SEQ ID NO: 48            moltype = AA   length = 8
FEATURE                  Location/Qualifiers
source                   1..8
                         mol_type = protein
                         organism = synthetic construct
VARIANT                  6
                         note = X can be "N", "H", "T", or "S"
SEQUENCE: 48
GYTFTXYW                                                              8

SEQ ID NO: 49            moltype = AA   length = 8
FEATURE                  Location/Qualifiers
source                   1..8
                         mol_type = protein
                         organism = synthetic construct
SEQUENCE: 49
GYTFTNYW                                                              8

SEQ ID NO: 50            moltype = AA   length = 8
FEATURE                  Location/Qualifiers
source                   1..8
                         mol_type = protein
                         organism = synthetic construct
SEQUENCE: 50
GYTFTHYW                                                              8

SEQ ID NO: 51            moltype = AA   length = 8
FEATURE                  Location/Qualifiers
source                   1..8
                         mol_type = protein
                         organism = synthetic construct
SEQUENCE: 51
GYNFNHYW                                                              8

SEQ ID NO: 52            moltype = AA   length = 8
FEATURE                  Location/Qualifiers
source                   1..8
                         mol_type = protein
                         organism = synthetic construct
SEQUENCE: 52
GFNIKNIY                                                              8

SEQ ID NO: 53            moltype = AA   length = 8
FEATURE                  Location/Qualifiers
source                   1..8
                         mol_type = protein
                         organism = synthetic construct
SEQUENCE: 53
GYTFITYW                                                              8

SEQ ID NO: 54            moltype = AA   length = 8
FEATURE                  Location/Qualifiers
source                   1..8
                         mol_type = protein
                         organism = synthetic construct
SEQUENCE: 54
GYTFTSYW                                                              8

SEQ ID NO: 55            moltype = AA   length = 8
FEATURE                  Location/Qualifiers
source                   1..8
                         mol_type = protein
                         organism = synthetic construct
SEQUENCE: 55
```

-continued

```
GYVFSTSW                                                                  8

SEQ ID NO: 56          moltype = AA   length = 8
FEATURE                Location/Qualifiers
source                 1..8
                       mol_type = protein
                       organism = synthetic construct
VARIANT                4
                       note = X can be "F", "S", "L", "A", "G", "N", or "R"
SEQUENCE: 56
IYPXDGYT                                                                  8

SEQ ID NO: 57          moltype = AA   length = 8
FEATURE                Location/Qualifiers
source                 1..8
                       mol_type = protein
                       organism = synthetic construct
SEQUENCE: 57
IDPFDTYI                                                                  8

SEQ ID NO: 58          moltype = AA   length = 8
FEATURE                Location/Qualifiers
source                 1..8
                       mol_type = protein
                       organism = synthetic construct
SEQUENCE: 58
IAPSDNYV                                                                  8

SEQ ID NO: 59          moltype = AA   length = 8
FEATURE                Location/Qualifiers
source                 1..8
                       mol_type = protein
                       organism = synthetic construct
SEQUENCE: 59
IYPLSHFT                                                                  8

SEQ ID NO: 60          moltype = AA   length = 8
FEATURE                Location/Qualifiers
source                 1..8
                       mol_type = protein
                       organism = synthetic construct
SEQUENCE: 60
IDPANGNS                                                                  8

SEQ ID NO: 61          moltype = AA   length = 8
FEATURE                Location/Qualifiers
source                 1..8
                       mol_type = protein
                       organism = synthetic construct
SEQUENCE: 61
IYPGGGRT                                                                  8

SEQ ID NO: 62          moltype = AA   length = 8
FEATURE                Location/Qualifiers
source                 1..8
                       mol_type = protein
                       organism = synthetic construct
SEQUENCE: 62
IHPNSGST                                                                  8

SEQ ID NO: 63          moltype = AA   length = 8
FEATURE                Location/Qualifiers
source                 1..8
                       mol_type = protein
                       organism = synthetic construct
SEQUENCE: 63
IYPRDGHS                                                                  8

SEQ ID NO: 64          moltype = AA   length = 13
FEATURE                Location/Qualifiers
source                 1..13
                       mol_type = protein
                       organism = synthetic construct
VARIANT                5..7
                       note = X can be "S", "N", "Y", "W", "G", "T", or absent
VARIANT                9
                       note = X can be "V", "R", "Y", "D", or absent
SEQUENCE: 64
ARPDXXXYXY FDY                                                            13
```

-continued

```
SEQ ID NO: 65              moltype = AA   length = 14
FEATURE                    Location/Qualifiers
source                     1..14
                           mol_type = protein
                           organism = synthetic construct
SEQUENCE: 65
ARPDSSGYPV YFDY                                                    14

SEQ ID NO: 66              moltype = AA   length = 14
FEATURE                    Location/Qualifiers
source                     1..14
                           mol_type = protein
                           organism = synthetic construct
SEQUENCE: 66
ARPDNSGYPV YFDY                                                    14

SEQ ID NO: 67              moltype = AA   length = 13
FEATURE                    Location/Qualifiers
source                     1..13
                           mol_type = protein
                           organism = synthetic construct
SEQUENCE: 67
ARWDYFDSRT FDY                                                     13

SEQ ID NO: 68              moltype = AA   length = 9
FEATURE                    Location/Qualifiers
source                     1..9
                           mol_type = protein
                           organism = synthetic construct
SEQUENCE: 68
ADEGWGFAN                                                          9

SEQ ID NO: 69              moltype = AA   length = 16
FEATURE                    Location/Qualifiers
source                     1..16
                           mol_type = protein
                           organism = synthetic construct
SEQUENCE: 69
ARYDGNYVGY YYAMDY                                                  16

SEQ ID NO: 70              moltype = AA   length = 16
FEATURE                    Location/Qualifiers
source                     1..16
                           mol_type = protein
                           organism = synthetic construct
SEQUENCE: 70
VRSGSYYGTT YDYFDY                                                  16

SEQ ID NO: 71              moltype = AA   length = 11
FEATURE                    Location/Qualifiers
source                     1..11
                           mol_type = protein
                           organism = synthetic construct
SEQUENCE: 71
ARDYGYYYFD Y                                                       11

SEQ ID NO: 72              moltype = AA   length = 6
FEATURE                    Location/Qualifiers
source                     1..6
                           mol_type = protein
                           organism = synthetic construct
VARIANT                    5
                           note = X can be "T", "N", or "S"
SEQUENCE: 72
QSVGXF                                                             6

SEQ ID NO: 73              moltype = AA   length = 6
FEATURE                    Location/Qualifiers
source                     1..6
                           mol_type = protein
                           organism = synthetic construct
SEQUENCE: 73
QDVGTY                                                             6

SEQ ID NO: 74              moltype = AA   length = 6
FEATURE                    Location/Qualifiers
source                     1..6
                           mol_type = protein
```

-continued

```
                        organism = synthetic construct
SEQUENCE: 74
QDVGTT                                                                    6

SEQ ID NO: 75           moltype = AA   length = 6
FEATURE                 Location/Qualifiers
source                  1..6
                        mol_type = protein
                        organism = synthetic construct
SEQUENCE: 75
QTIGTN                                                                    6

SEQ ID NO: 76           moltype = AA   length = 12
FEATURE                 Location/Qualifiers
source                  1..12
                        mol_type = protein
                        organism = synthetic construct
SEQUENCE: 76
QSLLNSGNQK NY                                                             12

SEQ ID NO: 77           moltype = AA   length = 10
FEATURE                 Location/Qualifiers
source                  1..10
                        mol_type = protein
                        organism = synthetic construct
SEQUENCE: 77
ESVDFYGNSF                                                                10

SEQ ID NO: 78           moltype = AA   length = 10
FEATURE                 Location/Qualifiers
source                  1..10
                        mol_type = protein
                        organism = synthetic construct
SEQUENCE: 78
ESVNIYGNSF                                                                10

SEQ ID NO: 79           moltype = AA   length = 6
FEATURE                 Location/Qualifiers
source                  1..6
                        mol_type = protein
                        organism = synthetic construct
SEQUENCE: 79
ENVYSF                                                                    6

SEQ ID NO: 80           moltype = AA   length = 9
FEATURE                 Location/Qualifiers
source                  1..9
                        mol_type = protein
                        organism = synthetic construct
VARIANT                 8
                        note = X can be "Y", "L", "R", "F", or "P"
SEQUENCE: 80
QQHYSTPXT                                                                 9

SEQ ID NO: 81           moltype = AA   length = 9
FEATURE                 Location/Qualifiers
source                  1..9
                        mol_type = protein
                        organism = synthetic construct
SEQUENCE: 81
QQHYSTPYT                                                                 9

SEQ ID NO: 82           moltype = AA   length = 9
FEATURE                 Location/Qualifiers
source                  1..9
                        mol_type = protein
                        organism = synthetic construct
SEQUENCE: 82
QQHYNTPYT                                                                 9

SEQ ID NO: 83           moltype = AA   length = 9
FEATURE                 Location/Qualifiers
source                  1..9
                        mol_type = protein
                        organism = synthetic construct
SEQUENCE: 83
QQINSWPLT                                                                 9

SEQ ID NO: 84           moltype = AA   length = 9
```

```
FEATURE              Location/Qualifiers
source               1..9
                     mol_type = protein
                     organism = synthetic construct
SEQUENCE: 84
QNDYSYPLT                                                             9

SEQ ID NO: 85        moltype = AA  length = 9
FEATURE              Location/Qualifiers
source               1..9
                     mol_type = protein
                     organism = synthetic construct
SEQUENCE: 85
QQSIEDPRT                                                             9

SEQ ID NO: 86        moltype = AA  length = 9
FEATURE              Location/Qualifiers
source               1..9
                     mol_type = protein
                     organism = synthetic construct
SEQUENCE: 86
HQSNEDPFT                                                             9

SEQ ID NO: 87        moltype = AA  length = 9
FEATURE              Location/Qualifiers
source               1..9
                     mol_type = protein
                     organism = synthetic construct
SEQUENCE: 87
QHHYGTPPT                                                             9

SEQ ID NO: 88        moltype = AA  length = 219
FEATURE              Location/Qualifiers
source               1..219
                     mol_type = protein
                     organism = synthetic construct
VARIANT              28
                     note = X can be any amino acid
VARIANT              75
                     note = X can be any amino acid
VARIANT              128
                     note = X can be any amino acid or absent
VARIANT              134
                     note = X can be any amino acid
VARIANT              160..162
                     note = X can be any amino acid or absent
VARIANT              168
                     note = X can be any amino acid
VARIANT              172
                     note = X can be any amino acid
VARIANT              215
                     note = X can be any amino acid or absent
SEQUENCE: 88
RVSPSTEVVR FPNITNLCPF GEVFNATXFP SVYAWERKRI SNCVADYSVL YNSTSFSTFK    60
CYGVSPTKLN DLCFXNVYAD SFVVKGDEVR QIAPGQTGVI ADYNYKLPDD FTGCVJAWNT   120
RNIDAGGXNY YYRXFRHGKL KPFERDISNV PYSPGGKPCX XXGLNCYXPL SXYGFYPTVG   180
VGYQPYRVVV LSFELLNAPA TVCGPKLSTD LVKNXCVNF                          219

SEQ ID NO: 89        moltype = AA  length = 219
FEATURE              Location/Qualifiers
source               1..219
                     mol_type = protein
                     organism = synthetic construct
SEQUENCE: 89
RVQPTESIVR FPNITNLCPF GEVFNATRFA SVYAWNRKRI SNCVADYSVL YNSASFSTFK    60
CYGVSPTKLN DLCFTNVYAD SFVIRGDEVR QIAPGQTGKI ADYNYKLPDD FTGCVIAWNS   120
NNLDSKVGGN YNYLYRLFRK SNLKPFERDI STEIYQAGST PCNGVEGFNC YFPLQSYGFQ   180
PTNGVGYQPY RVVVLSFELL HAPATVCGPK KSTNLVKNK                          219

SEQ ID NO: 90        moltype = AA  length = 214
FEATURE              Location/Qualifiers
source               1..214
                     mol_type = protein
                     organism = synthetic construct
SEQUENCE: 90
RTSPTTQVVR FPNITNLCPF GEVFNATTFA SVYAWNRRRI SNCVADYSVL YNTTSFSTFK    60
CYGVSPTKLN DLCFTNVYAD SFVVRGDEVR QIAPGQTGKI ADYNYKLPDD FMGCVIAWNS   120
ISLDAGGSYY YRLFRKSVLK PFERDISTQL YQAGDKPCSV EGPDCYYPLQ SYYFQSTNGV   180
GYQPYRVVVL SFELLNAPAT VCGPKKSTHL VVNK                               214
```

-continued

```
SEQ ID NO: 91              moltype = AA  length = 223
FEATURE                    Location/Qualifiers
source                     1..223
                           mol_type = protein
                           organism = synthetic construct
SEQUENCE: 91
RVQPTISIVR FPNITNLCPF GEVFNASKFA SVYAWNRKRI SNCVADYSVL YNSTSFSTFK    60
CYGVSPTKLN DLCFTNVYAD SFVVKGDEVR QIAPGQTGVI ADYNYKLPDD FTGCVIAWNS   120
VKQDALTGGN YGYLYRLFRK SKLKPFERDI STEIYQAGST PCNGQVGLNC YYPLERYGFH   180
PTTGVNYQPF RVVVLSFELL NGPATVCGPK LSTTLVKDKC VNF                     223

SEQ ID NO: 92              moltype = AA  length = 223
FEATURE                    Location/Qualifiers
source                     1..223
                           mol_type = protein
                           organism = synthetic construct
SEQUENCE: 92
RVQPTDSIVR FPNITNLCPF GEVFNATTFA SVYAWNRKRI SNCVADYSVL YNSTSFSTFK    60
CYGVSPTKLN DLCFTNVYAD SFVITGDEVR QIAPGQTGKI ADYNYKLPDD FTGCVIAWNS   120
KHIDAKEGGN FNYLYRLFRK ANLKPFERDI STEIYQAGSK PCNGQTGLNC YYPLYRYGFY   180
PTDGVGHQPY RVVVLSFELL NAPATVCGPK KSTNLVKNKC VNF                     223

SEQ ID NO: 93              moltype = AA  length = 193
FEATURE                    Location/Qualifiers
source                     1..193
                           mol_type = protein
                           organism = synthetic construct
SEQUENCE: 93
NITNLCPFGE VFNATKFPSV YAWERKKISN CVADYSVLYN STFFSTFKCY GVSATKLNDL    60
CFSNVYADSF VVKGDDVRQI APGQTGVIAD YNYKLPDDFM GCVLAWNTRN IDATSTGNYN   120
YKYRYLRHGK LRPFERDISN VPFSPDGKPC TPPALNCYWP LNDYGFYTTT GIGYQPYRVV   180
VLSFELLNAP ATV                                                     193

SEQ ID NO: 94              moltype = AA  length = 222
FEATURE                    Location/Qualifiers
source                     1..222
                           mol_type = protein
                           organism = synthetic construct
SEQUENCE: 94
RVAPSKEVVR FPNITNLCPF GEVFNATTFP SVYAWERKRI SNCVADYSVL YNSTSFSTFK    60
CYGVSATKLN DLCFSNVYAD SFVVKGDDVR QIAPGQTGVI ADYNYKLPDD FTGCVLAWNT   120
RNIDATQTGN YNYKYRSLRH GKLRPFERDI SNVPFSPDGK PCTPPAFNCY WPLNDYGFYI   180
TNGIGYQPYR VVVLSFELLN APATVCGPKL STDLIKNQCV NF                      222

SEQ ID NO: 95              moltype = AA  length = 218
FEATURE                    Location/Qualifiers
source                     1..218
                           mol_type = protein
                           organism = synthetic construct
SEQUENCE: 95
RVAPSKEVVR FPNITNLCPF GEVFNATTFP SVYAWERKRI SNCVADYSVL YNSTSFSTFK    60
CYGVSATKLN DLCFSNVYAD SFVVKGDDVR QIAPGQTGVI ADYNYKLPDD FLGCVLAWNT   120
NSKDSSTSGN YNYLYRWVRR SKLNPYERDL SNDIYSPGGQ SCSAVGPNCY NPLRPYGFFT   180
TAGVGHQPYR VVVLSFELLN APATVCGPKL STDLIKNQ                           218

SEQ ID NO: 96              moltype = AA  length = 218
FEATURE                    Location/Qualifiers
source                     1..218
                           mol_type = protein
                           organism = synthetic construct
SEQUENCE: 96
RVSPSREVVR FPNITNLCPF GEVFNATTFP SVYAWERKRI SNCVADYSVL YNSTSFSTFK    60
CYGVSAIKLN DLCFSNVYAD SFVVKGDDVR QIAPGQTGVI ADYNYKLPDD FMGCVLAWNT   120
RNIDATSSGN FHYKYRSLRH GKLRPFERDI SNVPFSPDGK PCTPPAFNCY WPLNDYGFYT   180
TNGIGYQPYR VVVLSFELLN APATVCGPKL STDLITNQ                           218

SEQ ID NO: 97              moltype = AA  length = 218
FEATURE                    Location/Qualifiers
source                     1..218
                           mol_type = protein
                           organism = synthetic construct
SEQUENCE: 97
RVVPSGDVVR FPNITNLCPF GEVFNATKFP SVYAWERKRI SNCVADYSVL YNSTSFSTFK    60
CYGVSATKLN DLCFSNVYAD SFVVKGDDVR QIAPGQTGVI ADYNYKLPDD FMGCVLAWNT   120
RNIDATSTGN YNYKYRYLRH GKLRPFERDI SNVPFSPDGK PCTPPAPNCY WPLRGYGFYT   180
TSGIGYQPYR VVVLSFELLN APATVCGPKL STDLIKNQ                           218

SEQ ID NO: 98              moltype = AA  length = 204
```

```
FEATURE              Location/Qualifiers
source               1..204
                     mol_type = protein
                     organism = synthetic construct
SEQUENCE: 98
RVSPTHEVVR FPNITNRCPF DKVFNASRFP NVYAWERTKI SDCVADYTVL YNSTSFSTFK    60
CYGVSPSKLI DLCFTSVYAD TFLIRSSEVR QVAPGETGVI ADYNYKLPDD FTGCVIAWNT   120
AKQDQGQYYY RSSRKTKLKP FERDLTSDEN GVRTLSTYDF YPNVPIEYQA TRVVVLSFEL   180
LNAPATVCGP KLSTALVKNQ CVNF                                          204

SEQ ID NO: 99        moltype = AA  length = 204
FEATURE              Location/Qualifiers
source               1..204
                     mol_type = protein
                     organism = synthetic construct
SEQUENCE: 99
RILPSTEVVR FPNITNFCPF DKVFNATRFP NVYAWQRTKI SDCIADYTVL YNSTSFSTFK    60
CYGVSPSKLI DLCFTSVYAD TFLIRFSEVR QIAPGETGVI ADYNYKLPDD FTGCVLAWNT   120
AQQDIGSYFY RSHRAVKLKP FERDLSSDEN GVRTLSTYDF NPNVPLDYQA TRVVVLSFEL   180
LNAPATVCGP KLSTQLVKNR CVNF                                          204

SEQ ID NO: 100       moltype = AA  length = 204
FEATURE              Location/Qualifiers
source               1..204
                     mol_type = protein
                     organism = synthetic construct
SEQUENCE: 100
RVSPVTEVVR FPNITNLCPF DKVFNATRFP SVYAWERTKI SDCVADYTVF YNSTSFSTFN    60
CYGVSPSKLI DLCFTSVYAD TFLIRFSEVR QVAPGQTGVI ADYNYKLPDD FTGCVIAWNT   120
AKQDVGSYFY RSHRSSKLKP FERDLSSEEN GVRTLSTYDF NQNVPLEYQA TRVVVLSFEL   180
LNAPATVCGP KLSTSLVKNQ CVNF                                          204

SEQ ID NO: 101       moltype = AA  length = 204
FEATURE              Location/Qualifiers
source               1..204
                     mol_type = protein
                     organism = synthetic construct
SEQUENCE: 101
RVSPSTEVIR FPNITNRCPF DRVFNASRFP SVYAWERTKI SDCVADYTVL YNSTSFSTFK    60
CYGVSPSKLI DLCFTSVYAD TFLIRFSEVR QIAPGETGVI ADYNYKLPDE FTGCVIAWNT   120
ANQDRGQYYY RSSRKTKLKP FERDLSSDEN GVRTLSTYDF YPSVPLEYQA TRVVVLSFEL   180
LNAPATVCGP KLSTSLIKNQ CVNF                                          204

SEQ ID NO: 102       moltype = AA  length = 219
FEATURE              Location/Qualifiers
source               1..219
                     mol_type = protein
                     organism = synthetic construct
SEQUENCE: 102
RVTPTTEVVR FPNITQLCPF NEVFNITSFP SVYAWERMRI TNCVADYSVL YNSSASFSTF    60
QCYGVSPTKL NDLCFSSVYA DYFVVKGDDV RQIAPAQTGV IADYNYKLPD DFTGCVIAWN   120
TNSLDSSNEF FYRRFRHGKI KPYGRDLSNV LFNPSGGTCS AEGLNCYKPL ASYGFTQSSG   180
IGFQPYRVVV LSFELLNAPA TVCGPKQSTE LVKNKCVNF                          219

SEQ ID NO: 103       moltype = AA  length = 222
FEATURE              Location/Qualifiers
source               1..222
                     mol_type = protein
                     organism = synthetic construct
SEQUENCE: 103
RVSPSTEVVR FPNITNLCPF GQVFNASNFP SVYAWERLRI SDCVADYAVL YNSSSSFSTF    60
KCYGVSPTKL NDLCFSSVYA DYFVVKGDDV RQIAPAQTGV IADYNYKLPD DFTGCVLAWN   120
TNSVDSKSGN NFYYRLFRHG KIKPYERDIS NVLYNSAGGT CSSISQLGCY EPLKSYGFTP   180
TVGVGYQPYR VVVLSFELLN APATVCGPKK STELVKNKCV NF                      222

SEQ ID NO: 104       moltype = AA  length = 220
FEATURE              Location/Qualifiers
source               1..220
                     mol_type = protein
                     organism = synthetic construct
SEQUENCE: 104
RVSPSLDVVR FPNMTNICPF DQVFNKTQFP SVYAWERVRI SDCVSDYTVL YNSSASFSTF    60
KCYGVSPTKL NDLCFSGVYA DYFVVKGDHV HQIAPGQTGV IADYNYKLPS EFVGCILAWN   120
TRTIDSKRGF YYRLFRHGNI RPYERDTSNV PYNAAGGTCN QPGTHNCYEP LQDYGFTSTS   180
GVGYQPFRVV VLSFELLNAP ATVCGPKQST DLVKNKCVNF                         220

SEQ ID NO: 105       moltype = AA  length = 16
FEATURE              Location/Qualifiers
source               1..16
```

-continued

```
                              mol_type = protein
                              organism = synthetic construct
SEQUENCE: 105
RGVPHIVMVD AYKRYK                                                  16
```

1

ANTIBODIES WHICH HAVE SPECIFICITY TO A SARBECOVIRUS SPIKE PROTEIN RECEPTOR-BINDING DOMAIN AND METHODS OF USE THEREOF FOR TREATING A CORONAVIRUS INFECTION

RELATED APPLICATIONS

This application claims the benefit under 35 U.S.C. § 119(e) of U.S. Provisional Patent Application Ser. No. 63/285,441, filed Dec. 2, 2021, U.S. Provisional Patent Application Ser. No. 63/341,314, filed May 12, 2022, and U.S. Provisional Patent Application Ser. No. 63/375,618, filed Sep. 14, 2022. The content of these related application is incorporated herein by reference in its entirety for all purposes.

STATEMENT REGARDING FEDERALLY SPONSORED R&D

This invention was made with government support under Grant No(s). AI138938 & CA033572 awarded by the National Institutes of Health. The government has certain rights in the invention.

REFERENCE TO SEQUENCE LISTING

The present application is being filed along with a Sequence Listing in electronic format. The Sequence Listing is provided as a file entitled 30KJ-302449-US_SeqList, created Dec. 1, 2022, which is 108 kilobytes in size. The information in the electronic format of the Sequence Listing is incorporated herein by reference in its entirety.

BACKGROUND

Field

The present disclosure relates generally to the field of biopharmaceuticals.

Description of the Related Art

Spillover of animal SARS-like betacoronaviruses (sarbecoviruses) resulted in two human health emergencies in the early 21$^{st}$ century: the SARS-CoV epidemic in the early 2000s and the COVID-19 pandemic caused by SARS-CoV-2. Large coronavirus reservoirs in bats are predictive of future cross-species transmission, necessitating vaccines and therapies that can protect against emerging coronaviruses. In addition, SARS-CoV-2 variants have emerged throughout the COVID-19 pandemic, with the Alpha, Beta, Delta, Gamma, and Omicron lineages designated as variants of concern (VOCs) due to apparent increased transmissibility and/or resistance to neutralizing antibodies elicited by infection or vaccination. In the case of Omicron VOCs, a large number of substitutions in the SARS-CoV-2 spike protein receptor-binding domain (RBD), the major target of neutralizing antibodies and detectable cross-variant neutralization, results in reduced efficacies of vaccines and therapeutic monoclonal antibodies (mAbs).

Comparison of the variability of RBDs across sarbecoviruses (FIG. 7A-FIG. 7E) and within SARS-CoV-2 VOCs and variants of interest (VOIs) suggest that vaccines and mAbs targeting the more conserved neutralizing antibody epitopes (class 4 and class ¼; nomenclature from (FIG. 1A-FIG. 1B) can protect against present and future SARS-CoV-2 VOCs and prevent future sarbecovirus spillover events from causing another epidemic or pandemic. By contrast, antibodies targeting the less conserved class 1 and class 2 RBD epitopes that directly overlap with the binding footprint for human ACE2, the SARS-CoV-2 host receptor, recognize a portion of the RBD that exhibits sequence variability between sarbecoviruses (FIG. 1A), which is also where VOC and VOI substitutions accumulate (FIG. 1B; FIG. 8A-FIG. 8C). Class 3 RBD epitopes are more conserved than class 1 and class 2 epitopes but exhibit some variation across sarbecoviruses (FIG. 1B; FIG. 8A-FIG. 8C), suggesting the potential for continued variability amongst SARS-CoV-2 VOCs.

There is a need for antibodies capable of broadly neutralizing for sarbecoviruses and be useful, for example, for treating or preventing SARS-Cov-2 infections, as well as infections due to emerging coronaviruses.

SUMMARY

Disclosed herein include antibodies or fragments thereof. In some embodiments, the antibody or fragment thereof has specificity to a sarbecovirus spike protein receptor binding domain (RBD) and comprises: (a) a heavy chain variable region (VH) CDR1 comprising an amino acid sequence selected from SEQ ID NOs: 49-55 or a variant thereof having a single substitution, deletion or insertion from any one of SEQ ID NOs: 49-55; (b) a VH CDR2 comprising an amino acid sequence selected from SEQ ID NOs: 57-63 or a variant thereof having a single substitution, deletion or insertion from any one of SEQ ID NOs: 57-63; (c) a VH CDR3 comprising an amino acid sequence selected from SEQ ID NOs: 65-71 or a variant thereof having a single substitution, deletion or insertion from any one of SEQ ID NOs: 65-71; (d) a light chain variable region (VL) CDR1 comprising an amino acid sequence selected from SEQ ID NOs: 73-79 or a variant thereof having a single substitution, deletion or insertion from any one of SEQ ID NOs: 73-79; (e) a VL CDR2 comprising an amino acid sequence selected from WAS, YAS, RAS and RAK; and (f) a VL CDR3 comprising an amino acid sequence selected from SEQ ID NOs: 81-87 or a variant thereof having a single substitution, deletion or insertion from any one of SEQ ID NOs: 81-87.

The antibody or fragment thereof can comprise: (a) a VH CDR1 comprising an amino acid sequence selected from SEQ ID NOs: 49-55; (b) a VH CDR2 comprising an amino acid sequence selected from SEQ ID NOs: 57-63; (c) a VH CDR3 comprising an amino acid sequence selected from SEQ ID NOs: 65-71; (d) a VL CDR1 comprising an amino acid sequence selected from SEQ ID NOs: 73-79; (e) a VL CDR2 comprising an amino acid sequence selected from WAS, YAS, RAS, and RAK; and (f) a VL CDR3 comprising an amino acid sequence selected from SEQ ID NOs: 81-87.

The antibody or fragment thereof can comprise: a VH CDR1 of SEQ ID NO: 49 or a variant thereof having a single substitution, deletion or insertion of SEQ ID NO: 49; a VH CDR2 of SEQ ID NO: 57 or a variant thereof having a single substitution, deletion or insertion of SEQ ID NO: 57; a VH CDR3 of SEQ ID NO: 65 or a variant thereof having a single substitution, deletion or insertion of SEQ ID NO: 65; a VL CDR1 of SEQ ID NO: 73 or a variant thereof having a single substitution, deletion or insertion of SEQ ID NO: 73; a VL CDR2 having the amino acid sequence WAS; and a VL CDR3 of SEQ ID NO: 81 or a variant thereof having a single substitution, deletion or insertion of SEQ ID NO: 81. The antibody or fragment thereof can comprise: a VH CDR1 of SEQ ID NO: 51 or a variant thereof having a single substitution, deletion or insertion of SEQ ID NO: 51; a VH CDR2 of SEQ ID NO: 59 or a variant thereof having a single substitution, deletion or insertion of SEQ ID NO: 59; a VH CDR3 of SEQ ID NO: 67 or a variant thereof having a single substitution, deletion or insertion of SEQ ID NO: 67; a VL CDR1 of SEQ ID NO: 75 or a variant thereof having a single substitution, deletion or insertion of SEQ ID NO: 75; a VL CDR2 having the amino acid sequence YAS; and a VL CDR3 of SEQ ID NO: 83 or a variant thereof having a single substitution, deletion or insertion of SEQ ID NO: 83. The antibody or fragment thereof can comprise: a VH CDR1 of SEQ ID NO: 52 or a variant thereof having a single substitution, deletion or insertion of SEQ ID NO: 52; a VH CDR2 of SEQ ID NO: 60 or a variant thereof having a single substitution, deletion or insertion of SEQ ID NO: 60; a VH CDR3 of SEQ ID NO: 68 or a variant thereof having a single substitution, deletion or insertion of SEQ ID NO: 68; a VL CDR1 of SEQ ID NO: 76 or a variant thereof having a single substitution, deletion or insertion of SEQ ID NO: 76; a VL CDR2 having the amino acid sequence WAS; and a VL CDR3 of SEQ ID NO: 84 or a variant thereof having a single substitution, deletion or insertion of SEQ ID NO: 84. The antibody or fragment thereof can comprise: a VH CDR1 of SEQ ID NO: 53 or a variant thereof having a single substitution, deletion or insertion of SEQ ID NO: 53; a VH CDR2 of SEQ ID NO: 61 or a variant thereof having a single substitution, deletion or insertion of SEQ ID NO: 61; a VH CDR3 of SEQ ID NO: 69 or a variant thereof having a single substitution, deletion or insertion of SEQ ID NO: 69; a VL CDR1 of SEQ ID NO: 77 or a variant thereof having a single substitution, deletion or insertion of SEQ ID NO: 77; a VL CDR2 having the amino acid sequence RAS; and a VL CDR3 of SEQ ID NO: 85 or a variant thereof having a single substitution, deletion or insertion of SEQ ID NO: 85.

The antibody or fragment thereof can comprise a heavy chain variable region comprising (i) an amino acid sequence selected from SEQ ID NOs: 1, 4, 27, 33, 35, 41, and 43, (ii) an amino acid sequence having at least 90% sequence identity to an amino acid sequence selected from SEQ ID NOs: 1, 4, 27, 33, 35, 41, and 43, or (iii) an amino acid sequence having one, two or three mismatches relative to an amino acid sequence selected from SEQ ID NOs: 1, 4, 27, 33, 35, 41, and 43. The antibody or fragment thereof can comprise a light chain variable region comprising (i) an amino acid sequence of SEQ ID NO: 2, 5, 28, 34, 36, 42, or 44, (ii) an amino acid sequence having at least 90% sequence identity to an amino acid sequence selected from SEQ ID NOs: 2, 5, 28, 34, 36, 42, and 44, (iii) an amino acid sequence having one, two or three mismatches relative to an amino acid sequence selected from SEQ ID NOs: 2, 5, 28, 34, 36, 42, and 44.

The antibody or fragment thereof can comprise a heavy chain variable region comprising the amino acid sequence of SEQ ID NO: 1 or a peptide having at least 90% sequence identity to the amino acid sequence of SEQ ID NO: 1, and a light chain variable region comprising the amino acid sequence of SEQ ID NO: 2 or a peptide having at least 90% sequence identity to the amino acid sequence of SEQ ID NO: 2. The antibody or fragment thereof can comprise a heavy chain variable region comprising the amino acid sequence of SEQ ID NO: 27 or a peptide having at least 90% sequence identity to the amino acid sequence of SEQ ID NO: 27, and a light chain variable region comprising the amino acid sequence of SEQ ID NO: 28 or a peptide having at least 90% sequence identity to the amino acid sequence of SEQ ID NO: 28. The antibody or fragment thereof can comprise a heavy chain variable region comprising the amino acid sequence of SEQ ID NO: 33 or a peptide having at least 90% sequence identity to the amino acid sequence of SEQ ID NO: 33, and a light chain variable region comprising the amino acid sequence of SEQ ID NO: 34 or a peptide having at least 90% sequence identity to the amino acid sequence of SEQ ID NO: 34.

The antibody or fragment thereof can comprise a heavy chain variable region comprising the amino acid sequence of SEQ ID NO: 35 or a peptide having at least 90% sequence identity to the amino acid sequence of SEQ ID NO: 35, and a light chain variable region comprising the amino acid sequence of SEQ ID NO: 36 or a peptide having at least 90% sequence identity to the amino acid sequence of SEQ ID NO: 36.

In some embodiments, the antibody or fragment thereof comprises an Fc domain. In some embodiments, the antibody or fragment thereof is a single-chain variable fragment (scFv), a single-domain antibody, an immunoglobulin molecule, a monoclonal antibody, a chimeric antibody, a CDR-grafted antibody, a humanized antibody, a Fab fragment, a Fab' fragment, a F(ab')$_2$ fragment, an Fv fragment, a disulfide linked Fv, an scFv, a single domain antibody, a diabody, a multispecific antibody, a dual specific antibody, an anti-idiotypic antibody, a bispecific antibody, or a functionally active epitope-binding fragment thereof.

In some embodiments, the antibody or fragment thereof specifically binds to two or more different sarbecovirus spike protein RBDs. In some embodiments, the antibody or fragment thereof binds to at least one of the two or more sarbecovirus spike protein RBDs with an EC50 of less than 10 µg/mL, less than 1 µg/mL, less than 0.1 µg/mL, or less than 0.01 µg/mL as assessed by an optofluidic system and/or an ELISA assay. In some embodiments, the antibody or fragment thereof binds to all of the two or more sarbecovirus spike protein RBDs with an EC50 of less than 10 µg/mL, less than 1 µg/mL, less than 0.1 µg/mL, or less than 0.01 µg/mL as assessed by an optofluidic system and/or an ELISA assay. In some embodiments, the antibody or fragment thereof binds to at least one of the two or more sarbecovirus spike protein RBDs with an EC50 of about 0.001 µg/mL to about 10 µg/mL, about 0.001 µg/mL to about 1 µg/mL, about 0.001 µg/mL to about 0.1 µg/mL, or about 0.001 µg/mL to about 0.01 µg/mL as assessed by an optofluidic system and/or an ELISA assay. In some embodiments, the antibody or fragment thereof binds to all of the two or more sarbecovirus spike protein RBDs with an EC50 of about 0.001 µg/mL to about 10 µg/mL, about 0.001 µg/mL to about 1 µg/mL, about 0.001 µg/mL to about 0.1 µg/mL, or about 0.001 µg/mL to about 0.01 µg/mL as assessed by an optofluidic system and/or an ELISA assay. In some embodiments, at least one of the two or more sarbecovirus spike protein RBDs is selected from SARS-CoV-2 RBD and variants thereof, RsSTT200 RBD and variants thereof, Pang17 RBD and variants thereof, RaTG13 RBD and variants thereof, SARS-CoV RBD and variants thereof, WIV1 RBD and variants thereof, SHCO14 RBD and variants thereof, LyRa3 RBD and variants thereof, C028 RBD and variants thereof, Rs4081 RBD and variants thereof, RmYNO2 RBD and variants thereof, Rfl RBD and variants thereof, Yun11 RBD and variants thereof, BM4831 RBD and variants thereof, BtKY72 RBD and variants thereof, and Khosta2 RBD and variants thereof.

In some embodiments, the antibody or fragment thereof inhibits infectivity of a virus comprising a sarbecovirus spike protein receptor binding domain (RBD) with an IC50 less than 10 µg/mL, less than 1 µg/mL, less than 0.1 µg/mL or less than 0.01 µg/mL. In some embodiments, IC50 is measured by a pseudovirus neutralization assay. In some embodiments, the antibody or fragment thereof inhibits infectivity of a virus comprising a sarbecovirus spike protein receptor binding domain (RBD) with an IC50 of about 0.001 µg/mL to about 10 µg/mL, about 0.001 µg/mL to about 1 µg/mL, about 0.001 µg/mL to about 0.1 µg/mL, or about 0.001 µg/mL to about 0.01 µg/mL. In some embodiments, IC50 is measured by a pseudovirus neutralization assay.

In some embodiments, the antibody or fragment thereof inhibits infectivity of two or more viruses each comprising a different sarbecovirus spike protein receptor binding domain (RBD). In some embodiments, the antibody or fragment thereof inhibits infectivity of at least one, at least two, or all of the two or more viruses with an IC50 less than 10 µg/mL, less than 1 µg/mL, less than 0.1 µg/mL, or less than 0.01 µg/mL. In some embodiments, the antibody or fragment thereof inhibits infectivity of at least one, at least two, or all of the two or more viruses with an IC50 of about 0.001 µg/mL to about 10 µg/mL, about 0.001 µg/mL to about 1 µg/mL, about 0.001 µg/mL to about 0.1 µg/mL, or about 0.001 µg/mL to about 0.01 µg/mL. In some embodiments, the antibody or fragment thereof inhibits infectivity of at least one, at least two, or all of the two or more viruses with an IC50 of about 0.005 µg/mL to about 9 µg/mL, for example an IC50 of about 0.001 µg/mL to about 0.06 µg/mL, an IC50 of about 0.02 µg/mL to about 6 µg/mL, or an IC50 of about 0.002 µg/mL to about 2 µg/mL. In some embodiments, the pseudovirus neutralization assay comprises target cells expressing hACE2 receptor protein.

The sarbecovirus spike protein RBD can be SARS-CoV-2 RBD or a variant thereof, SARS-CoV RBD and variants thereof, WIV1 RBD and variants thereof, SHC014 RBD and variants thereof, BtKY72 RBD and variants thereof, Khosta2/SARS-CoV Chimera RBD and variants thereof, and LyRa3/SARS-CoV RBD Chimera and variants thereof. In some embodiments, the SARS-CoV-2 variants comprise Wuhan (WA1 D614G), Beta, Delta, Omicron BA.1, Omicron BA.2, Omicron BA.4, and Omicron BA.5. In some embodiments, the antibody or fragment thereof is capable of binding to each of the three RBDs of a sarbecovirus spike trimer.

Disclosed herein include compositions comprising any of the antibodies or fragments thereof provided herein and a pharmaceutically acceptable carrier. Also disclosed herein are polynucleotides encoding one or more of the antibodies or fragments thereof provided herein. There are provided isolated cells comprising any of the polynucleotides provided herein. Disclosed herein include compositions comprising any of the polynucleotides and/or an isolated cells provided herein.

Disclosed herein include methods of treating or preventing a coronavirus infection in a patient in need thereof, e.g., administering to the patient an effective amount of any of the antibodies or fragments thereof, polynucleotides, isolated cells, and compositions provided herein, or a combination thereof.

In some embodiments, the coronavirus is a coronavirus in the genus of Alpha-coronavirus, Beta-coronavirus, or both. In some embodiments, the coronavirus is a coronavirus of the subgenus Sarbecovirus. In some embodiments, the coronavirus is SARS-CoV-2 and variants thereof, RsSTT200 and variants thereof, Pang17 and variants thereof, RaTG13 and variants thereof, SARS-CoV and variants thereof, WIV1 and variants thereof, SHC014 and variants thereof, LyRa3 and variants thereof, C028 and variants thereof, Rs4081 and variants thereof, RmYNO2 and variants thereof, Rfl and variants thereof, Yun11 and variants thereof, BM4831 and variants thereof, BtKY72 and variants thereof, or Khosta2 and variants thereof. In some embodiments, the coronavirus comprises a SARS-CoV-2 variant of concern, variant of interest, or both. In some embodiments, the SARS-CoV-2 variant of concern comprises SARS-CoV-2 Beta and variants thereof, SARS-CoV-2 Delta and variants thereof, or SARS-CoV-2 Omicron and variants thereof.

The method can comprise administering to the patient a second therapeutic agent. In some embodiments, the second therapeutic agent comprises an anti-viral compound, an immunosuppressant, an antibody, or any combination thereof. In some embodiments, the second therapeutic agent comprises remdesivir, molnupiravir, tocilizumab, favipiravir, merimepodib, artesunate, favipiravir, ribavirin, EIDD-2801, niclosamide, nitazoxanide, oseltamivir, AT-527, paxlovid, regdanvimab, ramdicivir, baricitinib, imatinib, casirivimab, imdevimab, bemcentinib, bamlanivimab, etesevimab, sotrovimab, leronlimab, bebtelovimab, cilgavimab, IMU-838, oseltamivir, or dexamethasone.

Disclosed herein include methods for identifying an antibody or fragment thereof that has specificity to a sarbecovirus spike protein receptor binding domain (RBD). In some embodiments, the method comprises screening B cells against one or more sarbecovirus spike protein RBDs; wherein the B cells are isolated from a mammal immunized with two or more different sarbecovirus spike protein RBDs.

In some embodiments, the B cells are isolated from a mammal immunized with four or more different sarbecovirus spike protein RBDs. In some embodiments, the B cells are isolated from a mammal immunized with a nanoparticle comprising the two or more sarbecovirus spike protein RBDs. In some embodiments, the nanoparticle comprises one or more sarbecovirus spike protein RBDs selected from a SARS-CoV-2 RBD, an SHC014 RBD, an RaTG13 RBD, an Rs4081 RBD, a WIV1 RBD, an Rfl RBD, an RmYNO2 RBD, a Pang17 RBD, a SARS-CoV RBD, a Yun11 RBD, a BM4831 RBD, and a BtKY72 RBD. In some embodiments, the immunizing comprises administration of an adjuvant. In some embodiments, the mammal a mouse, a rat, a rabbit, a goat, or a primate. In some embodiments, the B cells are CD138+ plasma B cells.

The method can comprise screening B cells for secretion of an antibody or fragment thereof that specifically binds to one or more sarbecovirus spike protein RBDs, wherein the one or more sarbecovirus spike protein RBDs are selected from a SARS-CoV-2 RBD and variants thereof, RsSTT200 RBD and variants thereof, Pang17 RBD and variants thereof, RaTG13 RBD and variants thereof, SARS-CoV RBD and variants thereof, WIV1 RBD and variants thereof, SHCO14 RBD and variants thereof, LyRa3 RBD and variants thereof, C028 RBD and variants thereof, Rs4081 RBD and variants thereof, RmYNO2 RBD and variants thereof, Rfl RBD and variants thereof, Yun11 RBD and variants thereof, BM4831 RBD and variants thereof, BtKY72 RBD and variants thereof, and Khosta2 RBD and variants thereof. In some embodiments, the binding is assessed by an optofluidic assay, an ELISA assay, or both. In some embodiments, the antibody or fragment thereof binds to the one or more sarbecovirus spike protein RBDs with an EC50 of less than 10 µg/mL, less than 1 µg/mL, less than 0.1 µg/mL, or less than 0.01 µg/mL. In some embodiments, the antibody or fragment thereof binds to the one or more sarbecovirus spike protein RBDs with an EC50 of about 0.001 µg/mL to about 10 µg/mL, about 0.001 µg/mL to about 1 µg/mL, about 0.001 µg/mL to about 0.1 µg/mL, or about 0.001 µg/mL to about 0.01 µg/mL. Disclosed herein include antibodies or fragments thereof identified by the methods provided herein.

BRIEF DESCRIPTION OF THE DRAWINGS

FIG. 1A shows exemplary models of the SARS-CoV-2 spike trimer and conserved sequences. Left: Structure of SARS-CoV-2 spike trimer (PDB 6VYB) with one RBD in an "up" position. Right: Sequence conservation of 16 sarbecovirus RBDs (FIG. 7A-FIG. 7E) calculated by the ConSurf Database plotted on a surface representation of the RBD structure (PDB 7BZ5). Class 1, 2, 3, 4, and ¼ epitopes are outlined in different shaded dots using information from structures of the representative monoclonal antibodies bound to RBD or spike trimer (Cl 02: PDB 7K8M; C002: PDB 7K8T, S309: PDB 7JX3; CR3022: PDB 7LOP; Cl 18: PDB 7RKV). A potential N-linked glycosylation site at position 370 (SARS-CoV-2 numbering) found in some sarbecovirus RBDs but not in the SARS-CoV-2 RBD is indicated by a hexagon. FIG. 1B shows RBD mutations of 13 SARS-CoV-2 VOCs and VOis (viralzone.expasy.org/9556) plotted onto the RBD structure (PDB 7BZ5) as spheres that are shaded according to the variability gradient shown. The N-linked glycan at position 343 of SARS-CoV-2 RBD is shown as small spheres. FIG. 1C depicts an exemplary structural model of a mosaic-8 nanoparticle formed by SpyCatcher-mi3 and eight SpyTagged RBDs made using coordinates of an RBD (PDB 7SC1), mi3 (PDB 7B3Y), and SpyCatcher (PDB 4MLI). FIG. 1D shows a non-limiting exemplary embodiment of preferential stimulation of B cells that encode cross-reactive antibodies by mosaic (right) versus homotypic (left) RBD nanoparticles. Left: Lighter shaded B cell receptors recognizing an accessible strain-specific epitope (lighter triangle) can crosslink between adjacent RBDs on a homotypic nanoparticle to enhance binding through avidity effects. Middle: Lighter shaded B cell receptors against a strain-specific epitope cannot crosslink between adjacent RBDs on a mosaic RBD nanoparticle that presents different versions of the epitope (differently shaded triangles). Right: Darker cross-reactive B cell receptors can crosslink between a conserved epitope (center dark circles) on adjacent RBDs in a mosaic RBD nanoparticle to enhance binding to a more occluded, but conserved, epitope through avidity effects.

FIG. 2A-FIG. 2B depict exemplary data showing that a subset of mAbs elicited in mosaic-8 and homotypic SARS-CoV-2 RBD nanoparticle-immunized mice show cross-reactive binding and neutralization properties. FIG. 2A shows data related to assays for RBD binding. Top four rows: RBDs used for screening of single B cells. Stars indicates binding was detected; no star indicates no binding was detected. Remaining rows: ELISA $EC_{50}$ values for mouse mAb binding to sarbecovirus RBDs from different clades. RBDs that were included on the mosaic-8 RBD-nanoparticles are highlighted. $EC_{50}$ values were derived from ELISAs conducted with duplicate samples at least twice (for first seven mAbs) or once (for remaining mAbs). M8a-11 and M8a-26 shared the same protein sequences, the same $EC_{50}$ values were presented twice. Darker boxes with a dagger symbol indicates an EC50 value greater than 10 μg/mL. FIG. 2B shows exemplary data related to neutralization potencies ($IC_{50}$ values) of mAbs against SARS-CoV-2 variants and indicated sarbecoviruses. $IC_{50}$ values are reported from neutralization assays that were conducted using duplicate samples at least twice except for a single assay for M8a-28 against Omicron BA.1.

(FIG. 3A) WA1 spike complexed with M8a-3. (FIG. 3B) WA1 spike complexed with M8a-6. (FIG. 3C) WA1 spike complexed with M8a-31. (FIG. 3D) Omicron BA.1 spike complexed with M8a-31. (FIG. 3E) WA1 spike complexed with M8a-34. (FIG. 3F) WA1 spike complexed with M8a-28.

FIG. 4A-FIG. 4F depict non-limiting exemplary cartoons showing epitopes of mAbs elicited by mosaic-8 immunization demonstrate targeting of non-class 1/class 2 RBD epitopes. FIG. 4A displays four views of RBD surface (dark gray) with overlay of mAb $V_H$-$V_L$ domains (different shaded cartoon representations) from Fab-spike structures. ACE2 (light cartoon representation comprising alpha helices) complexed with RBD (PDB 6M0J) is shown for comparison. FIG. 4B-FIG. 4F depict mAb epitopes on RBD surface shown with overlaid heavy and light chain CDRs (top, CDRs that do not interact with the RBD are shown in transparent cartoons; all CDRs were defined based on the IMGT definition), as different shaded areas for heavy and light chains as indicated by arrows (middle) and outlined with dotted lines on a sequence conservation surface plot (bottom; calculated using the 16 sarbecovirus RBD sequences shown in FIG. 7A-FIG. 7E). The N-glycan at RBD position Asn343 was shown as spheres. (FIG. 4B) M8a-3. (FIG. 4C) M8a-6. (FIG. 4D) M8a-31 from complex with WA1 spike trimer. (FIG. 4E) M8a-34. (FIG. 4F) M8a-28. Omicron BA.1 and BA.2 substitutions are in darker shading in the top panels of (FIG. 4B-FIG. 4F).

FIG. 5A shows EM density of single-particle cryo-EM structure of HSW-1 Fab-spike trimer complex shown from the side (upper left), the top (lower right), and as a cartoon diagram of the HSW-1 $V_H$-$V_L$ interaction with two adjacent RBDs (1° and 2°) (upper right). HSW-1 interacts mainly with an 'up' RBD (1° RBD, lighter shaded RBD) but also includes $V_L$ interactions with a 'down' RBD (2° RBD, darker shaded RBD). FIG. 5B shows a model of HSW-1 epitope on RBD surface shown with overlaid heavy and light chain CDRs (top, CDRs that do not interact with the RBD are shown in transparent cartoons; all CDRs were defined based on the IMGT definition), as differently shaded areas for heavy and light chains (middle) as indicated by arrows and outlined with dotted lines on a sequence conservation surface plot (bottom; calculated using the 16 sarbecovirus RBD sequences in FIG. 7A-FIG. 7E). Omicron BA.1 and BA.2 substitutions are in darker shading in the top panel. FIG. 5C depicts a model of EM density of single-particle cryo-EM structure of HSW-2-Fab S1 domain complex (top) and cartoon diagram of the HSW-2 $V_H$-$V_L$ interaction with the RBD (bottom). FIG. 5D shows a model of the HSW-1 epitope on RBD surface shown with overlaid heavy and light chain CDRs (top, all CDRs were defined based on the IMGT definition), as differently shaded areas for heavy and light chains (middle) as indicated by arrows and outlined with dotted lines on a sequence conservation surface plot (bottom; calculated using the 16 sarbecovirus RBD sequences shown in FIG. 7A-FIG. 7E). Omicron BA.1 and BA.2 substitutions are in darker shading in the top panel. FIG. 5E displays two views of RBD surface (dark gray) with overlays of mAb $V_H$-$V_L$ domains (lighter gray cartoon representations) from HSW Fab-spike structures and ACE2 (light gray cartoon representation at top comprising alpha helices from PDB 6M0J). FIG. 5F-FIG. 5G depict superpositions of HSW-2-RBD structure onto the RBD from a spike trimer structure showing that HSW-2 Fab is sterically hindered from binding to either an 'up' or 'down' RBD on an intact spike trimer due to clashes (indicated as starbursts) with the spike S2 domain. (FIG. 5F) HSW-2 Fab-RBD interaction modeled onto an 'up' RBD from the M8a-31-spike complex structure. (FIG. 5G) HSW-2 Fab-RBD interaction modeled onto a 'down' RBD from the M8a-28-spike complex structure.

FIG. 6A-FIG. 6G depict non-limiting illustrations of comparisons of M8a epitopes with human mAbs targeting class 3 or class ¼ RBD epitopes. FIG. 6A depicts locations of class 3 and class ¼ RBD epitopes mapped on an unliganded spike trimer structure with two 'down' and one 'up' RBDs (PDB 6VYB) showing that the class 3 epitope is exposed, whereas the class ¼ epitope is partially occluded in the context of the spike trimer. The binding epitopes of representative class 3 (5309/Sotrovimab, PDB 7JX3) and class ¼ (C118, PDB 7RKV) anti-RBD antibodies were identified by PDBePISA. FIG. 6B-FIG. 6F show RBD epitopes of M8a-28 and human mAbs. Left: $V_H$-$V_L$ domains of M8a-28 and currently or previously EUA-approved class 3 anti-RBD mAbs (cartoon representations) shown interacting with an RBD (gray surface representation with Omicron BA.1 and BA.2 substitutions in darker shading on the surface and the RBD Asn343 N-glycan shown as dark spheres). Right: mAb epitopes outlined with dotted lines on a sequence conservation surface plot (calculated using the 16 sarbecovirus RBD sequences shown in FIG. 7A-FIG. 7E). (FIG. 6B) M8a-28. (FIG. 6C) LY-CoV1404/Bebtelovimab (PDB 7MMO). (FIG. 6D) 5309/Sotrovimab (PDB 7JX3). (FIG. 6E) REGN10987/Imdevimab (PDB 6XDG). (FIG. 6F) AZD1061/Cilgavimab (PDB 7L7E). FIG. 6G depicts a comparison of the class ¼ epitopes of M8a mouse mAbs described herein with the epitopes of C118 (PDB 7RKV), a broadly cross-reactive human mAb, and S2X259 (PDB 7RAL), a broadly reactive and potent human class ¼ mAb.

FIG. 7A-FIG. 7E show data related to sarbecovirus RBDs and construction of RBD-nanoparticles. FIG. 7A depicts a sequence alignment of RBDs from 16 sarbecoviruses. FIG. 7B shows pairwise sequence identities (%) relating the RBDs in FIG. 7A. FIG. 7C depicts an SEC profile showing separation of conjugated SpyCatcher003-mi3 nanoparticles from free RBDs. RBDs were added at a 2-fold molar excess over SpyCatcher003-mi3 subunits. FIG. 7D shows exemplary SDS-PAGE analysis of free RBD, purified conjugated RBD-nanoparticles, and unconjugated SpyCatcher-mi3 nanoparticles. FIG. 7E depicts an exemplary negative stain EM of conjugated nanoparticles. Left: mosaic-8 RBD-nanoparticles. Right: homotypic SARS-CoV-2 RBD-nanoparticles.

(FIG. 8A) SARS- CoV-2 Alpha, Beta, Gamma and Delta variants. (FIG. 8B) SARS-CoV-2 Omicron BA.1 and BA.2 variants. (FIG. 8C) SARS-CoV-2 VOIs.

FIG. 9A illustrates how antigen-specific binding activity was assayed using biotinylated RBDs immobilized on streptavidin-coated beads and loaded into the main channel of the Beacon microfluidic chip, which contained single plasma B cells in individual culture compartments (Nanopens). The specificity of secreted antibodies for the antigen presented in the channel was detected via the local concentration of a fluorescently-labeled secondary above a Nanopen secreting an antigen-specific antibody. FIG. 9B depicts examples of detection of secreted antibody binding to different RBDs. The Nanopen(s) from which the secreted antibody signal was emanating over the assay time course is highlighted.

FIG. 10A-FIG. 10B show data related to a sequence alignment of seven mAbs isolated from RBD nanoparticle-immunized mice that bound two or more sarbecovirus RBDs. FIG. 10A depicts a sequence alignment of $V_H$ and $V_L$ domains. CDRs were assigned using IMGT definitions. VH and VL gene segment assignments for each mAb are shown in parentheses. FIG. 10B shows the pairwise sequence identities (%) between $V_H$ and $V_L$ domains in FIG. 10A.

FIG. 12A depicts a representative micrograph. FIG. 12B shows representative 2D classes. FIG. 12C depicts an exemplary workflow of single-particle data processing. FIG. 12D shows a fourier shell correlation (FSC) plot of the final reconstruction. FIG. 12E shows final reconstruction of M8a-3 Fab in complex with SARS-CoV-2 spike, shaded by local resolution.

FIG. 13A depicts a representative micrograph. FIG. 13B shows representative 2D classes. FIG. 13C depicts an exemplary workflow of single-particle data processing. FIG. 13D shows an FSC plot of the final reconstruction. FIG. 13E shows final reconstruction of M8a-6 Fab in complex with SARS-CoV-2 spike, shaded by local resolution.

FIG. 14A depicts a representative micrograph. FIG. 14B shows representative 2D classes. FIG. 14C depicts an exemplary workflow of single-particle data processing. FIG. 14D shows an FSC plot of the final reconstruction. FIG. 14E shows final reconstruction of M8a-31 Fab in complex with SARS-CoV-2 spike, shaded by local resolution.

FIG. 15A depicts a representative micrograph. FIG. 15B shows representative 2D classes. FIG. 15C depicts an exemplary workflow of single-particle data processing. FIG. 15D shows an FSC plot of the final reconstruction. FIG. 15E shows final reconstruction of M8a-3 Fab in complex with SARS-CoV-2 spike Omicron BA.1, shaded by local resolution.

FIG. 16A depicts a representative micrograph. FIG. 16B shows representative 2D classes. FIG. 16C depicts exemplary workflow of single-particle data processing. FIG. 16D shows an FSC plot of the final reconstruction. FIG. 16E depicts final reconstruction of M8a-34 Fab in complex with SARS-CoV-2 spike, shaded by local resolution.

FIG. 17A depicts a representative micrograph. FIG. 17B show representative 2D classes. FIG. 17C depicts an exemplary workflow of single-particle data processing. FIG. 17D shows an FSC plot of the final reconstruction. FIG. 17E shows final reconstructions of both states of M8a-28 Fab in complex with SARS-CoV-2 spike, shaded by local resolution. An 'up' RBD in state 2 is labeled with an arrow.

FIG. 18A depicts a representative micrograph. FIG. 18B shows representative 2D classes. FIG. 18C depicts an exemplary workflow of single-particle data processing. FIG. 18D depicts an FSC plot of the final reconstruction. FIG. 18E shows final reconstruction of HSW-1 Fab in complex with SARS-CoV-2 spike, shaded by local resolution.

FIG. 19A depicts a representative micrograph. FIG. 19B shows representative 2D classes. FIG. 19C depicts an exemplary workflow of single-particle data processing. FIG. 19D depicts an FSC plot of the final reconstruction. FIG. 19E shows final reconstruction of HSW-2 Fab in complex with SARS-CoV-2 spike S1 domain, shaded by local resolution.

(FIG. 20A) WA1 spike complexed with M8a-3. (FIG. 20B) SARS-CoV-2 WA1 spike complexed with M8a-6. (FIG. 20C) WA1 spike complexed with M8a-31. (FIG. 20D) Omicron BA.1 spike complexed with M8a-31. (FIG. 20E) WA1 spike complexed with M8a-34. (FIG. 20F) WA1 spike complexed with M8a-28.

(FIG. 21A) SARS-CoV-2 WA1 spike complexed with HSW-1. (FIG. 21B) WA1 spike S1 domain complexed with HSW-2.

FIG. 22A shows a model of unliganded spike (PDB 6VYB): closed prefusion conformation. FIG. 22B shows a model of C118 Fab-WA1 spike (PDB 7RKV): open trimer conformation with potential for intra-spike crosslink-ing by C118 IgG. FIG. 22C depicts a model of M8a-3 Fab-WA1 spike: open trimer confirmation with no potential for intra-spike crosslinking.

FIG. 22D shows a model of M8a-6-WA1 spike: open trimer conformation. Black dotted lines between the Ca atoms of C-terminal $C_H1$ residues are not shown because the reconstruction included only one Fab. FIG. 22E shows a model of M8a-31-WA1 spike: open trimer conformation with potential for intra-spike crosslinking by M8a-31 IgG. FIG. 22F depicts a model of M8a-31-Omicron BA.1 spike: open trimer conformation with potential for intra-spike crosslinking by M8a-31 IgG. FIG. 22G shows a model of M8a-34-WA1 spike: open trimer conformation with no potential for intra-spike crosslinking by M8a-34 IgG. FIG. 22H shows a model of HSW-1-WA1 spike: open trimer conformation. Black dotted lines between the Ca atoms of C-terminal $C_H1$ residues are not shown because the recon-struction included only one Fab. FIG. 22I depicts a model of M8a-28-WA1 spike: closed trimer conformation with no potential for intra-spike crosslinking.

FIG. 23A-FIG. 23G depict non-limiting exemplary data related to epitopes of mAbs mapped on a unliganded SARS-CoV-2 spike trimer. Binding epitopes for all mAbs were identified by PDBePISA and then mapped on to a unliganded spike trimer with two 'down' and one 'up' RBDs (PDB 6VYB). The spike trimer is shown as a surface representation with N-linked glycans shown as small dark gray spheres. The epitopes of (FIG. 23A) M8a-3, (FIG. 23B) M8a-6, (FIG. 23C) M8a-31 and (FIG. 23D) M8a-34 are blocked in the 'down' RBD conformation, but accessible in an 'up' RBD conformation. FIG. 23E depicts a cartoon showing that the epitope of M8a-28 is accessible in both 'down' and 'up' RBD conformations. FIG. 23F depicts a cartoon showing the epitope of HSW-1 is blocked in the 'down' RBD conformation, but accessible in an 'up' RBD conformation. FIG. 23G depicts a cartoon showing the epitope of HSW-2 is blocked in both 'down' and 'up' RBD conformations.

FIG. 24A-FIG. 24G depict non-limiting exemplary data related to the epitopes of mAbs mapped on a SARS-CoV-2 spike trimer with all 'up' RBDs. Binding epitopes for all mAbs were identified by PDBePISA and then mapped on to a spike trimer with three 'up' RBDs (PDB 7RKV; Fabs not shown). The spike trimer is shown as a surface representation with N-linked glycans shown as small dark gray spheres. The epitopes of (FIG. 24A) M8a-3, (FIG. 24B) M8a-6, (FIG. 24C) M8a-31, and (FIG. 24D) M8a-34 are all accessible in an 'up' RBD conformation. FIG. 24E depicts a cartoon showing the epitope of M8a-28 is accessible in 'up' RBD conformation. FIG. 24F depicts a cartoon showing the epitope of HSW-1 is accessible in an 'up' RBD conformation.

FIG. 24G depicts a cartoon showing the epitope of HSW-2 is sterically hindered in an 'up' RBD conformation.

(FIG. 25B) M8a-6 IgG interacting with two adjacent RBDs on a mosaic-8 RBD-nanoparticle. (FIG. 25C) M8a-31 IgG interacting with two adjacent RBDs on a mosaic-8 RBD-nanoparticle. (FIG. 25D) M8a-34 IgG interacting with two adjacent RBDs on a mosaic-8 RBD-nanoparticle. (FIG. 25E) M8a-28 IgG interacting with two adjacent RBDs on a mosaic-8 RBD-nanoparticle. (FIG. 25F) HSW-1 IgG interacting with two adjacent RBDs on a homotypic RBD-nanoparticle. (FIG. 25G) HSW-2 IgG interacting with two adjacent RBDs on a homotypic RBD-nanoparticle.

DETAILED DESCRIPTION

Figure 1A:
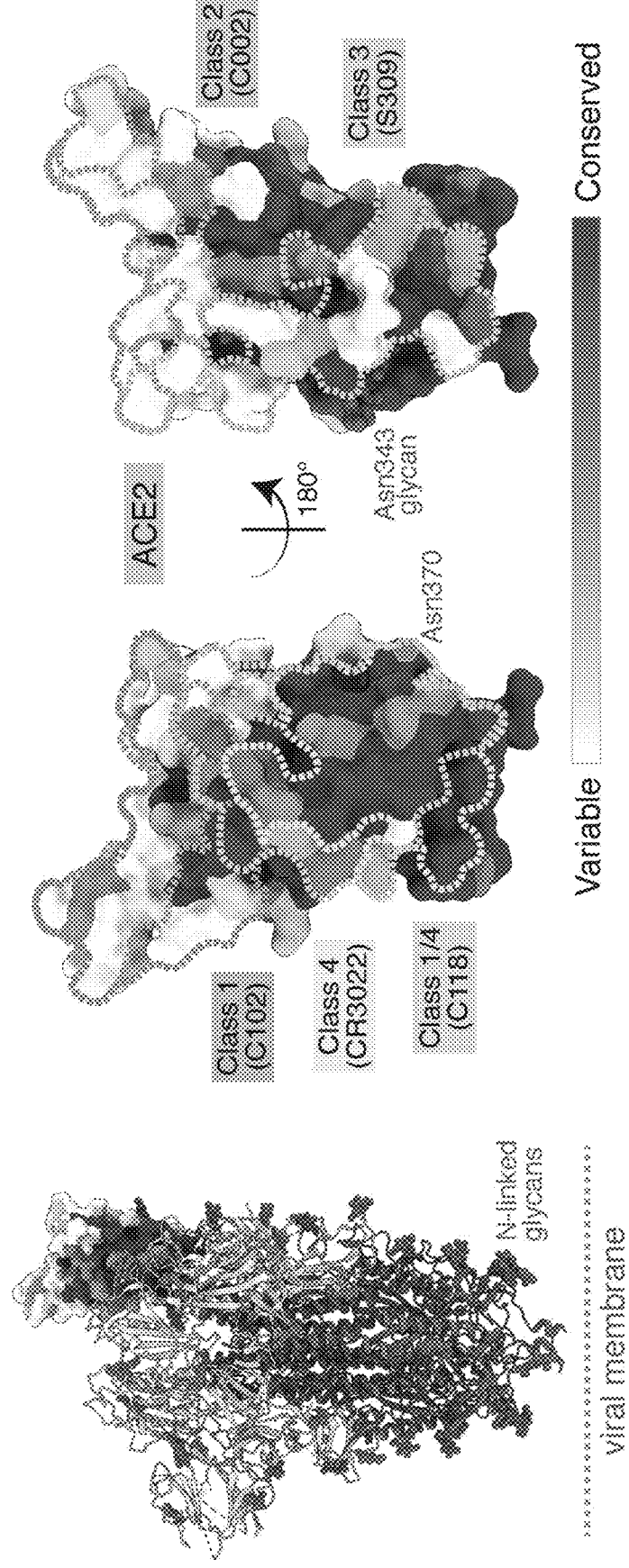
FIG. 1A-FIG. 1D depict non-limiting exemplary embodiments for utilizing antibody avidity effects as a strategy to target antibodies to conserved regions of sarbecovirus RBDs.
Figure 1B:
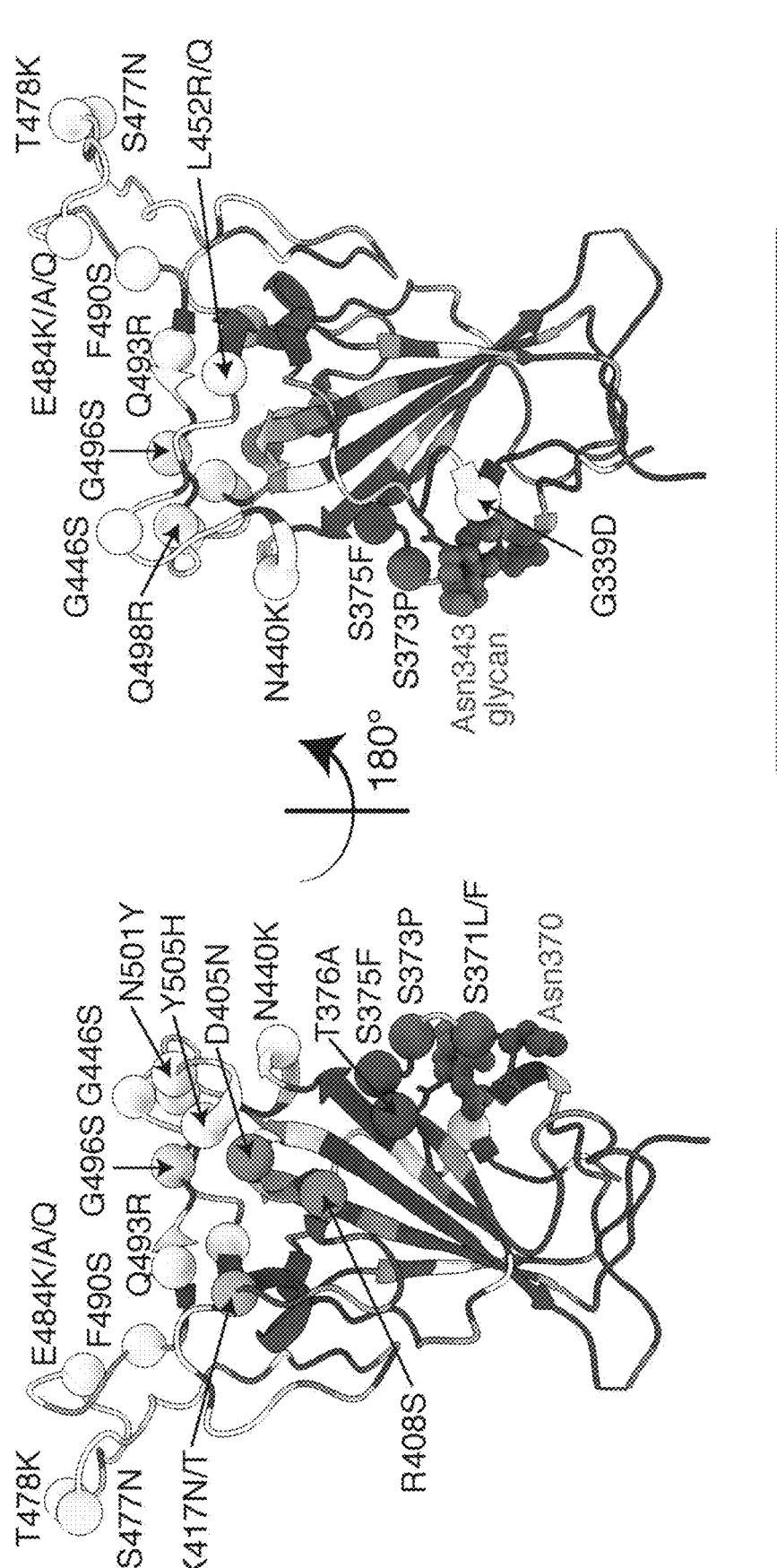

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include antibodies or fragments thereof. In some embodiments, the antibody or fragment thereof has specificity to a coronavirus antigen. In some embodiments, the antibody or fragment thereof has specificity to a coronavirus spike protein receptor binding domain. In some embodiments, the antibody or fragment thereof has specificity to a sarbecovirus spike protein receptor binding domain (RBD) and comprises: (a) a heavy chain variable region ($V_H$) CDR1 comprising an amino acid sequence selected from SEQ ID NOs: 49-55 or a variant thereof having a single substitution, deletion or insertion from any one of SEQ ID NOs: 49-55; (b) a $V_H$ CDR2 comprising an amino acid sequence selected from SEQ ID NOs: 57-63 or a variant thereof having a single substitution, deletion or insertion from any one of SEQ ID NOs: 57-63; (c) a $V_H$ CDR3 comprising an amino acid sequence selected from SEQ ID NOs: 65-71 or a variant thereof having a single substitution, deletion or insertion from any one of SEQ ID NOs: 65-71; (d) a light chain variable region ($V_L$) CDR1 comprising an amino acid sequence selected from SEQ ID NOs: 73-79 or a variant thereof having a single substitution, deletion or insertion from any one of SEQ ID NOs: 73-79; (e) a VL CDR2 comprising an amino acid sequence selected from WAS, YAS, RAS, or RAK; and (f) a VL CDR3 comprising an amino acid sequence selected from SEQ ID NOs: 81-87 or a variant thereof having a single substitution, deletion or insertion from any one of SEQ ID NOs: 81-87.

Disclosed herein include compositions comprising any of the antibodies or fragments thereof provided herein and a pharmaceutically acceptable carrier. Disclosed herein include polynucleotides encoding one or more of the antibody or fragment thereof provided herein. Disclosed herein include isolated cells comprising any of the polynucleotides provided herein. Disclosed herein include compositions comprising any of the polynucleotides and/or an isolated cells provided herein.

There are provided methods of treating or preventing a coronavirus infection in a patient in need thereof, e.g., administering to the patient an effective amount of any of the antibodies or fragments thereof, polynucleotides, isolated cells, and compositions provided herein, or a combination thereof.

Disclosed herein include methods for identifying an antibody or fragment thereof that has specificity to a sarbecovirus spike protein receptor binding domain (RBD). In some embodiments, the method comprises screening B cells against one or more sarbecovirus spike protein RBDs; wherein the B cells are isolated from a mammal immunized with two or more different sarbecovirus spike protein RBDs.

Disclosed herein include antibodies or fragments thereof identified by the methods provided herein.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

The terms "polynucleotide" and "nucleic acid" are used interchangeably herein and refer to a polymeric form of nucleotides of any length, either ribonucleotides or deoxyribonucleotides. A polynucleotide can be single-, double-, or multi-stranded DNA or RNA, genomic DNA, cDNA, DNA-RNA hybrids/triple helices, or a polymer including purine and pyrimidine bases or other natural, chemically or biochemically modified, non-natural, or derivatized nucleotide bases.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

As used herein, "sequence identity" or "identity" in the context of two nucleic acid or polypeptide sequences makes reference to the nucleotide bases or amino acid residues in the two sequences that are the same when aligned for maximum correspondence over a specified comparison window. When percentage of sequence identity or similarity is used in reference to proteins, it is recognized that residue positions which are not identical often differ by conservative amino acid substitutions, where amino acid residues are substituted with a functionally equivalent residue of the amino acid residues with similar physiochemical properties and therefore do not change the functional properties of the molecule.

A functionally equivalent residue of an amino acid used herein typically can refer to other amino acid residues having physiochemical and stereochemical characteristics substantially similar to the original amino acid. The physiochemical properties include water solubility (hydrophobicity or hydrophilicity), dielectric and electrochemical properties, physiological pH, partial charge of side chains (positive, negative or neutral) and other properties identifiable to a person skilled in the art. The stereochemical characteristics include spatial and conformational arrangement of the amino acids and their chirality. For example, glutamic acid is considered to be a functionally equivalent residue to aspartic acid in the sense of the current disclosure. Tyrosine and tryptophan are considered as functionally equivalent residues to phenylalanine. Arginine and lysine are considered as functionally equivalent residues to histidine.

As used herein, a polypeptide "variant" can refer to a biologically active polypeptide having at least about 80% amino acid sequence identity with the corresponding native sequence polypeptide, or fragment thereof. Such variants include, for instance, polypeptides wherein one or more amino acid residues are added, deleted, or substituted. Ordinarily, a variant will have at least about 80% amino acid sequence identity, or at least about 90% amino acid sequence identity, or at least about 95% or more amino acid sequence identity with the native sequence polypeptide, or fragment thereof. The term "variant" as used herein shall have its ordinary meaning, and can also refer to a protein variant as described herein and/or which includes one or more amino acid mutations in the native protein sequence. Optionally, the one or more amino acid mutations include amino acid substitution(s).

The term "isolated" as used herein with respect to cells, proteins, nucleic acids (such as DNA or RNA), refers to molecules separated from other cells, proteins, nucleic acids, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. In some embodiments, an "isolated nucleic acid" refers to nucleic acid fragments which are not naturally occurring as fragments and would not be found in the natural state. The term "isolated" is also used herein to refer to cells or polypeptides which are isolated from other cellular proteins or tissues. Isolated polypeptides can encompass both purified and recombinant polypeptides.

As used herein, the term "recombinant" in the context of polypeptides or polynucleotides refers to a form of the polypeptide or polynucleotide that does not exist naturally, a non-limiting example of which can be created by combining polynucleotides or polypeptides or by combining different polypeptides that would not normally occur together.

As used herein, an "antibody" or "antigen-binding polypeptide" can refer to a polypeptide or a polypeptide complex that specifically recognizes and binds to an antigen (e.g., a spike protein receptor binding domain). An antibody can be a whole antibody and any antigen binding fragment or a single chain thereof. Thus, the term "antibody" includes any protein or peptide-containing molecule that comprises at least a portion of an immunoglobulin molecule having biological activity of binding to the antigen. Examples of such include, but are not limited to, a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, L-RNA aptamers (also known as spiegelmers), and diabodies. The term "antibody fragment" also includes any synthetic or genetically engineered protein that acts like an antibody by binding to a specific antigen to form a complex.

As used herein, a "single-chain variable fragment" or "scFv" refers to a fusion protein of the variable regions of the heavy ($V_H$) and light chains ($V_L$) of immunoglobulins. In some embodiments, the regions are connected with a short linker peptide of ten to about 25 amino acids. The linker can be rich in glycine for flexibility, as well as serine or threonine for solubility, and can either connect the N-terminus of the VH with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

As used herein, the term "antibody" encompasses various broad classes of polypeptides that can be distinguished biochemically. Those of skill in the art will appreciate that heavy chains are classified as gamma, mu, alpha, delta, or epsilon ($\gamma$, $\mu$, $\alpha$, $\delta$, or $\varepsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight approximately 53,000-70,000 Daltons. The four chains are typically joined by disulfide bonds in a "Y" configuration wherein the light chains bracket the heavy chains starting at the mouth of the "Y" and continuing through the variable region.

Antibodies, antigen-binding polypeptides, fragments, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies. Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VL chains (i.e. VH CDR1, VH CDR2, VH CDR3, VL CDR1, VL CDR2 and VL CDR3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a $\beta$-sheet conformation and the CDRs form loops which connect, and in some cases form part of, the $\beta$-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.*, 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those of skill in the art can routinely determine which residues comprise a particular CDR given the variable region amino acid sequence of the antibody.

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

Kabat et al. also defined a numbering system for variable domain sequences that is applicable to any antibody. One of skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: VH CDR1 begins at approximately amino acid 31 (i.e., approximately 9 residues after the first cysteine residue), includes approximately 5-7 amino acids, and ends at the next tryptophan residue. VH CDR2 begins at the fifteenth residue after the end of VH CDR1, includes approximately 16-19 amino acids, and ends at the next arginine or lysine residue. VH CDR3 begins at approximately the thirty third amino acid residue after the end of VH CDR2; includes 3-25 amino acids; and ends at the sequence W-G-X-G, where X is any amino acid. VL CDR1 begins at approximately residue 24 (i.e., following a cysteine residue); includes approximately 10-17 residues; and ends at the next tryptophan residue. VL CDR2 begins at approximately the sixteenth residue after the end of VL CDR1 and includes approximately 7 residues. VL CDR3 begins at approximately the thirty third residue after the end of VL CDR2 (i.e., following a cysteine residue); includes approximately 7-11 residues and ends at the sequence F or W-G-X-G, where X is any amino acid.

Antibodies disclosed herein can be from any animal origin including vertebrates (e.g., birds, reptiles, amphibians, and mammals). In some embodiments, the antibodies are human, murine, donkey, rabbit, goat, guinea pig, camel, llama, horse, or chicken antibodies. In some embodiments, the variable region is condricthoid in origin (e.g., from sharks). In some embodiments, the antibody or fragment thereof is from a mammal.

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a $C_H1$ domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CH2 regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In some embodiments, the target binding region or site is from a non-human source (e.g. mouse or primate) and the constant region is human.

As used herein, the term "binding" refers to a non-covalent interaction between macromolecules (e.g., between a protein and a nucleic acid or between a first protein and a second protein). While in a state of non-covalent interaction, the macromolecules are said to be "associated" or "interacting" or "binding" (e.g., when a molecule X is said to interact with a molecule Y, it means that the molecule X binds to molecule Y in a non-covalent manner). Binding interactions can be characterized by a dissociation constant (Kd), for example a Kd of, or a Kd less than, $10^{-6}$ M, $10^{-7}$ M, $10^{-1}$ M, $10^{-9}$ M, $10^{-10}$ M, $10^{-11}$ M, $10^{-12}$ M, $10^{-13}$ M, $10^{-14}$ M, $10^{-15}$ M, or a number or a range between any two of these values. Kd can be dependent on environmental conditions, e.g., pH and temperature. "Affinity" refers to the strength of binding, and increased binding affinity is correlated with a lower Kd. Binding interactions can also be characterized by an EC50. As used herein, "EC50" can refer to the concentration of an agent (e.g., an antibody or fragment thereof) which produces 50% of the maximal response possible for that agent. As described herein, binding interactions can be characterized by an EC50 of, or an EC50 less than 10 µg/mL, less than 1 µg/mL, less than 0.1 µg/mL, or less than 0.01 µg/mL.

The term "IC50," as used herein, can refer to the half-maximal concentration of an antibody or an antigen-binding fragment thereof, which induces an inhibitory response (e.g., reduced infectivity, e.g. neutralization), either in an in vitro or an in vivo assay, which is 50% of the maximal response, i.e., halfway between the maximal response and the baseline. As used herein, "infectivity" shall have its ordinary meaning, and can also refer to the ability of a virus to enter or exit a cell. As described herein, the antibodies or fragments thereof provided herein can reduce, inhibit, block infectivity of a virus at an IC50 of, e.g., less than 10 µg/mL, less than 1 µg/mL, less than 0.1 µg/mL, or less than 0.01 µg/mL.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity (e.g., greater binding affinity) for a given epitope than antibody "B," or antibody "A" may be said to bind to epitope "C" with a higher specificity (e.g., greater binding affinity) than it has for related epitope "D."

Provided herein are antibodies and fragments thereof with specificity for coronavirus antigens (e.g., spike protein receptor binding domain). Also provided are compositions comprising said antibodies or fragments thereof, and methods for identifying and isolating said antibodies. There are provided methods of treating a subject suffering from a coronavirus infection using any of the antibodies or fragments thereof and compositions described herein.

Figure 1C:
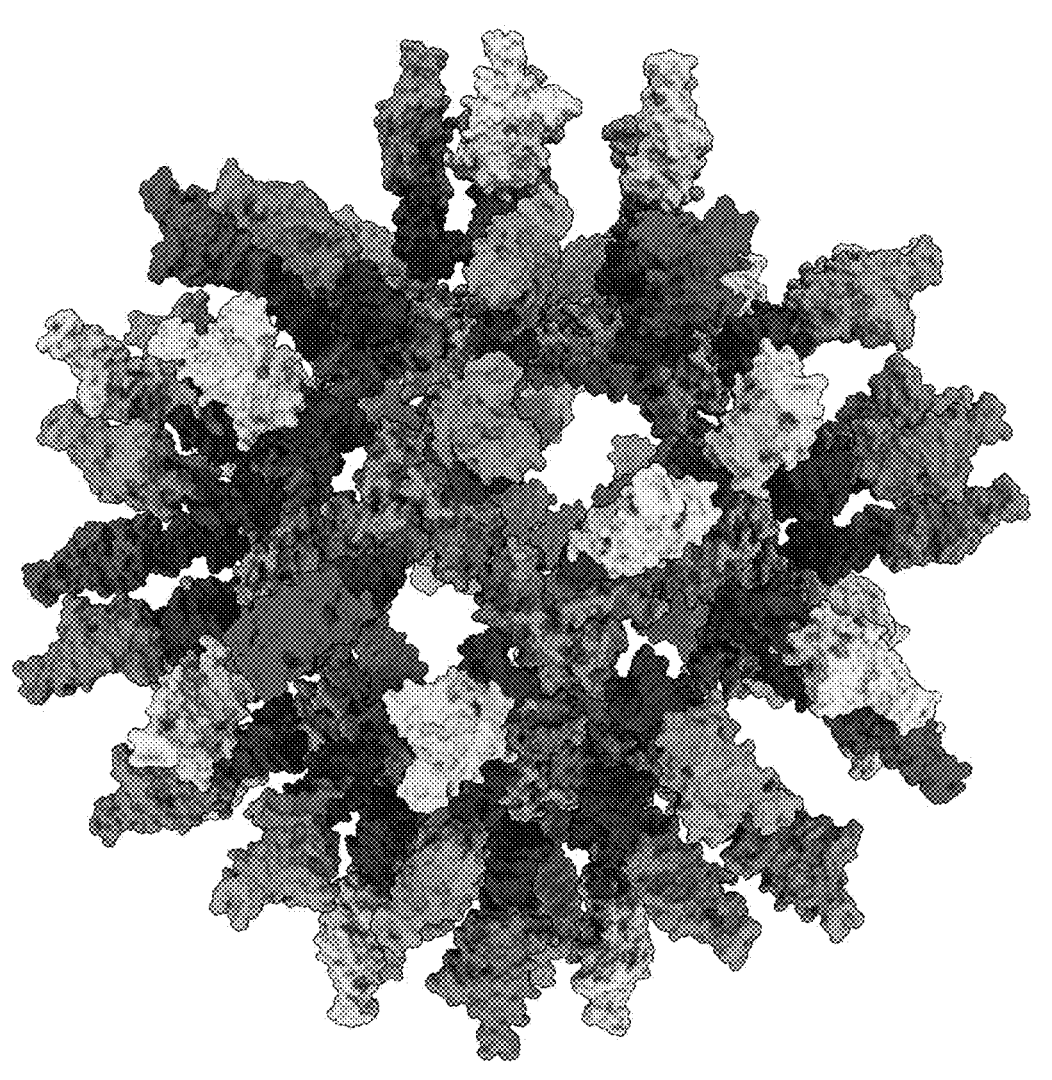
Figure 1D:
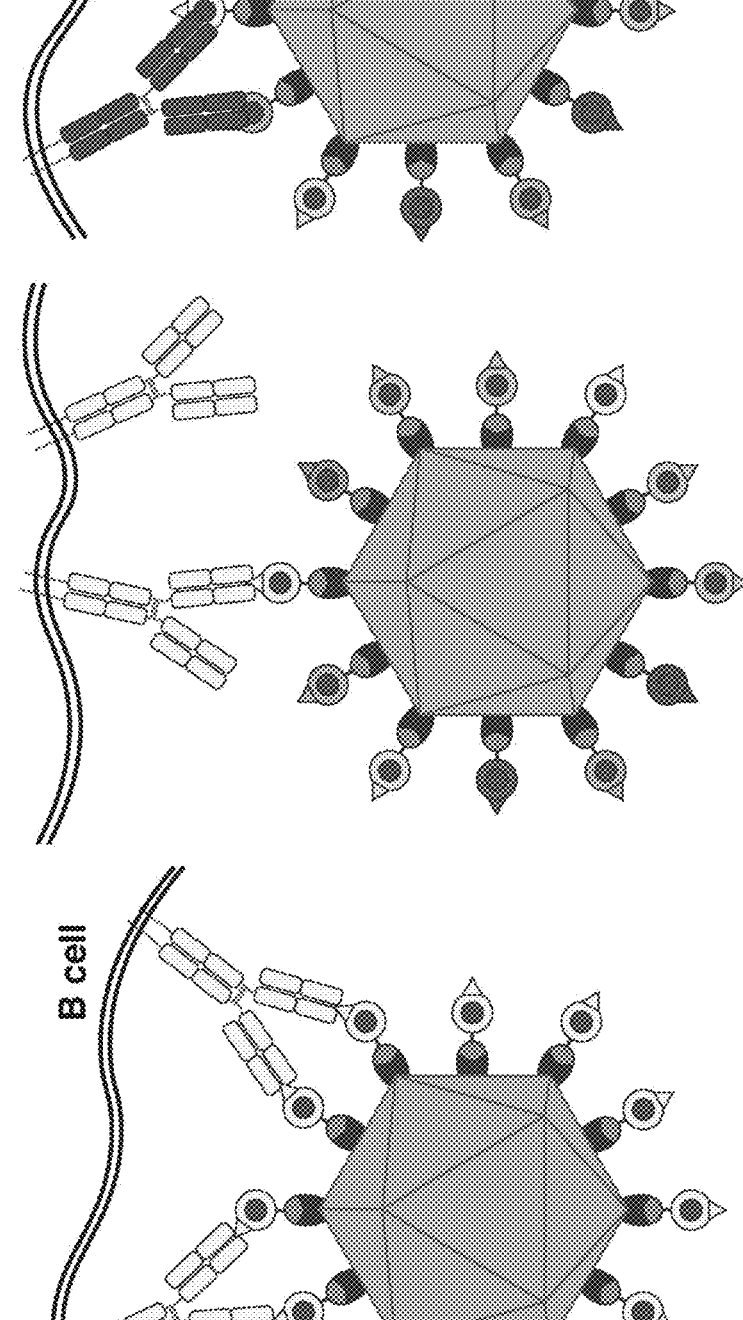

A vaccine approach involving simultaneous display of sarbecovirus RBDs on protein-based nanoparticles (FIG. 1C) showed enhanced heterologous binding, neutralization, and protection from sarbecovirus challenges compared with homotypic (SARS-CoV-2 RBD-only) nanoparticles in animal models (described in US Patent Publication No. 2022/0168414 which is hereby incorporated by reference in its entirety). The hypothesis behind enhanced elicitation of cross-reactive antibodies by mosaic RBD-nanoparticles is that B cell receptors (BCRs) that recognize conserved, but not readily accessible, RBD epitopes would be stimulated to proliferate to produce cross-reactive Abs through bivalent binding of BCRs to adjacent RBDs, whereas BCRs that bind to strain-specific epitopes could not bind bivalently to adjacent RBDs since these epitopes differ when RBDs are arranged randomly on a nanoparticle (FIG. 1D). By contrast, homotypic RBD-nanoparticles are predicted to stimulate BCRs against readily accessible, immunodominant strain-specific epitopes presented on all RBDs. Of relevance to the mAb potentials for sarbecovirus cross-reactivity, the more conserved class 4 and class ¼ epitopes targeted by polyclonal antibodies in mosaic-8 RBD-nanoparticle antisera are unlikely to vary in SARS-CoV-2 VOCs because, without being bound by any particular theory, they contact other portions of the spike trimer. This is in contrast to the class 1 and 2 RBD epitope regions targeted by homotypic SARS-CoV-2 RBD-nanoparticle antisera, which (in common with the class 3 RBD region) are not involved in contacts with non-RBD portions of spike. Although the epitopes of both class 4 and class ¼ anti-RBD mAbs fall outside of the ACE2-binding footprint within class 1 and class 2 RBD epitopes, these mAbs can directly compete with ACE2 for binding through steric effects, thereby rationalizing their increased neutralization potencies.

Described herein are mAbs isolated from mosaic RBD- and homotypic RBD-immunized mice. Binding and neutralization results, together with cryo-EM structures of antibody Fab-spike trimer complexes, show that the mosaic RBD-nanoparticle vaccine approach works as designed to target conserved epitopes, and can be used both for more broadly protective vaccines to elicit broadly neutralizing and potent antibodies. Provided herein are methods to produce therapeutic neutralizing mAbs that would not be affected by Omicron or future SARS-CoV-2 VOC substitutions.

Antibodies

The present disclosure provides sarbecovirus spike protein specific antibodies or fragments thereof with high affinity and specificity to the spike protein receptor binding domain (RBD). The spike protein of sarbecoviruses typically is in the form of a homotrimer, and the antibodies and fragments thereof provided herein can, in some embodiments, bind one, two, or all three of the RBDs of a single spike trimer. In some embodiments, the spike protein RBD-specific antibodies herein described are broadly neutralizing and potent. In some embodiments, the antibodies herein described can be used for treating a patient in need thereof, who is suffering from, e.g., a SARS-CoV-2 infection. There are provided, in some embodiments, compositions comprising one or more of the antibody or fragment thereof as described herein.

In some embodiments, the antibodies or fragments thereof disclosed herein contain CDR regions defined in SEQ ID NOs: 49-87 or variants thereof having one, two or three mismatches (e.g., a single substitution, deletion or insertion) in any one of SEQ ID NOs: 49-87.

Disclosed herein include antibodies or fragments thereof. In some embodiments, the antibody or fragment thereof has specificity to a sarbecovirus spike protein receptor binding domain (RBD) and comprises: (a) a heavy chain variable region (VH) CDR1 comprising an amino acid sequence selected from SEQ ID NOs: 49-55 or a variant thereof having a single substitution, deletion or insertion from any one of SEQ ID NOs: 49-55; (b) a VH CDR2 comprising an amino acid sequence selected from SEQ ID NOs: 57-63 or a variant thereof having a single substitution, deletion or insertion from any one of SEQ ID NOs: 57-63; (c) a VH CDR3 comprising an amino acid sequence selected from SEQ ID NOs: 65-71 or a variant thereof having a single substitution, deletion or insertion from any one of SEQ ID NOs: 65-71; (d) a light chain variable region (VL) CDR1 comprising an amino acid sequence selected from SEQ ID NOs: 73-79 or a variant thereof having a single substitution, deletion or insertion from any one of SEQ ID NOs: 73-79; (e) a VL CDR2 comprising an amino acid sequence selected from WAS, YAS, RAS, and RAK; and (f) a VL CDR3 comprising an amino acid sequence selected from SEQ ID NOs: 81-87 or a variant thereof having a single substitution, deletion or insertion from any one of SEQ ID NOs: 81-87.

The antibody or fragment thereof can comprise: (a) a VH CDR1 comprising an amino acid sequence selected from SEQ ID NOs: 49-55; (b) a VH CDR2 comprising an amino acid sequence selected from SEQ ID NOs: 57-63; (c) a VH CDR3 comprising an amino acid sequence selected from SEQ ID NOs: 65-71; (d) a VL CDR1 comprising an amino acid sequence selected from SEQ ID NOs: 73-79; (e) a VL CDR2 comprising an amino acid sequence selected from WAS, YAS, RAS, and RAK; and (f) a VL CDR3 comprising an amino acid sequence selected from SEQ ID NOs: 81-87.

The antibody or fragment thereof can comprise: a VH CDR1 of SEQ ID NO: 49 or a variant thereof having a single substitution, deletion or insertion of SEQ ID NO: 49; a VH CDR2 of SEQ ID NO: 57 or a variant thereof having a single substitution, deletion or insertion of SEQ ID NO: 57; a VH CDR3 of SEQ ID NO: 65 or a variant thereof having a single substitution, deletion or insertion of SEQ ID NO: 65; a VL CDR1 of SEQ ID NO: 73 or a variant thereof having a single substitution, deletion or insertion of SEQ ID NO: 73; a VL CDR2 having the amino acid sequence WAS; and a VL CDR3 of SEQ ID NO: 81 or a variant thereof having a single substitution, deletion or insertion of SEQ ID NO: 81.

The antibody or fragment thereof can comprise: a VH CDR1 of SEQ ID NO: 51 or a variant thereof having a single substitution, deletion or insertion of SEQ ID NO: 51; a VH CDR2 of SEQ ID NO: 59 or a variant thereof having a single substitution, deletion or insertion of SEQ ID NO: 59; a VH CDR3 of SEQ ID NO: 67 or a variant thereof having a single substitution, deletion or insertion of SEQ ID NO: 67; a VL CDR1 of SEQ ID NO: 75 or a variant thereof having a single substitution, deletion or insertion of SEQ ID NO: 75; a VL CDR2 having the amino acid sequence YAS; and a VL CDR3 of SEQ ID NO: 83 or a variant thereof having a single substitution, deletion or insertion of SEQ ID NO: 83.

The antibody or fragment thereof can comprise: a VH CDR1 of SEQ ID NO: 52 or a variant thereof having a single substitution, deletion or insertion of SEQ ID NO: 52; a VH CDR2 of SEQ ID NO: 60 or a variant thereof having a single substitution, deletion or insertion of SEQ ID NO: 60; a VH CDR3 of SEQ ID NO: 68 or a variant thereof having a single substitution, deletion or insertion of SEQ ID NO: 68; a VL CDR1 of SEQ ID NO: 76 or a variant thereof having a single substitution, deletion or insertion of SEQ ID NO: 76; a VL CDR2 having the amino acid sequence WAS; and a VL CDR3 of SEQ ID NO: 84 or a variant thereof having a single substitution, deletion or insertion of SEQ ID NO: 84.

The antibody or fragment thereof can comprise: a VH CDR1 of SEQ ID NO: 53 or a variant thereof having a single substitution, deletion or insertion of SEQ ID NO: 53; a VH CDR2 of SEQ ID NO: 61 or a variant thereof having a single substitution, deletion or insertion of SEQ ID NO: 61; a VH CDR3 of SEQ ID NO: 69 or a variant thereof having a single substitution, deletion or insertion of SEQ ID NO: 69; a VL CDR1 of SEQ ID NO: 77 or a variant thereof having a single substitution, deletion or insertion of SEQ ID NO: 77; a VL CDR2 having the amino acid sequence RAS; and a VL CDR3 of SEQ ID NO: 85 or a variant thereof having a single substitution, deletion or insertion of SEQ ID NO: 85.

The antibody or fragment thereof can comprise a heavy chain variable region comprising (i) an amino acid sequence selected from SEQ ID NOs: 1, 3-4, 6, 8, 11, 13-14, 16-19, 21, 24, 27, 29, 31, 33, 35, 37-38, 41, and 43, (ii) an amino acid sequence having, having about, having at least, or having at least about 90%, 91%, 92%, 93%, 94%, 95%, 96%, 97%, 98%, or 99% sequence identity to an amino acid sequence selected from SEQ ID NOs: 1, 3-4, 6, 8, 11, 13-14, 16-19, 21, 24, 27, 29, 31, 33, 35, 37-38, 41, and 43, or (iii) an amino acid sequence having one, two or three mismatches relative to an amino acid sequence selected from SEQ ID NOs: 1, 3-4, 6, 8, 11, 13-14, 16-19, 21, 24, 27, 29, 31, 33, 35, 37-38, 41, and 43.

The antibody or fragment thereof can comprise a light chain variable region comprising (i) an amino acid sequence selected from SEQ ID NOs: 2, 5, 7, 9-10, 12, 15, 20, 22-23, 25-26, 28, 30, 32, 34, 36, 39-40, 42, and 44-45, (ii) an amino acid sequence having, having about, having at least, or having at least about 90%, 91%, 92%, 93%, 94%, 95%, 96%, 97%, 98%, or 99% sequence identity to an amino acid sequence selected from SEQ ID NOs: 2, 5, 7, 9-10, 12, 15, 20, 22-23, 25-26, 28, 30, 32, 34, 36, 39-40, 42, and 44-45, (iii) an amino acid sequence having one, two or three mismatches relative to an amino acid sequence selected from SEQ ID NOs: 2, 5, 7, 9-10, 12, 15, 20, 22-23, 25-26, 28, 30, 32, 34, 36, 39-40, 42, and 44-45.

The antibody or fragment thereof can comprise a heavy chain variable region comprising (i) an amino acid sequence selected from SEQ ID NOs: 1, 4, 27, 33, 35, 41, and 43, (ii) an amino acid sequence having, having about, having at least, or having at least about 90%, 91%, 92%, 93%, 94%, 95%, 96%, 97%, 98%, or 99% sequence identity to an amino acid sequence selected from SEQ ID NOs: 1, 4, 27, 33, 35, 41, and 43, or (iii) an amino acid sequence having one, two or three mismatches relative to an amino acid sequence selected from SEQ ID NOs: 1, 4, 27, 33, 35, 41, and 43.

The antibody or fragment thereof can comprise a light chain variable region comprising (i) an amino acid sequence selected from SEQ ID NOs: 2, 5, 28, 34, 36, 42, and 44, (ii) an amino acid sequence having, having about, having at least, or having at least about 90%, 91%, 92%, 93%, 94%, 95%, 96%, 97%, 98%, or 99% sequence identity to an amino acid sequence selected from SEQ ID NOs: 2, 5, 28, 34, 36, 42, and 44, (iii) an amino acid sequence having one, two or three mismatches relative to an amino acid sequence selected from SEQ ID NOs: 2, 5, 28, 34, 36, 42, and 44.

The antibody or fragment thereof can comprise a heavy chain variable region comprising the amino acid sequence of SEQ ID NO: 1 or a peptide having, having about, having at least, or having at least about 90%, 91%, 92%, 93%, 94%, 95%, 96%, 97%, 98%, or 99% sequence identity to the amino acid sequence of SEQ ID NO: 1, and a light chain variable region comprising the amino acid sequence of SEQ ID NO: 2 or a peptide having, having about, having at least, or having at least about 90%, 91%, 92%, 93%, 94%, 95%, 96%, 97%, 98%, or 99% sequence identity to the amino acid sequence of SEQ ID NO: 2.

The antibody or fragment thereof can comprise a heavy chain variable region comprising the amino acid sequence of SEQ ID NO: 27 or a peptide having, having about, having at least, or having at least about 90%, 91%, 92%, 93%, 94%, 95%, 96%, 97%, 98%, or 99% sequence identity to the amino acid sequence of SEQ ID NO: 27, and a light chain variable region comprising the amino acid sequence of SEQ ID NO: 28 or a peptide having, having about, having at least, or having at least about 90%, 91%, 92%, 93%, 94%, 95%, 96%, 97%, 98%, or 99% sequence identity to the amino acid sequence of SEQ ID NO: 28.

The antibody or fragment thereof can comprise a heavy chain variable region comprising the amino acid sequence of SEQ ID NO: 33 or a peptide having, having about, having at least, or having at least about 90%, 91%, 92%, 93%, 94%, 95%, 96%, 97%, 98%, or 99% sequence identity to the amino acid sequence of SEQ ID NO: 33, and a light chain variable region comprising the amino acid sequence of SEQ ID NO: 34 or a peptide having, having about, having at least, or having at least about 90%, 91%, 92%, 93%, 94%, 95%, 96%, 97%, 98%, or 99% sequence identity to the amino acid sequence of SEQ ID NO: 34.

The antibody or fragment thereof can comprise a heavy chain variable region comprising the amino acid sequence of SEQ ID NO: 35 or a peptide having, having about, having at least, or having at least about 90%, 91%, 92%, 93%, 94%, 95%, 96%, 97%, 98%, or 99% sequence identity to the amino acid sequence of SEQ ID NO: 35, and a light chain variable region comprising the amino acid sequence of SEQ ID NO: 36 or a peptide having, having about, having at least, or having at least about 90%, 91%, 92%, 93%, 94%, 95%, 96%, 97%, 98%, or 99% sequence identity to the amino acid sequence of SEQ ID NO: 36.

The antibody or fragment thereof can comprise a heavy chain variable region comprising the amino acid sequence of SEQ ID NO: 4 or a peptide having, having about, having at least, or having at least about 90%, 91%, 92%, 93%, 94%, 95%, 96%, 97%, 98%, or 99% sequence identity to the amino acid sequence of SEQ ID NO: 4, and a light chain variable region comprising the amino acid sequence of SEQ ID NO: 5 or a peptide having, having about, having at least, or having at least about 90%, 91%, 92%, 93%, 94%, 95%, 96%, 97%, 98%, or 99% sequence identity to the amino acid sequence of SEQ ID NO: 5.

The antibody or fragment thereof can comprise a heavy chain variable region comprising the amino acid sequence of SEQ ID NO: 41 or a peptide having, having about, having at least, or having at least about 90%, 91%, 92%, 93%, 94%, 95%, 96%, 97%, 98%, or 99% sequence identity to the amino acid sequence of SEQ ID NO: 41, and a light chain variable region comprising the amino acid sequence of SEQ ID NO: 42 or a peptide having, having about, having at least, or having at least about 90%, 91%, 92%, 93%, 94%, 95%, 96%, 97%, 98%, or 99% sequence identity to the amino acid sequence of SEQ ID NO: 42.

The antibody or fragment thereof can comprise a heavy chain variable region comprising the amino acid sequence of SEQ ID NO: 43 or a peptide having, having about, having at least, or having at least about 90%, 91%, 92%, 93%, 94%, 95%, 96%, 97%, 98%, or 99% sequence identity to the amino acid sequence of SEQ ID NO: 43, and a light chain variable region comprising the amino acid sequence of SEQ ID NO: 44 or a peptide having, having about, having at least, or having at least about 90%, 91%, 92%, 93%, 94%, 95%, 96%, 97%, 98%, or 99% sequence identity to the amino acid sequence of SEQ ID NO: 44.

The antibody or fragment thereof can comprise a heavy chain variable region comprising the amino acid sequence of SEQ ID NO: 6 or a peptide having, having about, having at least, or having at least about 90%, 91%, 92%, 93%, 94%, 95%, 96%, 97%, 98%, or 99% sequence identity to the amino acid sequence of SEQ ID NO: 6, and a light chain variable region comprising the amino acid sequence of SEQ ID NO: 7 or a peptide having, having about, having at least, or having at least about 90%, 91%, 92%, 93%, 94%, 95%, 96%, 97%, 98%, or 99% sequence identity to the amino acid sequence of SEQ ID NO: 7.

The antibody or fragment thereof can comprise a heavy chain variable region comprising the amino acid sequence of SEQ ID NO: 8 or a peptide having, having about, having at least, or having at least about 90%, 91%, 92%, 93%, 94%, 95%, 96%, 97%, 98%, or 99% sequence identity to the amino acid sequence of SEQ ID NO: 8, and a light chain variable region comprising the amino acid sequence of SEQ ID NO: 9 or a peptide having, having about, having at least, or having at least about 90%, 91%, 92%, 93%, 94%, 95%, 96%, 97%, 98%, or 99% sequence identity to the amino acid sequence of SEQ ID NO: 9.

The antibody or fragment thereof can comprise a heavy chain variable region comprising the amino acid sequence of SEQ ID NO: 11 or a peptide having, having about, having at least, or having at least about 90%, 91%, 92%, 93%, 94%, 95%, 96%, 97%, 98%, or 99% sequence identity to the amino acid sequence of SEQ ID NO: 11, and a light chain variable region comprising the amino acid sequence of SEQ ID NO: 12 or a peptide having, having about, having at least, or having at least about 90%, 91%, 92%, 93%, 94%, 95%, 96%, 97%, 98%, or 99% sequence identity to the amino acid sequence of SEQ ID NO: 12.

The antibody or fragment thereof can comprise a heavy chain variable region comprising the amino acid sequence of SEQ ID NO: 14 or a peptide having, having about, having at least, or having at least about 90%, 91%, 92%, 93%, 94%, 95%, 96%, 97%, 98%, or 99% sequence identity to the amino acid sequence of SEQ ID NO: 14, and a light chain variable region comprising the amino acid sequence of SEQ ID NO: 15 or a peptide having, having about, having at least, or having at least about 90%, 91%, 92%, 93%, 94%, 95%, 96%, 97%, 98%, or 99% sequence identity to the amino acid sequence of SEQ ID NO: 15.

The antibody or fragment thereof can comprise a heavy chain variable region comprising the amino acid sequence of SEQ ID NO: 24 or a peptide having, having about, having at least, or having at least about 90%, 91%, 92%, 93%, 94%, 95%, 96%, 97%, 98%, or 99% sequence identity to the amino acid sequence of SEQ ID NO: 24, and a light chain variable region comprising the amino acid sequence of SEQ ID NO: 25 or a peptide having, having about, having at least, or having at least about 90%, 91%, 92%, 93%, 94%, 95%, 96%, 97%, 98%, or 99% sequence identity to the amino acid sequence of SEQ ID NO: 25.

The antibody or fragment thereof can comprise a heavy chain variable region comprising the amino acid sequence of SEQ ID NO: 29 or a peptide having, having about, having at least, or having at least about 90%, 91%, 92%, 93%, 94%, 95%, 96%, 97%, 98%, or 99% sequence identity to the amino acid sequence of SEQ ID NO: 29, and a light chain variable region comprising the amino acid sequence of SEQ ID NO: 30 or a peptide having, having about, having at least, or having at least about 90%, 91%, 92%, 93%, 94%, 95%, 96%, 97%, 98%, or 99% sequence identity to the amino acid sequence of SEQ ID NO: 30.

The antibody or fragment thereof can comprise a heavy chain variable region comprising the amino acid sequence of SEQ ID NO: 31 or a peptide having, having about, having at least, or having at least about 90%, 91%, 92%, 93%, 94%, 95%, 96%, 97%, 98%, or 99% sequence identity to the amino acid sequence of SEQ ID NO: 31, and a light chain variable region comprising the amino acid sequence of SEQ ID NO: 32 or a peptide having, having about, having at least, or having at least about 90%, 91%, 92%, 93%, 94%, 95%, 96%, 97%, 98%, or 99% sequence identity to the amino acid sequence of SEQ ID NO: 32.

The antibody or fragment thereof can comprise a heavy chain variable region comprising the amino acid sequence of SEQ ID NO: 38 or a peptide having, having about, having at least, or having at least about 90%, 91%, 92%, 93%, 94%, 95%, 96%, 97%, 98%, or 99% sequence identity to the amino acid sequence of SEQ ID NO: 38, and a light chain variable region comprising the amino acid sequence of SEQ ID NO: 39 or a peptide having, having about, having at least, or having at least about 90%, 91%, 92%, 93%, 94%, 95%, 96%, 97%, 98%, or 99% sequence identity to the amino acid sequence of SEQ ID NO: 39.

The antibody or fragment thereof can comprise an Fc domain. The antibody or fragment thereof can be a single-chain variable fragment (scFv), a single-domain antibody, an immunoglobulin molecule, a monoclonal antibody, a chimeric antibody, a CDR-grafted antibody, a humanized antibody, a Fab fragment, a Fab' fragment, a F(ab')₂ fragment, an Fv fragment, a disulfide linked Fv, an scFv, a single domain antibody, a diabody, a multispecific antibody, a dual specific antibody, an anti-idiotypic antibody, a bispecific antibody, or a functionally active epitope-binding fragment thereof.

In some embodiments, the antibody or fragment thereof is a single-chain variable fragment (scFv) or a single-domain antibody. Single-chain variable fragment can be formed by linking the heavy and light chain fragments of the Fv region via an amino acid bridge (e.g., a disulfide linkage), resulting in a single-chain fusion peptide. The heavy and light chain fragments of the Fv region can be selected from any of the heavy and light chain fragments and variants thereof described herein (e.g., SEQ ID NOs: 1-45 or variants thereof). Examples of techniques which can be used to produce scFvs and antibodies include those described in U.S. Pat. Nos. 4,946,778 and 5,258,498; Huston et al., *Methods in Enzymology* 203:46-88 (1991); Shu et al., *Proc. Natl. Sci. USA* 90:1995-1999 (1993); and Skerra et al., *Science* 240:1038-1040 (1988). In some embodiments, the antibody or fragment thereof is a single-domain antibody comprising a heavy chain variable region or a variant thereof described herein. For example, the single-domain antibody can comprise an amino acid sequence selected from SEQ ID NOs: 1, 3, 4, 6, 8, 11, 13, 14, 16-19, 21, 24, 27, 29, 31, 33, 35, 37-38, 41, 43 or variants thereof having about, at least or at least about 75%, 80%, 85%, 90%, 95%, 98%, or 99% sequence identity to any one of SEQ ID NOs: 1, 3, 4, 6, 8, 11, 13, 14, 16-19, 21, 24, 27, 29, 31, 33, 35, 37-38, 41, 43 or fragments thereof. The single-domain antibody can comprise an amino acid sequence selected from SEQ ID NOs: 49-71 or variants having one, two or three mismatches in one of SEQ ID NOs: 49-71.

In some embodiments, the antibodies or fragments thereof do not elicit an undesirable (e.g., deleterious) immune response in a subject to be treated, e.g., in a human. In some embodiments, antibodies, fragments, variants, or derivatives thereof of the disclosure are modified to reduce their immunogenicity using techniques recognized in the art. For example, antibodies can be humanized, primatized, deimmunized, or chimeric antibodies.

In some embodiments, the antibody or fragment thereof specifically binds to two or more different sarbecovirus spike protein RBDs. Binding of the antibodies and fragments thereof as disclosed herein can be assessed by any assay known in the art, including, but not limited to, precipitation assay, agglutination assay, ELISA, surface plasma resonance, western blot, and FACS. In some embodiments, binding can be assessed by an optofluidic system (e.g., Berkeley Light Beacon® Optofluidic System). As described herein, the optofluidic technology can comprise distributing cells within a sample into individual compartments using microfluidic devices, and detecting a signal associated with the subset of cells with the property of interest. The term "enzyme linked immunosorbent assay" (ELISA) as used herein can refer to an antibody-based assay in which detection of the antigen of interest is accomplished via an enzymatic reaction producing a detectable signal. An ELISA can be run as a competitive or non-competitive format.

In some embodiments, the antibody or fragment thereof binds to at least one of the two or more sarbecovirus spike protein RBDs with an EC50 of less than 10 μg/mL, less than 1 μg/mL, less than 0.1 μg/mL, or less than 0.01 μg/mL as assessed by an optofluidic system and/or an ELISA assay. In some embodiments, the antibody or fragment thereof binds to all of the two or more sarbecovirus spike protein RBDs with an EC50 of less than 10 μg/mL, less than 1 μg/mL, less than 0.1 μg/mL, or less than 0.01 μg/mL as assessed by an optofluidic system and/or an ELISA assay.

In some embodiments, the antibody or fragment thereof binds to at least one of the two or more sarbecovirus spike protein RBDs with an EC50 of about 0.001 μg/mL to about 10 μg/mL (e.g., 0.001, 0.005, 0.01, 0.05, 0.1, 0.5, 1, 1.5, 2, 3, 4, 5, 6, 7, 8, 9, 10 μg/mL or a number or a range between any two of these values), about 0.001 μg/mL to about 1 μg/mL (e.g., 0.001, 0.005, 0.01, 0.05, 0.1, 0.5, 1 μg/mL or a number or a range between any two of these values), about 0.001 μg/mL to about 0.1 μg/mL (e.g., 0.001, 0.005, 0.01, 0.05, 0.1 μg/mL or a number or a range between any two of these values), or about 0.001 μg/mL to about 0.01 μg/mL (e.g., 0.001, 0.0025, 0.005, 0.0075, 0.01 μg/mL or a number or a range between any two of these values) as assessed by an optofluidic system and/or an ELISA assay. In some embodiments, the antibody or fragment thereof binds to all of the two or more sarbecovirus spike protein RBDs with an EC50 of about 0.001 μg/mL to about 10 μg/mL (e.g., 0.001, 0.005, 0.01, 0.05, 0.1, 0.5, 1, 1.5, 2, 3, 4, 5, 6, 7, 8, 9, 10 μg/mL or a number or a range between any two of these values), about 0.001 μg/mL to about 1 μg/mL (e.g., 0.001, 0.005, 0.01, 0.05, 0.1, 0.5, 1 μg/mL or a number or a range between any two of these values), about 0.001 μg/mL to about 0.1 μg/mL (e.g., 0.001, 0.005, 0.01, 0.05, 0.1 μg/mL or a number or a range between any two of these values), or about 0.001 µg/mL to about 0.01 µg/mL (e.g., 0.001, 0.0025, 0.005, 0.0075, 0.01 µg/mL or a number or a range between any two of these values) as assessed by an optofluidic system and/or an ELISA assay.

In some embodiments, at least one of the two or more sarbecovirus spike protein RBDs is selected from SARS-CoV-2 RBD and variants thereof, RsSTT200 RBD and variants thereof, Pang17 RBD and variants thereof, RaTG13 RBD and variants thereof, SARS-CoV RBD and variants thereof, WIV1 RBD and variants thereof, SHCO14 RBD and variants thereof, LyRa3 RBD and variants thereof, C028 RBD and variants thereof, Rs4081 RBD and variants thereof, RmYNO2 RBD and variants thereof, Rfl RBD and variants thereof, Yun11 RBD and variants thereof, BM4831 RBD and variants thereof, BtKY72 RBD and variants thereof, and Khosta2 RBD and variants thereof.

In some embodiments, the antibodies and fragments thereof comprise potent and/or broad neutralization activities against, e.g., one or more coronaviruses. "Potency" as used herein can refer to a measure of how effective an antibody or fragment thereof is at producing the desired response (e.g., inhibiting infectivity) and can be expressed in terms of the concentration (e.g., IC50) which produces a particular level of the response attainable. Broadly neutralizing antibodies are antibodies that can neutralize coronaviruses from two or more taxonomic groups (e.g., subfamily, genus, subgenus, species, and/or strain) of coronavirus. Broadly neutralizing response can also be referred to as heterologous neutralizing response. In some embodiments, the methods described herein can elicit broadly neutralizing antibodies that neutralize one or more coronaviruses from a subfamily, genus, subgenus, species, and/or strain that differ from the subfamily, genus, subgenus, species, and/or strain of the coronaviruses from which the coronavirus antigens are derived to produce the multivalent nanoparticles (See, "Methods for identifying antibodies or fragments thereof that specifically bind coronavirus antigens" below).

The term "neutralizing," as used herein, in relation to the antibodies of the disclosure refers to antibodies that are capable of preventing, reducing or inhibiting infection of a cell by the virus, by neutralizing, inhibiting, or reducing its biological effect and/or reducing the infectious titer of the virus, regardless of the mechanism by which neutralization is achieved. Neutralization can, e.g., be achieved by inhibiting the attachment or adhesion of the virus to the cell surface, or by inhibition of the fusion of viral and cellular membranes following attachment of the virus to the target cell, and the like (e.g., by interfering with ACE2 binding). Neutralization potencies can be determined by any method known in the art. In some embodiments, reduced infectivity and IC50 values can be determined by, e.g., a pseudovirus neutralization assay (See Example 2 below).

In some embodiments, the antibody or fragment thereof inhibits infectivity of a virus comprising a sarbecovirus spike protein receptor binding domain (RBD) with an IC50 less than 10 µg/mL, less than 1 µg/mL, less than 0.1 µg/mL or less than 0.01 µg/mL. In some embodiments, IC50 is measured by a pseudovirus neutralization assay. In some embodiments, the antibody or fragment thereof inhibits infectivity of a virus comprising a sarbecovirus spike protein receptor binding domain (RBD) with an IC50 of about 0.001 µg/mL to about 10 µg/mL (e.g., 0.001, 0.005, 0.01, 0.05, 0.1, 0.5, 1, 1.5, 2, 3, 4, 5, 6, 7, 8, 9, 10 µg/mL or a number or a range between any two of these values), about 0.001 µg/mL to about 1 µg/mL (e.g., 0.001, 0.005, 0.01, 0.05, 0.1, 0.5, 1 µg/mL or a number or a range between any two of these values), about 0.001 µg/mL to about 0.1 µg/mL (e.g., 0.001, 0.005, 0.01, 0.05, 0.1 µg/mL or a number or a range between any two of these values), or about 0.001 µg/mL to about 0.01 µg/mL (e.g., 0.001, 0.025, 0.005, 0.075, 0.01 µg/mL or a number or a range between any two of these values). In some embodiments, IC50 is measured by a pseudovirus neutralization assay. The pseudovirus neutralization assay can comprise target cells expressing hACE2 receptor protein.

In some embodiments, the antibody or fragment thereof inhibits infectivity of two or more viruses each comprising a different sarbecovirus spike protein receptor binding domain (RBD). In some embodiments, the antibody or fragment thereof inhibits infectivity of at least one, at least two, or all of the two or more viruses with an IC50 less than 10 µg/mL, less than 1 µg/mL, less than 0.1 µg/mL, or less than 0.01 µg/mL.

In some embodiments, the antibody or fragment thereof inhibits infectivity of at least one, at least two, or all of the two or more viruses with an IC50 of about 0.001 µg/mL to about 10 µg/mL (e.g., 0.001, 0.005, 0.01, 0.05, 0.1, 0.5, 1, 1.5, 2, 3, 4, 5, 6, 7, 8, 9, 10 µg/mL or a number or a range between any two of these values), about 0.001 µg/mL to about 1 µg/mL (e.g., 0.001, 0.005, 0.01, 0.05, 0.1, 0.5, 1 µg/mL or a number or a range between any two of these values), about 0.001 µg/mL to about 0.1 µg/mL (e.g., 0.001, 0.005, 0.01, 0.05, 0.1 µg/mL or a number or a range between any two of these values), or about 0.001 µg/mL to about 0.01 µg/mL (e.g., 0.001, 0.005, 0.01 µg/mL or a number or a range between any two of these values).

In some embodiments, the antibody or fragment thereof inhibits infectivity of at least one, at least two, or all of the two or more viruses with an IC50 of about 0.005 µg/mL to about 9 µg/mL (e.g., 0.005, 0.01, 0.05, 0.1, 0.5, 1, 1.5, 2, 3, 4, 5, 6, 7, 8, 9 µg/mL or a number or a range between any two of these values). In some embodiments, the antibody or fragment thereof inhibits infectivity of at least one, at least two, or all of the two or more viruses with an IC50 of about 0.001 µg/mL to about 0.06 µg/mL (e.g., 0.001, 0.005, 0.0075, 0.01, 0.025, 0.05, 0.06 µg/mL or a number or a range between any two of these values). In some embodiments, the antibody or fragment thereof inhibits infectivity of at least one, at least two, or all of the two or more viruses with an IC50 of about 0.02 µg/mL to about 6 µg/mL (e.g., 0.02, 0.05, 0.1, 0.5, 1, 1.5, 2, 3, 4, 5, 6 µg/mL or a number or a range between any two of these values). In some embodiments, the antibody or fragment thereof inhibits infectivity of at least one, at least two, or all of the two or more viruses with an IC50 of about 0.002 µg/mL to about 2 µg/mL (e.g., 0.002, 0.005, 0.01, 0.05, 0.1, 0.5, 0.75, 1, 1.5, 1.75, 2 µg/mL or a number or a range between any two of these values).

In some embodiments, the sarbecovirus spike protein RBD is selected from SARS-CoV-2 RBD and variants thereof, SARS-CoV RBD and variants thereof, WIV1 RBD and variants thereof, SHC014 RBD and variants thereof, BtKY72 RBD and variants thereof, Khosta2/SARS-CoV Chimera RBD and variants thereof, and LyRa3/SARS-CoV RBD Chimera and variants thereof. The SARS-CoV-2 variants can comprise Wuhan (WA1 D614G), Beta, Delta, Omicron BA.1, Omicron BA.2, Omicron BA.4, and Omicron BA.5. The antibody or fragment thereof can be capable of binding to each of the three RBDs of a sarbecovirus spike trimer. Disclosed herein include compositions comprising any of the antibodies or fragments thereof provided herein and a pharmaceutically acceptable carrier.

There are also provided polynucleotides encoding one or more of the antibody or fragment thereof provided herein. Disclosed herein include isolated cells comprising any of the polynucleotides provided herein. There are provided compositions comprising any of the polynucleotides and/or an isolated cells provided herein.

The present disclosure provides isolated polynucleotides or nucleic acid molecules encoding the antibodies, fragments, variants or derivatives thereof of the disclosure. The polynucleotides of the present disclosure can encode the heavy and light chain variable regions of the antibodies, fragments, variants or derivatives thereof on the same polynucleotide molecule or on separate polynucleotide molecules. In some embodiments, the polynucleotides of the present disclosure can encode portions of the heavy and light chain variable regions of the antibodies (e.g., the CDR regions), fragments, variants or derivatives thereof on the same polynucleotide molecule or on separate polynucleotide molecules.

Methods of making antibodies are well known in the art and described herein. For example, polynucleotides encoding desired antibodies can be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA can be placed into expression vectors, which are then transfected into antibody-producing cells including prokaryotic or eukaryotic host cells such as *E. coli* cells, simian COS cells, Chinese Hamster Ovary (CHO) cells or myeloma cells that do not otherwise produce immunoglobulins. The isolated DNA can be used to clone constant and variable region sequences for the manufacture antibodies as described in Newman et al., U.S. Pat. No. 5,658,570 which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As described herein, transformed cells expressing the desired antibody can be grown up in relatively large quantities to provide clinical and commercial supplies of the immunoglobulin.

In some embodiments, mutations can be introduced in the nucleotide sequence encoding an antibody of the present disclosure using standard techniques known to those of skill in the art, including, but not limited to, site-directed mutagenesis and PCR-mediated mutagenesis which result in amino acid substitutions.

In some embodiments, the antibodies, fragments, variants, or derivatives thereof can further comprise a chemical moiety not naturally associated with an antibody. For example, the antibody or fragment thereof can comprise a flexible linker or can be modified to add a functional moiety such as a detectable label. The antibodies, fragments, variants, or derivatives thereof can be modified, i.e., by the covalent or non-covalent attachment of a chemical moiety to the antibody such that the attachment does not interfere or prevent the antibody from binding to the epitope. The chemical moiety can be conjugated to an antibody using any technique known in the art.

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

In some embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

In some embodiments, the prepared antibodies do not elicit a deleterious immune response in the subject to be treated, e.g., in a human. In one embodiment, antigen-binding polypeptides, variants, or derivatives thereof of the disclosure are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., Proc. Natl. Acad. Sci. USA 57:6851-6855 (1984); Morrison et al., Adv. Immunol. 44:65-92 (1988); Verhoeyen et al., Science 239:1534-1536 (1988); Padlan, Molec. Immun. 25:489-498 (1991); Padlan, Molec. Immun. 31:169-217 (1994), and U.S. Pat. Nos. 5,585,089, 5,693, 761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T-cell epitopes (see, e.g., International Application Publication Nos.: WO/9852976 A1 and WO/0034317 A2). For example, variable heavy chain and variable light chain sequences from the starting antibody are analyzed and a human T-cell epitope "map" from each V region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

The binding specificity of the antibodies or fragments thereof of the present disclosure can be determined by in vitro assays such as immunoprecipitation, radioimmunoassay (RIA) or enzyme-linked immunoabsorbent assay (ELISA).

Alternatively, techniques described for the production of single-chain units (U.S. Pat. No. 4,694,778; Bird, Science 242:423-442 (1988); Huston et al., Proc. Natl. Acad. Sci. USA 55:5879-5883 (1988); and Ward et al., Nature 334: 544-554 (1989)) can be adapted to produce single-chain units of the present disclosure. Single-chain units are formed by linking the heavy and light chain fragments of the Fv region via an amino acid bridge, resulting in a single-chain fusion peptide. Techniques for the assembly of functional Fv fragments in *E. coli* may also be used (Skerra et al., Science 242: 1038-1041 (1988)).

Examples of techniques which can be used to produce single-chain Fvs (scFvs) and antibodies include those described in U.S. Pat. Nos. 4,946,778 and 5,258,498; Huston et al., Methods in Enzymology 203:46-88 (1991); Shu et al., Proc. Natl. Sci. USA 90:1995-1999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816397, which are incorporated herein by reference in their entireties.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., Proc. Natl. Sci. USA 91:969-973 (1994)), and chain shuffling (U.S. Pat. No. 5,565,332, which is incorporated by reference in its entirety).

Completely human antibodies can be particularly desirable for therapeutic treatment of human patients. Human antibodies can be made by a variety of methods known in the art including phage display methods using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar Int. Rev. Immunol. 73:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies can be engaged to provide human antibodies directed against a selected antigen using technology similar to that described above.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope. (Jespers et al., Bio/Technology 72:899-903 (1988). See also, U.S. Pat. No. 5,565,332, which is incorporated by reference in its entirety.)

Additionally, using routine recombinant DNA techniques, one or more of the CDRs of the antibodies of the present disclosure, may be inserted within framework regions, e.g., into human framework regions to humanize a non-human antibody. The framework regions may be naturally occurring or consensus framework regions, and preferably human framework regions (see, e.g., Chothia et al., J. Mol. Biol. 278:457-479 (1998) for a listing of human framework regions). Preferably, the polynucleotide generated by the combination of the framework regions and CDRs encodes an antibody that specifically binds to at least one epitope of a desired polypeptide. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and within the skill of the art.

In addition, techniques developed for the production of "chimeric antibodies" (Morrison et al., Proc. Natl. Acad. Sci. USA:851-855 (1984); Neuberger et al., Nature 372:604-608 (1984); Takeda et al., Nature 314:452-454 (1985)) by splicing genes from a mouse antibody molecule, of appropriate antigen specificity, together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region.

Yet another highly efficient means for generating recombinant antibodies is disclosed by Newman, Biotechnology 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

Alternatively, antibody-producing cell lines may be selected and cultured using techniques well known to the skilled artisan. Such techniques are described in a variety of laboratory manuals and primary publications. In this respect, techniques suitable for use in the disclosure as described below are described in Current Protocols in Immunology, Coligan et al., Eds., Green Publishing Associates and Wiley-Interscience, John Wiley and Sons, New York (1991) which is herein incorporated by reference in its entirety, including supplements.

Additionally, standard techniques known to those of skill in the art can be used to introduce mutations in the nucleotide sequence encoding an antibody of the present disclosure, including, but not limited to, site-directed mutagenesis and PCR-mediated mutagenesis which result in amino acid substitutions. Preferably, the variants (including derivatives) encode fewer than 50 amino acid substitutions, fewer than 40 amino acid substitutions, fewer than 30 amino acid substitutions, fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the reference variable heavy chain region, CDR-H1, CDR-H2, CDR-H3, variable light chain region, CDR-L1, CDR-L2, and/or CDR-L3. In some embodiments, one or more mutations are introduced randomly along all or part of the coding sequence, such as by saturation mutagenesis, and the resultant mutants can be screened for biological activity to identify mutants that retain activity.

Methods of Treating Coronavirus Infections

Disclosed herein include methods of treating or preventing a coronavirus infection in a patient in need thereof, e.g., administering to the patient an effective amount of any of the antibodies or fragments thereof, polynucleotides, isolated cells, and compositions provided herein, or a combination thereof.

The compositions disclosed herein can be employed in a variety of therapeutic or prophylactic applications to treat or prevent a coronavirus infection in a subject in need, and/or to treat or prevent a disease or disorder caused by a coronavirus in a subject in need.

As used herein, the term "treatment" or "treat" refers to an intervention made in response to a disease, disorder or physiological condition (e.g., a coronavirus infection) manifested by a patient. The aim of treatment may include, but is not limited to, one or more of the alleviation or prevention of symptoms, slowing or stopping the progression or worsening of a disease, disorder, or condition and the remission of the disease, disorder or condition. The term "treat" and "treatment" includes, for example, therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. As used herein, the term "prevention" refers to any activity that reduces the burden of the individual later expressing those symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications. The term "prevent" does not require the 100% elimination of the possibility of an event. Rather, it denotes that the likelihood of the occurrence of the event has been reduced in the presence of the compound or method.

The term "condition" as used herein indicates a physical status of the body of an individual (as a whole or as one or more of its parts), that does not conform to a standard physical status associated with a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

Signs and symptoms manifesting a disease or disorder caused by a coronavirus infection can include, but not limited to, fever, cough, tiredness, a loss of taste or smell, shortness of breath or difficulty breathing, muscle aches, chills, sore throat, runny nose, headache, chest pain, pink eye (conjunctivitis), nausea, vomiting, diarrhea, rash, pneumonia and acute respiratory distress syndrome. Diseases or disorders caused by a coronavirus infection may also include severe complications including but not limited to heart disorders including arrhythmias, cardiomyopathy, acute cardiac injury, coagulation disorders including thromboembolism and pulmonary emboli, disseminated intravascular coagulation (DIC), hemorrhage, and arterial clot formation, Guillain-Barre syndrome, sepsis, shock, multiorgan failure, and multisystem inflammatory syndrome, and any combination thereof.

The terms "subject", "subject in need", and "individual" as used herein refer to an animal and in particular higher animals and in particular vertebrates such as mammals and more particularly human beings. In some embodiments, the subject or individual has been exposed to a coronavirus. The term "exposed" indicates the subject has come in contact with a person or an animal that is known to be infected with a coronavirus. In some embodiments, a subject in need can be a healthy subject exposed to or at risk of being exposed to a coronavirus. In some embodiments, subjects in need include those already suffering from the disease or disorder caused by a coronavirus infection or those diagnosed with a coronavirus infection.

Accordingly, the composition (e.g., comprising an antibody or fragment thereof described herein) can be administered in advance of any symptom, for example, in advance of a coronavirus infection. The composition can also be administered at or after the onset of a symptom of disease or infection, for example, after development of a symptom of infection or after diagnosis of the infection.

The phrase "therapeutically effective amount" as used herein means the amount of an antibody or fragment thereof disclosed herein which is effective for producing some desired therapeutic effect and/or generating a desired response, such as reduce or eliminate a sign or symptom of a condition or disease, such as pneumonia, at a reasonable benefit/risk ratio. The therapeutically effective amount also varies depending upon neutralization potency, the route of administration utilized, and the specific diseases or disorders to be treated as will be understood to a person skilled in the art. For example, if a given clinical treatment is considered effective when there is at least a 20% reduction in a measurable parameter associated with a disease or disorder, a therapeutically effective amount of a disclosed composition for the treatment of that disease or disorder is the amount necessary to achieve at least a 20% reduction in that measurable parameter.

In some embodiments, a therapeutically effective amount is necessary to inhibit coronavirus replication or to measurably alleviate outward symptoms of the viral infection or inhibiting further development of the disease, condition, or disorder. In some embodiments, a therapeutically effective amount is an amount that prevents one or more signs or symptoms that can be caused by a coronavirus infection. In some embodiments, a therapeutically effective amount can be an amount that prevents one or more signs or symptoms of a particular disease or condition from developing, such as one or more signs or symptoms associated with coronavirus infections.

A therapeutically effective amount of a composition herein described can be estimated from data obtained from cell culture assays and further determined from data obtained in animal studies, followed up by human clinical trials. For example, toxicity and therapeutic efficacy of the compositions described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred.

The compositions herein described can be administered using techniques well known to those skilled in the art, such as injection, inhalation or insulation or by oral, parenteral or rectal administration. The composition can be administered by means including, but not limited to, traditional syringes and needleless injection devices. Suitable routes of administration include, but are not limited to, parenteral delivery, such as intramuscular, intradermal, subcutaneous, intramedullary injections, as well as, intrathecal, direct intraventricular, intravenous, intraperitoneal, intranasal, or intraocular injections. For injection, the composition herein described can be formulated in aqueous solutions, preferably in physiologically compatible buffers such as Hanks' solution, Ringer's solution, or physiological saline buffer.

In some embodiments, the antibodies and compositions thereof can be administered to a subject systematically. The wording "systemic administration" as used herein indicates any route of administration by which a composition is brought in contact with the body of the individual, so that the resulting composition location in the body is systemic (i.e. non limited to a specific tissue, organ or other body part where the antibody or fragment thereof is administered). Systemic administration includes enteral and parenteral administration. Enteral administration is a systemic route of administration where the substance is given via the digestive tract, and includes but is not limited to oral administration, administration by gastric feeding tube, administration by duodenal feeding tube, gastrostomy, enteral nutrition, and rectal administration. Parenteral administration is a systemic route of administration where the substance is given by route other than the digestive tract and includes but is not limited to intravenous administration, intra-arterial administration, intramuscular administration, subcutaneous administration, intradermal, administration, intraperitoneal administration, and intravesical infusion.

The frequency of administration can vary. A subject can receive dosing for a period of about, less than about, or greater than about 1, 2, 3, 4, 5, 6, 7, 8, 9, 10, 11, 12, 13, 14, or more days, weeks or months. The compositions can be administered periodically. For example, the compositions can be administered one, two, three, four times a day, or even more frequent. The subject can be administered every 1, 2, 3, 4, 5, 6, or 7 days. In some embodiments, the compositions are administered three times daily. The period of treatment can be for about 1, 2, 3, 4, 5, 6, 7, 8, or 9 days, 2 weeks, 1-11 months, or 1 year, 2 years, 5 years, or even longer. In some embodiments disclosed herein, the dosages that are administered to a subject can change or remain constant over the period of treatment. For example, the daily dosing amounts can increase or decrease over the period of administration. Therefore, the composition can be administered to the subject in need two or more times. A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the compositions described herein include but are not limited to intradermal, intramuscular, intraperitoneal, intravenous, subcutaneous, intranasal, epidural, and oral routes. The antibodies or fragments thereof or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It can be desirable to administer the antibodies or fragments thereof or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialistic membranes, or fibers. Preferably, when administering a protein, including an antibody, of the disclosure, care must be taken to use materials to which the protein does not absorb.

In some embodiments, an antibody or fragment thereof or composition can be delivered in a controlled release system. For example, a pump may be used (see Sefton, 1987, CRC Crit. Ref. Biomed. Eng. 14:201; Buchwald et al., 1980, Surgery 88:507; Saudek et al., 1989, N. Engl. J. Med. 321:574). As another example, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another example, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Some other non-limiting examples of controlled release systems are discussed in the review by Langer (1990, Science 249:1527-1533).

In some embodiments where the composition of the disclosure comprises a nucleic acid or polynucleotide encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The amount of the antibodies of the disclosure which will be effective in the treatment, inhibition and prevention of a coronavirus infection can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antibodies or fragments thereof of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

The methods for treating a coronavirus infection comprising administration of an antibody, variant, or derivative thereof of the disclosure are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample. The effect of the antibody or fragment thereof on the cell line and/or tissue sample can be determined utilizing techniques known to those of skill in the art, such as the assays disclosed elsewhere herein. In accordance with the disclosure, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

Various delivery systems are known and can be used to administer an antibody of the disclosure or a polynucleotide encoding an antibody of the disclosure, e.g., encapsulation in liposomes, microparticles, microcapsules, recombinant cells capable of expressing the compound, receptor-mediated endocytosis (see, e.g., Wu and Wu, 1987, J. Biol. Chem.

262:4429-4432), construction of a nucleic acid as part of a retroviral or other vector, etc.

In some embodiments, a method for treating or preventing a coronavirus infection in a subject in need thereof is disclosed, the method comprising administering to the subject a pharmaceutically effective amount of the composition herein described, thereby treating or preventing the coronavirus infection in the subject. In some embodiments, administering the composition comprising an antibody or fragment thereof disclosed herein results in treating or preventing infection caused by a coronavirus different from the coronavirus RBDs used to identify and isolate said antibody or fragment thereof. In some embodiments, administering the composition results in treating or preventing infection caused by additional coronaviruses different from the coronaviruses from which the two or more coronavirus antigens are derived to produce the antibody or fragment thereof. In some embodiments, administering the composition results in treating or preventing infection caused by the coronaviruses from which the sarbecovirus RBDs are derived to identify and produce the antibody or fragment thereof.

In some embodiments, a method of treating or preventing a disease or disorder caused by a coronavirus infection in a subject in need thereof is disclosed, the method comprising administering to the subject a pharmaceutically effective amount of the compositions herein described, thereby treating or preventing the disease or disorder caused by the coronavirus infection in the subject. In some embodiments, administering the composition results in treating or preventing the disease or disorder caused by a coronavirus different from the coronavirus used to identify the antibody or fragment thereof comprising the composition. In some embodiments, administering the composition results in treating or preventing the disease or disorder caused by additional coronaviruses different from the coronaviruses from which the coronavirus antigens (e.g., sarbecovirus RBDs) are derived to produce the composition. In some embodiments, administering the composition results in treating or preventing the disease or disorder caused by the coronaviruses from which the two or more different coronavirus antigens are derived to produce the composition.

In some embodiments, the composition can be used for treating and preventing a broad spectrum of coronavirus infections or a disease or disorder caused by such infections due to the broadly neutralizing and potent activities of the antibodies disclosed herein. For example, the composition herein described can neutralize one or more coronaviruses from a subfamily, genus, subgenus, species, and/or strain that differ from the subfamily, genus, subgenus, species, and/or strain of the coronaviruses from which the coronavirus antigens (e.g., spike protein RBDs) are derived to produce the composition.

In some embodiments, the antibodies and compositions described herein can treat or prevent infection by an antigenically divergent coronavirus. Therefore, in some embodiments, a composition made using the antibodies or fragments thereof described herein can be used to treat an infection resulting from emerging coronaviruses and variants thereof. For example, an antibody identified and isolated from B-cells isolated from an animal immunized with coronavirus antigens of SARS-CoV2 and SHCO14 can protect an individual against infection by antigenically divergent coronavirus strains of Sarbecovirus and by diverging coronavirus strains of the future. The coronavirus can be a coronavirus in the genus of Alpha-coronavirus, Beta-coronavirus, or both. The coronavirus can be a coronavirus of the subgenus Sarbecovirus.

The coronavirus can be SARS-CoV-2 or a variant thereof, RsSTT200 or a variant thereof, Pang17 or a variant thereof, RaTG13 or a variant thereof, SARS-CoV or a variant thereof, WIV1 or a variant thereof, SHCO14 or a variant thereof, LyRa3 or a variant thereof, C028 or a variant thereof, Rs408l or a variant thereof, RmYN02 or a variant thereof, Rfl or a variant thereof, Yun11 or a variant thereof, BM4831 or a variant thereof, BtKY72 or a variant thereof, or Khosta2 or a variant thereof. The coronavirus can comprise a SARS-CoV-2 variant of concern, variant of interest, or both. The SARS-CoV-2 variant of concern can comprise SARS-CoV-2 Beta and variants thereof, SARS-CoV-2 Delta and variants thereof, or SARS-CoV-2 Omicron and variants thereof. The compositions described herein can be used to protect a subject against infection by heterologous coronaviruses (e.g., coronaviruses of different taxonomic groups). For example, a composition can comprise antibodies or fragments thereof capable of preventing or treating the subject for infection by not only WIV1, Rf1, RmYNO2 and pang17 at a comparable magnitude, but also coronavirus SARS-CoV2, SHC014, SARS-CoV, Yun 11, BM-4831 and BtKY72.

Co-Therapies

The method can comprise administering to the patient a second therapeutic agent. The second therapeutic agent can comprise an anti-viral compound, an immunosuppressant, an antibody, or any combination thereof. The second therapeutic agent can comprise remdesivir, molnupiravir, tocilizumab, favipiravir, merimepodib, artesunate, favipiravir, ribavirin, EIDD-2801, niclosamide, nitazoxanide, oseltamivir, AT-527, paxlovid, regdanvimab, ramdicivir, baricitinib, imatinib, casirivimab, imdevimab, bemcentinib, bamlanivimab, etesevimab, sotrovimab, leronlimab, bebtelovimab, cilgavimab, IMU-838, oseltamivir, or dexamethasone.

As disclosed herein, co-administration of particular ratios and/or amounts of the antibodies or fragments thereof or a composition comprising said antibodies or fragments thereof, and the second therapeutic agent can result in synergistic effects in reducing, treating, or preventing a coronavirus infection. These synergistic effects can be such that the one or more effects of the combination compositions are greater than the one or more effects of each component alone at a comparable dosing level, or they can be greater than the predicted sum of the effects of all of the components at a comparable dosing level, assuming that each component acts independently. The synergistic effect can be about, or greater than about, 5, 10, 20, 30, 50, 75, 100, 110, 120, 150, 200, 250, 350, or 500% better than the effect of treating a subject with one of the components alone, or the additive effects of each of the components when administered individually. The effect can be any of the measurable effects described herein. The composition comprising a plurality of components can be such that the synergistic effect is an enhancement in reducing, treating, or preventing a coronavirus infection and that efficacy is increased to a greater degree as compared to the sum of the effects of administering each component, determined as if each component exerted its effect independently, also referred to as the predicted additive effect herein. For example, if a composition comprising component (a) yields an effect of a 20% improvement in e.g., treating a coronavirus infection and a composition comprising component (b) yields an effect of 50% improvement in treating a coronavirus infection, then a composition comprising both component (a) and component (b) would have a synergistic effect if the combination composition's effect on treating a coronavirus infection was greater than 70%.

A synergistic combination composition can have an effect that is greater than the predicted additive effect of administering each component of the combination composition alone as if each component exerted its effect independently. For example, if the predicted additive effect is 70%, an actual effect of 140% is 70% greater than the predicted additive effect or is 1 fold greater than the predicted additive effect. The synergistic effect can be at least about 20, 50, 75, 90, 100, 150, 200 or 300% greater than the predicted additive effect. In some embodiments, the synergistic effect can be at least about 0.2, 0.5, 0.9, 1.1, 1.5, 1.7, 2, or 3 fold greater than the predicted additive effect.

In some embodiments, the synergistic effect of the combination compositions can also allow for reduced dosing amounts, leading to reduced side effects to the subject and reduced cost of treatment. Furthermore, the synergistic effect can allow for results that are not achievable through any other treatments. Therefore, proper identification, specification, and use of combination compositions can allow for significant improvements in the reduction and prevention of coronavirus infection.

Protection from SARS-related coronaviruses with spill-over potential and SARS-CoV-2 variants is important for preventing and/or ending pandemics. As described herein, mice immunized with nanoparticles co-displaying spike receptor-binding domains (RBDs) from eight sarbecoviruses (mosaic-8 RBD-nanoparticles) efficiently elicit cross-reactive anti-sarbecovirus antibodies against conserved class ¼ and class 3 RBD epitopes. Monoclonal antibodies (mAbs) identified from initial screening of <10,000 single B-cells secreting IgGs binding two or more sarbecovirus RBDs showed cross-reactive binding and neutralization of SARS-CoV-2 variants and animal sarbecoviruses. Single-particle cryo-EM structures of antibody-spike complexes, including a Fab-Omicron complex, mapped neutralizing mAbs to conserved class ¼ RBD epitopes and revealed neutralization mechanisms, potentials for intra-spike trimer crosslinking by single IgGs, and induced changes in trimer upon Fab binding. In addition, a mAb resembling Bebtelovimab, an EUA-approved human class 3 anti-RBD mAb was identified. These results support using mosaic RBD-nanoparticles to identify therapeutic pan-sarbecovirus and pan-variant mAbs and to elicit them by vaccination.

Compositions

Disclosed herein include compositions comprising any of the antibodies or fragments thereof provided herein and a pharmaceutically acceptable carrier. Disclosed herein include compositions comprising any of the polynucleotide and/or isolated cell provided herein. In some embodiments, the composition further includes a second therapeutic agent (e.g., an anti-viral agent). The second therapeutic agent can comprise an anti-viral compound, an immunosuppressant, an antibody, or any combination thereof. The second therapeutic agent can comprise remdesivir, molnupiravir, tocilizumab, favipiravir, merimepodib, artesunate, favipiravir, ribavirin, EIDD-2801, niclosamide, nitazoxanide, oseltamivir, AT-527, paxlovid, regdanvimab, ramdicivir, baricitinib, imatinib, casirivimab, imdevimab, bemcentinib, bamlanivimab, etesevimab, sotrovimab, leronlimab, bebtelovimab, cilgavimab, IMU-838, oseltamivir, or dexamethasone.

In a some embodiments, the term "pharmaceutically acceptable" means approved by a regulatory agency of the Federal or a state government or listed in the U.S. Pharmacopeia or other generally recognized pharmacopeia for use in animals, and more particularly in humans. A "pharmaceutically acceptable carrier" is generally a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In some embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Kits

The compositions described herein can be provided as components of a kit. The kit can include compositions of the present disclosure as well components for making such compositions. As such, kits can include, for example, primers, nucleic acid molecules, expression vectors, nucleic acid constructs encoding protein antigens and/or particle-forming subunits described herein, cells, buffers, substrates, reagents, administration means (e.g., syringes), and instructions for using any of said components. Kits can include compositions comprising one or more antibodies or fragments thereof disclosed herein. It should be appreciated that a kit may comprise more than one container comprising any of the aforementioned, or related, components. For example, certain parts of the kit may require refrigeration, whereas other parts can be stored at room temperature. Thus, as used herein, a kit can comprise components sold in separate containers by one or more entity, with the intention that the components contained therein be used together.

Methods for Identifying Antibodies or Fragments Thereof that Specifically Bind Coronavirus Antigens Disclosed herein include methods for identifying an antibody or fragment thereof that has specificity to one or more coronavirus antigens. Disclosed herein include methods for identifying an antibody or fragment thereof that has specificity to a sarbecovirus spike protein receptor binding domain (RBD). In some embodiments, the method comprises screening B cells against one or more sarbecovirus spike protein RBDs; wherein the B cells are isolated from a mammal immunized with two or more different sarbecovirus spike protein RBDs. The B cells can be isolated from a mammal immunized with four or more different sarbecovirus spike protein RBDs.

The B cells can be isolated from a mammal immunized with a nanoparticle comprising the two or more sarbecovirus spike protein RBDs. The nanoparticle can comprise one or more sarbecovirus spike protein RBDs selected from a SARS-CoV-2 RBD, an SHC014 RBD, an RaTG13 RBD, an Rs4081 RBD, a WIV1 RBD, an Rfl RBD, an RmYNO2 RBD, a Pang17 RBD, a SARS-CoV RBD, a Yun11 RBD, a BM4831 RBD, and a BtKY72 RBD.

The immunizing can comprise administration of an adjuvant. [0215] The mammal can be selected from a mouse, a rat, a rabbit, a goat, and a primate. The mammal can be selected from a mouse, human, donkey, rabbit, goat, guinea pig, camel, llama, and a horse. The B cells can be CD138+ plasma B cells.

Detailed methods for making and using vaccine compositions for immunizing an animal with two or more heterologous (e.g., different) coronavirus antigens is described in US Patent Publication No. 2022/0168414 which is hereby incorporated by reference in its entirety. The term "heterologous antigens" means that the antigens are of different origins, such as derived from pathogens of different taxonomic groups such as different strains, species, subgenera, genera, subfamilies or families and/or from antigenically divergent pathogens (e.g., variants thereof). Multivalent nanoparticles can also be referred to as mosaic nanoparticles. Classification of viruses into various taxonomic groups is well understood by those skilled in the art. In the embodiments herein described, the heterologous coronavirus antigens of the multivalent nanoparticles herein described are derived from coronaviruses of different strains, species, subgenera, genera, and/or subfamilies in the Coronaviridae family.

The term "coronavirus" as used herein refers to a virus in the family Coronaviridae, which is in turn classified within the order Nidovirales. The coronaviruses are large, enveloped, positive-stranded RNA viruses. The coronaviruses have the largest genomes of the RNA viruses known in the art and replicate by a unique mechanism that results in a high frequency of recombination. The coronaviruses include antigenic groups I, II, and III. Nonlimiting examples of coronaviruses include SARS coronavirus (e.g., SARS-CoV and SARS-CoV-2), MERS coronavirus, transmissible gastroenteritis virus (TGEV), human respiratory coronavirus, porcine respiratory coronavirus, canine coronavirus, feline enteric coronavirus, feline infectious peritonitis virus, rabbit coronavirus, murine hepatitis virus, sialodacryoadenitis virus, porcine hemagglutinating encephalomyelitis virus, bovine coronavirus, avian infectious bronchitis virus, and turkey coronavirus, as well as chimeras thereof. Additional information related to coronavirus including classification, virion structure, genome structure, genetics and pathology is described, for example, in K V Holmes, Encyclopedia of Virology, 1999: 291-298, the content of which is incorporated herein by reference.

In some embodiments, a coronavirus described herein is in the genus of Alpha-coronavirus and the coronavirus antigens can be of or derived from any species or strains in the genus of Alpha-coronavirus. In some embodiments, a coronavirus described herein is in the genus of Beta-coronavirus and the coronavirus antigens can be of or derived from any species or strains in the genus of Beta-coronavirus. Member viruses in the genus of Alpha-coronavirus and Beta-coronavirus are enveloped, positive-strand RNA viruses that can infect mammals.

A coronavirus described herein can be of any subgenus of Alpha-coronavirus genus, including but not limited to Colacovirus (e.g. Bat coronavirus CDPHE15), Decacovirus (e.g. Bat coronavirus HKU10 and *Rhinolophus ferrumequinum* alphacoronavirus HuB-2013), Duvinacovirus (Human coronavirus 229E), Luchacovirus (e.g. Lucheng Rn rat coronavirus), Minacovirus (e.g. Mink coronavirus 1), Minunacovirus (e.g. Miniopterus bat coronavirus 1 and Miniopterus bat coronavirus HKU8), Myotacovirus (e.g. *Myotis ricketti* alphacoronavirus Sax-2011), Nyctacovirus (e.g. *Nyctalus velutinus* alphacoronavirus SC-2013 and *Pipistrellus kuhlii* coronavirus 3398), Pedacovirus (e.g. Porcine epidemic diarrhea virus and Scotophilus bat coronavirus 512), Rhinacovirus (e.g. Rhinolophus bat coronavirus HKU2), Setracovirus (e.g. Human coronavirus NL63 and NL63-related bat coronavirus strain BtKYNL63-9b), Soracovirus (e.g. *Sorex araneus* coronavirus T14), Sunacovirus (e.g. *Suncus murinus* coronavirus X74), and Tegacovirus (e.g. Alphacoronavirus 1).

Within the genus Beta-coronavirus, five subgenera or lineages have been recognized, including Embecovirus (lineage A), Sarbecovirus (lineage B), Merbecovirus (lineage C), Nobecovirus (lineage D), and Hibecovirus. Accordingly, in some embodiments, a coronavirus described herein can be any strain or species in any of the subgenera or lineages of Beta-coronavirus.

For example, a coronavirus antigen can be of or derived from any species or strains in the subgenus of Embecovirus, including but not limited to Beta-coronavirus 1 (e.g. Bovine coronavirus and human coronavirus OC43), China *Rattus* coronavirus HKU24, Human coronavirus HKUJ, Murine coronavirus (e.g. mouse hepatitis virus), and Myodes coronavirus 2JL14. The coronavirus antigen can be of or derived from any species or strains in the subgenus of Sarbecovirus, including but not limited to SARS-CoV, SARS-CoV-2, 16B0133, Bat SARS CoV Rf1, Bat coronavirus HKU3 (BtCoV HKU3), LYRa11, Bat SARS-CoV/Rp3, Bat SL-CoV YNLF_31C, Bat SL-CoV YNLF_34C, SHCO14-CoV, WIV1, WIV16, Civet SARS-CoV, Rc-o319, SL-ZXC21, SL-ZC45, Pangolin SARSr-CoV-GX, Pangolin SARSr-CoV-GD, RshSTT182, RshSTT200, RacCS203, RmYNO2, RpYN06, RaTG13, Bat CoV BtKY72, and Bat CoV BM48-31. The coronavirus antigen can be of any species or strains in the subgenus of Merbecovirus, including but not limited to Hedgehog coronavirus 1, MERS-CoV, Pipistrellus bat coronavirus HKU5, and Tylonycteris bat coronavirus HKU4. The coronavirus antigen can be of any species or strains in the subgenus of Nobecovirus, including but not limited to Eidolon bat coronavirus C704, Rousettus bat coronavirus GCCDC1, and Rousettus bat coronavirus HKU9. The coronavirus antigen can be of any species or strains in the subgenus of Hibecovirus, including but not limited to Bat Hp-betacoronavirus Zhejiang 2013.

The coronaviruses described herein can be, for example, phylogenetically clustered in functionally distinct clades. For example, the coronaviruses of lineage B Beta-coronavirus (Sarbecovirus) can be clustered into clade 1, clade 2, clade ½, or clade 3 using the nucleotide sequences of nonstructural protein gene ORF1a and ORF1b (see, for example, Hu et al., PLoS Pathog 13(11): e1006698). Accordingly, the coronavirus antigens can be of or derived from any species or strain in any one of these clades. For example, the coronavirus antigens can be of any species or strain in clade 1, including but not limited to SARS-CoV, WIV1, LYRa11, Rs7327, Rs4231, Rs4084, and SHC014. The coronavirus antigens can be of any species or strain in clade 2, including but not limited to As6526, Yunnan 2011, Shaanxi 2011, 279-2005, Rs4237, Rs4081, Rp3, Rs4247, HKU3-8, HKU3-13, GX2013, Longquan-140, YN2013, Rf4092, ZXC21, ZC45, JL2012, HuB2013, Rf1, HeB2013, and 273-2005. The coronavirus antigens can be of any species or strain in clade ½, including but not limited to SARS-CoV2. The coronavirus antigens can be of any species or strain in clade 3, including but not limited to BM48-31. The coronavirus antigen described herein can be of a coronavirus, for example, SARS, SARS-2, WIV1, SHC014, Rf1, RmYN02, pang17, RaTG13, and Rs408l.

As exemplified herein, SARS virus (e.g., SARS-CoV and SARS-CoV-2) is an enveloped coronavirus carrying a single-stranded positive-sense RNA genome (~30 kb), belonging to the genus Betacoronavirus from the Coronaviridae family. The virus RNA encodes four structural proteins including spike (S), envelope (E), membrane (M), and nucleocapsid (N) proteins, 16 non-structural proteins, and nine accessory proteins. The S glycoprotein contains an ectodomain that can be processed into S1 and S2 subunits, a transmembrane domain, and an intracellular domain. Both SARS-CoV and SARS-CoV-2 bind the human ACE2 via the receptor binding domain within the S1 subunit to facilitate entry into host cells, followed by membrane fusion mediated by the S2 subunit.

A coronavirus antigen of a coronavirus herein described can be any of a variety of coronavirus proteins capable of inducing an immune response against a coronavirus. Suitable coronavirus antigens are those that can elicit a protective immune response, such as producing broadly neutralizing antibodies. For example, the coronavirus antigen can comprise a coronavirus spike (S) protein, spike receptor binding domain (RBD), S1 subunit, S2 subunit, spike full ectodomain proteins, papain-like proteases, 3CL proteases, nucleocapsid proteins, envelope proteins, membrane proteins, or any of the structural, non-structural or accessory proteins that form a coronavirus.

In some embodiments, a coronavirus antigen used herein comprises a spike (S) protein or a portion thereof. An S protein is one of four major structural proteins covering the surface of each virion. The S protein, comprising an S1 subunit and an S2 subunit, is a highly glycosylated, type I transmembrane protein capable of binding to a host-cell receptor and mediates viral entry. The S protein comprises a domain referred to as the RBD that mediates the interaction with the host-cell receptor to enter the host cell after one or more RBDs adopts an "up" position to bind the host receptor. It is believed that after binding the receptor, a nearby host protease cleaves the spike, which releases the spike fusion peptide, facilitating virus entry. Known host receptors for coronaviruses (e.g., Beta-coronaviruses) include angiotensin-converting enzyme 2 (ACE2), dipeptidyl peptidase-4 (DPP4) or sialic acids. For example, the RBDs of human coronaviruses SARS-CoV-2, SARS-CoV, HCoV-NL63, and related animal coronaviruses (WIV1 and SCH014) use ACE2 as their host receptor, while MERS-CoV uses DPP4 as its host receptor.

The coronavirus antigen used herein can, for example, comprise a coronavirus nucleocapsid protein (N protein) or a portion thereof. The N protein is a multifunctional RNA-binding protein required for viral RNA transcription, replication, and packaging. The N protein consists of three domains, an N-terminal RNA-binding domain, a central intrinsically disordered region, followed by a C-terminal dimerization domain. The RNA-binding domain contains multiple positively charged binding surfaces that form charged interactions with RNA promoting its helical arrangement. The coronavirus antigen used herein can comprise any of these N protein domains or a portion thereof.

In some embodiments, the coronavirus antigen used herein comprises a coronavirus membrane protein (M protein) or a portion thereof. The M protein is the most abundant structural protein and defines the shape of the viral envelope. The M protein is regarded as the central organizer of the viral assembly, interacting with other major coronaviral structural proteins. In some embodiments, the coronavirus antigen used herein comprises a coronavirus envelope protein (E protein) or a portion thereof. The E protein is a small membrane protein and minor component of the virus particles. Without being bound to any theory, it is believed that the E protein plays roles in virion assembly and morphogenesis, alteration of the membrane of host cells and virus-host cell interaction. In some embodiments, the coronavirus antigen used herein comprises a coronavirus hemagglutinin-esterase protein (HE protein) or a portion thereof. The HE protein, which is another envelope protein, mediates reversible attachment to O-acetylated sialic acids by acting both as lectins and receptor-destroying enzymes.

The coronavirus antigen used herein can comprise a coronavirus papain-like protease or a portion thereof. The coronavirus papain-like protease is one of several nonstructural proteins, and is responsible for processing of viral proteins into functional, mature subunits during maturation. For example, the coronavirus papain-like protease can cleave a site at the amino-terminal end of the viral replicase region. In addition to its role in viral protein maturation, papain-like protease exhibits both a deubiquitinating and deISGylating activity. In vivo, this protease antagonizes innate immunity by acting on IFN beta and NF-kappa B signaling pathways.

In some embodiments, the coronavirus antigen used herein comprises a coronavirus 3CL protease or a portion thereof. The 3CL protease is another main protease in addition to the papain-like protease and is required for processing of viral polypeptides into distinct, functional proteins. In some embodiments, the 3CL protease is a SARS-CoV-2 3CL Protease, which is a C30-type cysteine protease located within the non-structural proteins 3 (NS3) region of the viral polypeptide. Analysis of the Coronavirus genome reveals at least 11 sites of cleavage for the 3CL protease, many containing the amino acid sequence LQ[S/A/G].

The coronavirus antigen disclosed herein can, in some embodiments, comprise an S protein or a portion thereof, an N protein or a portion thereof, an HE protein or a portion thereof, a papain-like protease or a portion thereof, a coronavirus 3CL protease or a portion thereof, an M protein or a portion thereof, or a combination thereof.

In some embodiments, the coronavirus antigen can be an immunogenic portion of a coronavirus protein herein described. It will be appreciated by those skilled in the art that an immunogenic portion of a coronavirus antigen can be fragments of the S protein (e.g., spike protein RBD), N protein, HE protein, papain-like protease, 3CL protease, or M protein capable of eliciting an immune response against one or more coronaviruses. The immunogenic portion can comprise about, at least or at least about, at most or at most about, 50, 60, 70, 80, 90, 100, 110, 120, 130, 140, 150, 160, 170, 180, 190, 200, 210, 220, 230, 240, 250, or a number or a range between any two of these values, contiguous amino acid residues from the coronavirus proteins. In some embodiments, the immunogenic portion comprises an S protein RBD or a portion thereof. The portion of the S protein RBD can comprise the receptor binding motif of the S protein RBD.

The coronavirus antigen can be a Spike protein or a portion thereof comprising or consisting of an amino acid sequence having, having about, having at least, or having at least about, 80%, 85%, 90%, 95%, 98%, 99%, or more sequence identity to the amino acid sequence of any of the coronavirus S proteins from one or more coronaviruses selected from SARS-CoV, SARS-CoV2, WIV1, LYRa11, Rs7327, Rs4231, Rs4084, SHC014, As6526, Yunnan 2011, Shaanxi 2011, 279-2005, Rs4237, Rs4081, Rp3, Rs4247, HKU3-8, HKU3-13, GX2013, Longquan-140, YN2013, Rf4092, ZXC21, ZC45, JL2012, HuB2013, Rf1, HeB2013, 273-2005, and BM48-31, optionally selected from SARS, SARS-2, WIV1, SHC014, Rf1, RmYNO2, pang17, RaTG13, and Rs4081.

The coronavirus antigen can be an N protein or a portion thereof comprising or consisting of an amino acid sequence having, having about, having at least, or having at least about, 80%, 85%, 90%, 95%, 98%, 99% or more, sequence identity to the amino acid sequence of any of the coronavirus N proteins from one or more coronaviruses selected from SARS-CoV, SARS-CoV2, WIV1, LYRa11, Rs7327, Rs4231, Rs4084, SHC014, As6526, Yunnan 2011, Shaanxi 2011, 279-2005, Rs4237, Rs4081, Rp3, Rs4247, HKU3-8, HKU3-13, GX2013, Longquan-140, YN2013, Rf4092, ZXC21, ZC45, JL2012, HuB2013, Rf1, HeB2013, 273-2005, and BM48-31, optionally selected from SARS, SARS-2, WIV1, SHC014, Rf1, RmYNO2, pang17, RaTG13, and Rs4081.

The coronavirus antigen can be an HE protein or a portion thereof comprising or consisting of an amino acid sequence having, having about, having at least, having at least about, 80%, 85%, 90%, 95%, 98%, 99% or more, sequence identity to the amino acid sequence of any of the coronavirus HE proteins from one or more coronaviruses selected from SARS-CoV, SARS-CoV2, WIV1, LYRa11, Rs7327, Rs4231, Rs4084, SHC014, As6526, Yunnan 2011, Shaanxi 2011, 279-2005, Rs4237, Rs4081, Rp3, Rs4247, HKU3-8, HKU3-13, GX2013, Longquan-140, YN2013, Rf4092, ZXC21, ZC45, JL2012, HuB2013, Rf1, HeB2013, 273-2005, and BM48-31, optionally selected from SARS, SARS-2, WIV1, SHC014, Rf1, RmYNO2, pang17, RaTG13, and Rs4081.

The coronavirus antigen can be a papain-like protease or a portion thereof comprising or consisting of an amino acid sequence having, having about, having at least, having at least about, 80%, 85%, 90%, 95%, 98%, 99% or more, sequence identity to the amino acid sequence of any of the coronavirus papain-like proteases from one or more coronaviruses selected from SARS-CoV, SARS-CoV2, WIV1, LYRa11, Rs7327, Rs4231, Rs4084, SHC014, As6526, Yunnan 2011, Shaanxi 2011, 279-2005, Rs4237, Rs4081, Rp3, Rs4247, HKU3-8, HKU3-13, GX2013, Longquan-140, YN2013, Rf4092, ZXC21, ZC45, JL2012, HuB2013, Rf1, HeB2013, 273-2005, and BM48-31, optionally selected from SARS, SARS-2, WIV1, SHC014, Rf1, RmYN02, pang17, RaTG13, and Rs4081.

The coronavirus antigen can be a 3CL protease or a portion thereof comprising or consisting of an amino acid sequence having, having about, having at least, having at least about, 80%, 85%, 90%, 95%, 98%, 99% or more, sequence identity to the amino acid sequence of any of the coronavirus 3CL proteases from one or more coronaviruses selected from SARS-CoV, SARS-CoV2, WIV1, LYRa11, Rs7327, Rs4231, Rs4084, SHC014, As6526, Yunnan 2011, Shaanxi 2011, 279-2005, Rs4237, Rs4081, Rp3, Rs4247, HKU3-8, HKU3-13, GX2013, Longquan-140, YN2013, Rf4092, ZXC21, ZC45, JL2012, HuB2013, Rf1, HeB2013, 273-2005, and BM48-31, optionally selected from SARS, SARS-2, WIV1, SHC014, Rf1, RmYNO2, pang17, RaTG13, and Rs4081.

The coronavirus antigen can be a M protein or a portion thereof comprising or consisting of an amino acid sequence having, having about, having at least, having at least about, 80%, 85%, 90%, 95%, 98%, 99% or more, sequence identity to the amino acid sequence of any of the coronavirus M proteins from one or more coronaviruses selected from SARS-CoV, SARS-CoV2, WIV1, LYRa11, Rs7327, Rs4231, Rs4084, SHC014, As6526, Yunnan 2011, Shaanxi 2011, 279-2005, Rs4237, Rs4081, Rp3, Rs4247, HKU3-8, HKU3-13, GX2013, Longquan-140, YN2013, Rf4092, ZXC21, ZC45, JL2012, HuB2013, Rf1, HeB2013, 273-2005, and BM48-31, optionally selected from SARS, SARS-2, WIV1, SHC014, Rf1, RmYNO2, pang17, RaTG13, and Rs4081.

In some embodiments, a coronavirus antigen comprises a coronavirus spike RBD or a portion or a variant thereof. The coronavirus spike RBD is known to have a three-dimensional structure of a twisted five-stranded antiparallel β sheet (e.g. β1, β2, β3, β4 and β7 in SARS-CoV-2) with short connecting helices and loops that form a core. Between two β strands (e.g. β4 and β7 strands in SARS-CoV-2) in the core, there is an extended insertion containing two short β strands (e.g. β5 and β6 in SARS-CoV-2), two α helices (e.g., α4 and α5 in SARS-CoV-2) and loops connecting the two β strands and/or the two α helices. This extended insertion is referred to as receptor binding motif (RBM), which contains residues that are capable of binding to host-cell receptors (e.g., ACE2). In the embodiments herein described, the coronavirus spike RBD, and particularly RBM, is capable of recognizing and binding to a host-cell receptor in order to initiate the spike protein-mediated viral entry. Detailed information of the coronavirus spike RBD and the host-cell receptor (e.g., ACE2) interface and related contacting residues is described, for example, in Lan et al., *Nature* volume 581, pages 215-220 (2020), the content of which is incorporated by reference it its entirety.

The coronavirus spike RBD or a portion thereof used herein can be of, or derived from, any viral species or strains in the family of Coronaviridae. The coronavirus spike RBD or a portion thereof used herein can be of any species or strains in the genus of Alpha-coronavirus. The coronavirus spike RBD or a portion thereof used herein can be of any species or strains in the genus of Beta-coronavirus. The coronavirus spike RBD or a portion thereof used herein can be of any viral species or strains in the subgenera Embecovirus (lineage A), Sarbecovirus (lineage B), Merbecovirus (lineage C), Nobecovirus (lineage D), and Hibecovirus of Beta-coronavirus.

For example, the coronavirus spike RBD protein or a portion thereof can be of any species or strains in the subgenus of Embecovirus, including but not limited to Beta-coronavirus 1 (e.g., Bovine coronavirus and human coronavirus OC43), China *Rattus* coronavirus HKU24, Human coronavirus HKUJ, Murine coronavirus (e.g., mouse hepatitis virus), and Myodes coronavirus 2JL14. The coronavirus spike RBD protein or a portion thereof can be of any viral species or strains in the subgenus of Sarbecovirus, including but not limited to SARS-CoV, SARS-CoV2, 16B0133, Bat SARS CoV Rf1, Bat coronavirus HKU3 (BtCoV HKU3), LYRa11, Bat SARS-CoV/Rp3, Bat SL-CoV YNLF_31C, Bat SL-CoV YNLF_34C, SHCO14-CoV, WIV1, WIV16, Civet SARS-CoV, Rc-o319, SL-ZXC21, SL-ZC45, Pangolin SARSr-CoV-GX, Pangolin SARSr-CoV-GD, RshSTT182, RshSTT200, RacCS203, RmYNO2, RpYN06, RaTG13, Bat CoV BtKY72, and Bat CoV BM48-31. The coronavirus spike RBD protein or a portion thereof can be of any viral species or strains in the subgenus of Merbecovirus, including but not limited to Hedgehog coronavirus 1, MERS-CoV, *Pipistrellus* bat coronavirus HKU5, and *Tylonycteris* bat coronavirus HKU4. The coronavirus spike RBD protein or a portion thereof can be of any viral species or strains in the subgenus of Nobecovirus, including but not limited to, Eidolon bat coronavirus C704, Rousettus bat coronavirus GCCDC1, and Rousettus bat coronavirus HKU9. The coronavirus spike RBD protein or a portion thereof can be of any viral species or strains in the subgenus of Hibecovirus, including but not limited to Bat Hp-beta-coronavirus Zhejiang 2013.

The coronavirus spike RBD protein or a portion thereof can be of any viral species or strain in any one of the phylogenetically clustered clades of lineage B coronavirus (Sarbecovirus). For example, the coronavirus spike RBD protein or a portion thereof can be of any species or strain in clade 1, including but not limited to SARS-CoV, WIV1, LYRa11, Rs7327, Rs4231, Rs4084, and SHC014. The coronavirus spike RBD protein or a portion thereof can be of any species or strain in clade 2, including but not limited to As6526, Yunnan 2011, Shaanxi 2011, 279-2005, Rs4237, Rs4081, Rp3, Rs4247, HKU3-8, HKU3-13, GX2013, Longquan-140, YN2013, Rf4092, ZXC21, ZC45, JL2012, HuB2013, Rf1, HeB2013, and 273-2005. The coronavirus spike RBD protein or a portion thereof can be of any species or strain in clade ½, including but not limited to SARS-CoV2. The coronavirus spike RBD protein or a portion thereof can be of any species or strain in clade 3, including but not limited to BM48-31.

In some embodiments, the coronavirus spike RBD protein or a portion thereof can be from a coronavirus selected from: SARS-CoV, SARS-CoV2, WIV1, LYRa11, Rs7327, Rs4231, Rs4084, SHC014, As6526, Yunnan 2011, Shaanxi 2011, 279-2005, Rs4237, Rs4081, Rp3, Rs4247, HKU3-8, HKU3-13, GX2013, Longquan-140, YN2013, Rf4092, ZXC21, ZC45, JL2012, HuB2013, Rf1, HeB2013, 273-2005, and BM48-31. In some embodiments, the coronavirus spike RBD protein or a portion thereof is from a coronavirus selected from SARS, SARS-2, WIV1, SHC014, Rf1, RmYNO2, pang17, RaTG13, and Rs4081.

The coronavirus (e.g., sarbecovirus) spike RBD protein or a portion or a variant thereof can, for example, comprise, or consist of, an amino acid sequence having at least 65% sequence identity to an amino acid sequence of any of the coronavirus spike protein RBDs disclosed herein (e.g., the coronavirus spike protein RBD of any one of SEQ ID Nos: 88-104). In some embodiments, the coronavirus spike protein RBD or a variant thereof comprises, or consists of, an amino acid sequence having, having about, having at least, having at least about, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, sequence identity to an amino acid sequence selected from SEQ ID Nos: 88-104. In some embodiments, the coronavirus spike protein RBD or a variant thereof comprises, or consists of, an amino acid sequence having at least, or having at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a range between any two of these values, sequence identity to an amino acid sequence selected from SEQ ID Nos: 88-104. In some embodiments, the coronavirus spike protein RBD or a variant thereof comprises, or consists of, an amino acid sequence having, having about, having at least, or having at least about, 90%, 91%, 92%, 93%, 94%, 95%, 96%, 97%, 98%, 99%, 100%, or a range between any two of these values, sequence identity to an amino acid sequence selected from SEQ ID Nos: 88-104. In some embodiments, the coronavirus spike protein RBD herein described comprises or consists of an amino acid sequence selected from any one of SEQ ID Nos: 88-104. In some embodiments, the amino acid sequence of the coronavirus spike protein RBD is selected from SEQ ID Nos: 88-104.

The coronavirus spike RBD or a variant thereof can, for example, comprise, or consist of, an amino acid sequence having, or having about, one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, or a range between any two of these values, mismatches compared to an amino acid sequence of any of the coronavirus spike RBDs disclosed herein (e.g., the coronavirus spike RBDs having an amino acid sequence of any one of SEQ ID Nos: 88-104). In some embodiments, the coronavirus spike RBD or a variant thereof comprises, or consists of, an amino acid sequence having at most, or having at most about, one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty mismatches compared to an amino acid sequence selected from SEQ ID Nos: 88-104. In some embodiments, the mismatch(es) herein described occurs in the RBM of the coronavirus spike RBD.

The sarbecovirus spike RBD or a variant thereof can, for example, comprise, or consist of, an amino acid sequence having, having about, having at most, or having at most about one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, or a range between any two of these values, deletions or insertions compared to an amino acid sequence of any of the coronavirus spike RBDs disclosed herein (e.g., the coronavirus spike RBDs having an amino acid sequence of any one of SEQ ID Nos: 88-104).

Accordingly, the coronavirus antigens in the context of the present disclosure can contain amino acid substitutions relative to the coronavirus proteins disclosed herein. Any amino acid substitution is permissible so long as the immunogenic activity of the protein is not significantly altered (e.g., at most 10%, 20%, 30%, 40% or 50% decrease relative to the coronavirus protein antigens disclosed herein) and the variants retain the desired activity. Preferred variants typically contains substitutions with one or more amino acids substituted with their functional equivalents.

In some embodiments, B cells can be isolated from a mammal immunized with a nanoparticle comprising the two or more sarbecovirus spike protein RBDs. As used herein, the term "nanoparticle" can refer to a nanoscopic particle having a size measured in nanometers (nm). Size of the nanoparticles may be characterized by their maximal dimension. The term "maximal dimension" as used herein can refer to the maximal length of a straight line segment passing through the center of a nanoparticle and terminating at the periphery. In the case of nanospheres, the maximal dimension of a nanosphere corresponds to its diameter. The term "mean maximal dimension" can refer to an average or mean maximal dimension of the nanoparticles, and may be calculated by dividing the sum of the maximal dimension of each nanoparticle by the total number of nanoparticles. Accordingly, value of maximal dimension may be calculated for nanoparticles of any shape, such as nanoparticles having a regular shape such as a sphere, a hemispherical, a cube, a prism, or a diamond, or an irregular shape. The nanoparticles provided herein can need not be spherical and can comprise, for example, a shape such as a cube, cylinder, tube, block, film, and/or sheet. In some embodiments, the maximal dimension of the nanoparticles is in the range from about 1 nm to about 5000 nm, such as between about 20 nm to about 1000 nm, about 20 nm to about 500 nm, about 50 nm to about 300 nm, or about 100 nm to about 200 nm.

The nanoparticle can be, but is not limited to, any one of lipid-based nanoparticles (nanoparticles where the majority of the material that makes up their structure are lipids, e.g., liposomes or lipid vesicles), polymeric nanoparticles, inorganic nanoparticles (e.g., magnetic, ceramic and metallic nanoparticles), surfactant-based emulsions, silica nanoparticles, virus-like particles (particles primarily made up of viral structural proteins that are not infectious or have low infectivity), peptide or protein-based particles (particles where the majority of the material that makes up their structure are peptides or proteins) and/or nanoparticles that are developed using a combination of nanomaterials such as lipid-polymer hybrid nanoparticles formed by polymer cores and lipid shells or nanolipoprotein particles formed by a membrane forming lipid arranged in a membrane lipid bilayer stabilized by a scaffold protein as will be understood by one skilled in the art.

In some embodiments, the nanoparticles described herein comprise a virus-like particle (VLP). VLP refers to a non-replicating, viral shell, derived from any of several viruses. VLPs can be naturally occurring or synthesized through the individual expression of viral structural proteins, which can then self-assemble into the virus-like structure. VLPs are generally composed of one or more viral proteins, such as particle-forming proteins referred to as capsid, coat, shell, surface and/or envelope proteins, or particle-forming polypeptides derived from these proteins. In some embodiments, VLPs can form spontaneously upon recombinant expression of the protein in an appropriate expression system. VLPs can differ in morphology, size and number of subunits. Methods for producing particular VLPs are known in the art. The presence of VLPs following recombinant expression of viral proteins can be detected using conventional techniques also known in the art, such as by electron microscopy, biophysical characterization, and the like (See e.g., Baker et al. (1991) Biophys. J. 60:1445-1456; and Hagensee et al. (1994) J. Virol. 68:4503-4505). For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions. Any of a variety of VLPs known in the art can be used herein, including but not limited to, *Aquifex aeolicus* lumazine synthase, *Thermotoga maritima* encapsulin, *Myxococcus xanthus* encapsulin, bacteriophage Qbeta virus particle, Flock House Virus (FHV) particle, ORSAY virus particle, and infectious bursal disease virus (IBDV) particle. In some embodiments, the nanoparticle used herein can be a bacteriophage VLP, such as Ap205 VLP.

In some embodiments, the nanoparticles described herein comprise a self-assembling nanoparticle. A self-assembling nanoparticle typically refers to a ball-shape protein shell with a diameter of tens of nanometers and well-defined surface geometry that is formed by identical copies of a non-viral protein capable of automatically assembling into a nanoparticle with a similar appearance to VLPs. Examples of self-assembling nanoparticles include but are not limited to ferritin (FR) (e.g., *Helicobacter pylori* ferritin), which is conserved across species and forms a 24-mer, as well as *B. stearothermophilus* dihydrolipoyl acyltransferase (E2p), *Aquifex* aeolicus lumazine synthase (LuS), and *Thermotoga maritima* encapsulin, which all form 60-mers.

In some embodiments, the self-assembling nanoparticles comprise a plurality of particle-forming proteins of 2-keto-3-deoxy-phosphogluconate (KDPG) aldolase from the Entner-Doudoroff pathway of the hyperthermophilic bacterium Theremotoga *Maritima* or a variant thereof. In some embodiments, mutations are introduced to the KDPG aldolase for improved particle yields, stability, and uniformity. For example, in some embodiments mutations can introduced to alter the interface between the wild-type protein trimer of KDPG aldolase. In some embodiments, the nanoparticle used herein is an i301 nanoparticle or a variant thereof. In some embodiments, the nanoparticle used herein is a mutated i301 nanoparticle (for example, mi3 nanoparticle). The self-assembling nanoparticles can form spontaneously upon recombinant expression of the protein in an appropriate expression system. Methods for nanoparticle production, detection, and characterization can be conducted using the same techniques developed for VLPs.

In some embodiments herein described, the nanoparticles used herein are multivalent. As opposed to a monovalent nanoparticle which presents a single species of a coronavirus antigen, a multivalent nanoparticle presents a heterologous population of immunogens, comprising at least two coronavirus antigens of or derived from different coronavirus strains or species in the family of Coronaviridae including subfamilies, genera, or subgenera described herein. Accordingly, the heterologous immunogens presented on a multivalent nanoparticle herein described have different protein sequences.

The term "present" as used herein with reference to a compound (e.g., an antigen) or functional group indicates attachment performed to maintain the chemical reactivity of the compound or functional group attached. Accordingly, a functional group presented on a nanoparticle is able to perform under the appropriate conditions the one or more chemical reactions that chemically characterize the functional group. A compound presented on a nanoparticle is able to perform under the appropriate conditions the one or more chemical reactions that chemically characterize the compound. For example, where the compound is, or comprises, a coronavirus antigen, the coronavirus antigen presented by a nanoparticle maintains the complex of reactions that are associated with the immunological activity characterizing the coronavirus antigen. Accordingly, presentation of a coronavirus antigen indicates an attachment such that the immunological activity associated to the coronavirus antigen attached is maintained.

The heterologous coronavirus antigens presented on the multivalent nanoparticle herein described can be displayed on its surface. Alternatively, the heterologous coronavirus antigens presented on the multivalent nanoparticle herein described can be partially encapsulated or embedded such that at least an immunogenic portion of the coronavirus antigen is exposed and accessible by a host cell receptor so as to induce an immune response.

Coupling of Coronavirus Antigens and Nanoparticles

The coronavirus antigens can be covalently or non-covalently attached to a nanoparticle. The terms "attach", "attached", "couple" and "coupled" are used interchangeably to refer to a chemical association of one entity (e.g., a chemical moiety) with another. The attachment can be direct or indirect such that for example where a first entity is directly bound to a second entity or where a first entity is bound to a second entity via one or more intermediate entity. In some embodiments, the C-terminus of a coronavirus antigens is attached to the N-terminus of a subunit forming the nanoparticle.

In some embodiments, the attachment or coupling is covalent such that the attachment occurs in the context of the presence of a covalent bond between two entities. In some embodiments, the attachment or coupling is mediated by non-covalent interactions including but not limited to charge interactions, affinity interactions, metal coordination, hydrophobic interactions, hydrogen bonding interactions, van der Waals interactions, magnetic interactions, electrostatic interactions, dipole-dipole interactions, or combinations thereof. In some embodiments, encapsulation is a form of attachment. In some embodiments, the plurality of coronavirus antigens are conjugated to the multivalent nanoparticle.

The nanoparticle herein described can, for example, be functionalized with a functional group or a reactive moiety that is presented for binding with a corresponding functional group or a corresponding reactive moiety of a coronavirus antigen. Accordingly, the attachment between the coronavirus antigen and the multivalent nanoparticle can occur through the binding between the functional group pair or reactive moiety pair. Exemplary functional group pairs or reactive moiety pairs include but are not limited to avidin (e.g., streptavidin, NeutrAvidin, CaptAvidin) and biotin pair, Strep-Tactin and Strep-tag pair, a thiol and a thiol-reactive moiety (e.g., maleimide, haloacetamide, iodoacetamid, benzylic halides and bromomethylketones) pair, and an amine and an amine-reactive moiety (e.g., active esters such as succinimidyl, tetrafluorophenyl, Carbodiimide, isothiocyanates, sulfonyl chlorides, dichlorotriazines, acryl halides, acyl azides).

The coronavirus antigen can be attached to the multivalent nanoparticle via chemical and/or photoreactive crosslinkers (e.g., crosslinking reagents) that contain two reactive groups, thereby providing a means of covalently linking the antigen and the nanoparticle. The reactive groups in a chemical crosslinking reagent typically belong to the classes of functional groups, including succinimidyl esters, maleimides and iodoacetamides and others identifiable to a skilled person. Additional examples of crosslinking and photoactivatable reagents are described, for example, in thermofisher.com/us/en/home/references/molecular-probes-the-handbook/crosslinking-and-photoactivatable-reagents.html, the content of which is incorporated by reference.

In some embodiments, the coronavirus antigen can be attached to the multivalent nanoparticle via a click chemistry moiety. The term "click chemistry," as used herein, can refer to a chemical philosophy introduced by K. Barry Sharpless of The Scripps Research Institute, describing chemistry tailored to generate covalent bonds quickly and reliably by joining small units comprising reactive groups together. Click chemistry does not refer to a specific reaction, but to a concept including reactions that mimic reactions found in nature. In some embodiments, click chemistry reactions are modular, wide in scope, give high chemical yields, generate non-toxic byproducts, are stereospecific, exhibit a large thermodynamic driving force >84 kJ/mol to favor a reaction with a single reaction product, and/or can be carried out under physiological conditions. In particular, click chemistry reactions that can be carried out under physiological conditions and that do not produce toxic or otherwise harmful side products are suitable for the generation of hydrogels in situ. Reactive moieties that can partake in a click chemistry reaction are well known to those of skill in the art, and include, but are not limited to alkyne and azide, alkene and tetrazole or tetrazine, or diene and dithioester. Other suitable reactive click chemistry moieties suitable for use in the context of antigen binding are known to those of skill in the art.

In some embodiments, the coronavirus antigen is attached to the multivalent nanoparticle through a Spytag/SpyCatcher binding pair. The Spytag/SpyCatcher binding pair refers to a protein ligation system that is based on the internal isopeptide bond of the CnaB2 domain of FbaB from *Streptococcus pyogenes* (see, e.g., Zakeri et al., Proc. Natl. Acad. Sci. USA. 2012; 109:E690-E697). CnaB2 is split and engineered into two complementary fragments, such that the first fragment (SpyCatcher) is able to bind and form a covalent isopeptide bond with the second fragment (SpyTag) through the side chains of a lysine in SpyCatcher and an aspartate in SpyTag. Multivalent nanoparticles presenting a plurality of coronavirus antigens can then be generated as a result of SpyTag/SpyCatcher mediated conjugation of the antigens to the nanoparticles. The SpyTag/SpyCather binding system can in some embodiments provide improved stability and specificity of the interaction between the coronavirus antigens and the particle-forming proteins of the multivalent particle.

In some embodiments, the particle-forming protein of the multivalent nanoparticle is a fusion protein containing amino acid sequences from at least two unrelated proteins that have been joined together, via peptide bond, to make a single protein. For example, the coronavirus protein antigen can be fused to a SpyTag motif and the nanoparticle subunit sequence can be fused to a SpyCatcher motif. Alternatively, the coronavirus protein antigen can be fused to a SpyCatcher motif and the subunit sequence can be fused to a SpyTag motif. The coronavirus antigen of the plurality of coronavirus antigens can comprise a SpyTag at the C-terminal of the coronavirus antigen and the particle-forming protein of a plurality of particle-forming proteins comprises a Spy-Catcher at the N-terminal of the particle-forming protein.

In some embodiments, the particle-forming protein can be a fusion protein containing a mi3 monomeric subunit protein at the C-terminal of the particle-forming protein and a SpyCatcher protein at the N-terminal of the particle-forming protein or a fusion protein containing a AP205-CP3 monomeric subunit protein at the C-terminal of the particle-forming protein and a SpyCatcher protein at the N-terminal of the particle forming protein such that the SpyCatcher proteins are presented or displayed for binding to the SpyTag of a coronavirus antigen.

In some embodiments, the coronavirus antigen of the plurality of coronavirus antigens comprises a coronavirus S protein RBD, and the coronavirus S protein RBD comprises a Spy tag at the C-terminal of the coronavirus S protein RBD and the particle-forming protein of a plurality of particle-forming proteins comprises a SpyCatcher at the N-terminal of the particle-forming protein.

In some embodiments, the nanoparticle used herein can comprise two or more coronavirus antigens derived from two or more coronaviruses, the antigens of the two or more coronaviruses being different from one another. The two or more coronavirus antigens (e.g., sarbecovirus RBDs) can comprise at least a first coronavirus antigen of a first coronavirus and a second coronavirus antigen of a second coronavirus that is different from the first coronavirus.

One coronavirus is considered being different from another coronavirus when the two coronaviruses are from different taxonomic groups, including from different strains, species, subgenera, genera, subfamilies in the Coronaviridae family. One coronavirus is also considered being different from another coronavirus when the two coronaviruses are antigenically divergent viruses. The term "antigenically divergent coronavirus" refers to a strain of coronavirus that has a tendency to mutate or has developed mutations over time, thus changing the amino acids that are displayed to the immune system. Such mutation over time can also be referred to as "antigenic drift".

In some embodiments, the at least first coronavirus and second coronavirus of the two or more coronaviruses (e.g., sarbecoviruses) are from different genera within the Coronaviridae family. In some embodiments, the at least first coronavirus and second coronavirus of the two or coronaviruses are from different subgenera within the same Coronaviridae family. In some embodiments, the at least first coronavirus and second coronavirus of the two or more coronviruses are from different species within the same Coronaviridae family. In some embodiments, the at least first coronavirus and second coronavirus of the two or more coronaviruses are different strains within the same Coronaviridae family.

The multivalent nanoparticle can comprise two or more coronavirus antigens (e.g., spike protein RBDs), comprising at least two, three, four, five, six, seven, eight or more heterologous coronavirus antigens. The number of heterologous coronavirus antigens presented by a multivalent nanoparticle can be different in different embodiments. In some embodiments, the nanoparticle herein described can present at least 2, 3, 4, 5, 6, 7, 8, 9, 10, 11, 12, 13, 14, 15, 16, 17, 18, 19, 20, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a number or a range between any two of these values, heterologous coronavirus antigens (e.g., sarbecovirus RBDs).

The total number of coronavirus antigens presented by a multivalent nanoparticle can be different in different embodiments. In some embodiments, the multivalent nanoparticle can comprise a total number of coronavirus antigens about, at least, at least about, at most, or at most about 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, or a number or a range between any two of these values.

It should be understood that in some embodiments the total number of coronavirus antigens presented by a nanoparticle is limited by the number of particle-forming subunits that make up the nanoparticle, such as the number of particle-forming lipids in lipid-based nanoparticles and the number of particle-forming proteins in protein-based nanoparticles. For example, encapsulin proteins from *Thermotoga maritima* form nanoparticles having 60-mers. Therefore, encapsulin-based nanoparticles (e.g., mi3 nanoparticle and i301 nanoparticle) can present a maximum of 60 protein antigens. In some embodiments, a particle-forming subunit of a nanoparticle can be attached with more than one coronavirus antigen.

One or more of the coronavirus antigens, or each of the two or more coronavirus antigens, can have a sequence identity of about, at least, or at least about 65%, 70%, 75%, 80%, 85%, 90%, 95%, 98%, or 99% with one another. In some embodiments, the plurality of coronavirus antigens each comprise a coronavirus S protein RBD or a portion thereof, the coronavirus S protein RBDs or portions thereof having a sequence identity of about, at least, or at least about, 65%, 70%, 75%, 80%, 85%, 90%, 95%, 98%, or 99% with one another. In some embodiments, the plurality of coronavirus antigens each comprise an amino acid sequence having at least 65%, 70%, 75%, 80%, 85%, 90%, 95%, or 98% sequence identity to an amino acid sequence selected from SEQ ID Nos: 88-104. In some embodiments, the plurality of coronavirus antigens each comprise an amino acid sequence selected from SEQ ID Nos: 88-104.

The number of attached coronavirus antigens of different coronaviruses can be the same or different. For example, the number of the first coronavirus antigens of the first coronavirus and the number of the second coronavirus antigens of the second coronavirus can be in a ratio from 1:50 to 50:1. In some embodiments, the ratio can be, be about, be at least, be at least about, be at most, be at most about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, or a number or a range between any two of the values. In some embodiments, the ratio can be, be about, be at least, be at least about, be at most, be at most about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, or a number or a range between any two of the values.

In some embodiments, the number of the coronavirus antigens of a coronavirus and the number of the coronavirus antigens of another coronavirus can be in a ratio from 1:50 to 50:1. In some embodiments, the ratio can be, be about, be at least, be at least about, be at most, be at most about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, or a number or a range between any two of the values. In some embodiments, the ratio can be, be about, be at least, be at least about, be at most, be at most about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, or a number or a range between any two of the values.

The multivalent nanoparticle herein described can induce broadly protective anti-coronavirus responses by eliciting broadly neutralizing antibodies. Broadly neutralizing antibodies are antibodies that can neutralize coronaviruses from a taxonomic group that is not only the same as but also differs from the taxonomic groups of the coronaviruses from which the coronavirus antigens used to elicit the antibodies are derived. Broadly neutralizing response can also be referred to as heterologously neutralizing response. In some embodiments, the multivalent nanoparticle herein described can elicit broadly neutralizing antibodies that neutralize one or more coronaviruses from a subfamily, genus, subgenus, species, and/or strain that differ from the subfamily, genus, subgenus, species, and/or strain of the coronaviruses from which the coronavirus antigens are derived to produce the multivalent nanoparticles.

In some embodiments, the multivalent nanoparticle comprising heterologous coronavirus antigens from a plurality of coronaviruses including a first coronavirus and a second coronavirus can induce heterologous binding and neutralizing responses against not only the first coronavirus and the second coronavirus, but also against one or more coronaviruses different from the first coronavirus and the second coronavirus (e.g., a third coronavirus, a fourth coronavirus, etc.). In particular, the multivalent nanoparticle comprising heterologous coronavirus antigens from a plurality of coronaviruses not including one or more particular coronaviruses can induce heterologous binding and neutralizing responses against the one or more particular coronaviruses.

For example, if a multivalent nanoparticle is constructed using sarbecovirus RBDs from SARS-CoV2 and SHC014-CoV, antibodies elicited by such multivalent nanoparticle are able to neutralize one or more coronaviruses of genera, subgenera, species and/or strains other than SARS-CoV2 and SHC014-CoV. As another example, a multivalent nanoparticle constructed using coronavirus antigens from SARS-CoV-2, WIV1, Rf1, RmYN02, pang17, RaTG13, SHC014, and Rs4081 can elicit heterologous binding and neutralizing responses against not only SARS-CoV-2, WIV1, Rf1, RmYN02, pang17, RaTG13, SHC014, and Rs4081 but also other coronaviruses such as SARS-CoV, Yun 11, BM-4831 and BtKY72 (see, for example, FIG. 2A-FIG. 2B).

In some embodiments, the multivalent nanoparticle comprising heterologous (e.g., different) coronavirus antigens from two or more different coronaviruses including a first coronavirus and a second coronavirus can induce about the same or comparable magnitude (e.g., about, at least, at least about 80%, 85%, 90%, 95%, 100%, 105%, 110%, 115%, 120%, 125%, 130%, 140%, 150%, or a number or a range between any two of these values, relative to one another) of immune response against the first coronavirus and/or the second coronavirus when compared to a monovalent nanoparticle (also referred to as a "homotypic nanoparticle") comprising a homologous population of a single coronavirus antigen from the first coronavirus or the second coronavirus. In other words, co-display of coronavirus antigens from coronaviruses of different taxonomic groups does not diminish the immune response against a coronavirus (e.g., SARS-CoV-2) relative to homotypic nanoparticles presenting antigens from the coronavirus (e.g., homotypic SARS-CoV2 nanoparticle). In a non-limiting example, in terms of the magnitude of immune response against SARS-CoV-2, it can be advantageous for conducting immunization with a mosaic nanoparticle that includes SARS-CoV-2 protein antigen as well as other coronavirus protein antigens versus a homotypic SARS-CoV-2 nanoparticle (see e.g., FIG. 2B).

The multivalent nanoparticle comprising different coronavirus antigens from two or more coronaviruses (e.g. sarbecoviruses) including a first coronavirus and a second coronavirus can induce an increased magnitude of immune response against the first coronavirus and/or the second coronavirus when compared to a monovalent nanoparticle comprising a homologous population of a single coronavirus antigen from the first coronavirus or the second coronavirus. The magnitude of immune response induced by the multivalent nanoparticle can be about, at least, or at least about 0.2, 0.5, 0.9, 1.1, 1.5, 1.7, 2, 3, 4, 5, 6, 7, 8, 9, 10, fold(s), or a number or a range between any of these values, greater than by the monovalent nanoparticle. In some embodiments, the magnitude of immune response induced by the multivalent nanoparticle can be increased by about, at least, or at least about 5%, 10%, 20%, 30%, 50%, 75%, 100%, 110%, 120%, 150%, 200%, 250%, 300%, 400%, 500%, 600%, 700%, 800%, 900%, 1000%, or a number or a range between any of these values, as compared to that by the monovalent nanoparticle.

In some embodiments, the multivalent nanoparticle does not present a coronavirus antigen from a particular coronavirus, but can still produce broadly neutralizing antibodies against that particular coronavirus, for example, at a comparable or even enhanced magnitude as compared to a monovalent nanoparticle presenting coronavirus antigens from that particular coronavirus. For example, the multivalent nanoparticle comprising two or more different coronavirus antigens not including a first coronavirus can induce about the same or comparable magnitude (e.g., about, at least, at least about 80%, 85%, 90%, 95%, 100%, 105%, 110%, 115%, 120%, 125%, 130%, 140%, 150%, or a number or a range between any of these values, relative to one another) of immune response against the first coronavirus when compared to a monovalent nanoparticle comprising a homologous population of a single coronavirus antigen from the first coronavirus.

In some embodiments, the multivalent nanoparticle comprising two or more different coronavirus antigens from a plurality of coronaviruses not including a first coronavirus can elicit an enhanced heterologous binding and neutralizing response against the first coronavirus when compared to a monovalent nanoparticle comprising a homologous population of a single coronavirus antigen from a second coronavirus. The first and second coronaviruses are different from one another. The magnitude of neutralizing response induced by the multivalent nanoparticle can be about, at least, or at least about 0.2, 0.5, 0.9, 1.1, 1.5, 1.7, 2, 3, 4, 5, 6, 7, 8, 9, 10 fold, or a number or a range between any of these values, greater than by the monovalent nanoparticle. In some embodiments, the magnitude of immune response induced by the multivalent nanoparticle can be increased by about, at least, or at least about 5%, 10%, 20%, 30%, 50%, 75%, 100%, 110%, 120%, 150%, 200%, 250%, 300%, 400%, 500%, 600%, 700%, 800%, 900%, 1000%, or a number or a range between any of these values, as compared to that by the monovalent nanoparticle.

In some embodiments, the multivalent nanoparticle comprising two or more different coronavirus antigens including a first coronavirus and a second coronavirus can elicit a substantially enhanced neutralizing response against the first coronavirus and/or the second coronavirus when compared to a soluble coronavirus antigen from the first coronavirus or the second coronavirus. The magnitude of neutralizing response induced by the multivalent nanoparticle can be about, at least, or at least about 1, 2, 3, 4, 5, 6, 7, 8, 9, 10, 50, 100, 200, 300, 400, 500, 600, 700, 800, 900, 1000 fold, or a number or a range between any of these values, greater than by the soluble coronavirus antigen.

The multivalent nanoparticles herein described can be prepared using any standard molecular biology procedures known to the person skilled in the art as well as the protocols exemplified herein (see e.g., Example 2 and US20220168414A1). In some embodiments, particle-forming subunits and/or the coronavirus protein antigens can be produced by liquid-phase or solid-phase chemical protein synthetic methods known in the art.

Production of the particle-forming subunits and/or the coronavirus protein antigens can use recombinant DNA technology well known in the art. For example, a tagged coronavirus protein antigen or a coronavirus protein antigen functionalized with a protein tag can be synthesized using biosynthetic methods such as cell-based or cell-free methods known to the person skilled in the art. A tagged coronavirus protein antigen can be produced using an expression vector comprising a nucleic acid molecule encoding the coronavirus protein antigen. The nucleic acid molecule can be operably linked to appropriate regulatory elements including, but not limited to, a promoter, enhancer, transcription initiation site, termination site, and translation initiation site.

The vector can also comprise a nucleic acid molecule encoding one or more protein tags (e.g., a poly(His) tag, SpyTag). In some embodiments, the vector can additionally include a nucleic acid molecule encoding a trimerization motif (e.g., a foldon trimerization domain from T4 fibritin or viral capsid protein SHP). The vector can also comprise a nucleic acid molecule encoding a signal peptide that directs the protein into the proper cellular pathway, such as a signal peptide for secretion of the expressed protein into supernatant medium. The vector may comprise one or more selectable marker genes such as gene providing ampicillin resistance or kanamycin resistance. Methods for the construction of nucleic acid constructs are well known. See, for example, *Molecular Cloning: a Laboratory Manual*, 3$^{rd}$ edition, Sambrook et al. 2001 Cold Spring Harbor Laboratory Press, and *Current Protocols in Molecular Biology*, Ausubel et al. eds., John Wiley & Sons, 1994. Protein biosynthesis of tagged coronavirus protein antigens can be performed by providing cell-based or cell-free protein translation systems with the expression vectors encoding the tagged coronavirus protein antigens. Similarly, a tagged particle-forming protein can be produced using an expression vector comprising a nucleic acid molecule encoding a particle-forming subunit and a nucleic acid molecule encoding a protein tag (e.g., SpyCatcher). In an exemplary embodiment, the multivalent nanoparticles are produced following the protocols described in Cohen A A et al, 2021, PloS ONE 16(3): e0247963, the content of which is incorporated herein by reference.

In some embodiments, constructs expressing the nanoparticle subunit and the coronavirus antigens can be introduced together into a host or transformation-competent cell. Multivalent nanoparticles can be generated as a result of conjugation of the expressed coronavirus antigens to the self-assembled nanoparticles through a functional group pair or a reactive moiety pair described herein (e.g., SpyTag/SpyCatcher).

Nanoparticles (e.g., nanoparticles with SpyCatcher) and coronavirus antigens (e.g., SpyTagged protein antigens) can, for example, be prepared separately and then incubated under a condition (e.g., in a TBS buffer at room temperature) for a certain time period (e.g., about, at least, or at least about 1 hour, 2 hours, 5 hours, 10 hours, 12 hours, 15 hours) to allow for the conjugation of the nanoparticles and the coronavirus antigens. In some embodiments, the coronavirus protein antigens are provided in an excess amount as compared to the particle-forming subunits of the nanoparticles, such as 1-fold, 2-fold, 3-fold, 4-fold, 5-fold or greater than the particle-forming subunits.

Following, e.g., immunization, CD138+ plasma B cells can be isolated from the immunized mammal using any method known in the art. This can include, e.g., column purification, fluorescence activated cells sorting (FACS) and the like. The method can comprise screening B cells (e.g., derived from mouse spleen) for secretion of an antibody or fragment thereof that specifically binds to one or more sarbecovirus spike protein RBDs, wherein the one or more sarbecovirus spike protein RBDs are selected from a SARS-CoV-2 RBD and variants thereof, RsSTT200 RBD and variants thereof, Pang17 RBD and variants thereof, RaTG13 RBD and variants thereof, SARS-CoV RBD and variants thereof, WIV1 RBD and variants thereof, SHC014 RBD and variants thereof, LyRa3 RBD and variants thereof, C028 RBD and variants thereof, Rs4081 RBD and variants thereof, RmYNO2 RBD and variants thereof, Rfl RBD and variants thereof, Yun11 RBD and variants thereof, BM4831 RBD and variants thereof, BtKY72 RBD and variants thereof, and Khosta2 RBD and variants thereof.

Binding can be assessed by any method known in the art. In some embodiments, an EC50 value is measured. The binding can be assessed by an optofluidic assay, an ELISA assay, or both. As described herein, the optofluidic technology can comprise distributing cells within a sample into individual compartments using microfluidic devices, and detecting a signal associated with the subset of cells with the property of interest. The optofluidic system can be, for example, the Berkeley Light Beacon® Optofluidic System. In some embodiments, the antibody or fragment thereof binds to the one or more sarbecovirus spike protein RBDs with an EC50 of less than 10 µg/mL, less than 1 µg/mL, less than 0.1 µg/mL, or less than 0.01 µg/mL. In some embodiments, the antibody or fragment thereof binds to the one or more sarbecovirus spike protein RBDs with an EC50 of about 0.001 µg/mL to about 10 µg/mL (e.g., 0.001, 0.005, 0.01, 0.05, 0.1, 0.5, 1, 1.5, 2, 3, 4, 5, 6, 7, 8, 9, 10 µg/mL or a number or a range between any two of these values), about 0.001 µg/mL to about 1 µg/mL (e.g., 0.001, 0.005, 0.01, 0.05, 0.1, 0.5, 1 µg/mL or a number or a range between any two of these values), about 0.001 µg/mL to about 0.1 µg/mL (e.g., 0.001, 0.005, 0.01, 0.05, 0.1 µg/mL or a number or a range between any two of these values), or about 0.001 µg/mL to about 0.01 µg/mL (e.g., 0.001, 0.005, 0.01 µg/mL or a number or a range between any two of these values).

Also disclosed herein include antibodies or fragments thereof produced and/or identified by any of the methods provided herein.

EXAMPLES

Some aspects of the embodiments discussed above are disclosed in further detail in the following examples, which are not in any way intended to limit the scope of the present disclosure.

Example 1

Antibodies and Methods to Treat SARS Coronavirus Infections

Mice were immunized with Mosaic-8, a nanoparticle comprising SARS coronavirus receptor binding domains from SARS-CoV-2, SHC014, RaTG13, Rs4081, WIV1, Rfl, RmYNO2, and pang 17. Briefly, ten B6 mice received Mosaic-8a at week 0 and week 4, and ten B6 mice received SARS-CoV-2 receptor binding domain (RBD) at week 0 and week 4. Mosaic-8a and the process for immunizing mice are described in detail in US2022/0168414 which is hereby incorporated by reference in its entirety.

Spleens were collected from two mice per each immunogen (i.e., two mice immunized with Mosaic-8 and two mice immunized with SARS-CoV-2 RBD). CD138 positive plasma B cells were isolated using CD138 positive plasma cell isolation kit, mouse (Miltenyi Biotec). Cells were loaded on the 11k chip and individual cells were penned into each well through the light technology on BEACON® (Berkeley Lights). After incubating cells for 30 minutes in the culture media on the chip, the assay bead was loaded with the detecting antibody onto the chip.

Assay was run for 45 minutes by capturing the fluorescent images every 4 minutes. Pens underneath a fluorescent booming and with a single cell were selected. Individual cells from the selected pens were unloaded and exported from the chip for gene recovery and sequencing analysis. For antibody generation from mice immunized with Mosaic-8a, four different assays were performed sequentially on the sample chip with four different RBDs (i.e., SARS-CoV-2 RBD, SARS-CoV-1 RBD, Yun11 RBD, and BtKY72 RBD) in order to screen the cross-reactive antibodies. VH and VL was amplified with cDNA synthesized from extracted mRNA of exported individual cells, and sequencing was done by Sanger sequencing. The results are shown in Table 9.

TABLE 9

ANTIBODIES ISOLATED BY OPTOFLUIDIC SCREENING

| | | | Positive to | | | |
|---|---|---|---|---|---|---|
| ID | VH SEQ ID NO: | VL SEQ ID NO: | SARS-CoV-2 | SARS-CoV-1 | Yunll | BtKY72 |
| SRl | 41 | 42 | X | X | X | X |
| SR2 | 43 | 44 | X | X | X | X |
| SR3 | — | 45 | X | X | X | X |
| 8a-3 | 1 | 2 | X | X | X | X |
| 8a-4 | 3 | — | | X | | |
| 8a-6 | 4 | 5 | X | | X | |
| 8a-7 | 6 | 7 | | X | | |
| 8a-9 | 8 | 9 | | | X | |
| 8a-10 | — | 10 | | X | | |
| 8a-11 | 11 | 12 | | | X | |
| 8a-14 | 13 | — | | | X | |
| 8a-15 | 14 | 15 | | | X | |
| 8a-16 | 16 | — | | | X | |
| 8a-17 | 17 | — | | | X | |
| 8a-18 | 18 | — | X | | | |
| 8a-19 | 19 | — | X | | | |
| 8a-20 | — | 20 | X | | | |
| 8a-21 | 21 | — | | X | | |
| 8a-22 | — | 22 | X | X | X | X |
| 8a-24 | — | 23 | | | X | |
| 8a-25 | 24 | 25 | | X | | |
| 8a-26 | 11 | 12 | | | X | |
| 8a-27 | — | 26 | | | X | |
| 8a-28 | 27 | 28 | X | X | | |
| 8a-29 | 29 | 30 | | | X | |
| 8a-30 | 31 | 32 | | | X | |
| 8a-31 | 33 | 34 | | X | X | |
| 8a-34 | 35 | 36 | X | X | X | |
| 8a-35 | 37 | — | | X | | |
| 8a-36 | 38 | 39 | X | | | X |
| 8a-40 | — | 40 | X | | X | |

"VH" is variable heavy chain domain, "VL" is variable light chain domain, and the dashed lines "—" indicate not determined.

Example 2

Figure 9A:
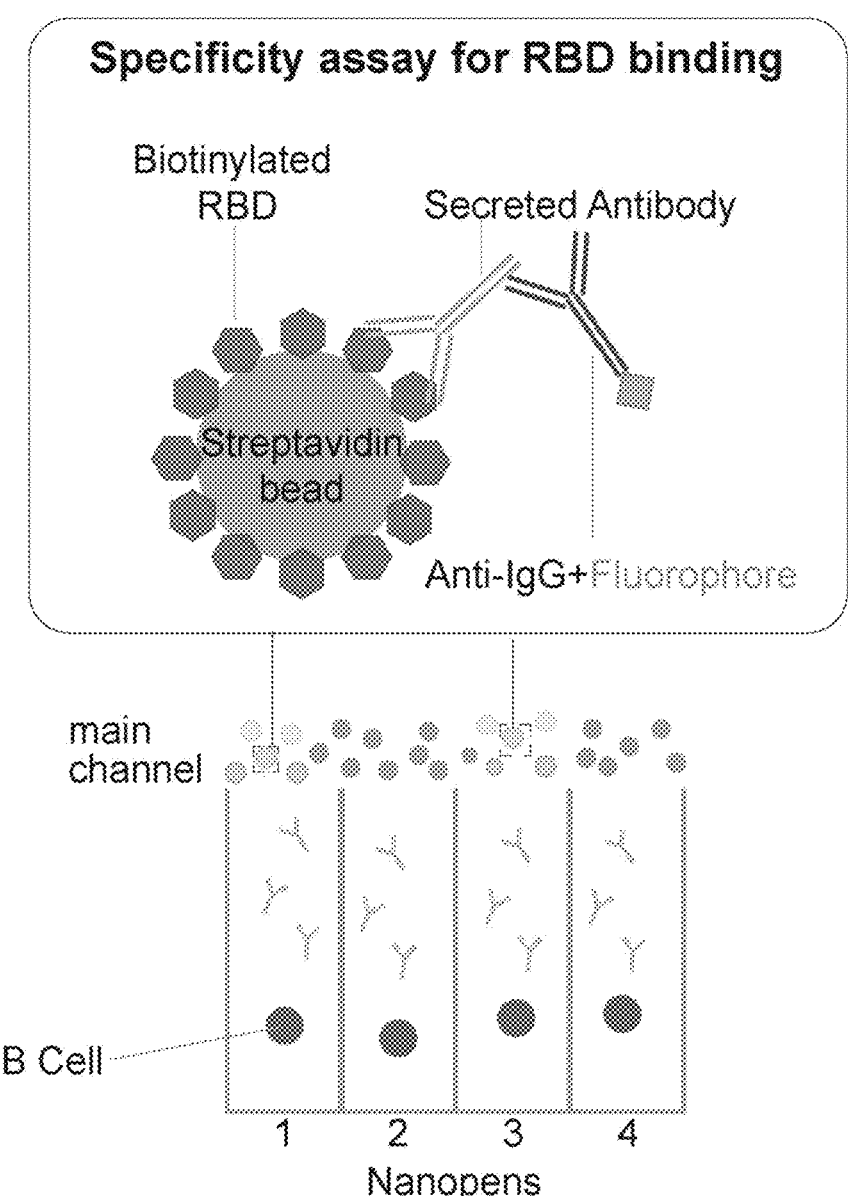
FIG. 9A-FIG. 9B show data related to the beacon setup. Individual plasma cells were isolated, cultured, and assayed for RBD binding activities using the Beacon optofluidic system.
Figure 9B:
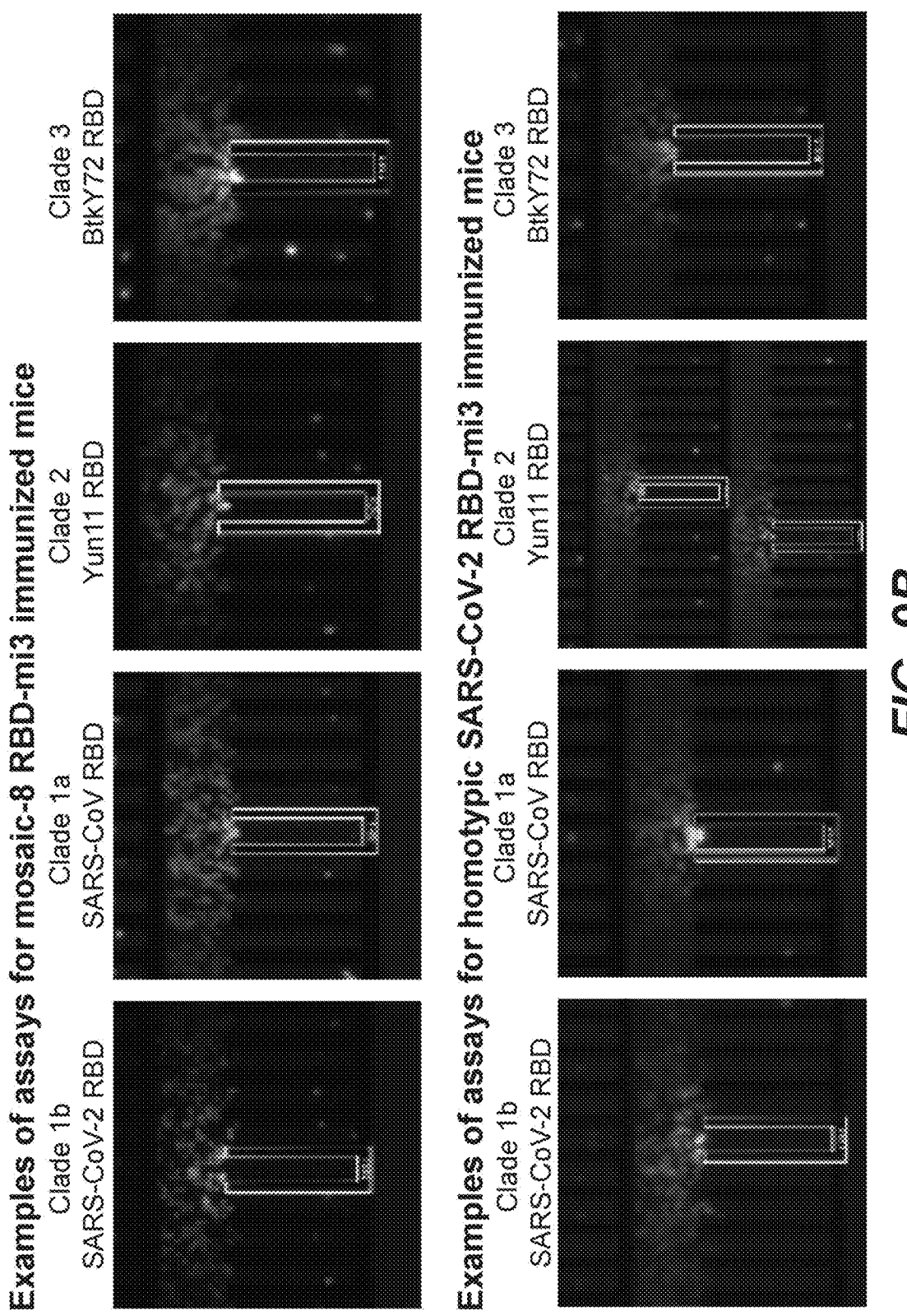

Neutralizing Monoclonal Antibodies Elicited by Mosaic RBD Nanoparticles Bind Conserved Sarbecovirus Epitopes The Majority of Mosaic-8 Elicited Mouse mAbs Identified as Binding Two or More RBDs are Cross-Neutralizing Multimerized RBD-nanoparticles were made using the SpyCatcher-SpyTag system to covalently attach RBDs with C-terminal SpyTag003 sequences to a 60-mer nanoparticle (SpyCatcher003-mi3). Nanoparticles presenting randomly arranged RBDs from SARS-CoV-2 and seven animal sarbecovirus spikes (mosaic-8 RBD-mi3) as well as nanoparticles presenting only SARS-CoV-2 RBDs (homotypic SARS-CoV-2 RBD-mi3) were produced and characterized (FIG. 7A-FIG. 7E). Mice were primed and boosted with either mosaic-8 or homotypic SARS-CoV-2 RBD-nanoparticles in AddaVax adjuvant. A Berkeley Lights Beacon Optofluidic system was used to screen a subset of B cells for binding to one or more labeled RBDs (FIG. 9A-FIG. 9B3, Table 5-Table 7).

65

TABLE 5

MOSAIC-8 RBD-MI3 IMMUNIZED MICE ASSAY RESULTS

| Among positive pens with single cell | SARS-2 RBD | SARS-RBD | Yun11-RBD | BtKY72-RBD | Total |
|---|---|---|---|---|---|
| SARS-2 RBD | | 9 | 9 | 6 | 18 |
| SARS-RBD | 9 | | 7 | 7 | 20 |
| Yun11-RBD | 9 | 7 | | 5 | 24 |
| BtKY72-RBD | 6 | 7 | 5 | | 9 |

TABLE 6

HOMOTYPIC SARS-COV2 RBD-MI3 IMMUNIZED MICE ASSAY RESULTS

| Among positive pens with single cell | SARS-2 RBD | SARS-RBD | Yun11-RBD | BtKY72-RBD | Total |
|---|---|---|---|---|---|
| SARS-2 RBD | | 11 | 12 | 9 | 130 |
| SARS-RBD | 11 | | 7 | 14 | 47 |
| Yun11-RBD | 12 | 7 | | 17 | 39 |
| BtKY72-RBD | 9 | 14 | 17 | | 36 |

TABLE 7

SUMMARY OF BEACON RESULTS

| | Immunization | |
|---|---|---|
| Assay Outcome | Homotypic SARS-CoV-2 RBD-mi3 immunized mice | Mosaic-8 RBD-mi3 immunized mice |
| Positive for all 4 RBDs | 3 | 5 |
| Positive for 3 RBDs (negative for SARS-1 RBD) | 3 | 0 |

66

TABLE 7-continued

SUMMARY OF BEACON RESULTS

| | Immunization | |
|---|---|---|
| Assay Outcome | Homotypic SARS-CoV-2 RBD-mi3 immunized mice | Mosaic-8 RBD-mi3 immunized mice |
| Positive for 3 RBDs (negative for Yun11-RBD) | 3 | 2 |
| Positive for 3 RBDs (negative for BtKY72-RBD) | 1 | 1 |
| Positive for 3 RBDs (negative for SARS-2-RBD) | 2 | 0 |

Figure 2A:
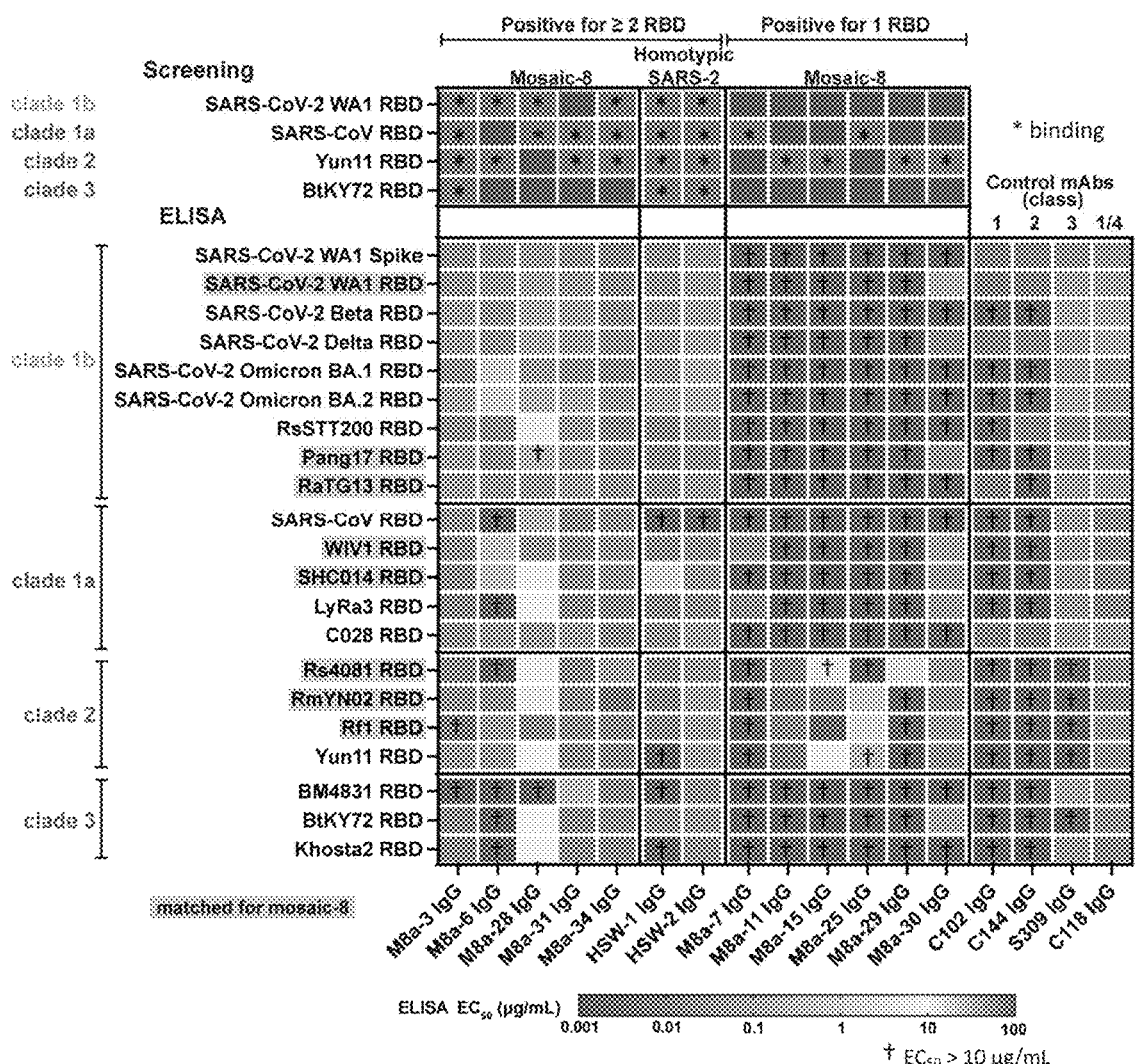

B cells secreting IgGs that bound to at least one RBD were exported from the instrument, and the variable domains of heavy and light chain genes were sequenced and subcloned into expression vectors containing genes encoding human IgG $C_H1$-$C_H2$-$C_H3$ domains, human $C_H1$, or human $C_L$ domains. From 39 exported cells, genes for 15 RBD-binding mAbs were isolated (Table 1) that were expressed as IgGs and corresponding Fabs. The 15 unique IgG sequences included 13 that were derived from mosaic-8 immunized mice and identified during the screen as binding to two or more labeled RBDs (six mAbs) or to one labeled RBD (seven mAbs), and two were derived from homotypic RBD-nanoparticle immunized mice and identified as binding to two or more labeled RBD (FIG. 2A, Table 1). Two mAbs from mosaic-8 immunized mice were excluded from analyses after showing no detectable binding to purified RBDs (Table 1).

TABLE 1

SEQUENCES AND V GENE SEGMENT LINEAGES FOR 15 MABS IDENTIFIED AS BINDING AT LEAST ONE RBD DURING SCREENING

| mAbs | $V_H$ (sequences) | SEQ ID NO | $V_L$ (sequences) | SEQ ID NO | Lineages |
|---|---|---|---|---|---|
| M8a-3 | QVQLQQPGAELVLPGA SVKLSCKASGYTFTNY WMHWVKQRPGHGLEWI GEIDPFDTYIKINQKF KGKSTLTVDTSSSTAY MQLSSLTSEDSAVYYC ARPDSSGYPVYFDYWG QGTTLTVSS | 1 | DIVMTQSHKFMSTSVGDRVSITCKA SQDVGTYIAWYQQKPGQSPKLLIYW ASTRHTGVPDRFTGSGSGTNYTLTI SSVQAEDLALYHCQQHYSTPYTFGG GTKLEIK | 2 | IgHV1-69 IgκV6-25 |
| M8a-6 | QVQLQQPGTELVMPGA SVKLSCKTSGYTFTHY WMHWVKQRPGEGLEWI GEIAPSDNYVKYNQKF KGKSTLSVDRSSSTAY MQLSSLTSEDSAVYFC ARPDNSGYPVYFDYWG QGTSLTVSS | 4 | DIVMTQSQKFMSTSLGDRVSISCKA SQDVGTTVAWYQQKPGQSPKLLIYW ASTRHTGVPDRFTGTGSGTDYTLTI SSVAAEDLALYYCQQHYNTPYTFGG GTKLEIE | 5 | IgHV1-69 IgκV6-25 |
| M8a-7 | QAYLQQSGAEMVRPGA SVKMSCKASGYTFNNY NMHWVKQTPSQGLEWI GGFYPGNDDTAYSQKF KGKATLTVDKSSSTAF MHLSSLTSEDSAVYFC ARSLGRYYAMDYWGQG TSVTVSS | 6 | DIVLTQSPASLAVSLGQRATISCRA SESVDDFGISYMNWFQQKPGQTPKL LIYGASNQGSGVPARFSGSGSGTDF SLNIHPMEEDDPAMYFCQQSKEVPY TFGGGTKLEIK | 7 | IgHV1-12 IgκV3-2 |

TABLE 1-continued

SEQUENCES AND V GENE SEGMENT LINEAGES FOR 15 MABS IDENTIFIED
AS BINDING AT LEAST ONE RBD DURING SCREENING

| mAbs | V_H (sequences) | SEQ ID NO | V_L (sequences) | SEQ ID NO | Lineages |
|---|---|---|---|---|---|
| M8a-9 | QVQLQQPGAELVRPGS SVKLSCKASGYTFTSY WIHWVRQRPIEGPEWI GMIDPSDSGNHFNQNF KDKATWTVDKSSNTAY MQLSSLTTEDSAVYYC ARGSGSTYRGYFDYWG HGTTLTVSS | 8 | DIQMTQSSSYLSVSLGGRVTITCKA SDHINNWLAWYQQKPGNTPRLLISG ATNLETGVPSRFSGSGSGKDYTLSI TSLQTEDVATYYCQQYWSSPLTFGA GTKLELK | 9 | IgHV1-52 IgκV13-85 |
| M8a-11 | EVQLQQSGPELVKPGA SVKIPCKASGYTFTDY NMDWVKQSHEKSLEWI GEIDPNNGDTIYNQKF KGKASLTVDKSSSTAY MELRSLTSEDTAVYYC AKRGYYGSSLWWYFDV WGTGTTVTVSS | 11 | DIQMTQSSSSFSVSLGDRVTITCKA SEDIYIRLAWYQQRPGNAPRLLISN AISLETGVPSRFSGSGSGKDYTLSI TSLQTEDVATYYCQQYWSTPWTFGG GTKLEIK | 12 | IgHV1-18 IgκV13-84 |
| M8a-15 | QVQLQQSGPELARPGA SVKLSCRASGYTVTSF GLSWMKQRTGQGLEWI GETYPTSKNTYYNDKF RTKATLTADKSSSTAY MELRSLTSEDSAVYFC VLYDYFDYWGQGTTLT VSS | 14 | QIVLTQSPAIMSASPGEKVTISCSA SSSVSYMYWYQQKTGSSPKPWIYRT SNLASGVPVRFSGSGSGTSYSLTIS SMEAEDAATYYCQQYQSYPRTFGGG TKLEIK | 15 | IgHV1-81 IgκV4-61 |
| M8a-25 | EVQLQQSVAELVRPGA SVKLSCTASGFNIKNT YMHWVKQRPEQGLEWI GRIDPSIDHTRYAPKF QGKAVITAFTSSNTAY LQLSSLTSEDTAIYYC AREGGGNYPYYYAIDY WGQGTSVTVSS | 24 | DIQMTQSSSSFSVSLGDRVTITCKA SEDIYIRLAWYQQRPGNAPRLLISN AISLETGVPSRFSGSGFGKDHTLSI TSLQTEDVATYYCQQYWSTPWTFGG GTKLEIK | 25 | IgHV14-3 IgκV13-84 |
| M8a-28 | QVQLQQPGAELVKPGA SVKMSCKASGYNFNHY WISWVKQRPGQGLEWI GDIYPLSHFTTYNEKF TNRATLTVDTSSTTAY MQLNSLTSDDSAVFYC ARWDYFDSRTFDYWGQ GTTLTVSS | 27 | DILLTQFPAILSVSPGERVSFSCRA SQTIGTNIHWYQQRINGSPRLLIKY ASESISGIPSRFSGSGSGTDFSLSI NNVESEDIADYYCQQINSWPLTFGA GTKLDLK | 28 | IgHV1-55 IgκV5-48 |
| M8a-29 | EVQLQQSVAELVRPGA SVKLSCTASGFNIKNT YMHWVKQRPEQGLEWI GRIDPSIDHTRYAPKF QGKAVITAFTSSNTAY LQLSSLTSEDTAIYYC AREGGGNYPYYYAIDY WGQGTSVTVSS | 29 | DIVMTQAAFSNPVTLGTSASISCRS TKSLLHSNGITYLYWYLQKPGQSPQ LLIYQMSNLASGVPDRFSSSGSGTD FTLRISRVEAEDVGVYYCAQNLELP YTFGGGTKLEIK | 30 | IgHV14-3 IgκV2-109 |
| M8a-30 | QVHLQQSGPELVKPGA SVKISCKASGYGFSSS WMNWVKQRPGKGLEWI GRIYPGDGDTNYNDKF QGKATLTADRSSSTAY MHLTSLTSADSAVYFC ARSLLYSFDYWGQGTT LTVSS | 31 | DVVVTQTPLSLPVSFGDQVSISCRS SQSLAGSYGHTYLSWYLHKSGQSPQ LLIYGISNRFSGVPDRFSGSGSGTD FTLKISTIKPEDLGMYYCLQGTHQP LTFGAGTKLELK | 32 | IgHV1-82 IgκV1-88 |
| M8a-31 | EVQLKQSVAELVRPGA SVKVSCTASGFNIKNI YMHWVKQRPEQGLDWI GRIDPANGNSRYAPKF QDKATITADTSSNTAY LQLSSLTSEDTAIYYC ADEGWGFANWGQGTLV TVSA | 33 | DIVMTQSPSSLTVTAGEKVTMSCKS SQSLLNSGNQKNYLTWYQQKVGQPP KLLIYWASTRDPGVPDRFTGSGFGT DFTLTISSVQAEDLAVYYCQNDYSY PLTFGAGTKVELK | 34 | IgHV14-3 IgκV8-19 |

TABLE 1-continued

| | | | | | |
|---|---|---|---|---|---|
| | | SEQUENCES AND V GENE SEGMENT LINEAGES FOR 15 MABS IDENTIFIED AS BINDING AT LEAST ONE RBD DURING SCREENING | | | |
| mAbs | V$_H$ (sequences) | SEQ ID NO | V$_L$ (sequences) | SEQ ID NO | Lineages |
| M8a-34 | QVQLQQPGAELVKPGA SVKMSCKASGYTFITY WITWVKQRPGQGLEWI GDIYPGGGRTNYNEKF KSKATLTVDTSSSTAY MQLRSLTSEDSAVYYC ARYDGNYVGYYYAMDY WGQGTSVTVSS | 35 | DIVLTQSPVSLAVSLGQRATISCRA SESVDFYGNSFIYWYQQKPGQAPKL LIYRASNLESGIPARFSGSGSRTDF TLTIHPVEADDVATYYCQQSIEDPR TFGGGTKLEIK | 36 | IgHV1-55 IgκV3-5 |
| M8a-36 | QVQLQQTGAELVKPGA SVKMSCKASGYTFTSY WIIWVKKRPGQGLEWI GDIYPGSGSTNYNEKF KSKATLTVDTSSSTAY MQLSSLTSEDSAVYYC TRGGSRFAMDYWGQGT SVTVSS | 38 | DIVMTQAAPSVPVTPGESVSISCRS SKSLLHSNGNTYLYWFLQRPGQSPQ LLIYRMSNLASGVPDRFSGSGSGTA FTLRISRVEAEDVGVYYCMQHLEYP YTFGGGTKLEIK | 39 | IgHV1-55 IgκV2-137 |
| HSW-1 | QVQLQQPGAELVKPGT SMKLSCKASGYTFTSY WMHWVKQRPGQGLEWI GMIHPNSGSTKYNENF KSKATLTVDKSSSTAY MQFSSLTSEDSAVYYC VRSGSYYGTTYDYFDY WGQGTTLTVSS | 41 | DIVLTQSPASLAVSLGQRATISCRA SESVNIYGNSFMHWYQQKPGQPPKL LIFRASNLESGIPVRFSGSGSRTDF TLTINPVEADDVATYYCHQSNEDPF TFGSGTKLEIK | 142 | IgHV1-64 IgκV3-5 |
| HSW-2 | QVQLQQSGPELVKPGA SVKISCKASGYVESTS WMSWVKQRPGEGPEWI GRIYPRDGHSSSTGKF KDKATLTADKSSNTAY IHLSSLTSEDSAVYFC ARDYGYYYFDYWGQGT TLTVSS | 43 | DIQMTQSPASLSASVGEAVTITCRL SENVYSFLAWYQQKQGKSPQLLVYR AKTLAEGVPSRFSGSGSGTQFSLKI NSLQPEDFGTYYCQHHYGTPPTFGG GTKLEIK | 44 | IgHV1-82 IgκV12-44 |

M8a-9 and M8a-36 did not exhibit binding to purified RBDs by ELISA (data not shown). M8a-11 and M8a-26 are identical sequences.

Binding of the 13 purified mAb IgGs to RBDs from SARS-CoV-2 variants and other sarbecoviruses was first evaluated using enzyme-linked immunosorbent assays (ELISAs). RBDs were included from sarbecovirus clades 1a, 1b, 2, and 3 (FIG. 2A). The mAb binding profiles were compared to four human anti-RBD IgGs with known epitopes: C118, a broadly cross-reactive class ¼ mAb isolated from a convalescent COVID-19 donor, 5309 (Sotrovimab), a cross-reactive class 3 mAb isolated from a SARS-CoV-infected donor, and mAbs isolated from COVID-19 donors that bind to more variable RBD epitopes overlapping with the ACE2-binding footprint: C102 (class 1) and C144 (class 2) (FIG. 2A). Of the seven mAbs isolated from B cells from vaccinated mice that were identified during screening as secreting IgGs that bound to more than one RBD (FIG. 2A), five were isolated from mosaic-8 RBD-nanoparticle-immunized mice (names with M8a prefixes), and two were isolated from homotypic RBD-nanoparticle-immunized mice (names with HSW prefixes). These seven mAbs showed binding to SARS-CoV-2 spike trimer and SARS-CoV-2 RBDs including Beta, Delta, and Omicrons BA.1 and BA.2 in addition to the SARS-CoV-2 WA1 variant included in the mosaic-8 RBD nanoparticles. These seven mAbs also showed cross-reactive binding to animal sarbecovirus RBDs (FIG. 2A). The half maximal effective concentrations (EC$_{50}$ values) for binding of these mAbs to most of the RBDs ranged from 1 to 10,000 ng/mL (FIG. 2A). By comparison, six mAbs isolated from B cells that secreted IgGs that bound only one RBD during screening recognized a smaller subset of RBDs evaluated in the ELISA panel, and none bound to SARS-CoV-2 spike (FIG. 2A). These mAbs can be useful for detecting whether particular RBDs are present on a mosaic RBD-nanoparticle: for example, M8a-7 and M8a-29 can be used to detect WIV1 or Rs4081, respectively, on mosaic-8 RBD-nanoparticles. The seven mAbs that were isolated from B cells secreting IgGs that bound to two or more RBDs during screening were analyzed further (FIG. 2A).

The five M8a IgGs and two HSW IgGs that showed cross-reactive RBD binding during screening and by ELISA shared amino acid sequence identities of ~50% to 90% in their V$_H$ and V$_L$ domains (FIG. 10A-FIG. 10B) and had varied lengths for their complementarity-determining regions 3 (CDR3s), which are often critical in antigen recognition. The mAb CDR3s ranged from 9-16 residues for the heavy chain CDR3 (CDRH3) and all were 9 residues for the light chain CDR3 (CDRL3) (Table 8, Table 10), compared with 11 (IgH) and 9 (Igk) for average C57Bl/6 mouse antibody CDR3s. The CDRH1, CDRH2, and CDRL2 regions were the same lengths across the seven mAbs, whereas the CDRL1 ranged from 6-12 residues (FIG. 10A-FIG. 10B, Table 8). M8a-34 and HSW-1 both had long (16 residues) CDRH3s, and M8a-31 had the shortest (9 residues) CDRH3. By contrast to its shorter than average CDRH3, M8a-31 had the longest CDRL1 (12 residues) compared with M8a-3, M8a-6, M8a-28, and HSW-2, which all included six-residue CDRL1s (Table 8). M8a-3 and M8a-6, related by high sequence identities (87.6% for $V_H$ and 89.7% for $V_L$) (FIG. 10B) and the shared V gene segments (IgH V1-69 and Igk V6-25) (FIG. 10A, Table 1), both contained 14-residue CDRH3s and six-residue CDRL1s (Table 8), yet M8a-3 showed a broader RBD binding profile by ELISA, such that it bound all RBDs evaluated except for the clade 2 Rf1 and clade 3 BM4831 RBDs. However, M8a-6 did not bind detectably to any of the three clade 3 RBDs or to three of the clade 1a and clade 2 RBDs (FIG. 2A). M8a-28 showed weak binding to some non-SARS-2 RBDs of clade 1b (RsSTT200 and Pang17), clade 1a (SHC014 and LyRa3) and clade 2 (Rs4081, RmYNO2 and Yun 11), and weak or no binding to RBDs of clade 3 (weak for BtKY72 and Khosta-2, and no binding to BM4831 RBD of clade 3 (FIG. 2A)). In contrast, HSW-2 showed binding to RBDs from all clades except SARS-CoV from clade 1a (FIG. 2A). M8a-31 and M8a-34 recognized all RBDs in the ELISA panel (FIG. 2A). Although M8a-34 and HSW-1 shared a sequence identity of 75.3% for VH and 88.3% for VL with the same light chain IgkV3-5 V gene segment (FIG. 10A, Table 1), and both had 16-residue CDRH3s and 10-residue CDRL1s (FIG. 10B, Table 8), HSW-1 was not as broadly cross-reactive by ELISA, showing no detectable binding to RBDs of SARS-CoV (clade 1a), Yun 11 (clade 2), or BM4831 and Khosta2 (cade 3) (FIG. 2A).

TABLE 8

NUMBER OF RESIDUES IN CDRS

|  | CDRH1 | CDRH2 | CDRH3 | CDRL1 | CDRL2 | CDRL3 |
|---|---|---|---|---|---|---|
| M8a-3 | 8 | 8 | 14 | 6 | 3 | 9 |
| M8a-6 | 8 | 8 | 14 | 6 | 3 | 9 |
| M8a-28 | 8 | 8 | 13 | 6 | 3 | 9 |
| M8a-31 | 8 | 8 | 9 | 12 | 3 | 9 |
| M8a-34 | 8 | 8 | 16 | 10 | 3 | 9 |
| HSW-1 | 8 | 8 | 16 | 10 | 3 | 9 |
| HSW-2 | 8 | 8 | 11 | 6 | 3 | 9 |

TABLE 10

CDR SEQUENCES

| Name | Sequence | SEQ ID NO |
|---|---|---|
| CDHR1 consensus | GYTFTXYW | 48 |
| M8a-3 CDRH1 | GYTFTNYW | 49 |
| M8a-6 CDRH1 | GYTFTHYW | 50 |
| M8a-28 CDRH1 | GYNFNHYW | 51 |
| M8a-31 CDRH1 | GFNIKNIY | 52 |
| M8a-34 CDRH1 | GYTFITYW | 53 |
| HSW-1 CDRH1 | GYTFTSYW | 54 |
| HSW-2 CDRH1 | GYVFSTSW | 55 |
| CDRH2 Consensus | IYPXDGYT | 56 |
| M8a-3 CDRH2 | IDPFDTYI | 57 |
| M8a-6 CDRH2 | IAPSDNYV | 58 |
| M8a-28 CDRH2 | IYPLSHFT | 59 |
| M8a-31 CDRH2 | IDPANGNS | 60 |
| M8a-34 CDRH2 | IYPGGGRT | 61 |
| HSW-1 CDRH2 | IHPNSGST | 62 |
| HSW-2 CDRH2 | IYPRDGHS | 63 |
| CDRH3 Consensus | ARPDXXXYXYFDY | 64 |
| M8a-3 CDRH3 | ARPDSSGYPVYFDY | 65 |
| M8a-6 CDRH3 | ARPDNSGYPVYFDY | 66 |
| M8a-28 CDRH3 | ARWDYFDSRTFDY | 67 |
| M8a-31 CDRH3 | ADEGWGFAN | 68 |
| M8a-34 CDRH3 | ARYDGNYVGYYYAMDY | 69 |
| HSW-1 CDRH3 | VRSGSYYGTTYDYFDY | 70 |
| HSW-2 CDRH3 | ARDYGYYYFDY | 71 |
| CDRL1 Consensus | QSVGXF | 72 |
| M8a-3 CDRL1 | QDVGTY | 73 |
| M8a-6 CDRL1 | QDVGTT | 74 |

TABLE 10-continued

CDR SEQUENCES

| Name | Sequence | SEQ ID NO |
|---|---|---|
| M8a-28 CDRL1 | QTIGTN | 75 |
| M8a-31 CDRL1 | QSLLNSGNQKNY | 76 |
| M8a-34 CDRL1 | ESVDFYGNSF | 77 |
| HSW-1 CDRL1 | ESVNIYGNSF | 78 |
| HSW-2 CDRL1 | ENVYSF | 79 |
| CDRL2 Consensus | XAS | N/A |
| M8a-3 CDRL2 | WAS | N/A |
| M8a-6 CDRL2 | WAS | N/A |
| M8a-28 CDRL2 | YAS | N/A |
| M8a-31 CDRL2 | WAS | N/A |
| M8a-34 CDRL2 | RAS | N/A |
| HSW-1 CDRL2 | RAS | N/A |
| HSW-2 CDRL2 | RAK | N/A |
| CDRL3 Consensus | QQHYSTPXT | 80 |
| M8a-3 CDRL3 | QQHYSTPYT | 81 |
| M8a-6 CDRL3 | QQHYNTPYT | 82 |
| M8a-28 CDRL3 | QQINSWPLT | 83 |
| M8a-31 CDRL3 | QNDYSYPLT | 84 |
| M8a-34 CDRL3 | QQSIEDPRT | 85 |
| HSW-1 CDRL3 | HQSNEDPFT | 86 |
| HSW-2 CDRL3 | QHHYGTPPT | 87 |

Neutralization potencies were measured next using a pseudovirus neutralization assay against sarbecoviruses known to use human ACE2 for target cell entry, including SARS-CoV-2 WA1 D614G, SARS-CoV-2 Beta, SARS-CoV-2 Delta, SARS-CoV-2 Omicron BA.1 and BA.2, SARS-CoV, WIV1, SHC014, a modified BtKY72 Khosta2/ SARS-CoV Chimera, and LyRa3/SARS-CoV Chimera (FIG. 2B). Among all, M8a-3 was the most consistently cross-reactively potent, with low half-maximal inhibitory concentrations ($IC_{50}$ values) against all pseudoviruses evaluated (FIG. 2B). Despite sharing high sequence identity, the same V gene segments, and similar CDR characteristics with M8a-3 (FIG. 10A-FIG. 10B, Table 8), M8a-6 showed no neutralizing activity except for weak activity against SHC014 and BtKY72. A less related mAb, M8a-28, was a potent neutralizer, but only against SARS-CoV-2 variants. The M8a-31 and M8a-34 mAbs were less potent against SARS-CoV-2 variants, but were more broadly cross-reactive, correlating with their ELISA profiles (FIG. 2B). By contrast to the five M8a mAbs, the HSW-1 and HSW-2 mAbs isolated from homotypic SARS-CoV-2 RBD nanoparticle-immunized mice identified as binding two or more RBDs during screening showed overall weaker neutralizing potencies, with eight of 18 assays showing no neutralizing activity and most of the remaining assays showing $IC_{50}$ values above 10 μg/mL (FIG. 2B).

To identify RBD epitopes for the mAbs, a binding assay was used to assess potential competition with proteins that bind to known RBD epitopes. For this competition assay, the four human anti-RBD mAbs with known epitopes were used that were also used as controls for ELISAs (FIG. 2A): C118 (class 4), S309 (class 3), C102 (class 1), and C144 (class 2), along with other potential competitor mAbs or control mAbs: C022 (class 14), CR3022 (class 4), COVA1-16, C135 (class 3), C110 (class 3), C105 (class 1), and a soluble human ACE2-Fc construct. The ELISA revealed the expected competition for the characterized human mAbs (FIG. 11), validating its use for mapping RBD epitopes for the seven mouse mAbs elicited by RBD-nanoparticle immunization. Three of the five m8a mAbs (M8a-3, M8a-31, and M8a-34) mapped to class ¼ and/or class 4 epitopes, M8a-28 mapped to the class 3 RBD region, and Ma-6 did not compete with any of the labeled anti-RBD IgGs. Without being bound by any particular theory, the identification of a class 3 RBD epitope for M8a-28 rationalized its potent neutralization of SARS-CoV-2 WA1 and VOCs and limited cross-reactive neutralization of animal sarbecoviruses (FIG. 2B). This contrasted with the class 1%4 RBD epitope identification for the remaining less potently neutralizing M8a mAbs (M8a-3, M8a-31, and M8a-34), since this class of anti-RBD mAb tends to show less potent neutralization, but broader sarbecovirus cross-reactivity, than other classes due to the more occluded nature of the class ¼ epitope. Of the two HSW mAbs, HSW-1 did not exhibit any detectable competition, and HSW-2 showed competition with CR3022, a class 4 anti-RBD mAb. Overall, these results demonstrated that the majority of the mAbs identified during Beacon screening mapped to the more conserved class 1%4, 4, and 3 RBD epitopes.

Cryo-EM Structures of Fab-Spike Trimer Complexes Reveal Cross-Reactive Recognition and Rationalize Neutralization Results To deduce recognition and neutralization mechanisms, structural analyses of the seven mAbs identified as binding two or more RBDs during the Beacon isolation was performed (FIG. 2A). Single-particle cryo-EM was used to solve structures of complexes of a SARS-CoV-2 6P spike trimer and a mAb Fab, five of which were derived from M8a IgGs isolated in mosaic-8 nanoparticle-immunized mice (FIG. 3A-FIG. 4A) and two from HSW IgGs elicited in homotypic SARS-CoV-2 RBD nanoparticle-immunized mice (FIG. 5A-FIG. 5G, FIG. 12A-FIG. 19E, Table 2).

Figure 3A:
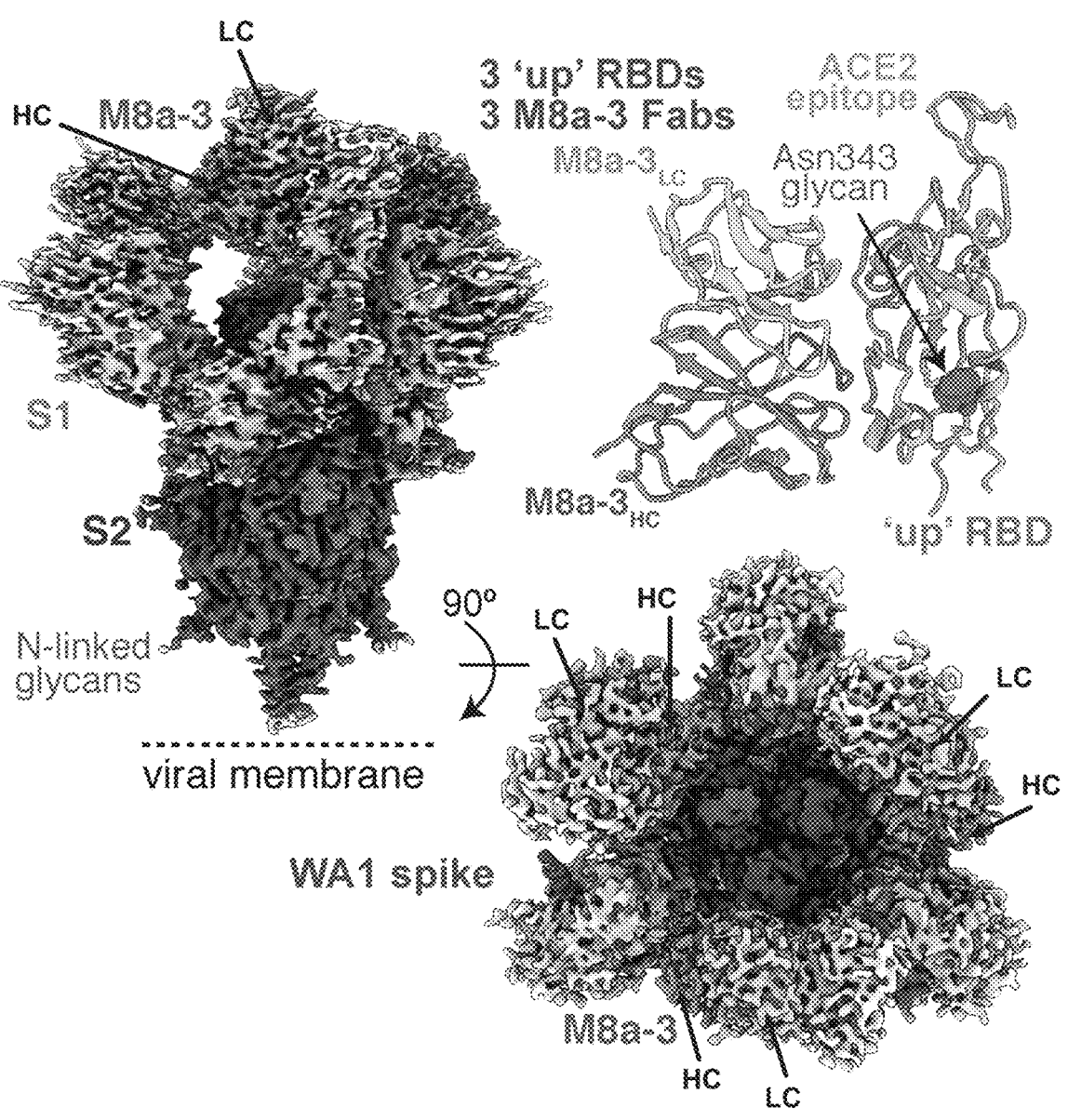
FIG. 3A-FIG. 3F depict non-limiting exemplary illustrations showing mAbs isolated from mice immunized with mosaic-8 nanoparticles target epitopes outside of the ACE2 binding footprint. EM densities of single-particle cryo-EM structures of Fab-spike trimer complexes are shown from the side (upper left), top (lower right), and as cartoon diagrams of the Fab $V_H$-$V_L$ interaction with the RBD. Only $V_H$-$V_L$ domains are shown for each Fab and the heavy and light chains are pointed out by arrows.
Figure 3B:
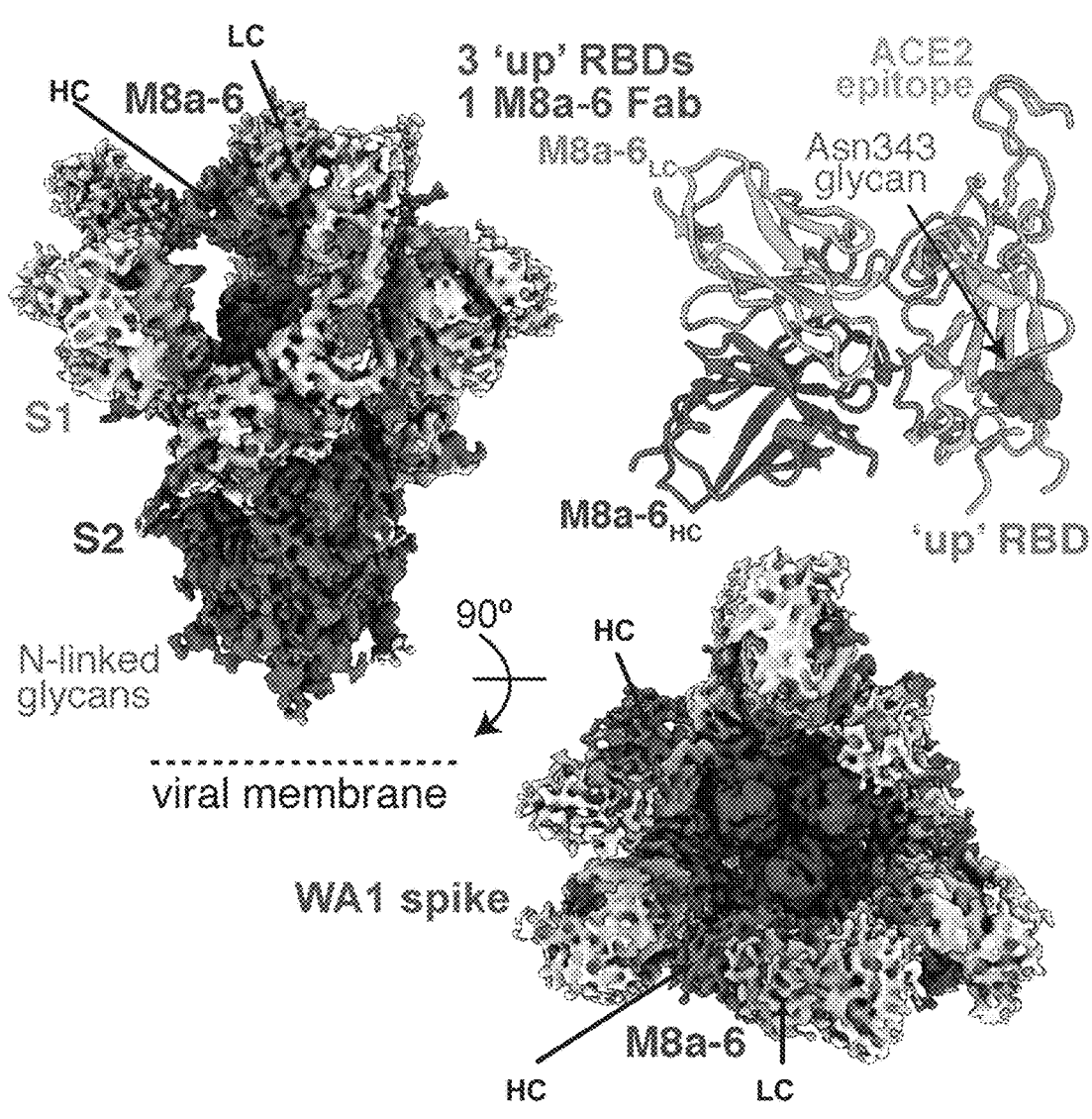
Figure 3C:
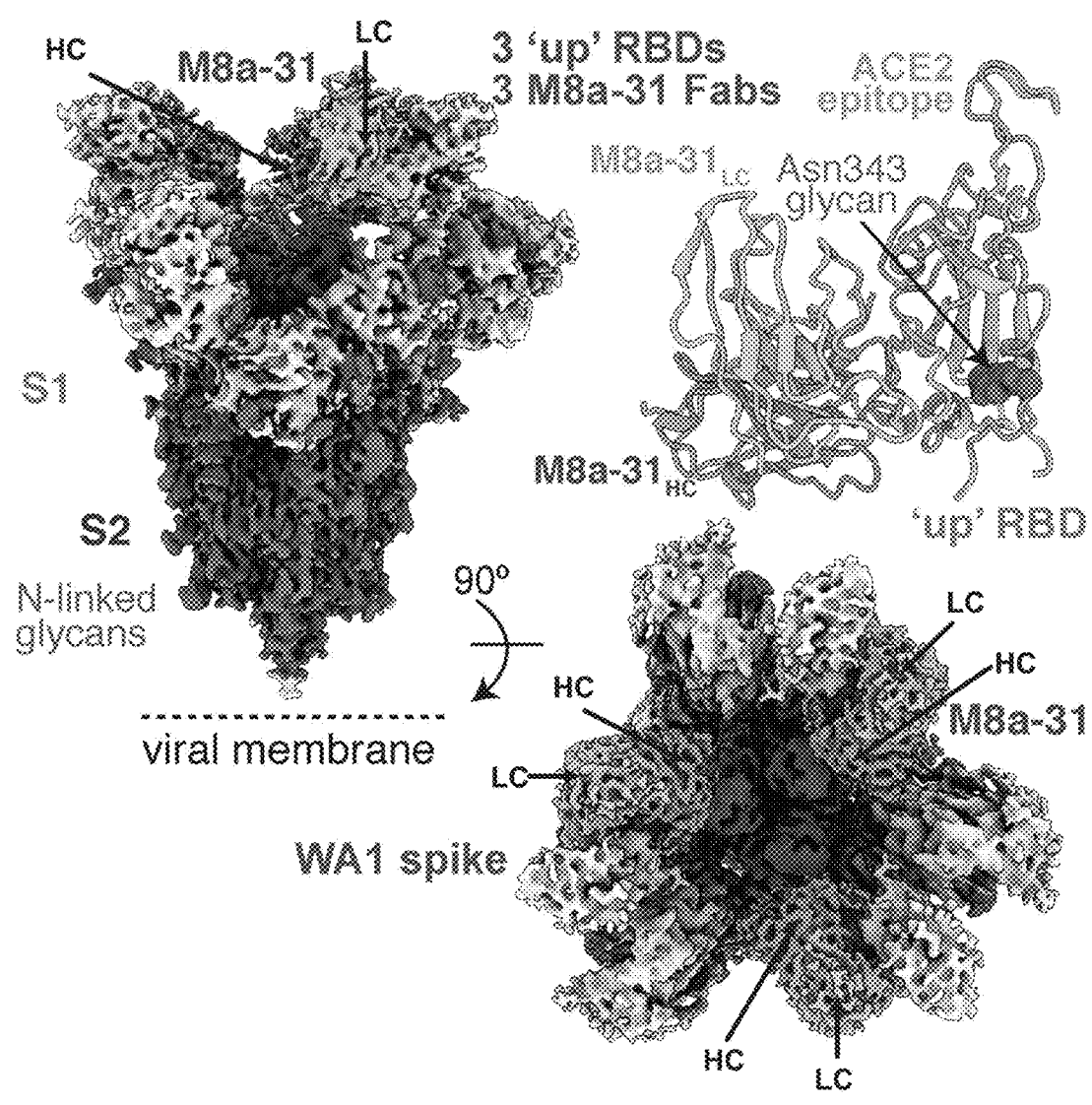
Figure 3D:
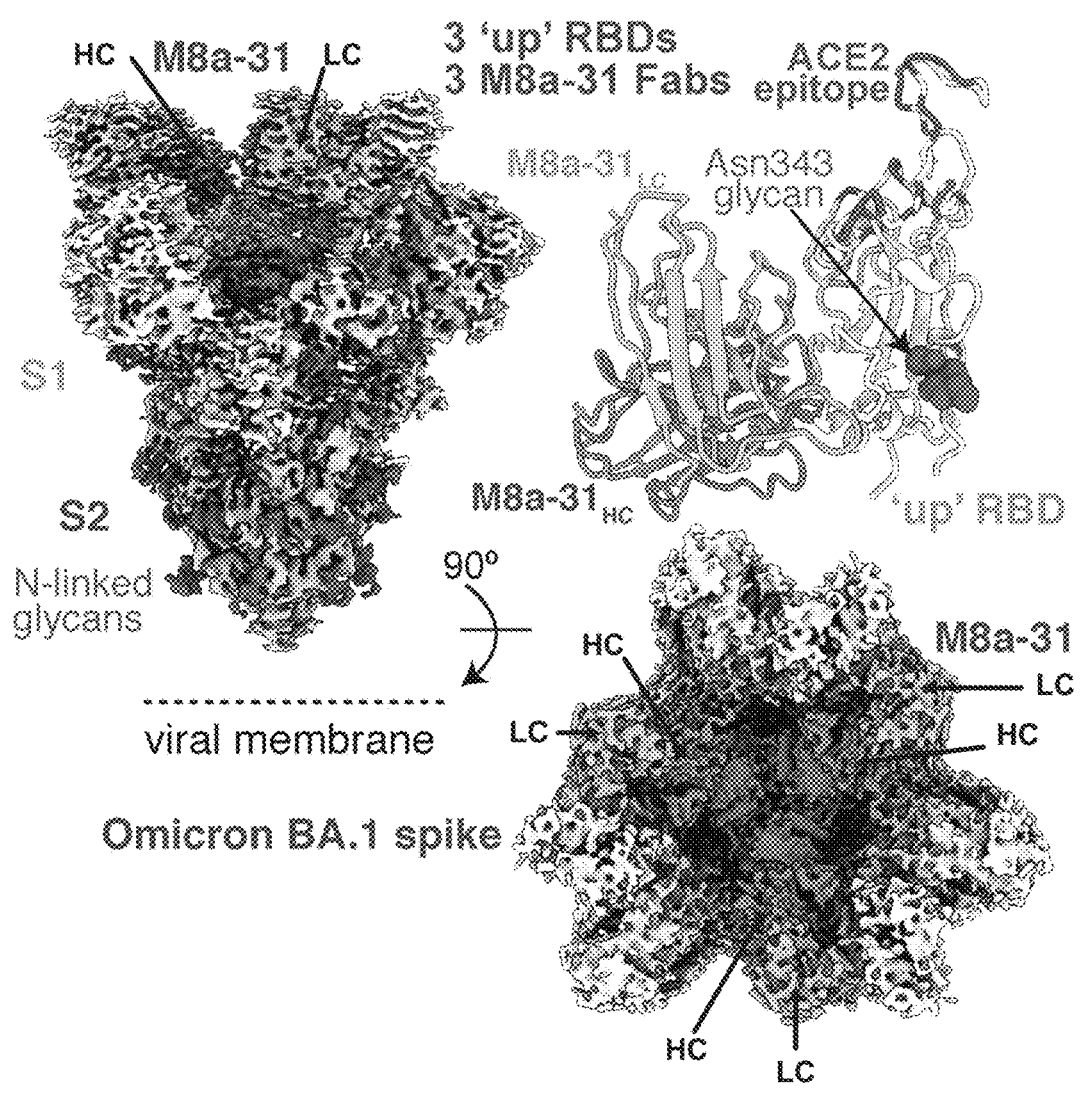
Figure 3E:
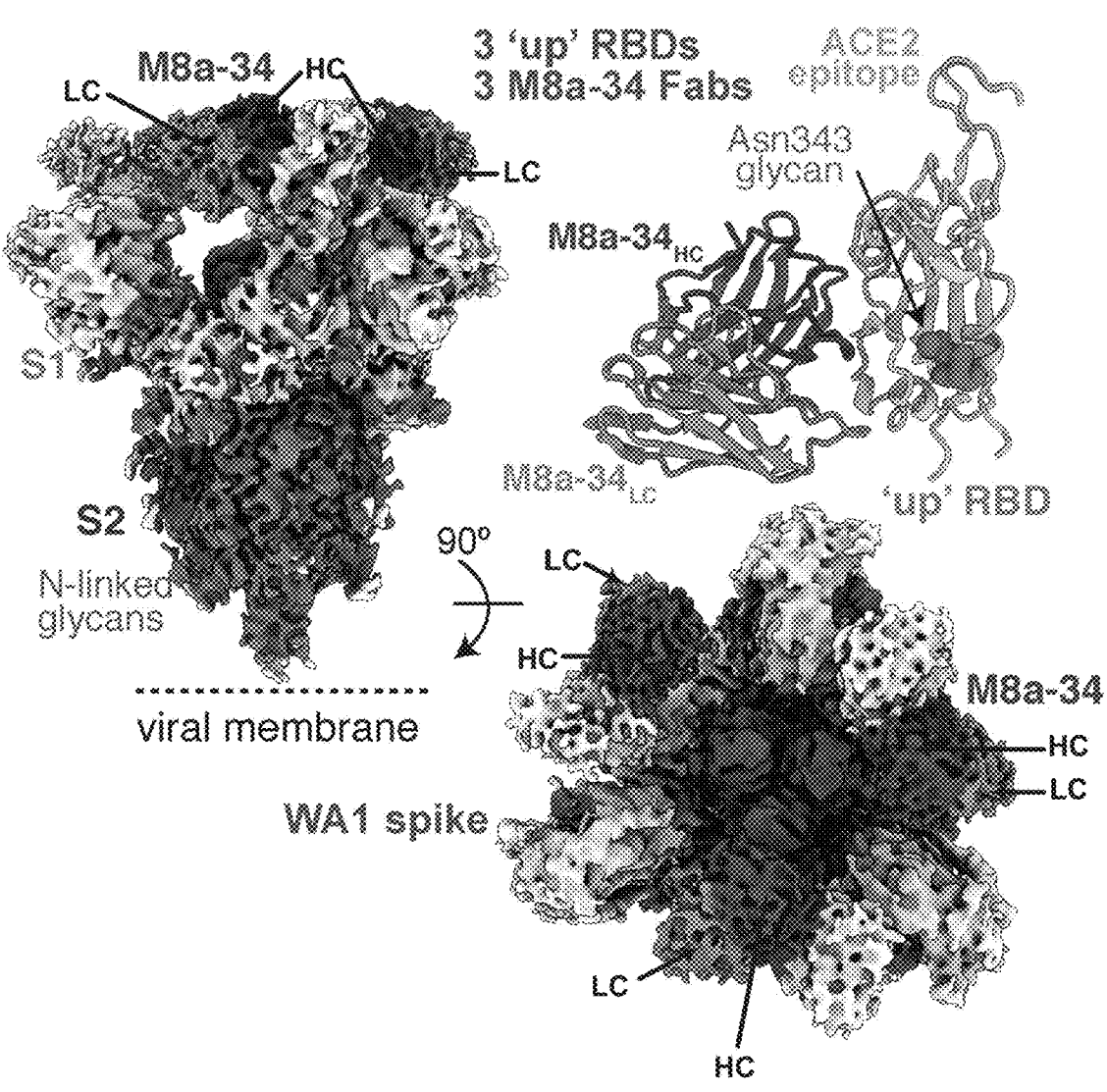
Figure 3F:
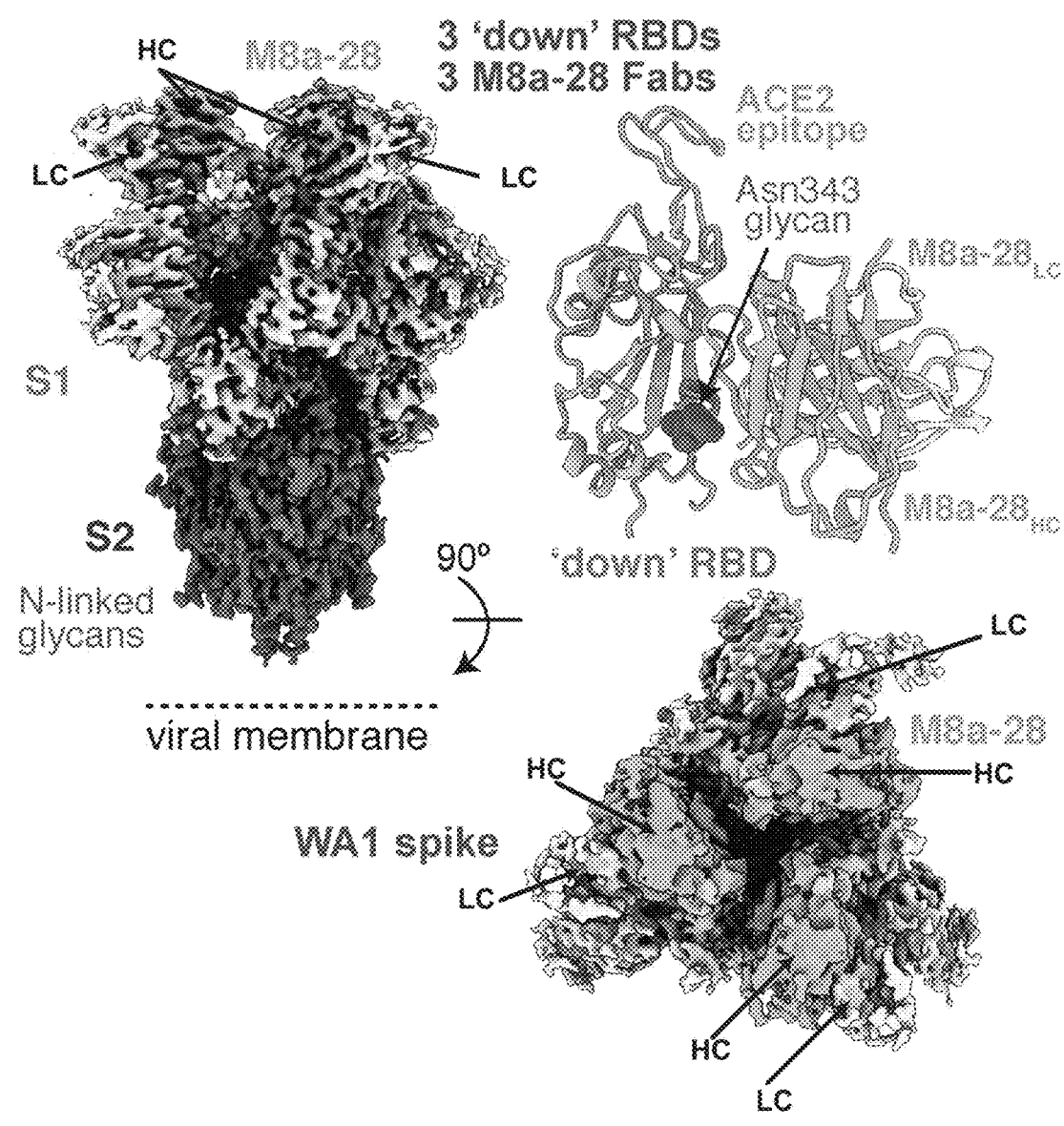

Each of the five M8a mAb Fab structures were solved as complexes with the SARS-CoV-2 WA1 spike trimer, and the M8a-31 Fab was also solved complexed with the Omicron BA.1 spike (FIG. 3A-FIG. 3F; FIG. 12A-FIG. 17E; Table 2). For five of the six M8a-spike structures (WA1 spike plus Fabs from M8a-3, M8a-31, M8a-34, M8a-28 and Omicron BA.1 spike plus M8a-31 Fab), one Fab was observed bound to each of the three RBDs, which were in 'up' positions in all cases except for the M8a-28-spike structure in which all three RBDs were in the 'down' conformation (FIG. 3C). In the remaining structure (M8a-6-spike), only one well-resolved Fab per trimer was found.

Figure 11:
FIG. 11 shows non-limiting exemplary data related to mAb epitope mapping. Competition ELISA experiments were performed in which a test set of biotinylated IgGs of known epitopes or human ACE2-Fc (y-axis) were assayed for binding to SARS-CoV-2 RBD in the presence of unlabeled M8a, HSW, control IgGs, or ACE2-Fc (x-axis). The heat map shows shading indicating the percent binding of the tested IgGs or ACE2-Fc in the presence of competitor. M8a-3, M8a-31, M8a-34, and HSW-2 IgGs competed with biotinylated class ¼ and/or class 4 anti-RBD, with HSW-2 competing with the biotinylated class 4 antibody only. M8a-3 IgG competed with biotinylated class 1 antibodies and ACE2-Fc in addition to the biotinylated class ¼ and class 4 antibodies. M8a-28 IgG competed with biotinylated class 3 antibodies. M8a-6 and HSW-1 IgGs showed no competition in this assay.
Figure 11:
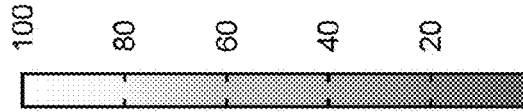
Figure 11:
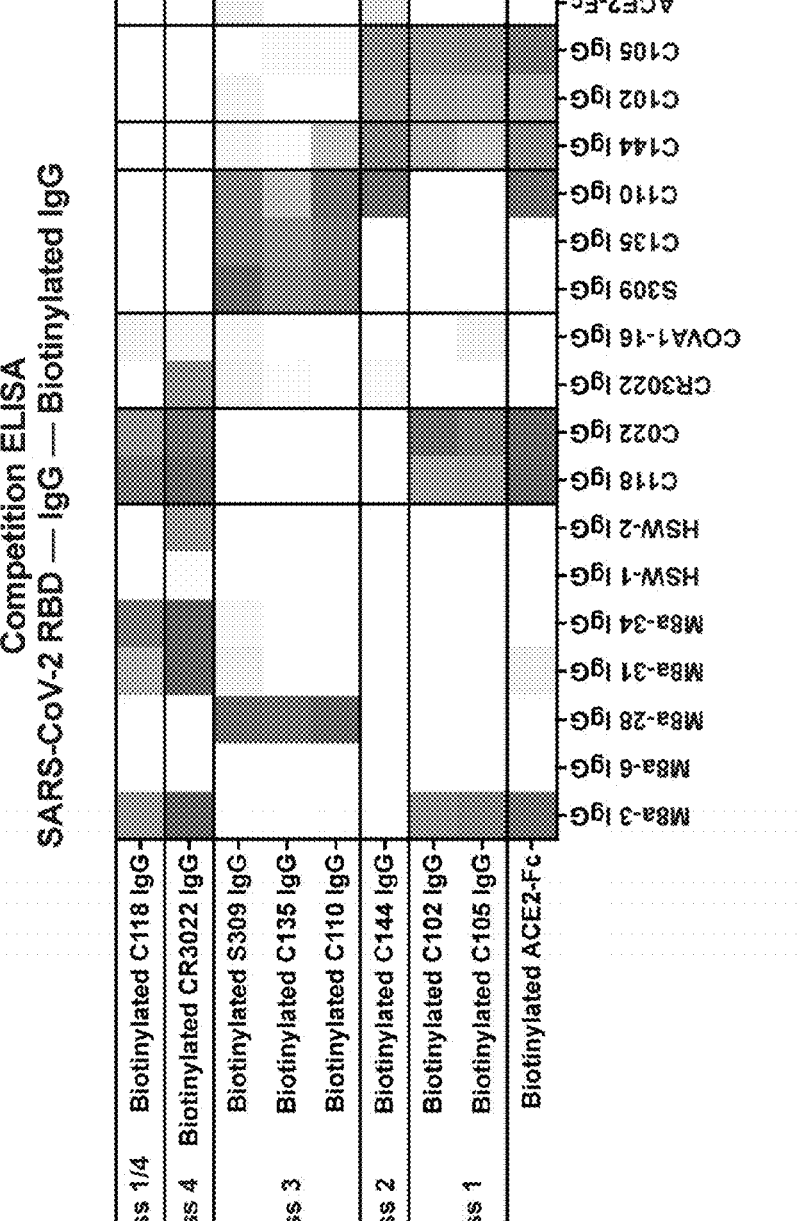
Figure 12A:
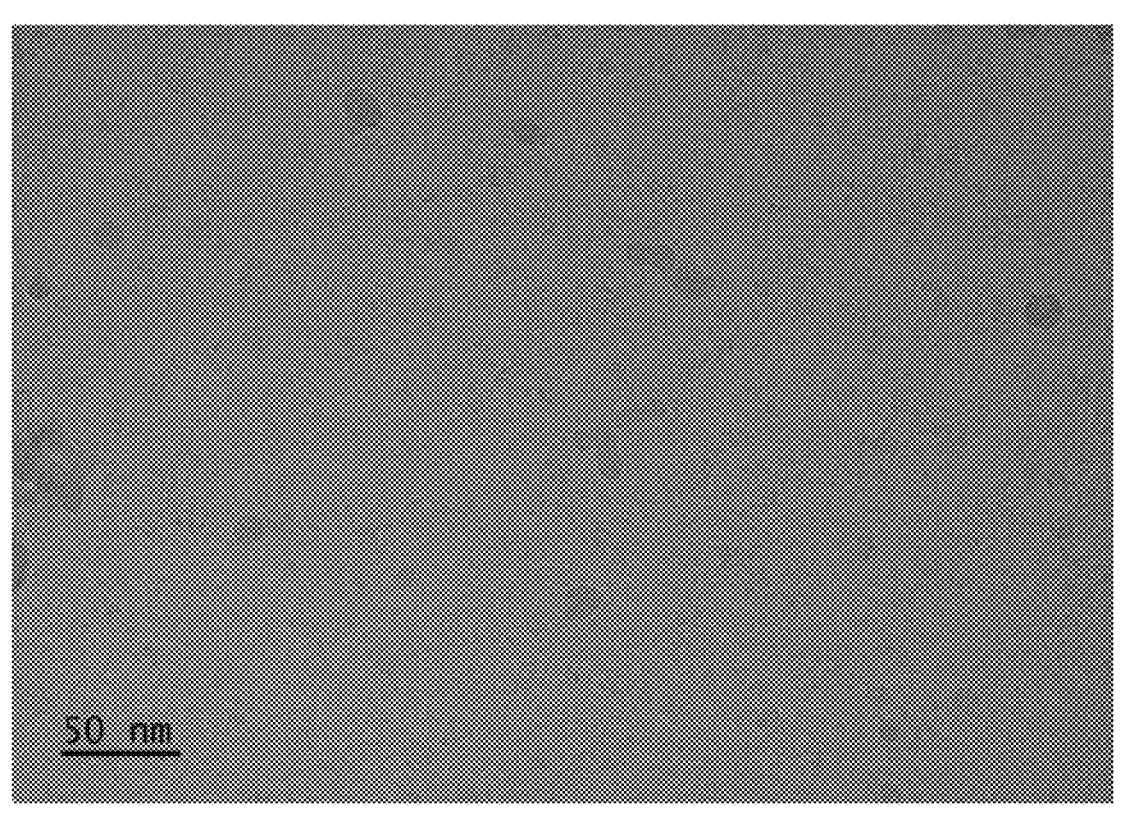
FIG. 12A-FIG. 12E show non-limiting exemplary data related to Cryo-EM data processing and validation for M8a-3 Fab in complex with SARS-CoV-2 WA1 spike.
Figure 12B:
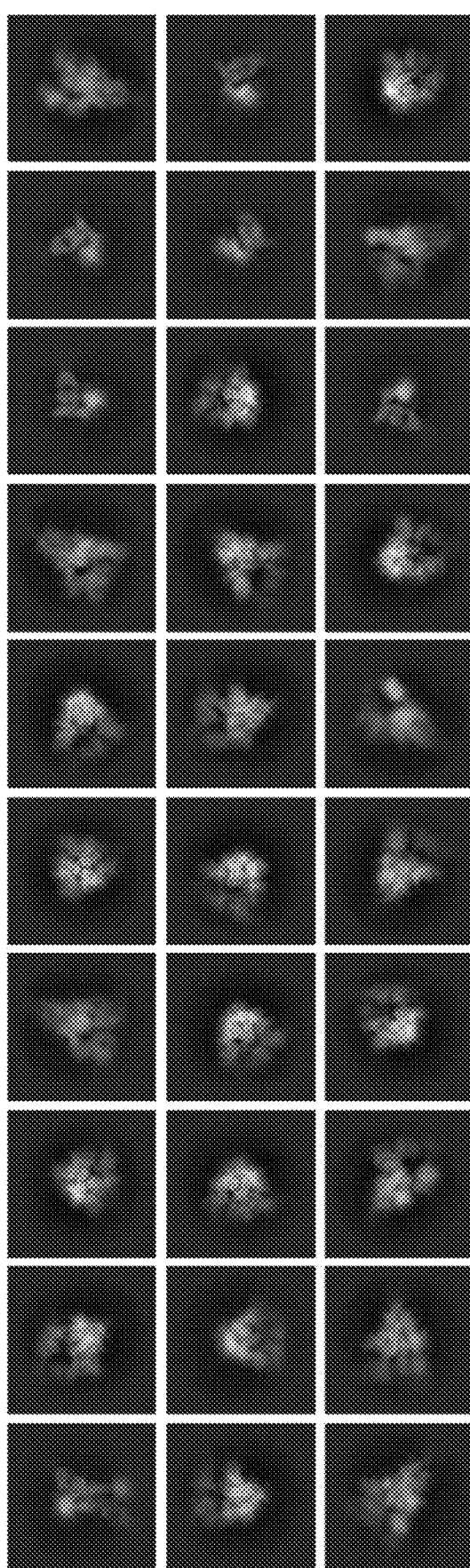
Figure 12C:
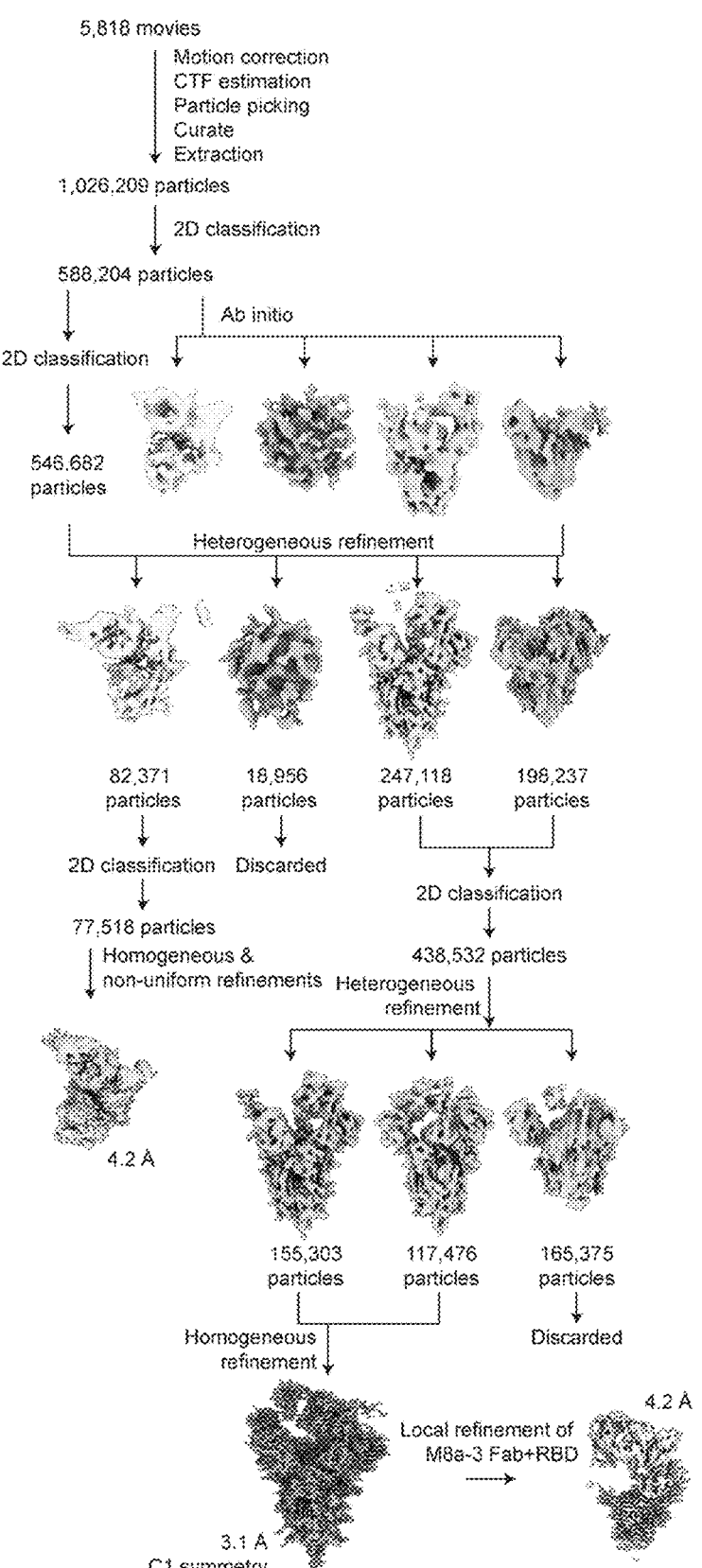
Figure 12D:
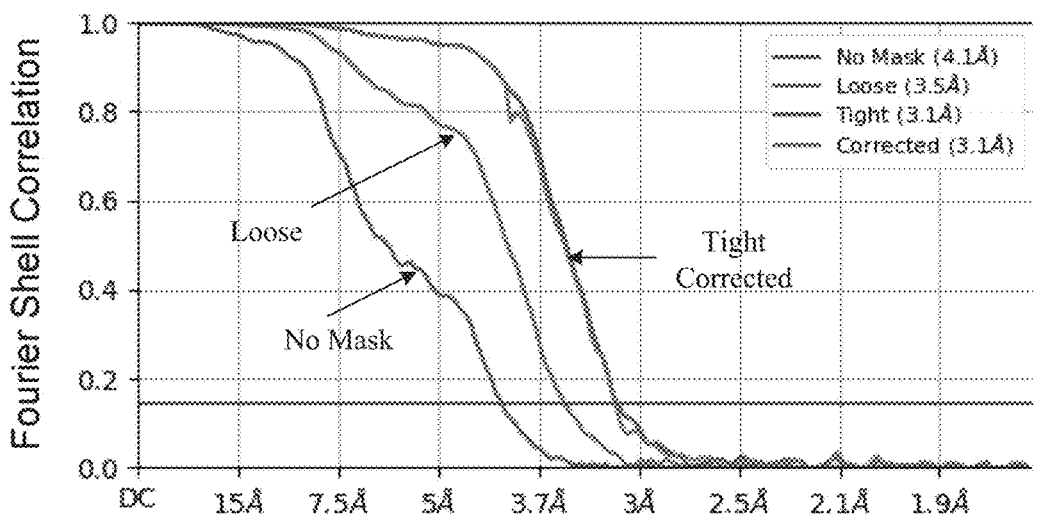
Figure 12E:
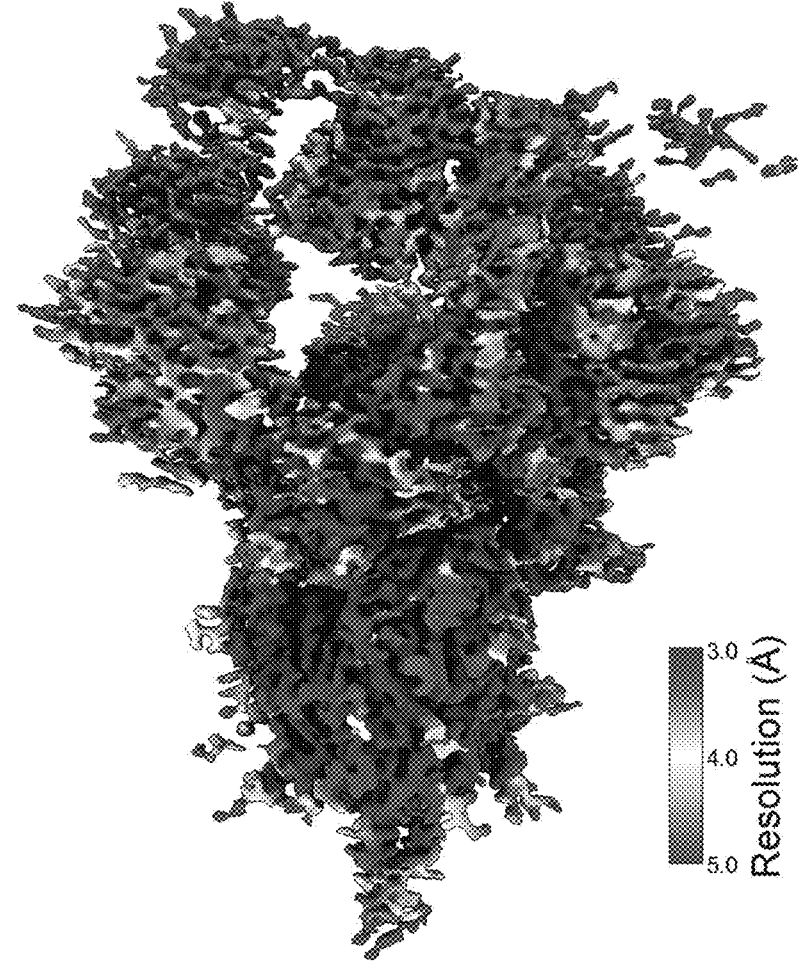
Figure 13A:
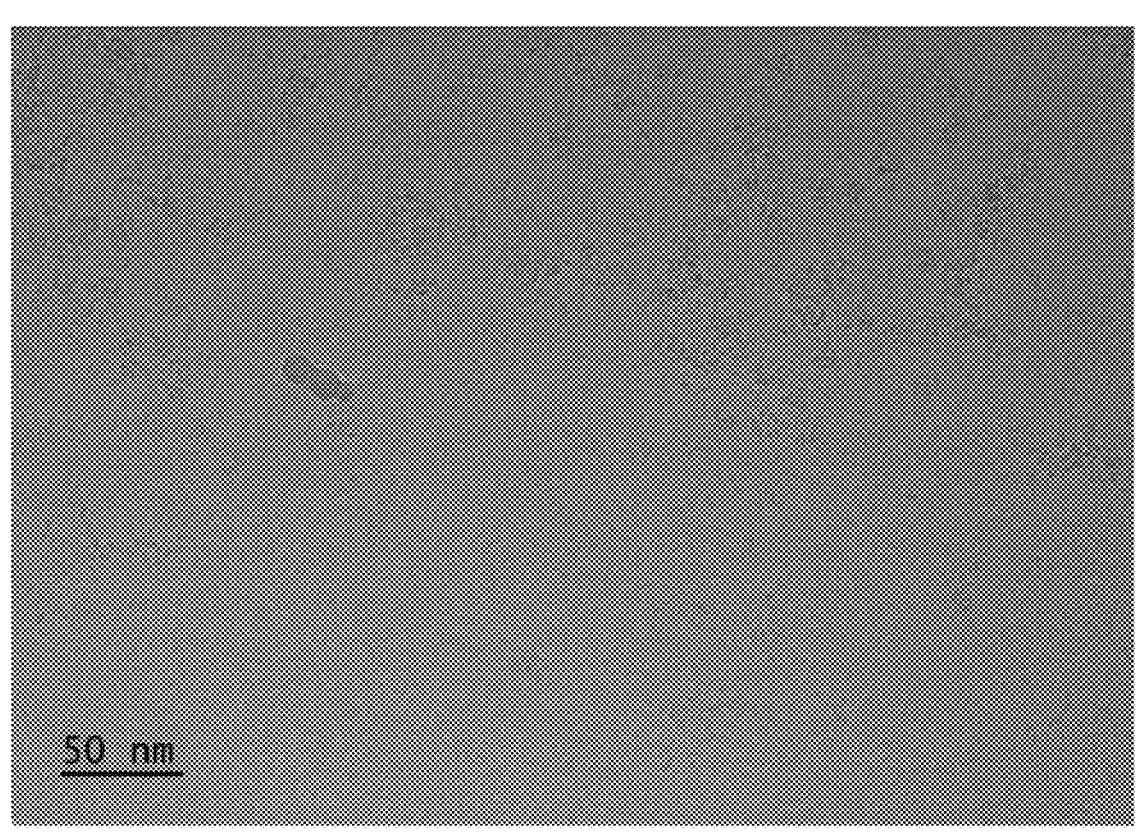
FIG. 13A-FIG. 13E show non-limiting exemplary data related to Cryo-EM data processing and validation for M8a-6 Fab in complex with SARS-CoV-2 WA1 spike.
Figure 13B:
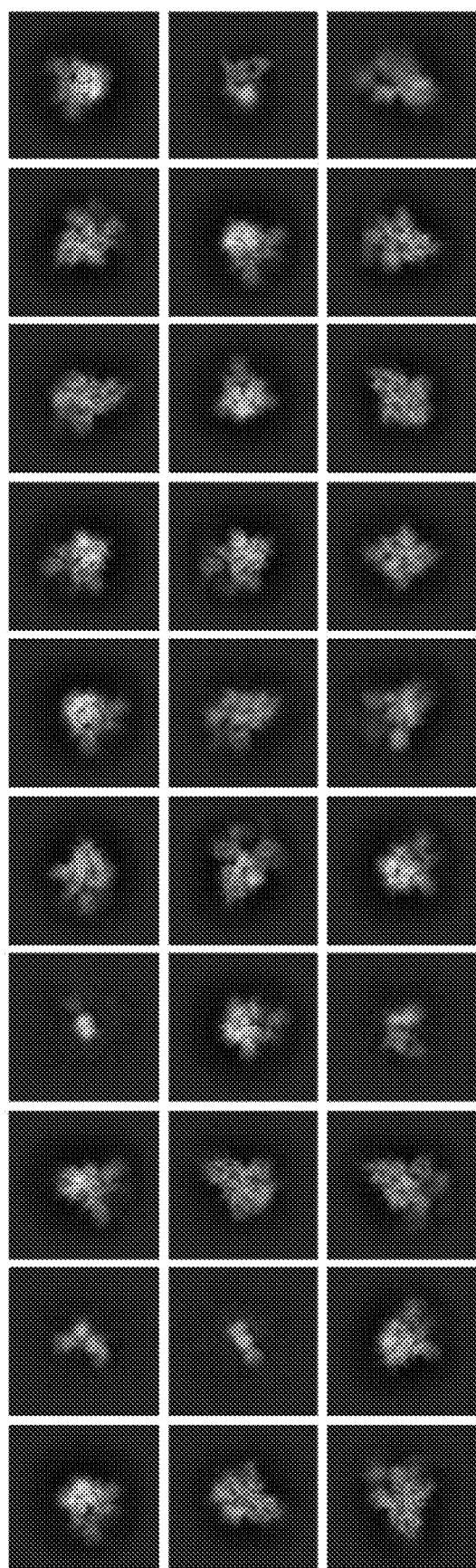
Figure 13C:
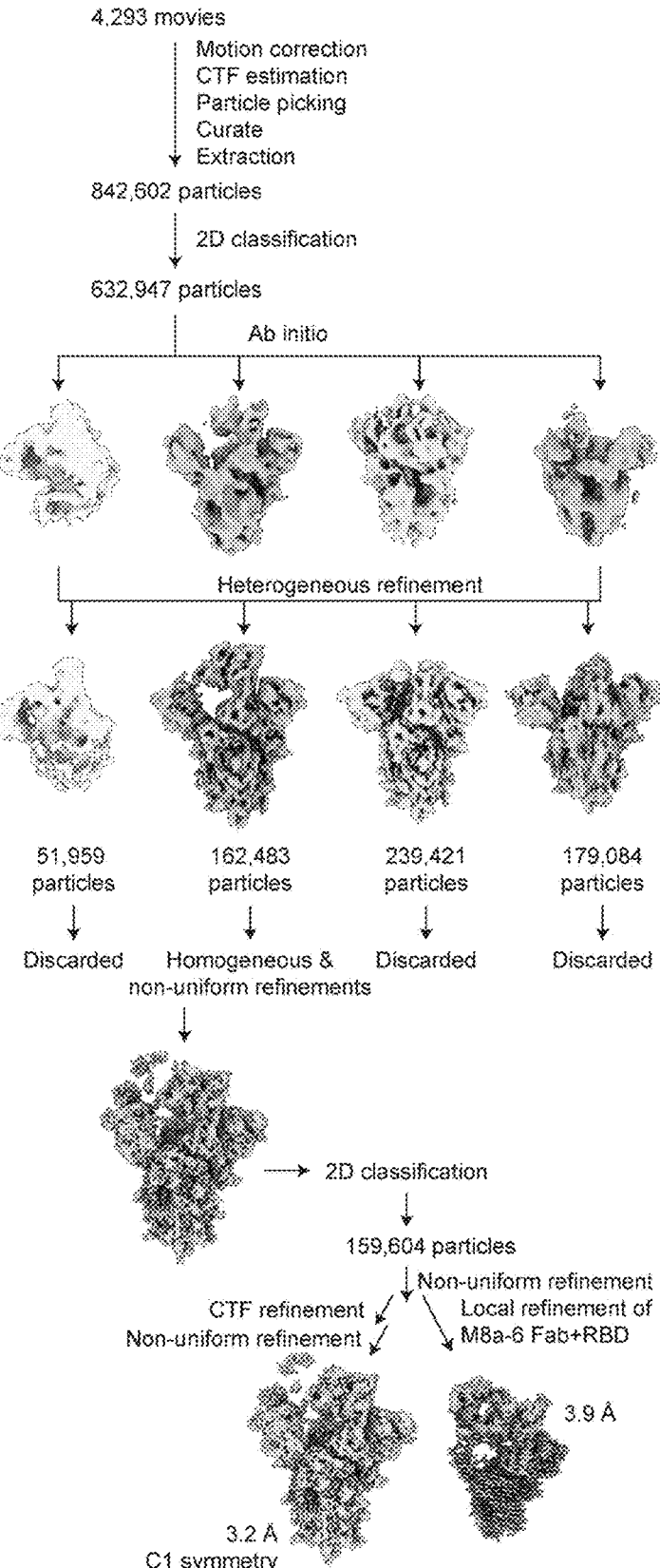
Figure 13D:
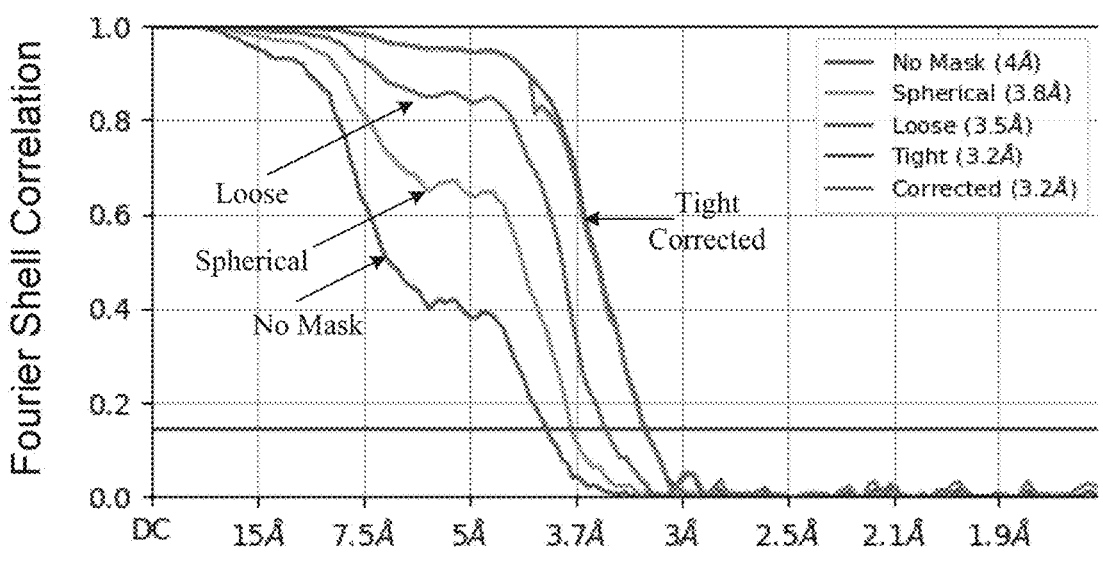
Figure 13E:
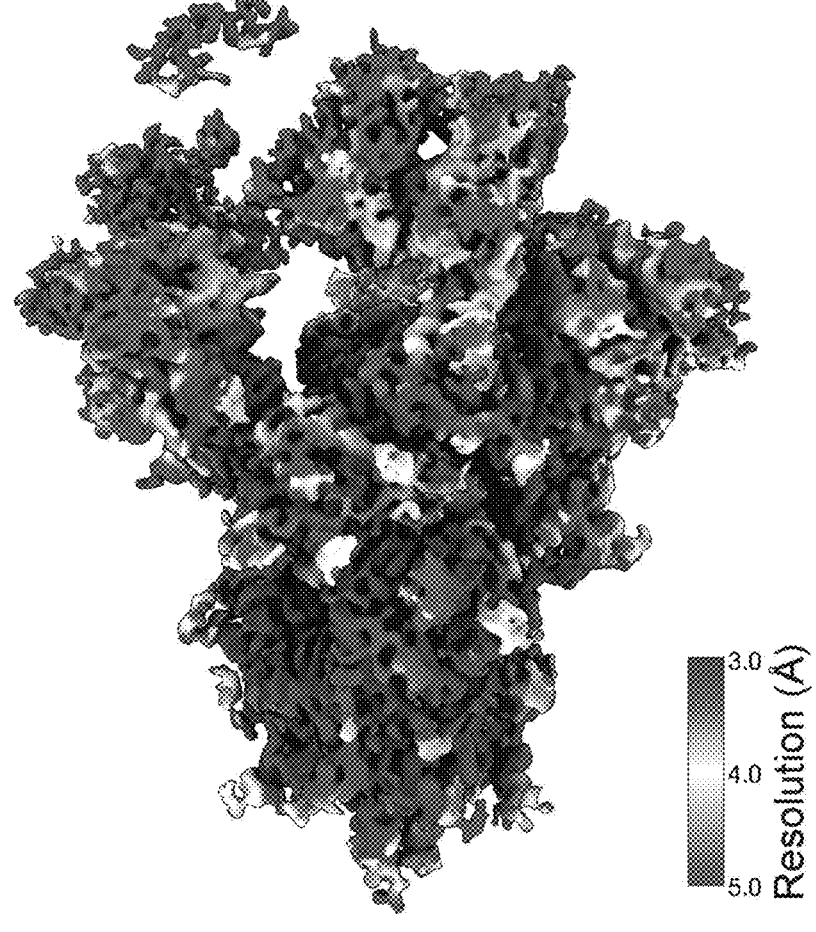
Figure 14A:
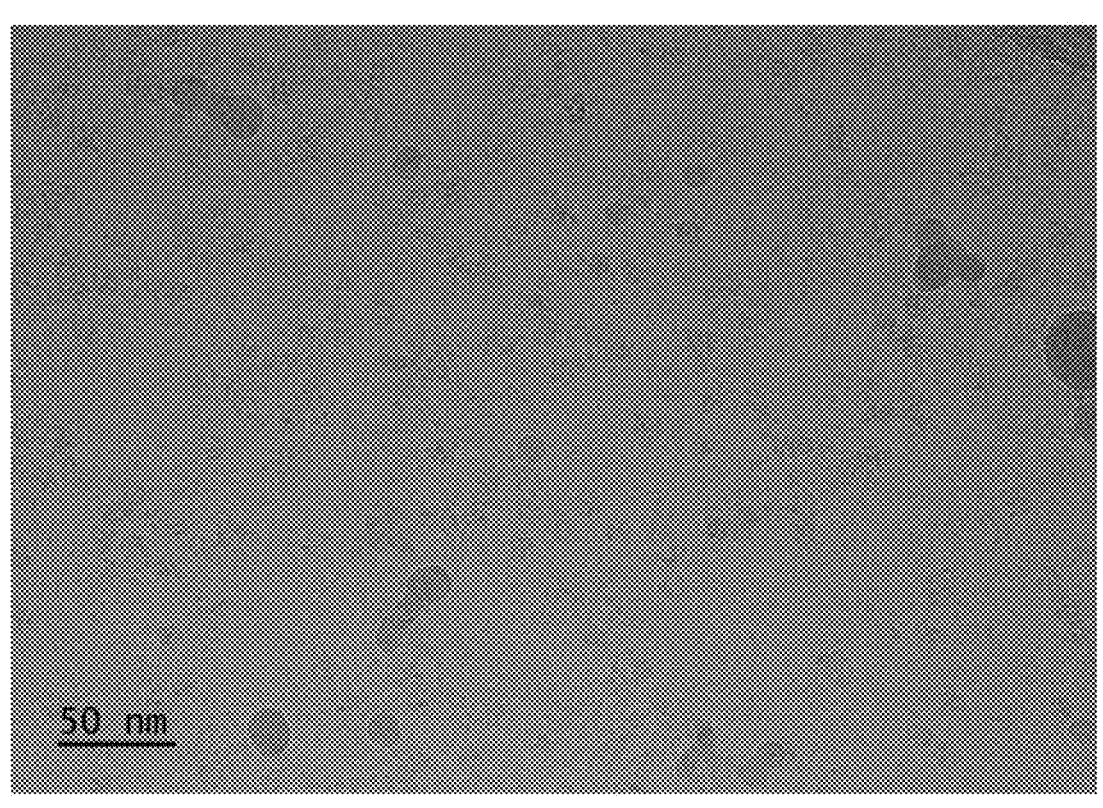
FIG. 14A-FIG. 14E show non-limiting exemplary data related to Cryo-EM data processing and validation for M8a-31 Fab in complex with SARS-CoV-2 WA1 spike.
Figure 14B:
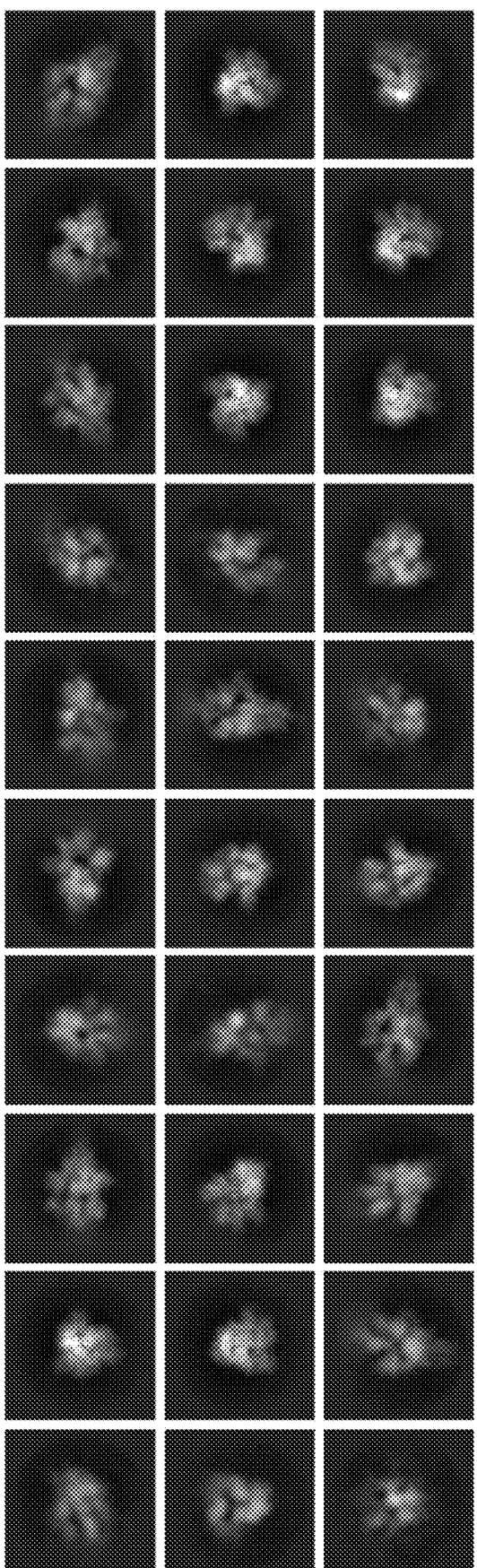
Figure 14C:
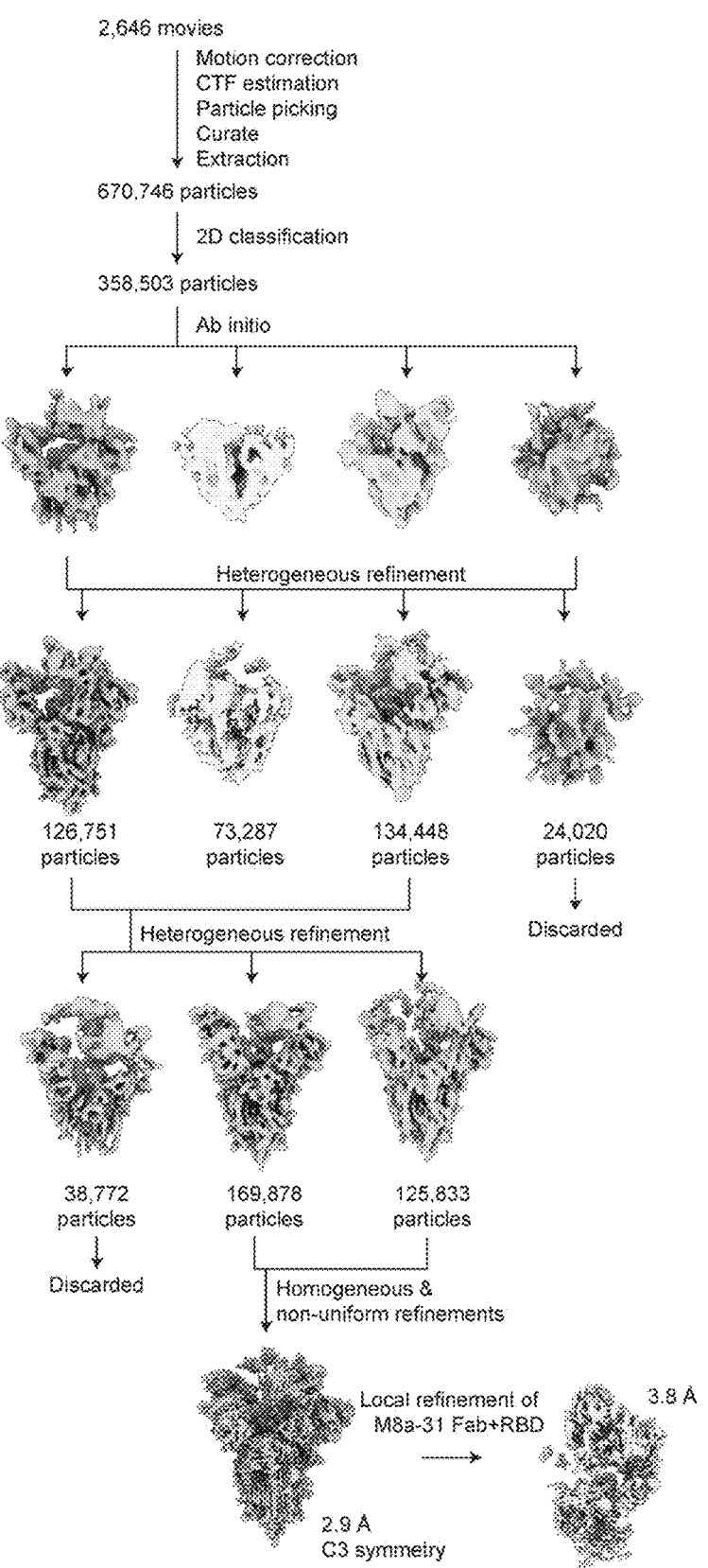
Figure 14D:
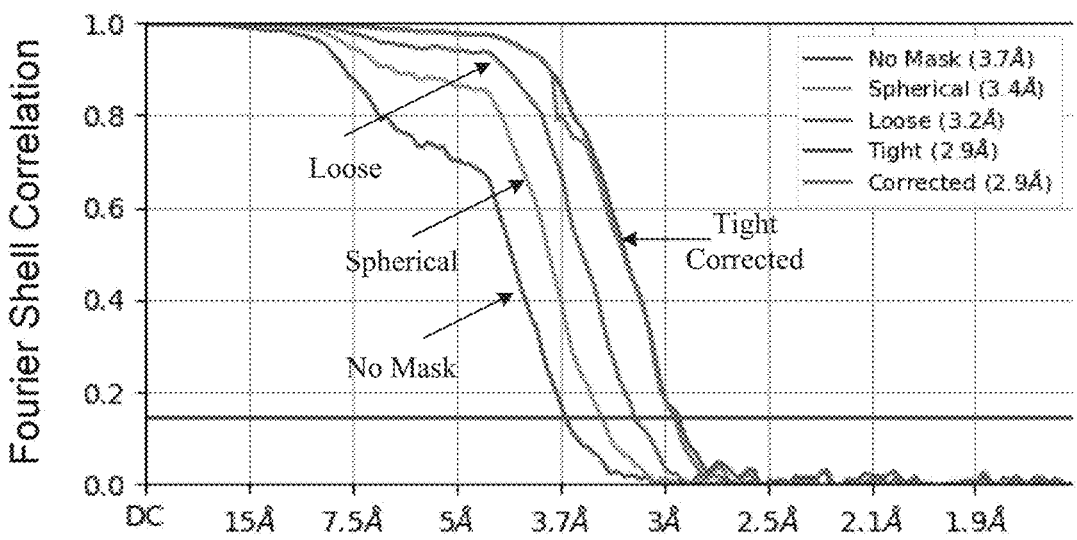
Figure 14E:
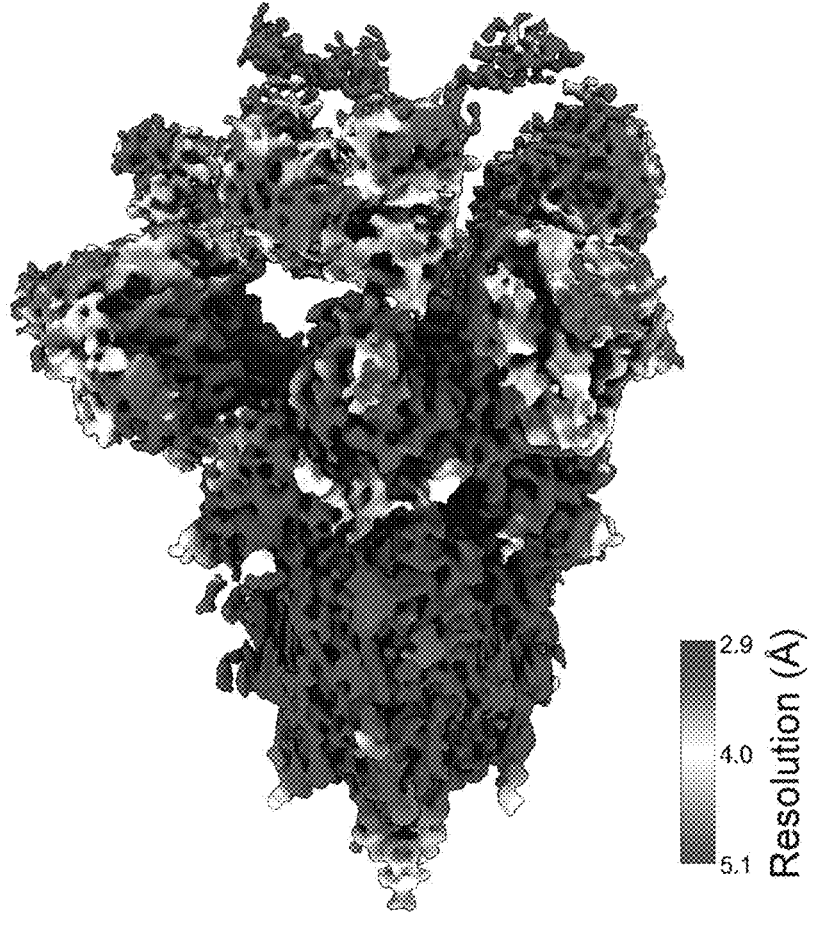
Figure 15A:
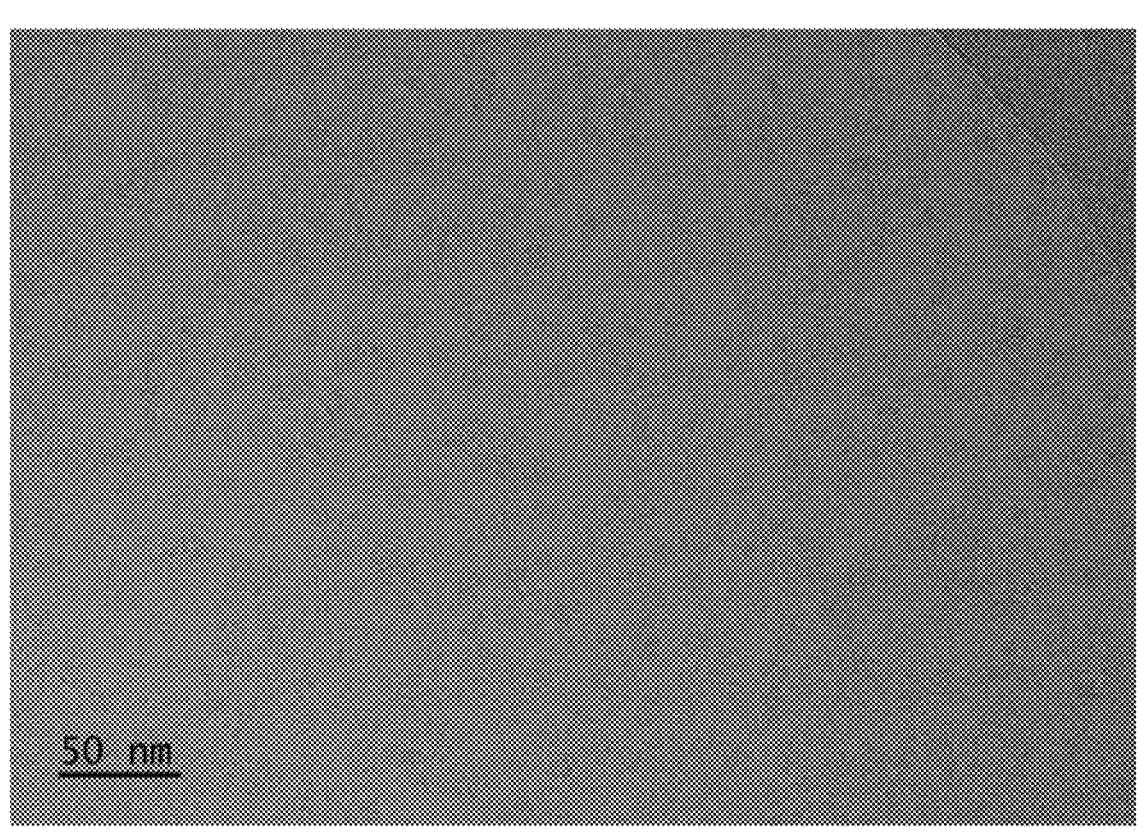
FIG. 15A-FIG. 15E show non-limiting exemplary data related to Cryo-EM data processing and validation for of M8a-31 Fab in complex with SARS-CoV-2 Omicron BA.1 spike.
Figure 15B:
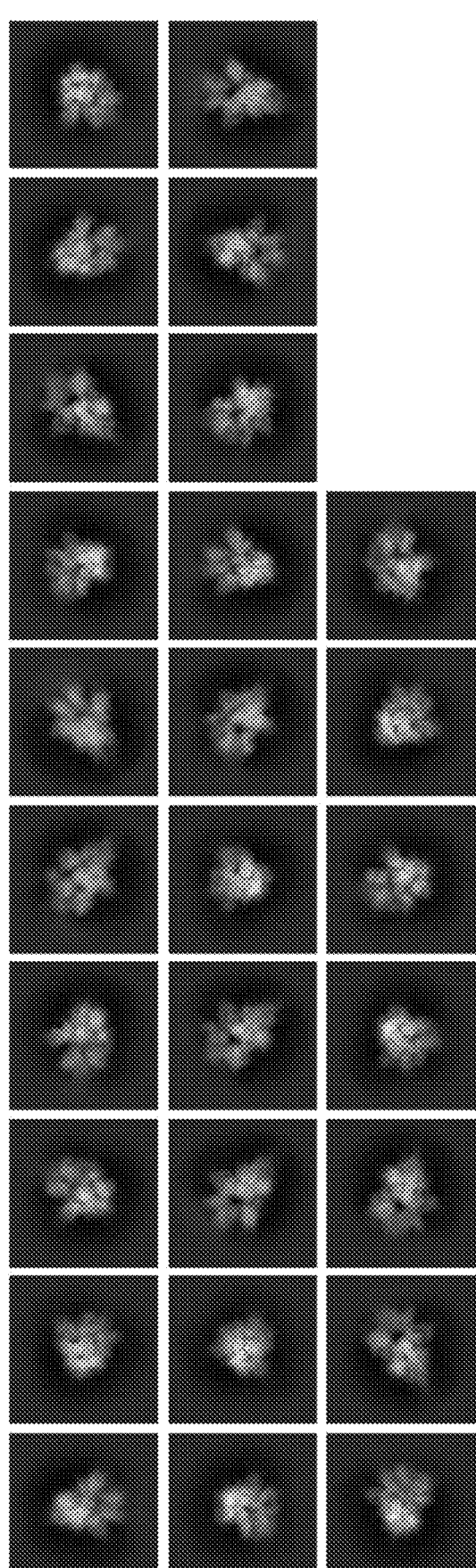
Figure 15B:
Figure 15C:
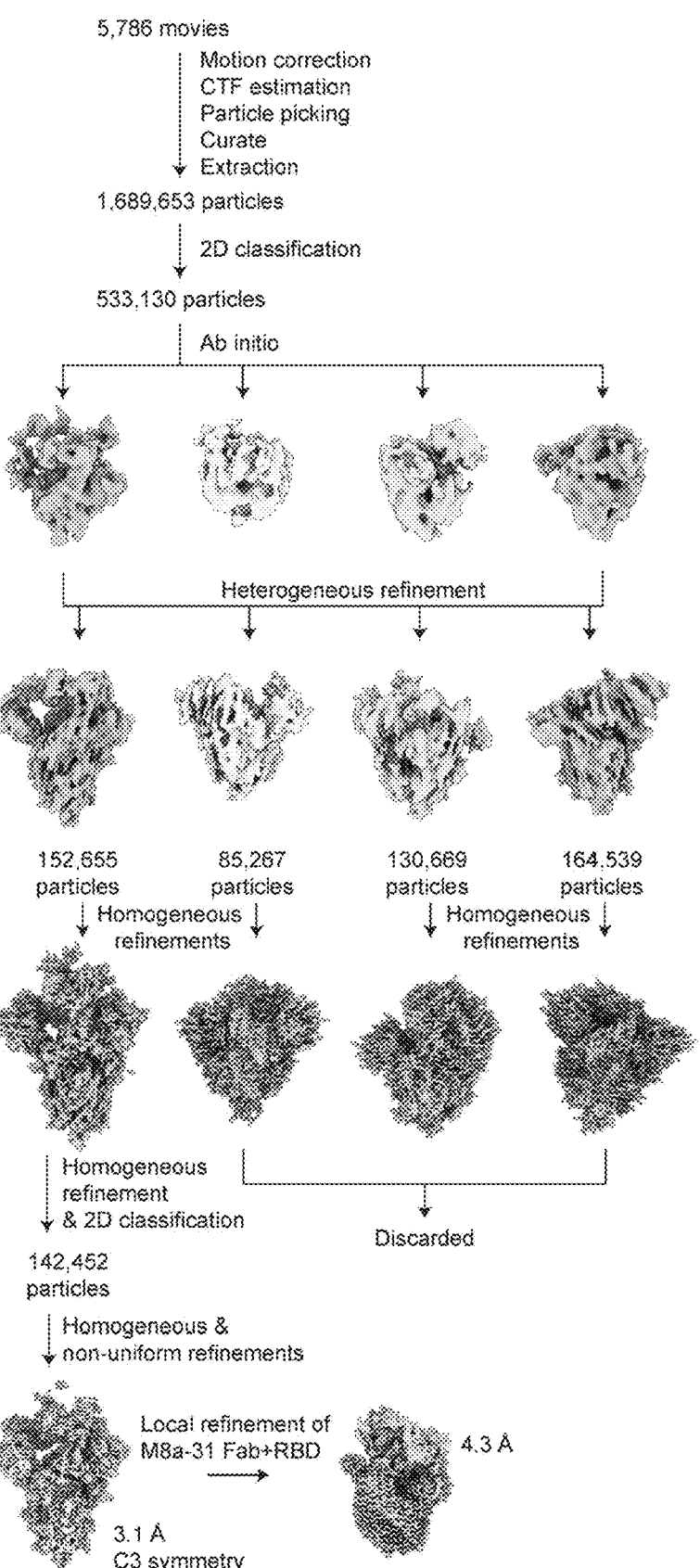
Figures 15D, 15E:
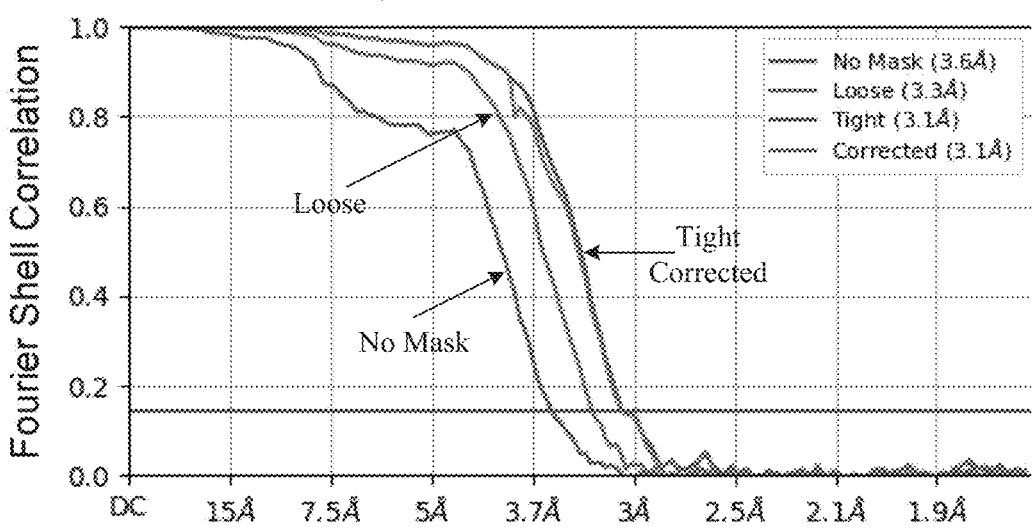
Figure 16A:
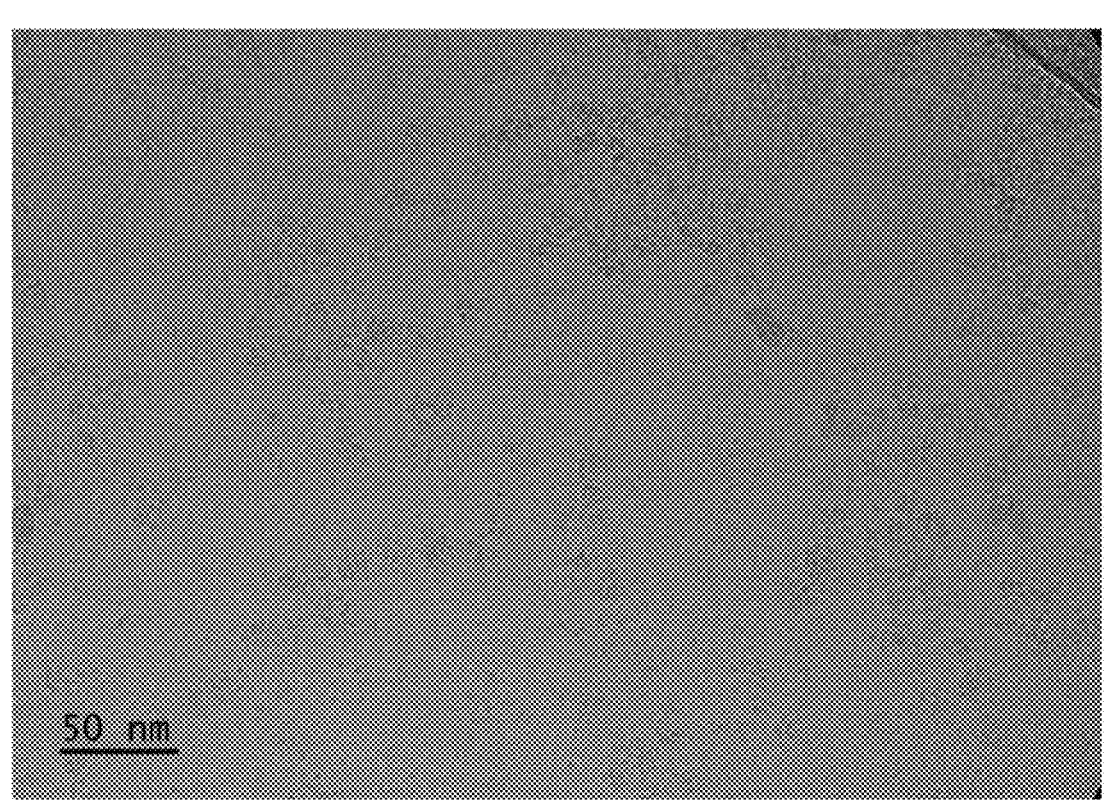
FIG. 16A-FIG. 16E show non-limiting exemplary data related to Cryo-EM data processing and validation for M8a-34 Fab in complex with SARS-CoV-2 WA1 spike.
Figure 16B:
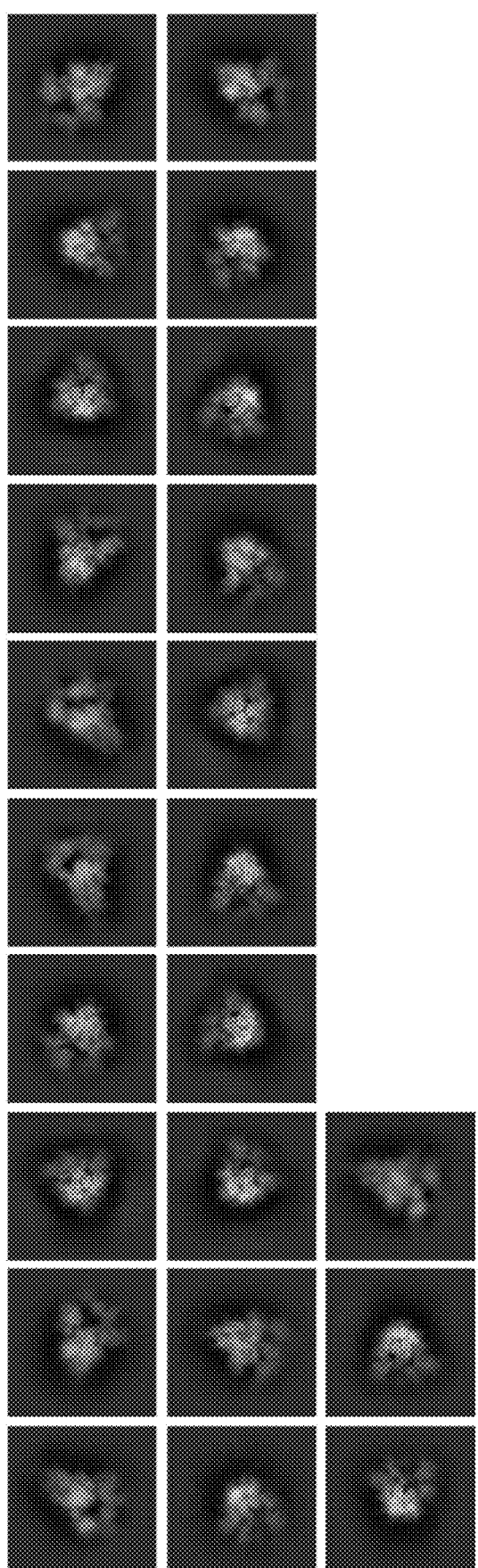
Figure 16B:
Figure 16C:
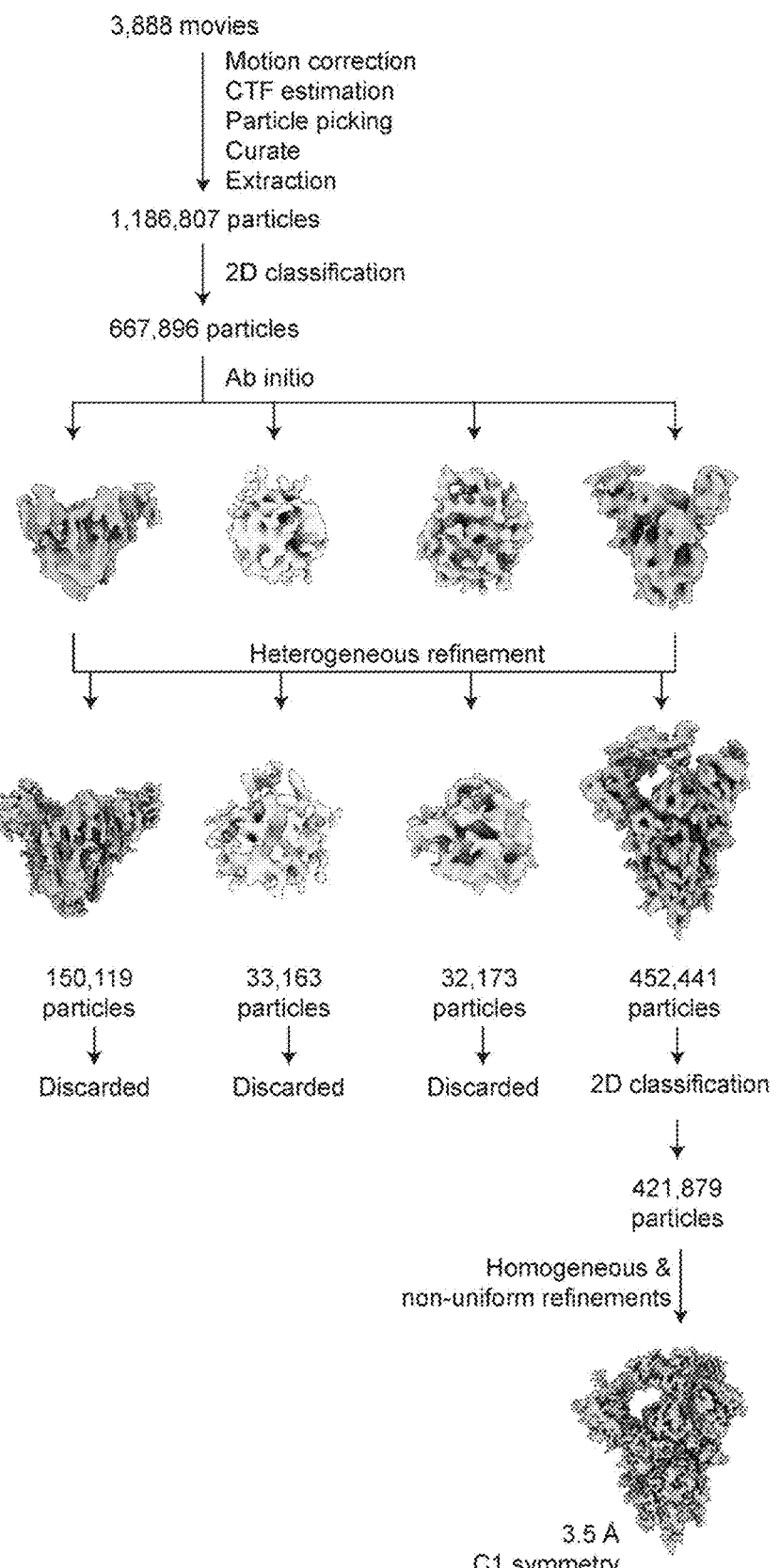
Figure 16D:
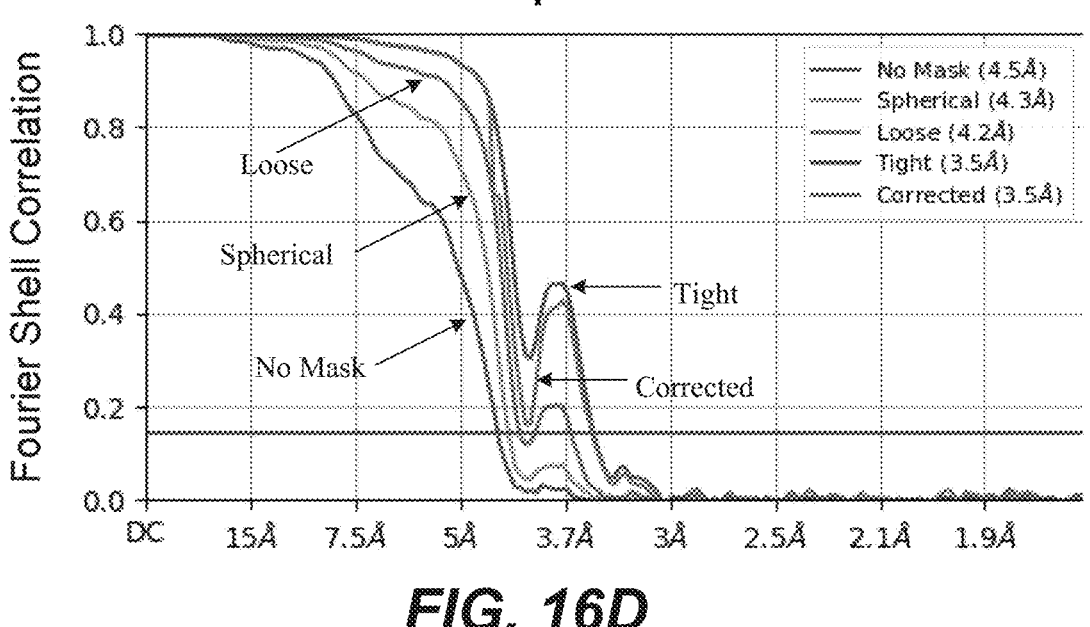
Figure 16E:
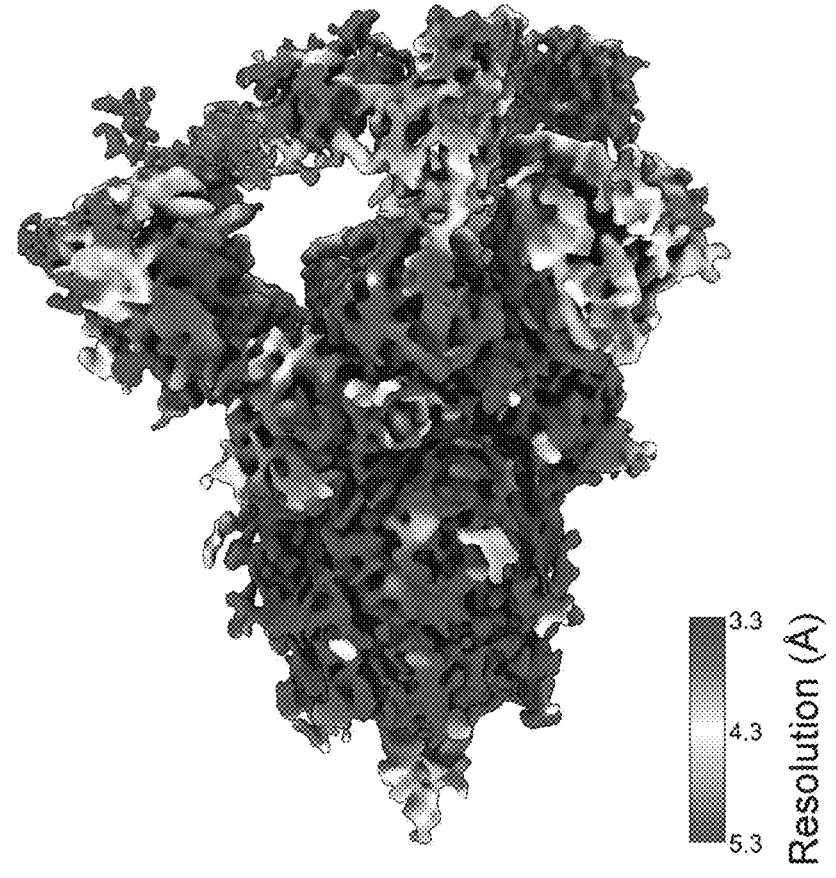
Figure 17A:
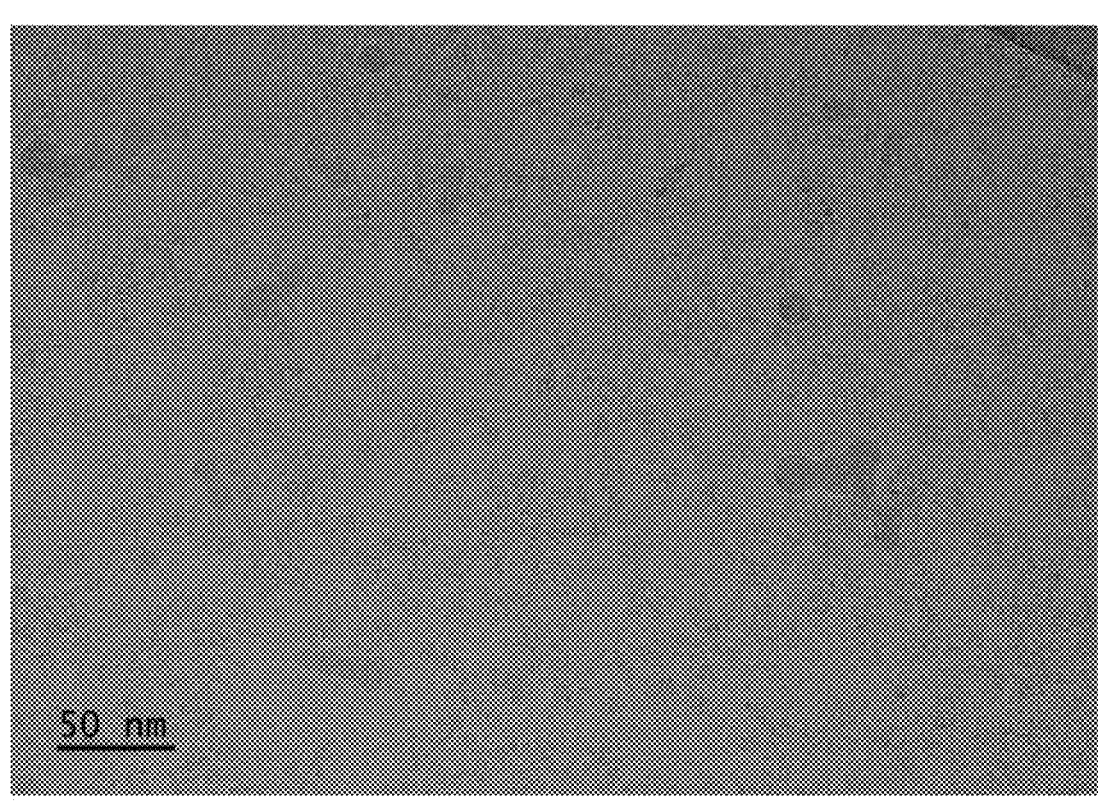
FIG. 17A-FIG. 17E show non-limiting exemplary data related to Cryo-EM data processing and validation for M8a-28 Fab in complex with SARS-CoV-2 WA1 spike.
Figure 17B:
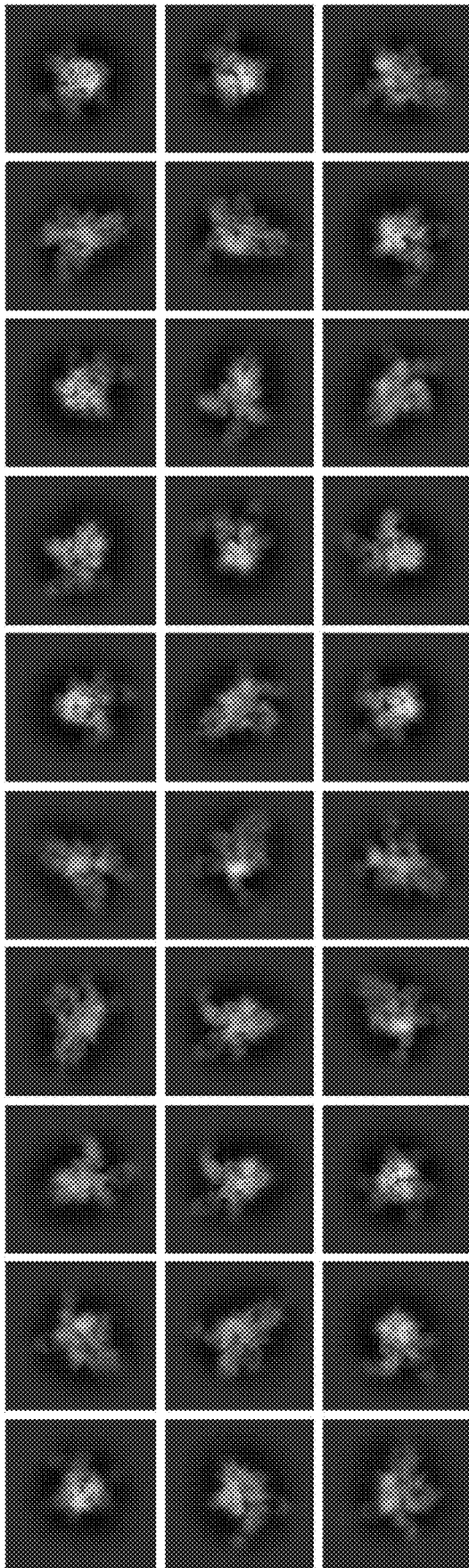
Figure 17C:
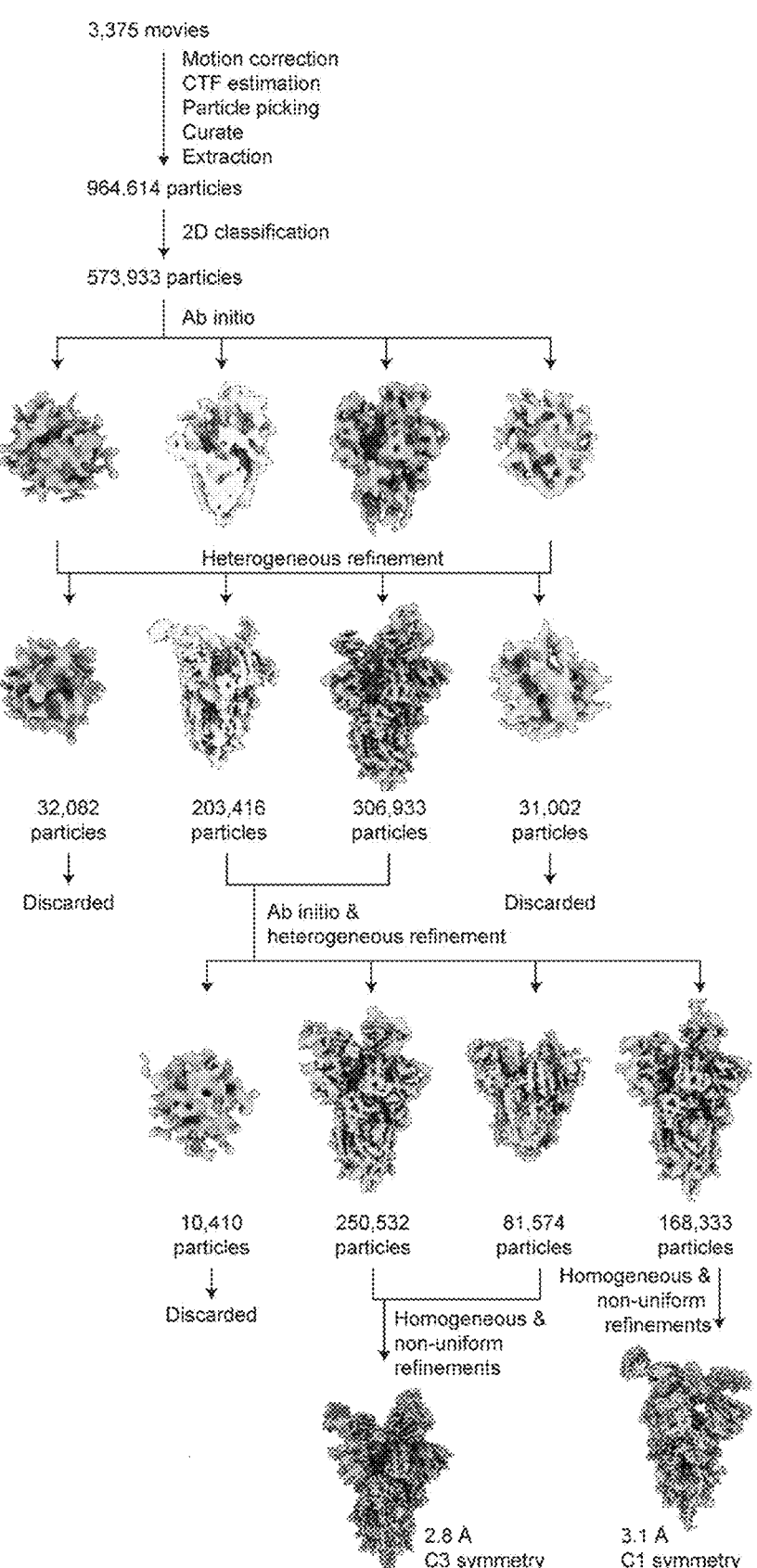
Figure 17D:
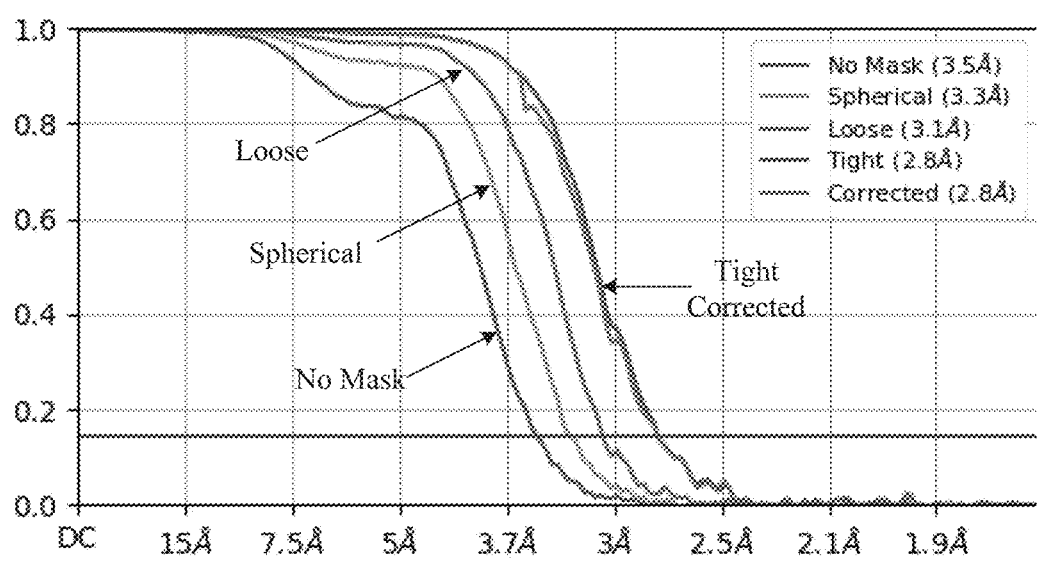
Figure 17D:
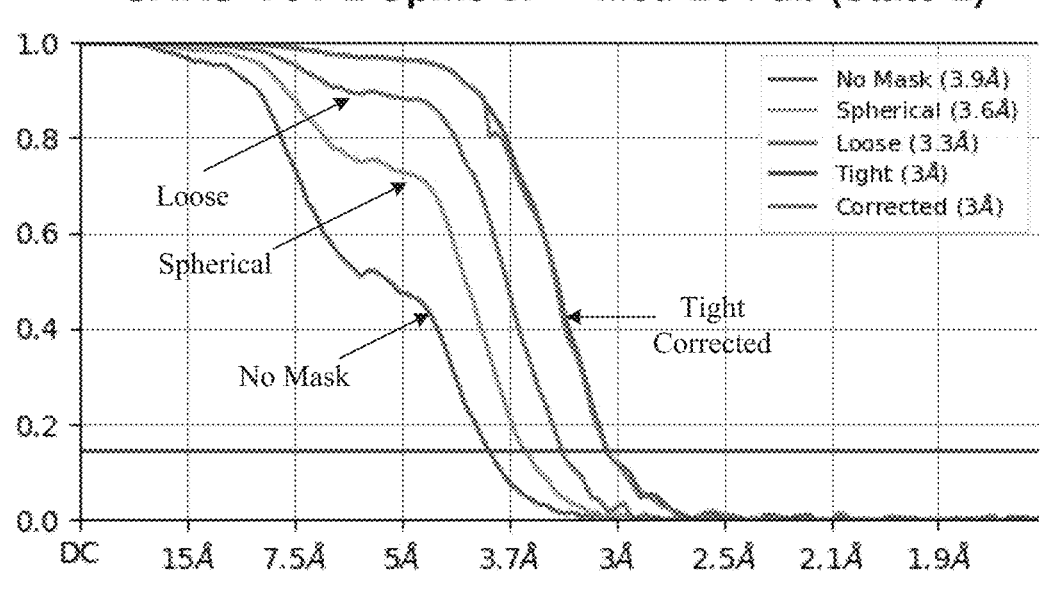
Figure 17E:
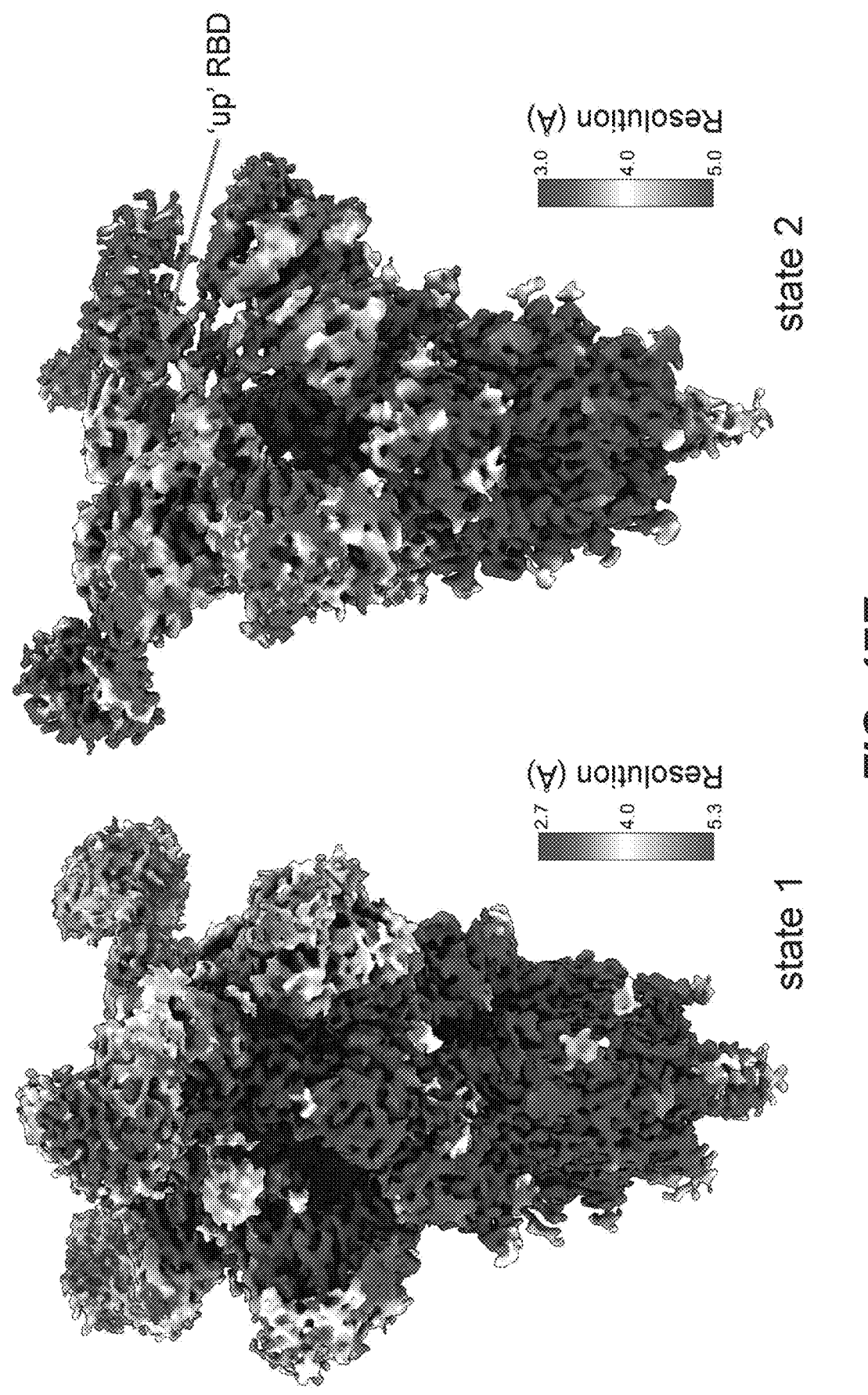
Figure 18A:
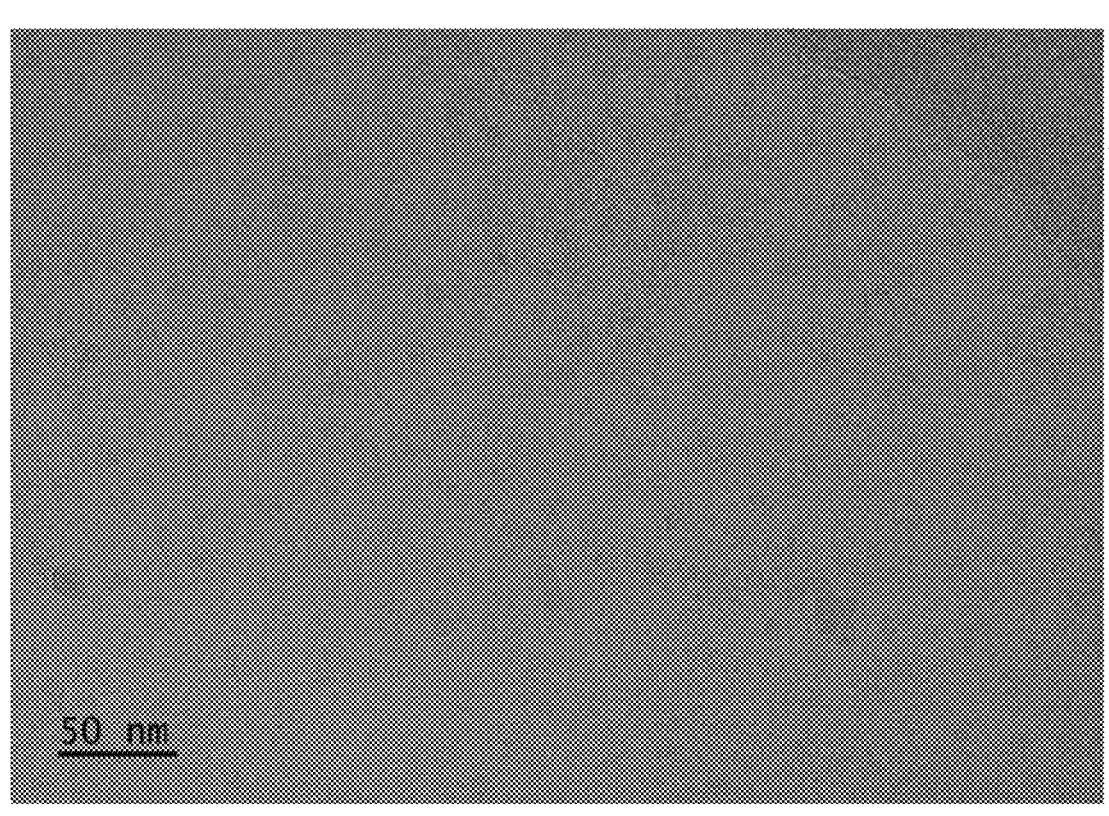
FIG. 18A-FIG. 18E show non-limiting exemplary data related to Cryo-EM data processing and validation for HSW-1 Fab in complex with SARS-CoV-2 WA1 spike.
Figure 18B:
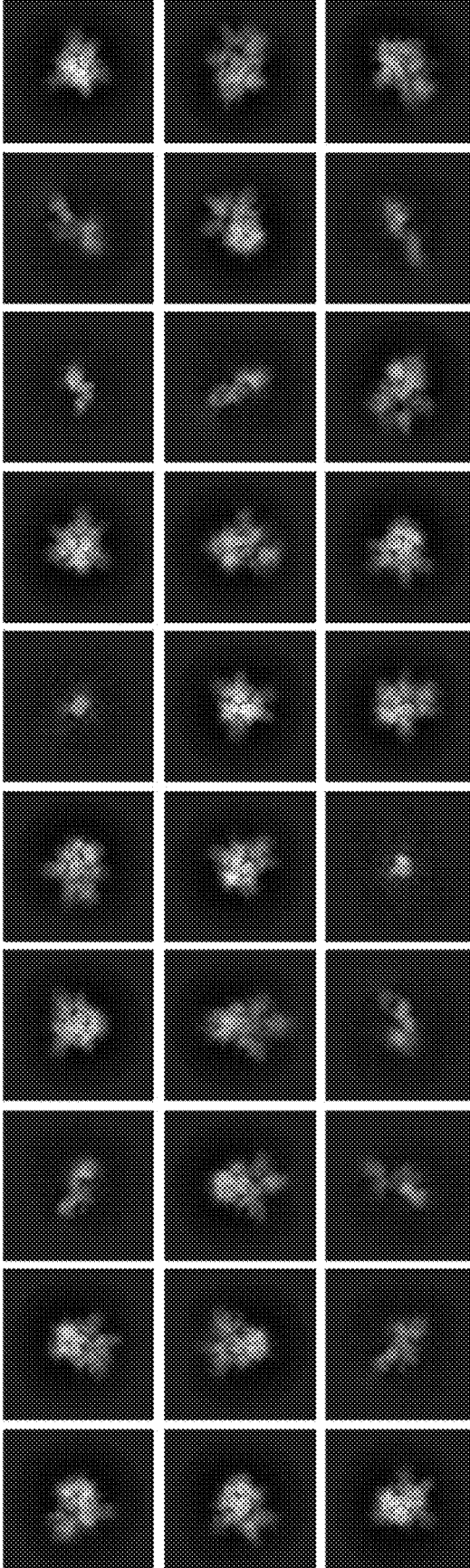
Figure 18C:
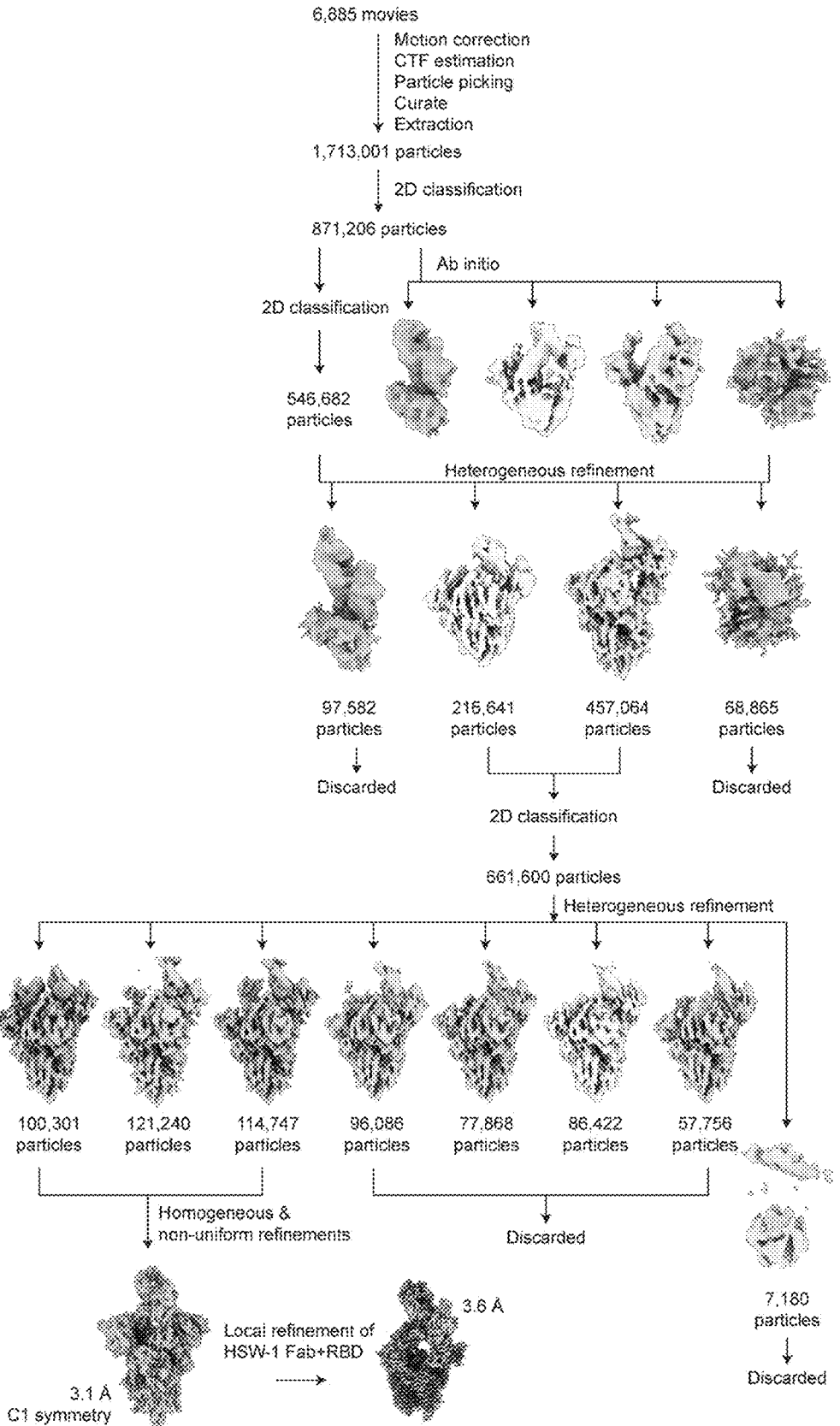
Figure 18D:
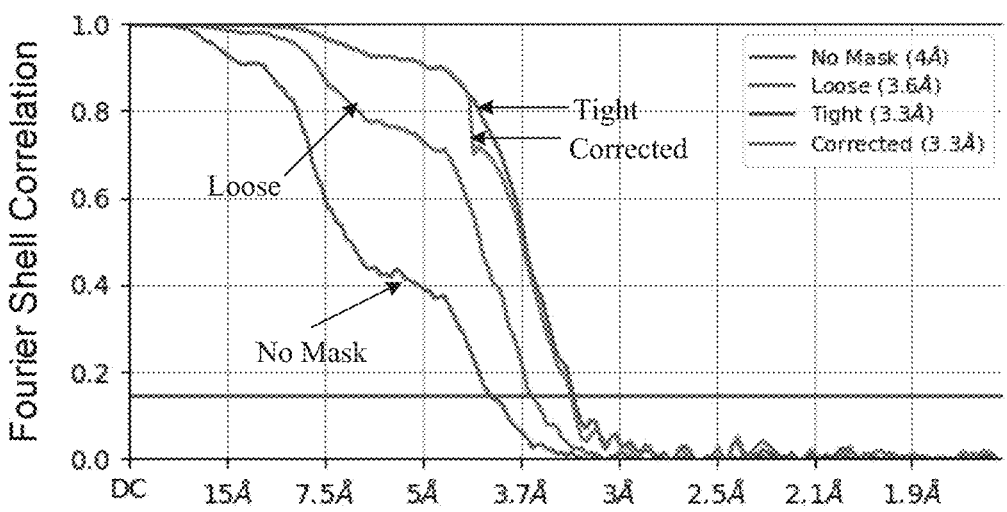
Figure 18E:
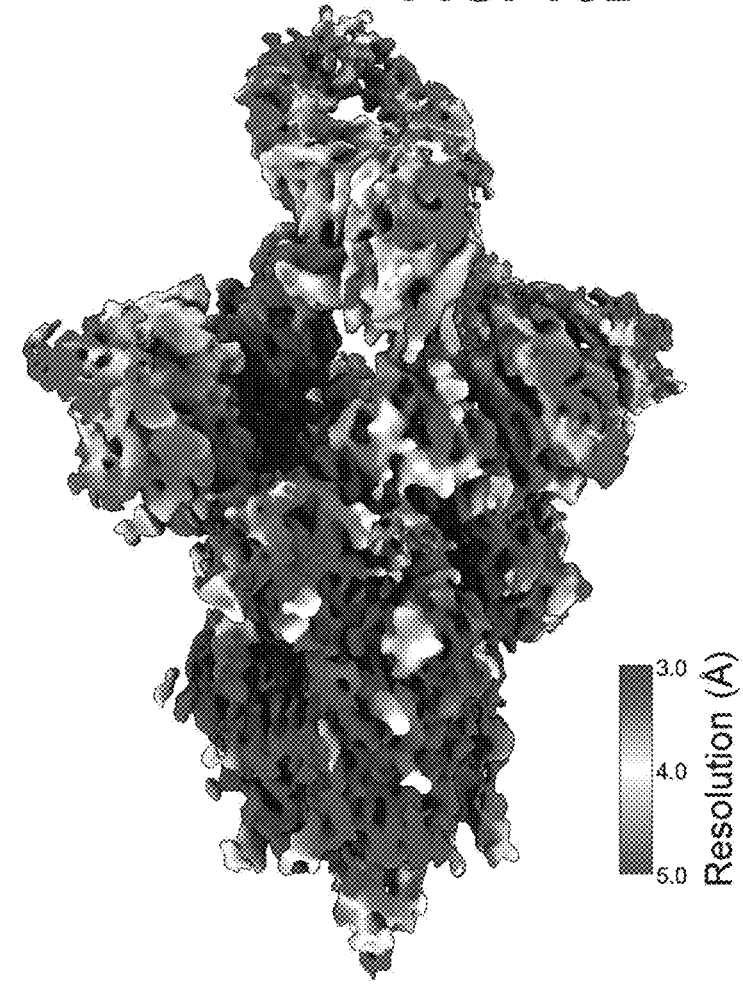
Figure 19A:
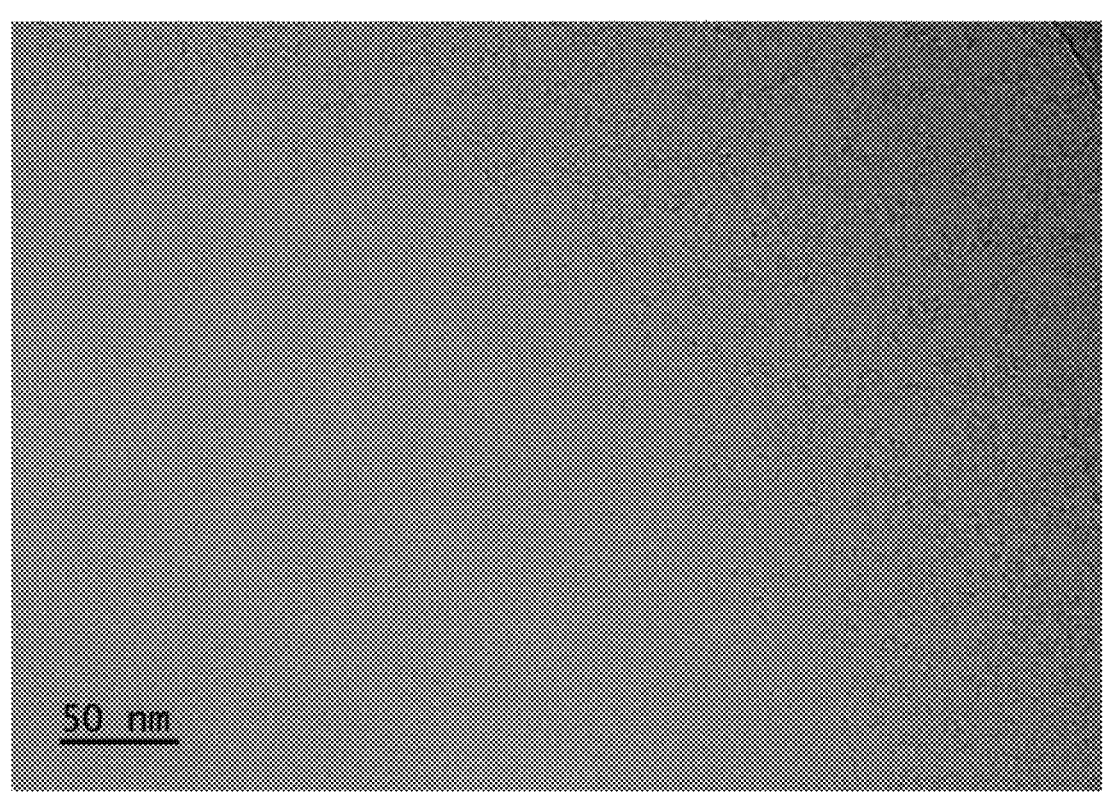
FIG. 19A-FIG. 19E show non-limiting exemplary data related to Cryo-EM data processing and validation for HSW-2 Fab in complex with SARS-CoV-2 WA1 spike.
Figure 19B:
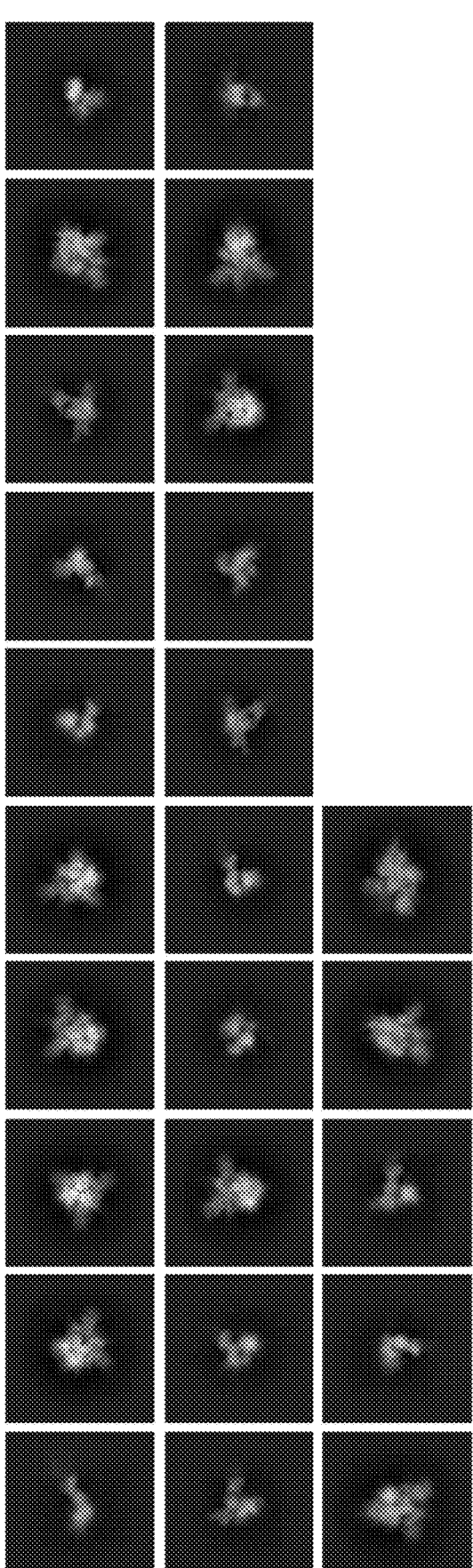
Figure 19B:
Figure 19C:
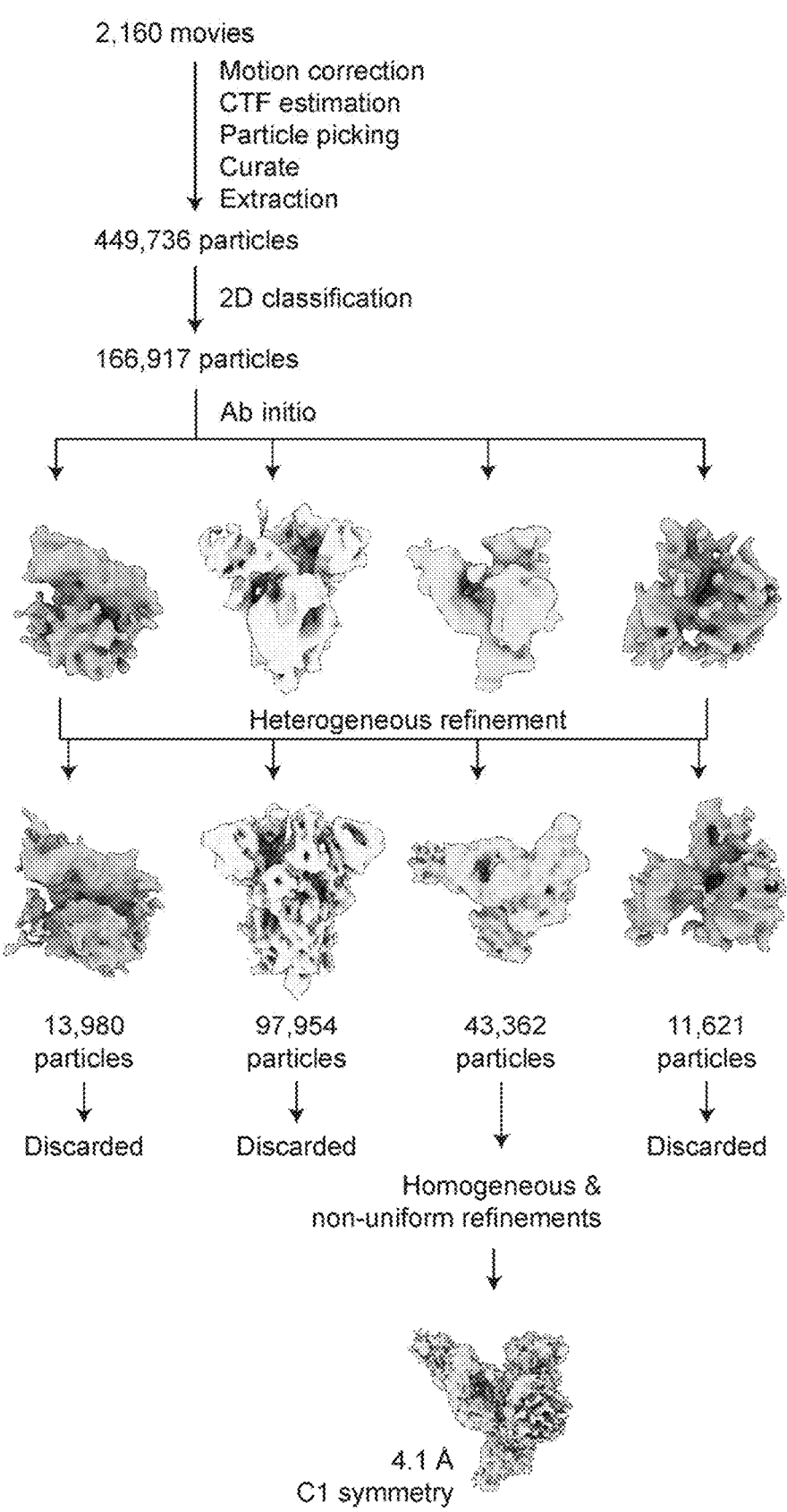
Figure 19D:
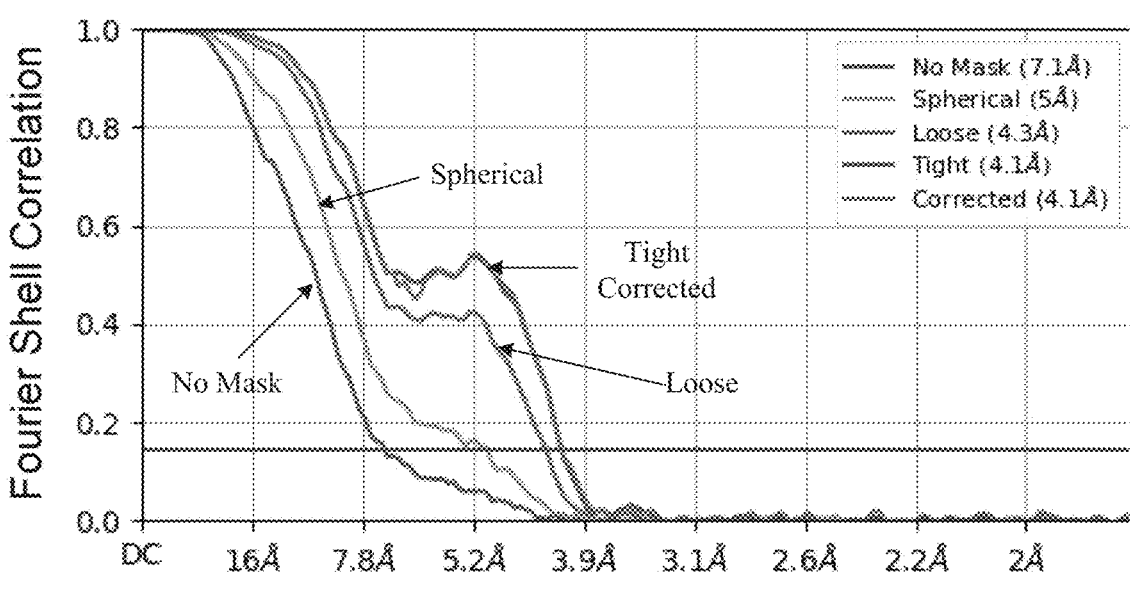
Figure 19E:
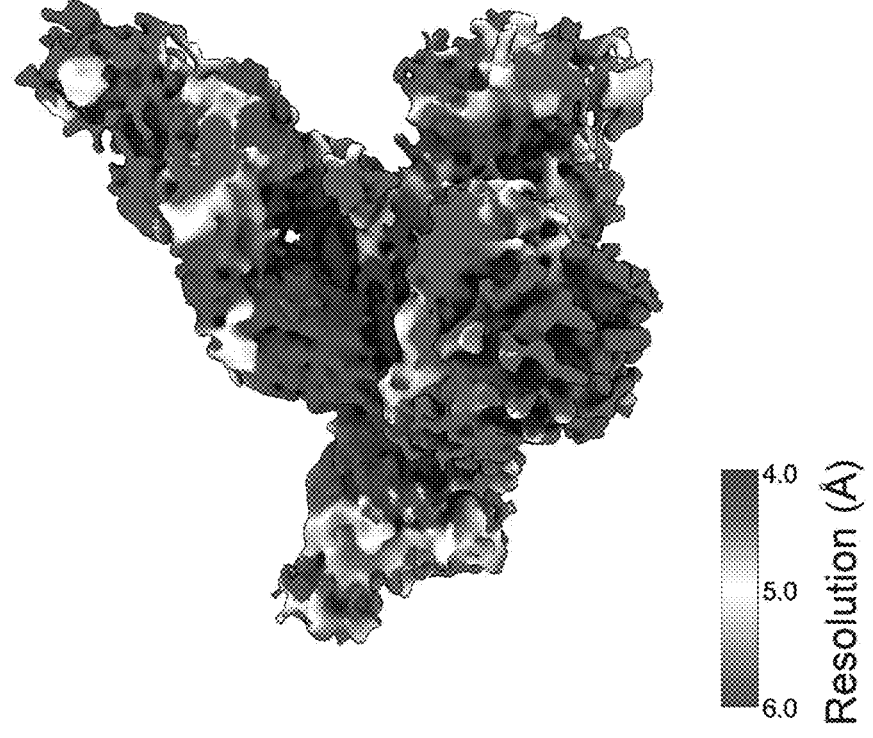

A 3.1 Å resolution M8a-3 Fab-spike complex structure revealed Fab $V_H$-$V_L$ interactions with 'up' RBDs using all six CDRs along with residues within the light chain framework region 2 and 3 (FWRL2 and FWRL3) (FIG. 3A, FIG. 4B, FIG. 12A-FIG. 12E, FIG. 20A). Consistent with the competition ELISA results (FIG. 11), comparison of the M8a-3 Fab-RBD interaction with previously-characterized representative anti-RBD antibodies in different structural classes showed overlap with the class 1 and class 4 RBD epitopes (FIG. 20A) and a binding footprint adjacent to that of ACE2 (FIG. 3A, FIG. 4A), similar to the human mAb C118, a class ¼ anti-RBD antibody that blocks ACE2 binding without substantially overlapping with the ACE2 binding footprint and that competes for binding to RBD with M8a-3 (FIG. 11). The M8a-3-spike structure showing recognition of a largely conserved region of the RBD (FIG. 4B) was consistent with ELISA and neutralization results demonstrating that M8a-3 neutralized and/or bound to most of the sarbecoviruses and the SARS-CoV-2 variants tested (FIG. 2A-FIG. 2B).

Figure 4A:
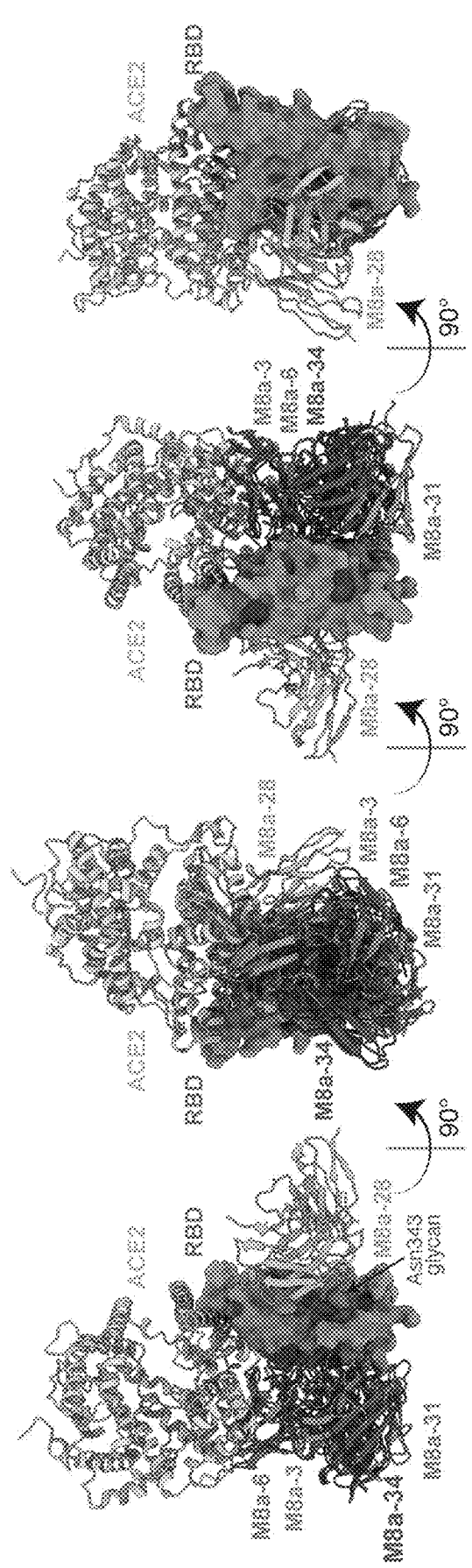
Figures 4B, 4C:
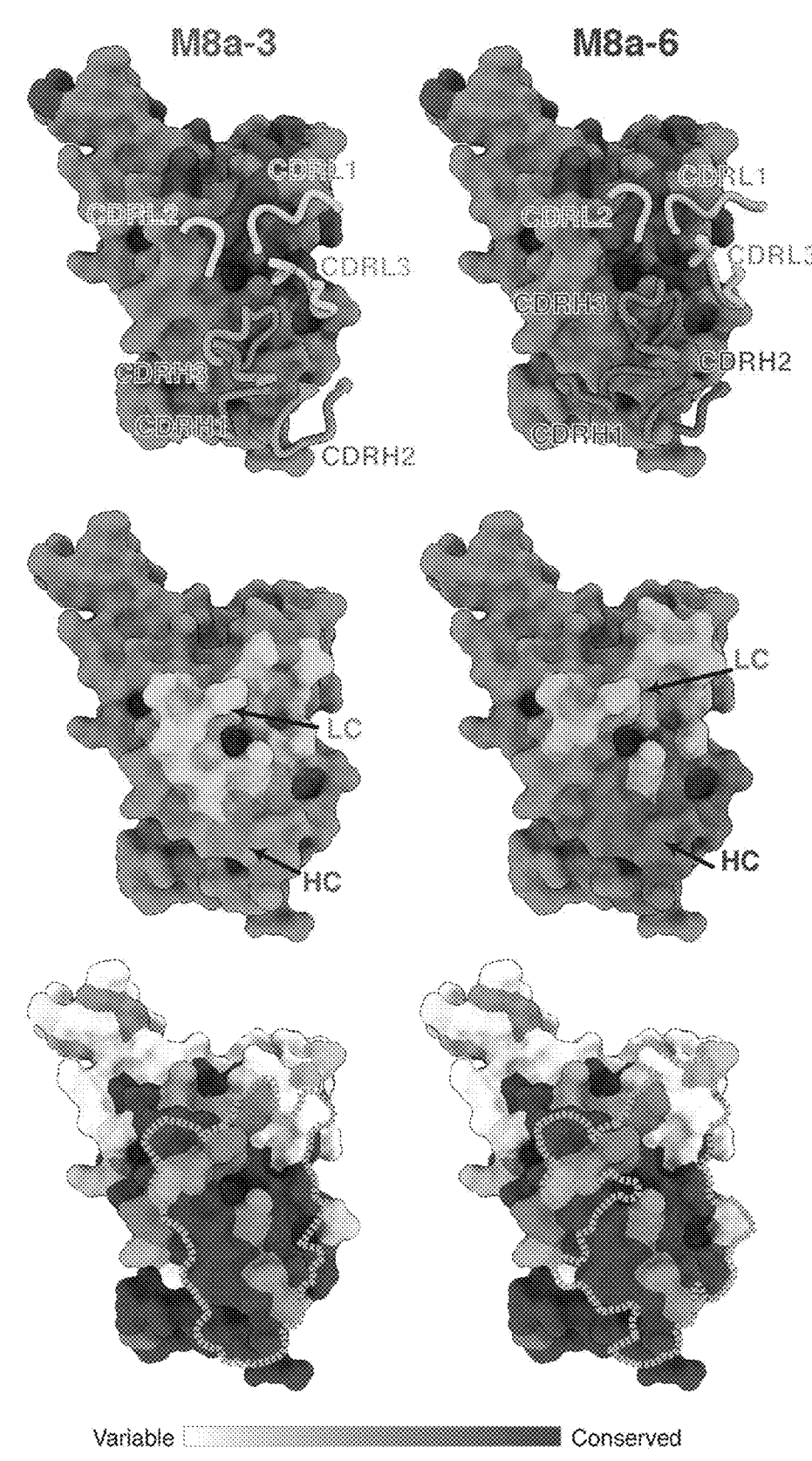
Figure 20A:
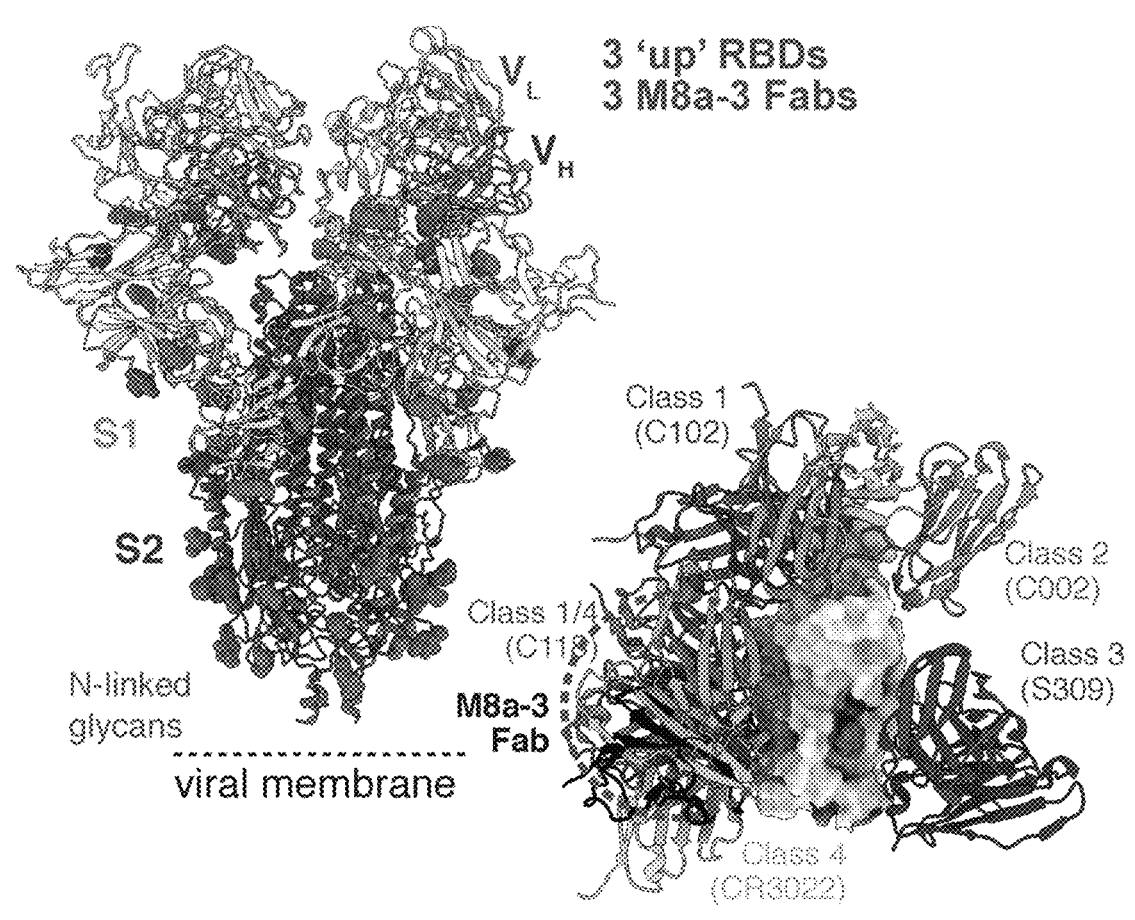
FIG. 20A-FIG. 20F depict non-limiting exemplary data related to mAbs isolated from mice immunized with mosaic-8 nanoparticles. Cartoon representations of single particle cryo-EM structures of Fab-spike trimer complexes are shown from the side (left) with a comparison of binding epitopes of the Fab with representative anti-RBD antibodies: class 1 (C102, PDB 7K8M), class 2 (C002, PDB 7K8T), class 3 (S309, PDB 7JX3), class 4 (CR3022, PDB 7LOP), and class ¼ (C118, PDB 7RKV)) aligned on an RBD in surface representation (right). Only $V_H$-$V_L$ domains are shown for each Fab. Fabs of interests (in black and circled with a dotted line) and the anti-RBD antibodies used for classification are aligned on a surface representation of the RBD. N-linked glycans are shown as small spheres.
Figure 20B:
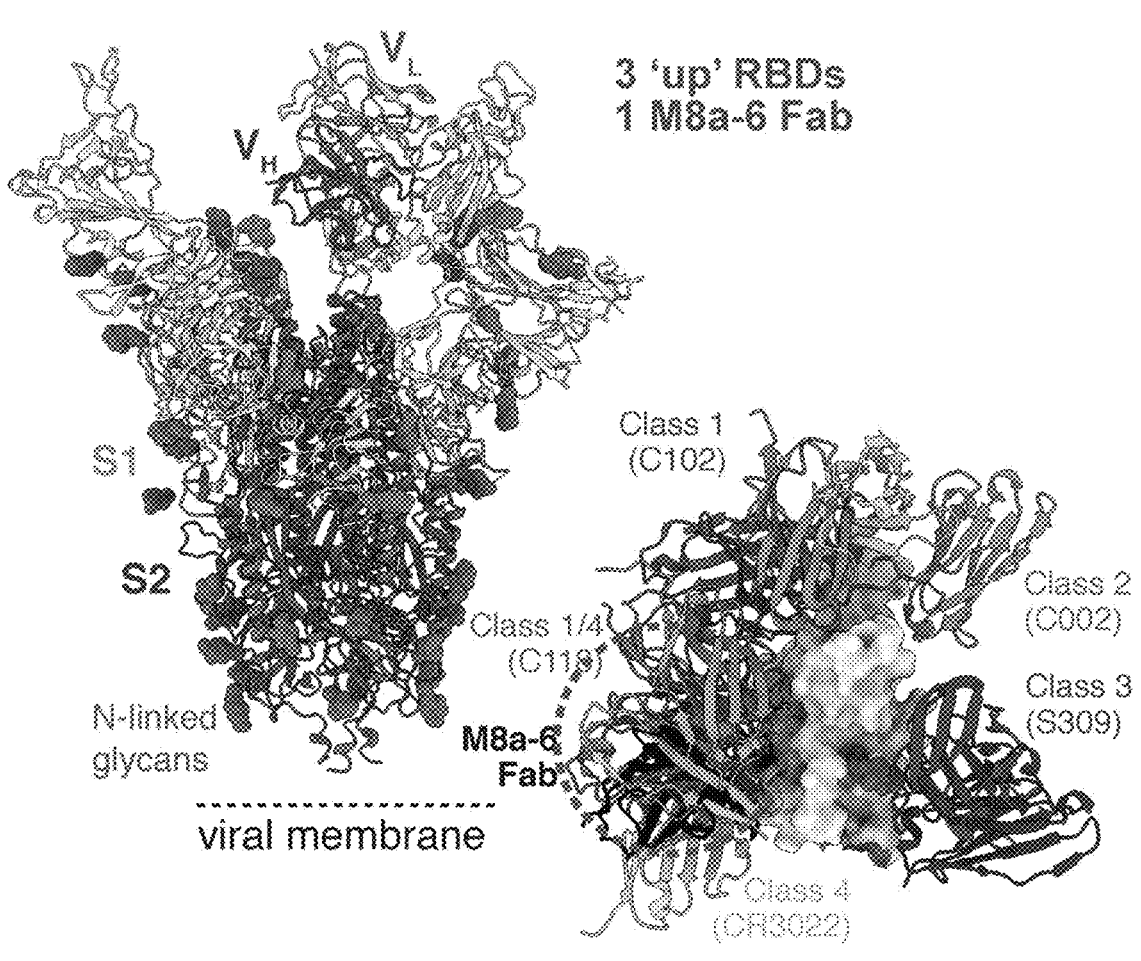
Figure 20C:
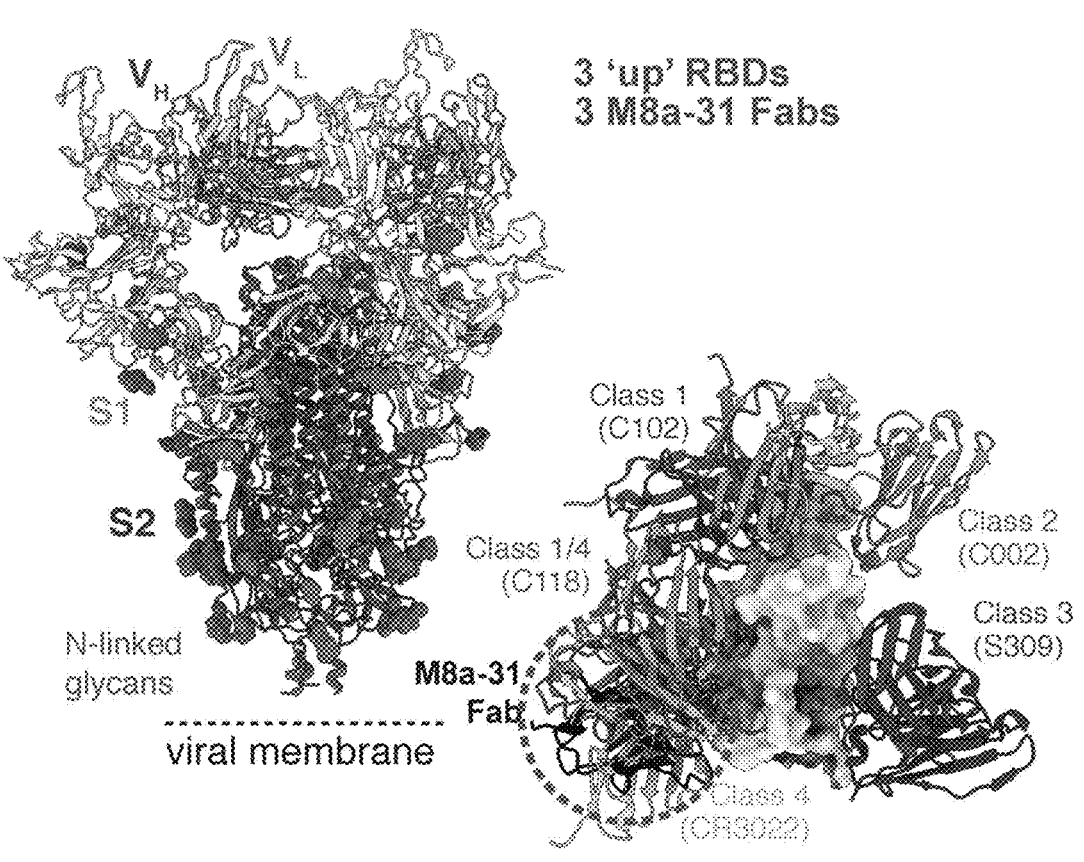
Figure 20D:
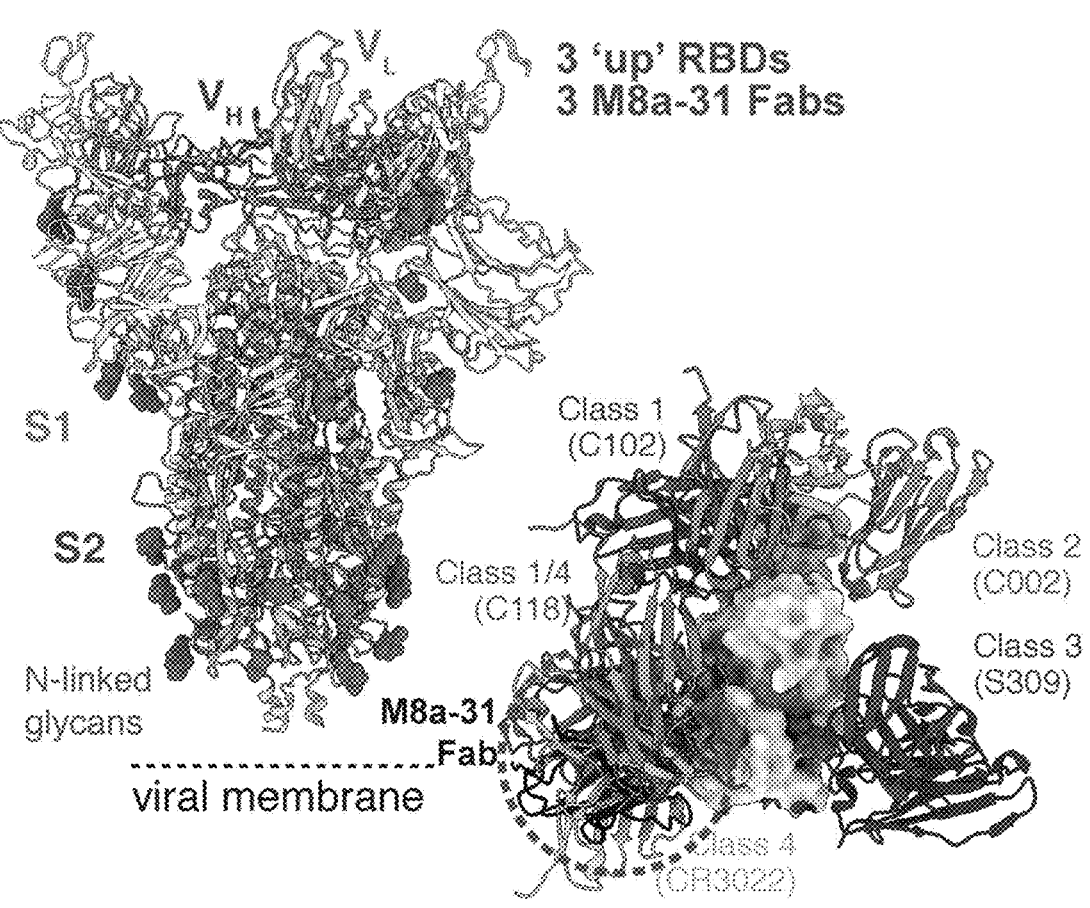

A 3.2 Å spike trimer structure complexes with the related, but mostly non-neutralizing M8a-6 mAb, showed three 'up" RBDs, but only one well-resolved Fab (FIG. 3B, FIG. 13A-FIG. 13E, FIG. 20B), which was modeled using information from a partially-refined 3.0 Å M8a-6 Fab-RBD crystal structure. The M8a-6 Fab shared a similar RBD binding epitope and approach angle as M8a-3 (FIG. 3A, FIG. 4A, FIG. 20B), interacting with the RBD using all six CDRs plus framework regions FWRH2, FWRL2, and FWRL3 (FIG. 4C). Furthermore, M8a-6 also recognized a similar epitope as the C118 and M8a-3 mAbs, involving mostly conserved RBD residues (FIG. 4C, FIG. 20B). Despite sharing high sequence identity and similar binding epitopes on SARS-CoV-2 RBD with M8a-3, M8a-6 was non-neutralizing against SARS-CoV-2 and only weakly neutralizing against SHC014, whereas M8a-3 neutralized SARS-CoV-2 D614G with a 0.18 µg/mL IC$_{50}$ (FIG. 2B). These different neutralization profiles likely result from a weaker interaction of M8a-6 as compared with M8a-3 with CoV spikes, as demonstrated by incomplete binding of Fabs in the M8a-6-spike complex cryo-EM structure and the lack of competition of M8a-6 IgG with any of the biotinylated IgGs, including C118, with known epitopes (FIG. 11).

Figure 4D:
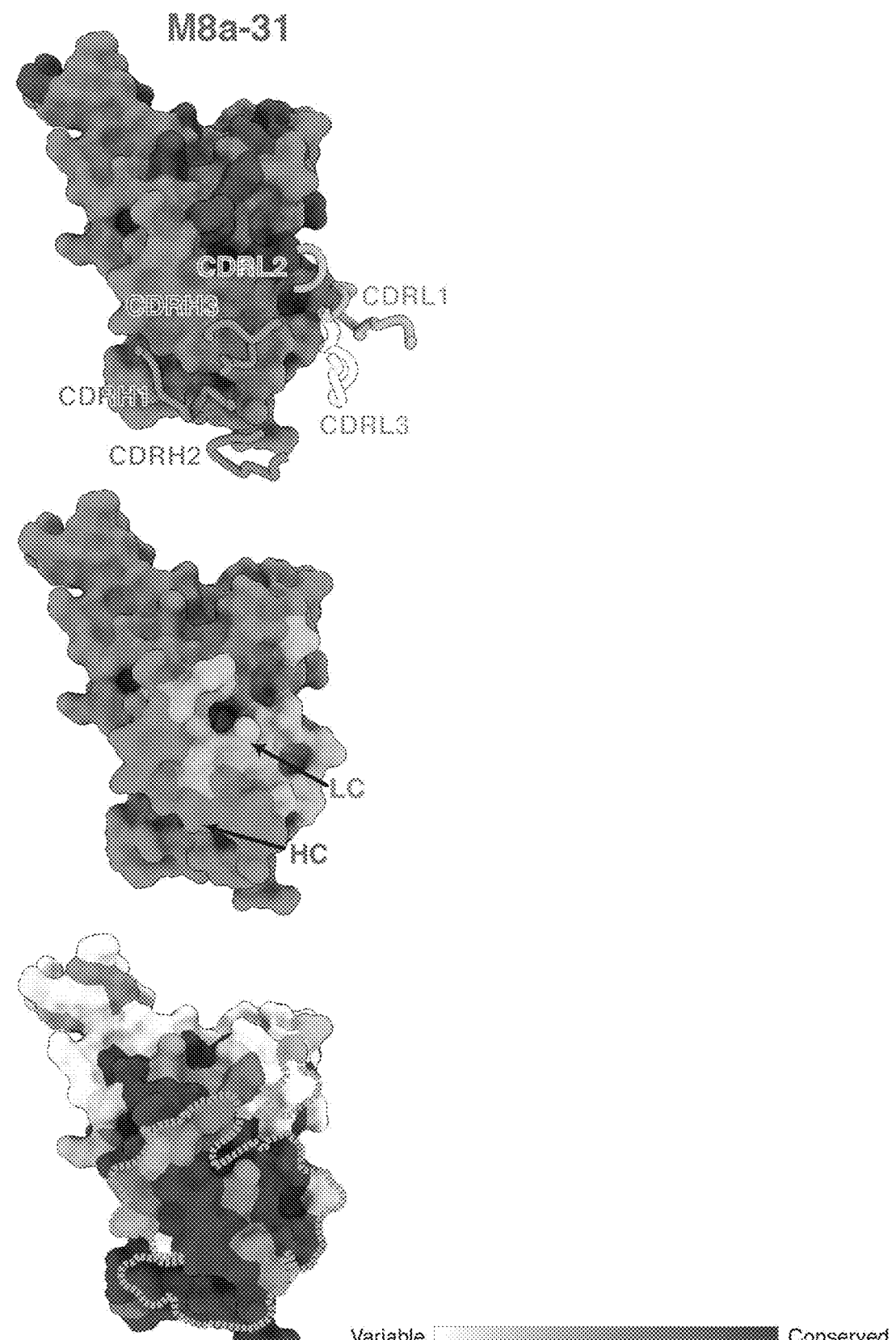

In common with M8a-3, M8a-31 exhibited broadly cross-reactive binding and neutralization across SARS-CoV-2 variants and other sarbecoviruses (FIG. 2A-FIG. 2B) and competed with class ¼ and class 4 anti-RBD antibodies (FIG. 11). Single-particle cryo-EM structures were determined for M8a-31 Fab bound to SARS-CoV-2 WA1 (FIG. 3C, FIG. 14A-FIG. 14E) and to Omicron BA.1 (FIG. 3D, FIG. 15A-FIG. 15E) spike trimers at resolutions of 2.9 Å and 3.5 Å, respectively. In both structures, three M8a-31 Fabs interacted with 'up' RBDs (FIG. 3C-FIG. 3D, FIG. 20C-FIG. 20D). Despite the 15 substitutions in the Omicron BA.1 RBD compared with the WA1 RBD, the epitope and binding pose of the M8a-31 Fab in both structures were similar (FIG. 20C-FIG. 20D) with a root mean square deviation (RMSD) of 1.0 Å (calculated using all 1,267 resolved Ca atoms in each Fab-spike protomer structure). The binding of M8a-31 Fab to both the SARS-CoV-2 WA1 and Omicron BA.1 RBDs was mainly stabilized through interactions with all CDRs except for CDRL3 along with FWRH1, FWRH2, FWRL2, and FWRL3 (FIG. 4D). The M8a-31 epitope overlapped with class 4 anti-RBD antibodies, but was shifted towards the ACE2 binding site compared with the CR3022 class 4 mAb (FIG. 20C-FIG. 20D), consistent with its competition with the C118 class ¼ mAb (FIG. 11). The mainly conserved nature of the M8a-31 epitope (FIG. 4D) is consistent with its broadly cross-reactive binding and neutralization properties (FIG. 2A-FIG. 2B).

Figure 20E:
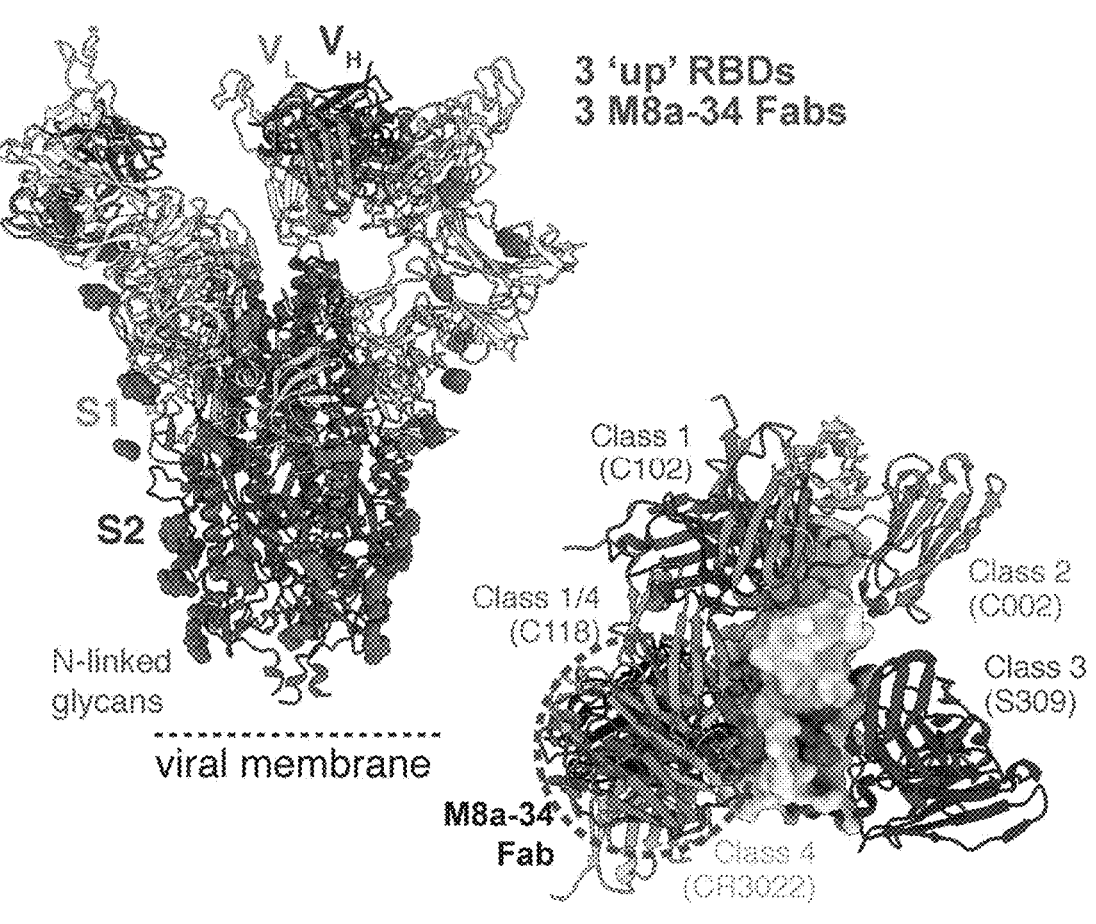

In common with M8a-3 and M8a-31, M8a-34 bound and neutralized most sarbecoviruses across different clades and SARS-CoV-2 variants (FIG. 2A-FIG. 2B) and exhibited a similar competition profile (FIG. 11). To map its epitope, a single-particle cryo-EM structure of M8a-34 Fab bound to the SARS-CoV-2 WA1 spike trimer at 3.5 Å resolution was determined (FIG. 3E, FIG. 16A-FIG. 16E), revealing interactions of three Fabs with three 'up' RBDs (FIG. 3E, FIG. 20E) that were modeled using an M8a-34 Fab-RBD crystal structure (Table 3). M8a-34 Fab interacted with the RBD through all three CDRHs as well as CDRL1 and CDRL3 (FIG. 4E). The M8a-34 Fab epitope was similar to epitopes of other class 1%4 mAbs including M8a-3, M8a-6 and M8a-31, which overlapped with the binding epitopes of CR3022 (class 4) and C118 (class ¼) (FIG. 4A, FIG. 20E), again consistent with its broad binding and neutralizing properties (FIG. 2A-FIG. 2B) and competition ELISA results (FIG. 11).

Figure 20F:
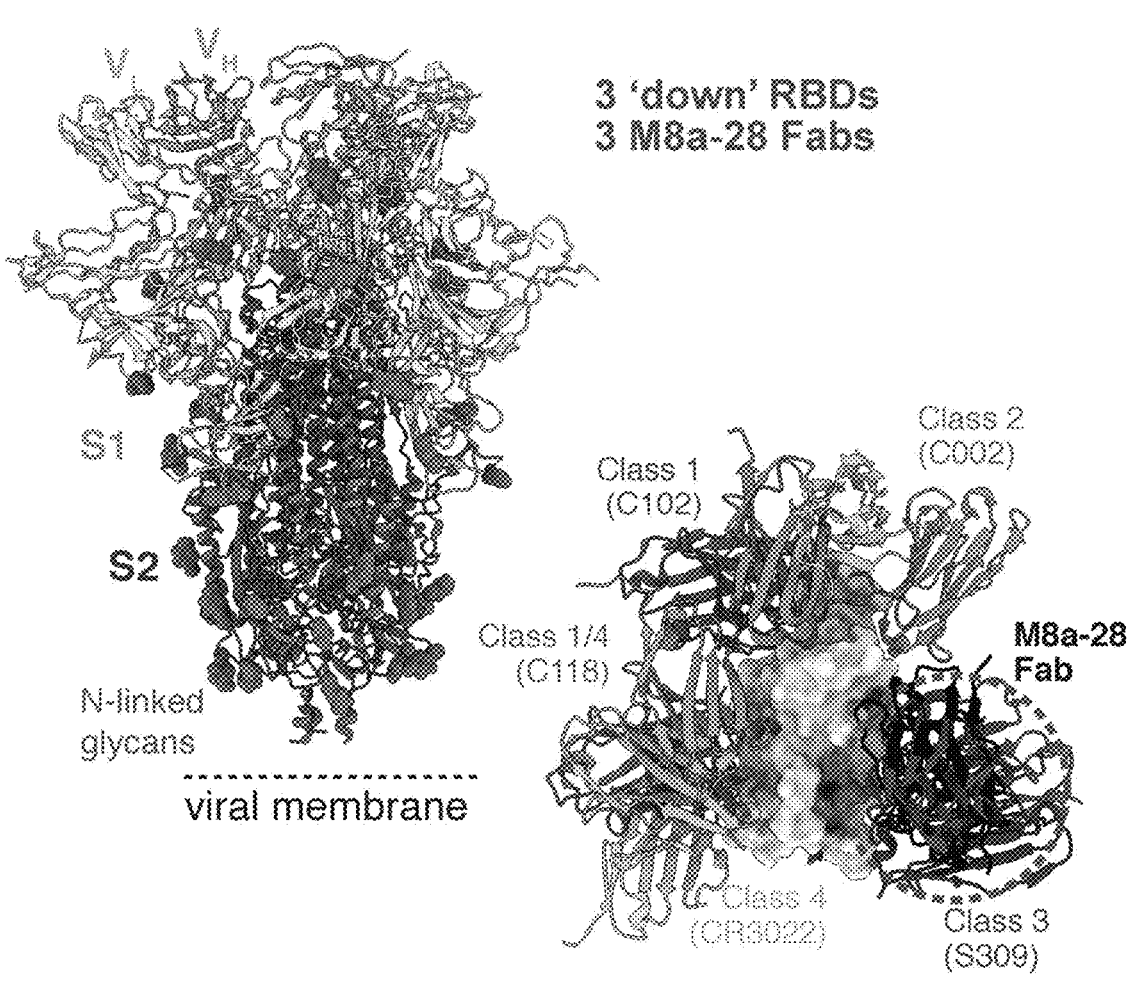

The M8a-28 mAb showed the lowest degree of cross-reactive RBD binding (FIG. 2A). M8a-28 mapped to the class 3 epitope instead of the more conserved class ¼ and class 4 epitopes (FIG. 11), and except for M8a-6 (a weakly/ non-neutralizing mAb), it showed the lowest levels of cross-reactive sarbecovirus neutralization of the five mAbs isolated from mosaic-8 immunized mice (FIG. 2B). Single-particle cryo-EM structures of the M8a-28 Fab in complex with the SARS-CoV-2 spike were determined in two conformational states: a 2.8 Å structure with each of three Fabs binding to a 'down' RBD (FIG. 3F) and a 3.1 Å structure with two Fabs bound to adjacent 'down' RBDs and a third Fab at lower occupancy bound to a flexible 'up' RBD (FIG. 17A-FIG. 17E). The Fab-RBD interaction was mediated by all six CDRs, plus FWRH3 and FWRL1 (FIG. 4F). Notably, the M8a-28 Fab approached the RBD from the opposite direction compared with Fabs from the other M8a mAbs (FIG. 4A, FIG. 20F), interacting with more variable RBD regions (FIG. 4F) that overlapped with the epitope of the class 3 anti-RBD mAb, S309 (FIG. 20F). Although M8a-28 potently neutralized SARS-CoV-2 WA1 D614G, Beta, Delta, Omicron BA.1 and BA.2, it was only weakly neutralizing or non-neutralizing against other sarbecoviruses (FIG. 2B), consistent with its epitope spanning more variable RBD residues than epitopes of class 4 and class ¼ anti-RBD mAbs.

Figure 5A:
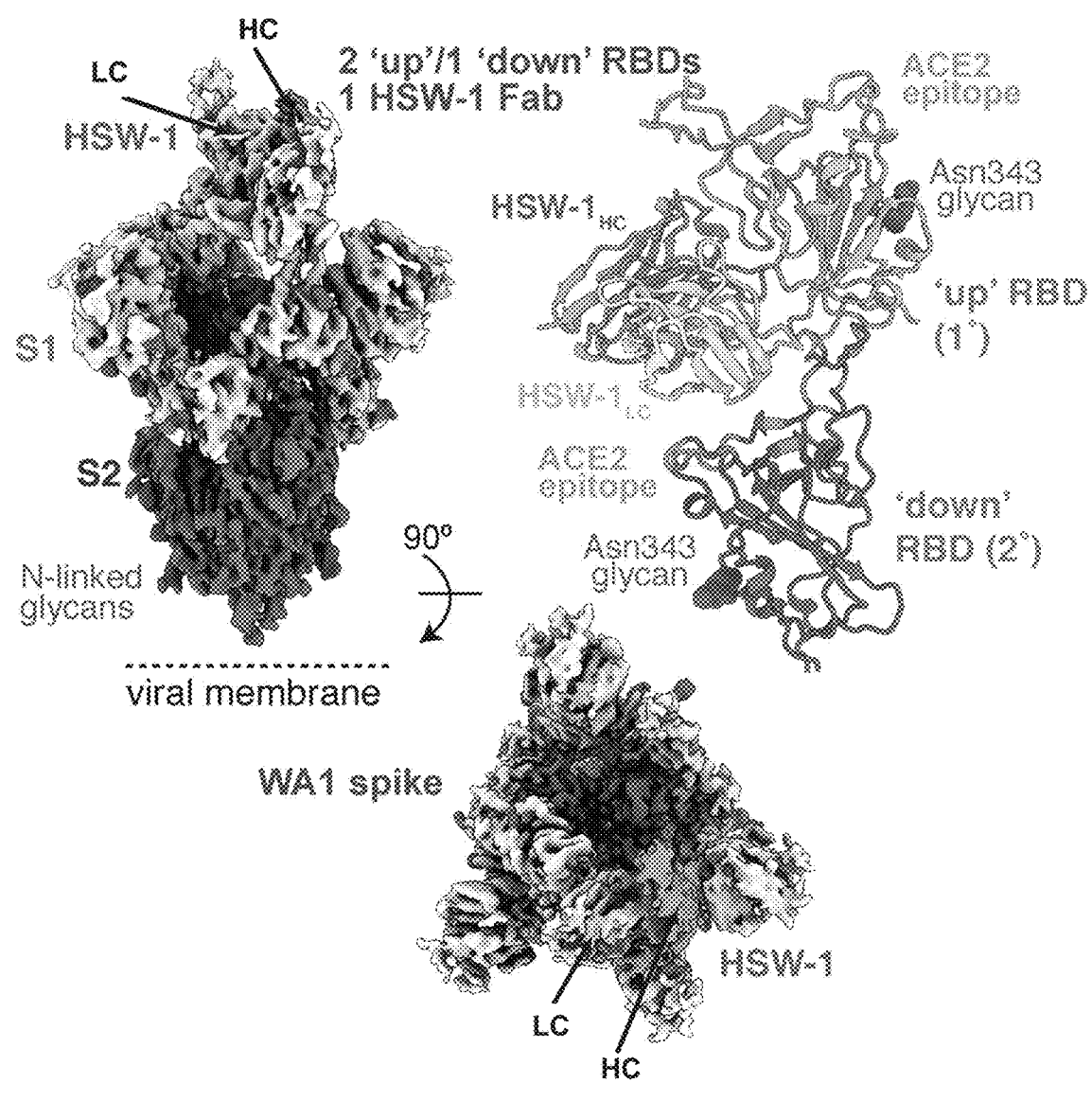
FIG. 5A-FIG. 5G depict non-limiting exemplary cartoons showing mAbs isolated from mice immunized with homotypic SARS-CoV-2 nanoparticles that target conserved RBD epitopes.
Figure 5B:
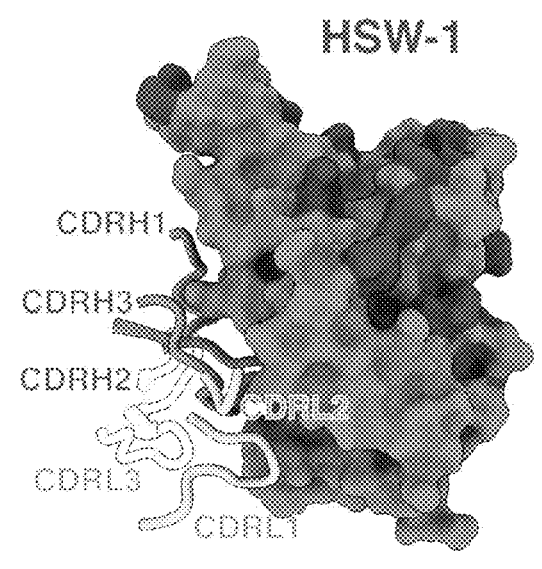
Figure 5B:
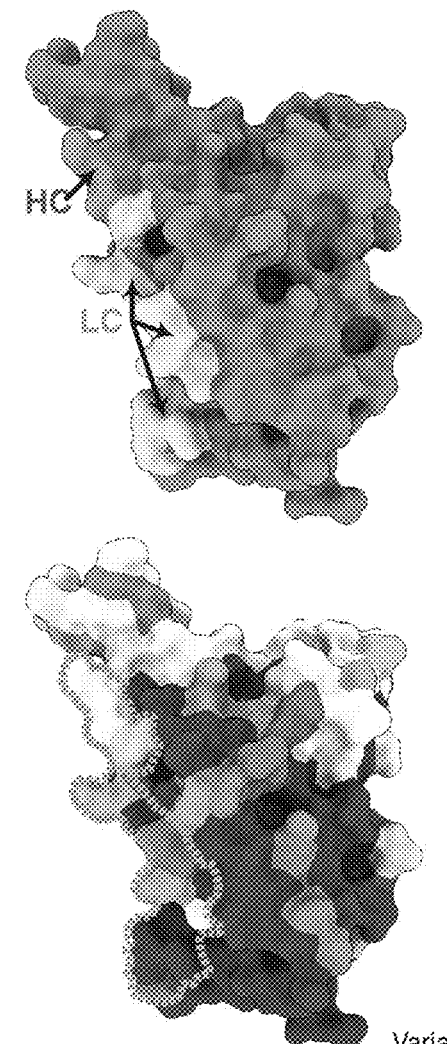
Figure 21A:
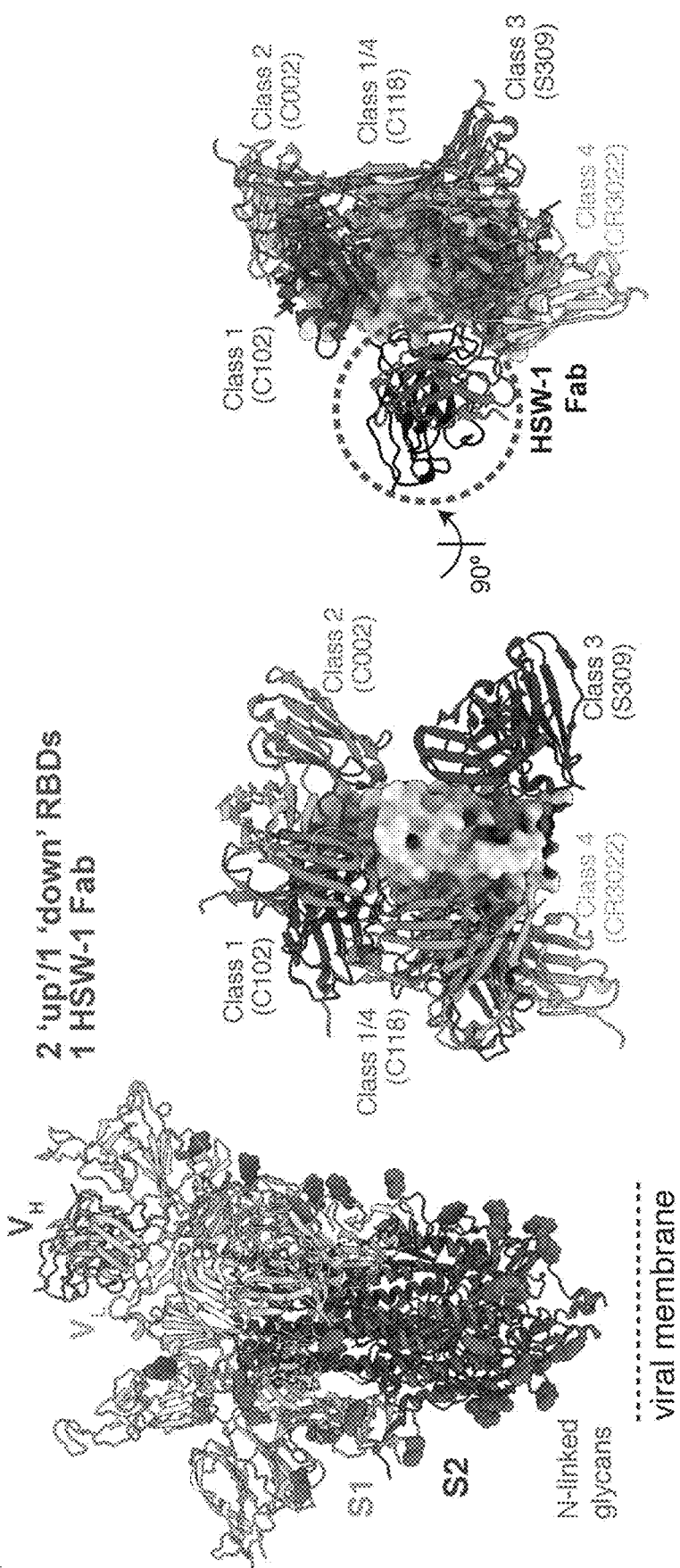
FIG. 21A-FIG. 21B depict non-limiting exemplary data related to mAbs isolated from mice immunized with homo-typic nanoparticles. Cartoon representations of single par-ticle cryo-EM structures of Fab-spike trimer complexes are shown from the side (left) with a comparison of binding epitopes of the Fab with representative anti-RBD antibodies: class 1 (C102, PDB 7K8M), class 2 (C002, PDB 7K8T), class 3 (5309, PDB 7JX3), class 4 (CR3022, PDB 7LOP) and class ¼ (C118, PDB 7RKV)) aligned on an RBD in surface representation (middle and right). Only $V_H$-$V_L$ domains are shown for each Fab. Fabs of interests (in black and circled with a dotted line) and the anti-RBD antibodies used for classification are aligned on a surface representation of the RBD. N-linked glycans are shown as small spheres.

The HSW-1 and HSW-2 mAbs, isolated from homotypic SARS-CoV-2 RBD nanoparticle-immunized mice, were each isolated from B cells secreting IgGs that bound to all four RBDs used during screening. Accordingly, they exhibited broad cross-reactive binding to sarbecovirus RBDs by ELISA, with HSW-2 binding to all tested RBDs except for SARS-CoV RBD and HSW-1 also not interacting detectably with SARS-CoV-1 RBD and three other RBDs from clade 2 and 3 sarbecoviruses (FIG. 2A). Despite broad recognition of sarbecovirus RBDs, the HSW mAbs, especially HSW-2, exhibited overall weaker neutralization potencies across the sarbecoviruses tested, with all $IC_{50}$ values being above 10 μg/mL (FIG. 2B). To compare recognition properties with the M8a Fabs, a single-particle cryo-EM structure of HSW-1 bound to SARS-CoV-2 WA1 spike trimer at 3.1 Å resolution was determined, revealing a single well-ordered Fab bound to a trimer with two 'up' RBDs and one 'down' RBD (FIG. 5A, FIG. 18A-FIG. 18E, FIG. 21A). In common with the M8a-6 mAb, for which the Fab-spike structure also revealed only a single bound Fab per trimer (FIG. 3B), HSW-1 showed no detectable competition with anti-RBD mAbs with known epitopes (FIG. 11). The bound HSW-1 Fab interacted with two RBDs: one 'up' RBD (1° RBD) and the adjacent 'down' RBD (2° RBD) (FIG. 5A, FIG. 21A). Interactions between the HSW-1 Fab and 1° RBD were mediated by both the heavy chain through FWRH1, CDRH1 and CDRH3, and the light chain through CDRL1, CDRL2, CDRL3 and FWRL2 (FIG. 5A-FIG. 5B). The interactions between HSW-1 and the 2° RBD were mediated by the HSW-1 light chain (FIG. 5A). Structural comparisons showed the epitope of HSW-1 overlapped somewhat with the binding epitopes of C118 (class ¼) and CR3022 (class 4) and included mostly conserved residues (FIG. 21A).

Figure 21B:
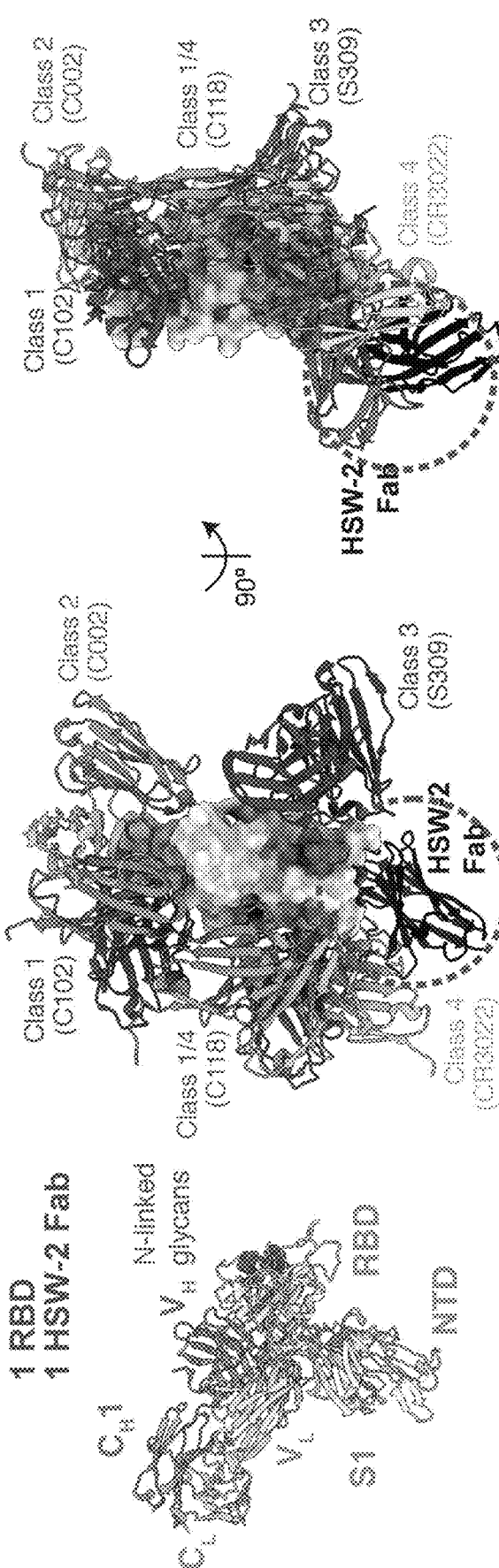

Next, single-particle cryo-EM was used to investigate the interactions of HSW-2 with spike trimer. Two main populations of particles were observed. One population of unliganded intact spike trimer, and a second HSW-2 Fab complexed with spike S1 domain protomers (FIG. 19A-FIG. 19E). From the second population, an EM reconstruction at 4.1 Å resolution of the HSW-2 Fab bound to the S1 domain of the SARS-CoV-2 WA1 spike was obtained (FIG. 5C, FIG. 21B) using a crystal structure of an HSW-2 Fab-RBD complex (Table 3) to derive detailed interactions. HSW-2 used its six CDRs plus FWRH2, FWRL1, FWRL2 and FWRL3 to recognize the bottom of the RBD (FIG. 5D-FIG.

Figure 5C:
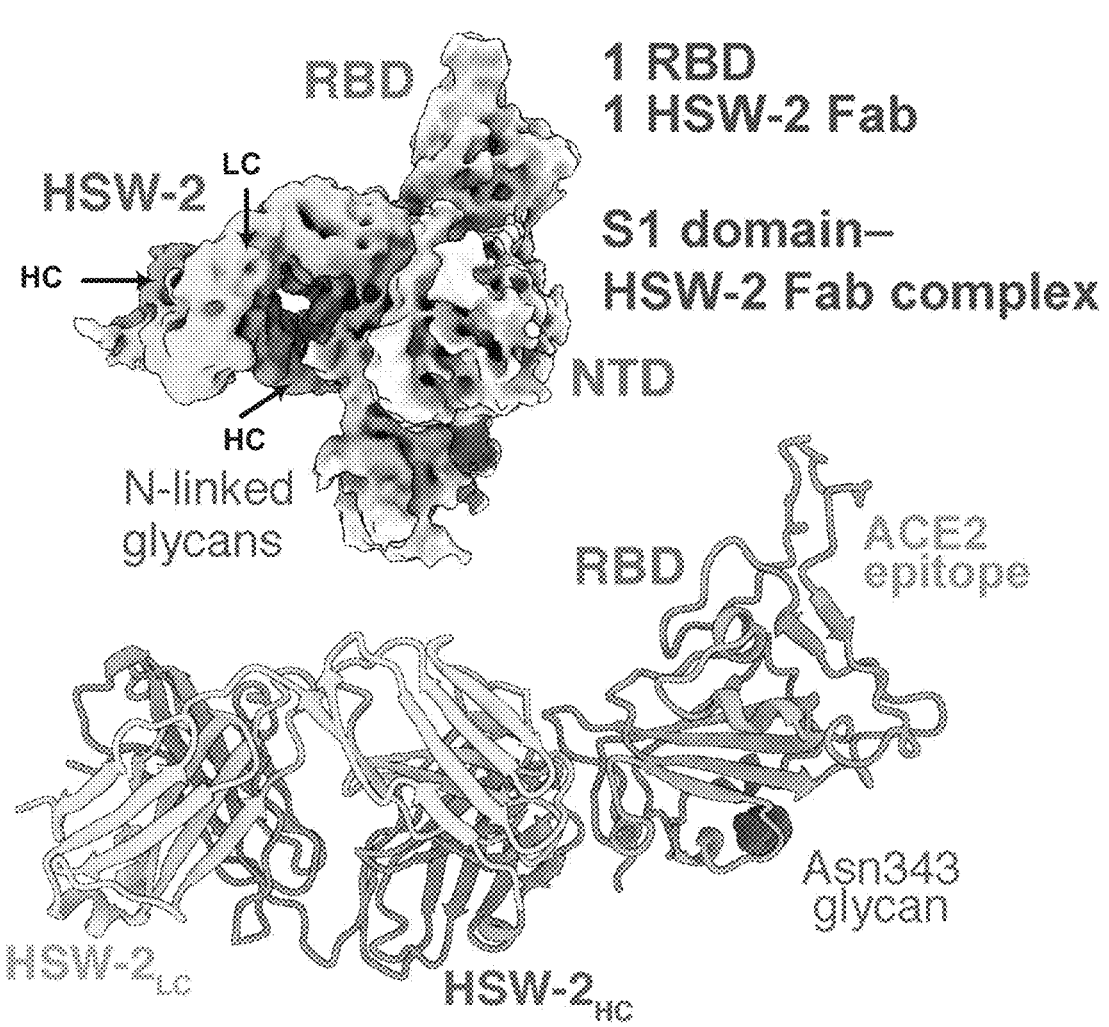

5E), consistent with its competition with the class 4 anti-RBD antibody CR3022 (FIG. 11). Although their binding poses differed, the HSW-2 epitope overlapped with the largely-conserved epitope of the class 4 mAb, CR3022 (FIG. 21B), a mAb isolated from a SARS-CoV patient that also induces dissociation of the SARS-CoV-2 spike trimer. Although S1 shedding resulting from mAb binding has been suggested as a possible neutralization mechanism for CR3022 and other class 4 anti-RBD mAbs, HSW-2 was largely non-neutralizing (FIG. 2B). To determine whether HSW-2 was raised against an RBD epitope that is inaccessible in an intact spike trimer, the RBD portion of the HSW-2 Fab-RBD structure was aligned to RBDs from a spike trimer structure with all 'up' RBDs and to a spike structure with all 'down' RBDs, and steric clashes were found in both cases (FIG. 5F-FIG. 5G). Without being bound by any particular theory, the inability of the HSW-2 Fab to access either 'up' or 'down' RBDs in the context of an intact spike trimer is consistent with the observation that although HSW-2 bound to almost all RBDs evaluated by ELISA (FIG. 2A), it showed weak or no neutralization activity against the tested strains (FIG. 2B).

Figure 22A:
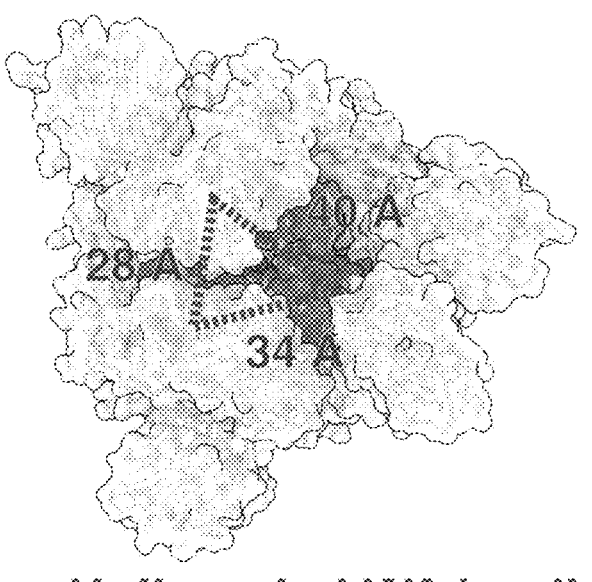
FIG. 22A-FIG. 22I depict non-limiting exemplary data showing Spike-mAb complex structures show increased trimer openness and the potential for intra-spike IgG cross-linking. Lighter dotted lines: Trimer openness was assessed by measuring distances between the Ca atoms of RBD residue 428 in each RBD of a spike trimer from the indicated Fab-spike complex structures (top-down views). Distances of 39 Å or less indicate a typical closed, prefusion spike trimer conformation (FIG. 22A). Binding of class ¼ anti-RBD antibodies such as C118 and S2X259 result in larger inter-RBD distances: 53 Å for C118 (panel B) and 43 Å for S2X259 (PDB 7RA8), indicating a more open trimer con-formation. Black dotted lines: The potential for intra-spike crosslinking by the two Fabs of a single bound IgG was assessed by measuring distances between the Ca atoms of C-terminal $C_H1$ residues (black) on adjacent bound Fabs on the RBDs of a spike trimer. Distances less than 65 Å are considered compatible with the potential for intra-spike crosslinking.
Figure 22B:
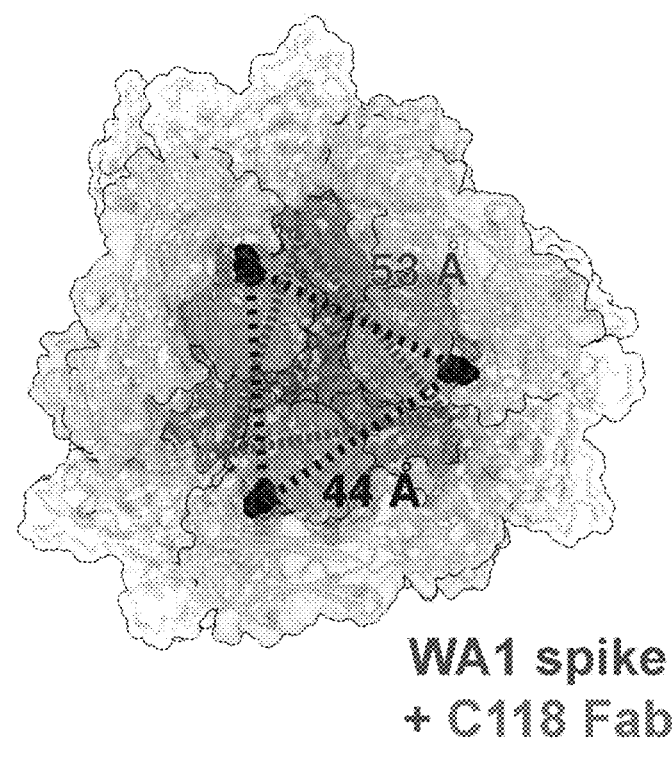
Figure 22C:
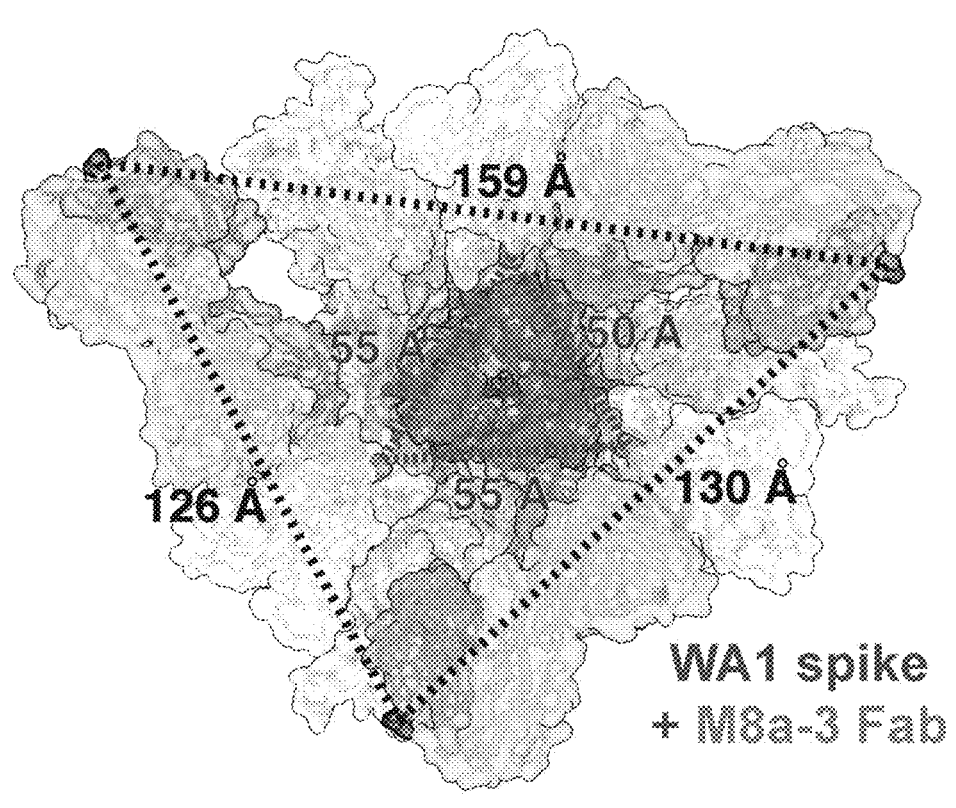
Figure 22D:
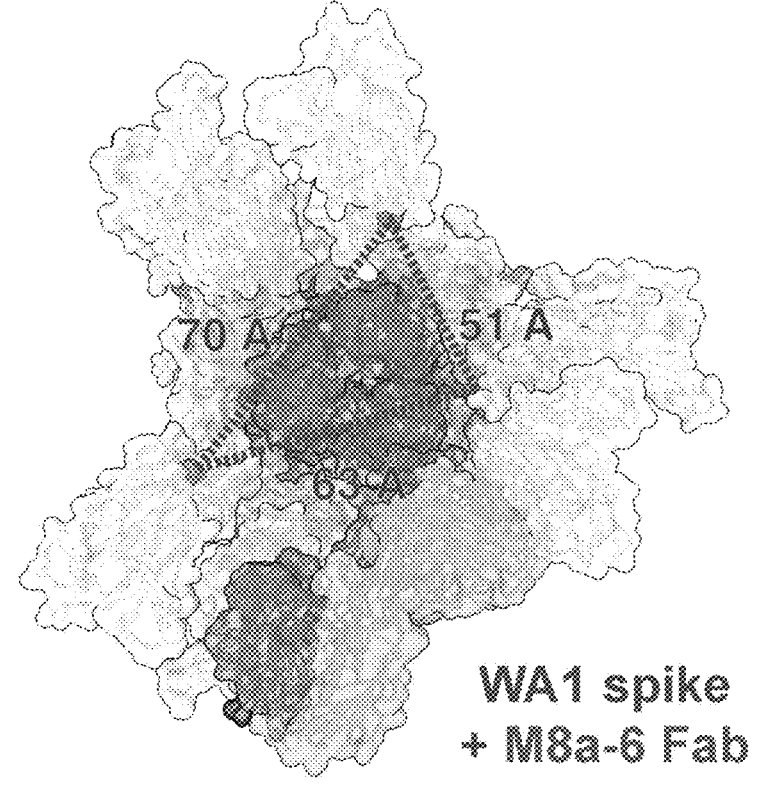
Figure 22E:
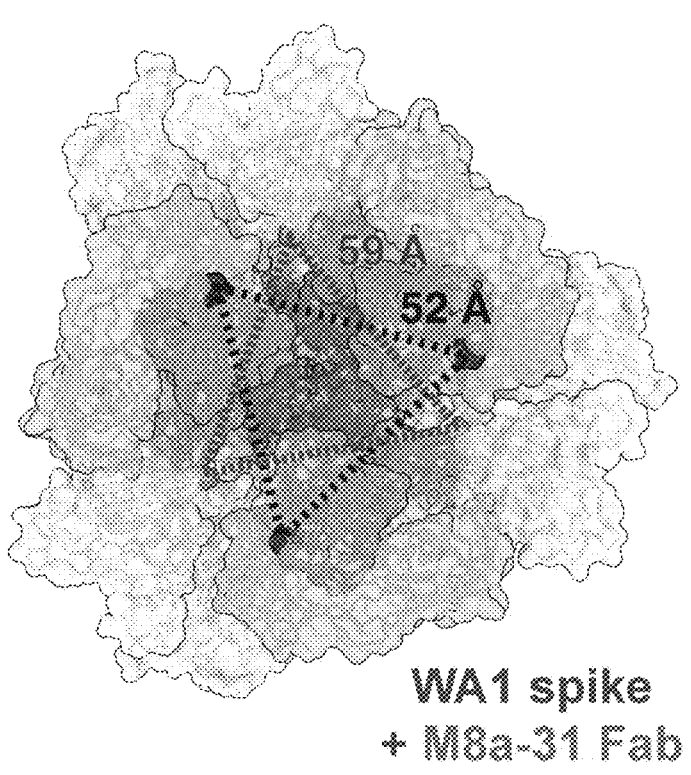
Figure 22F:
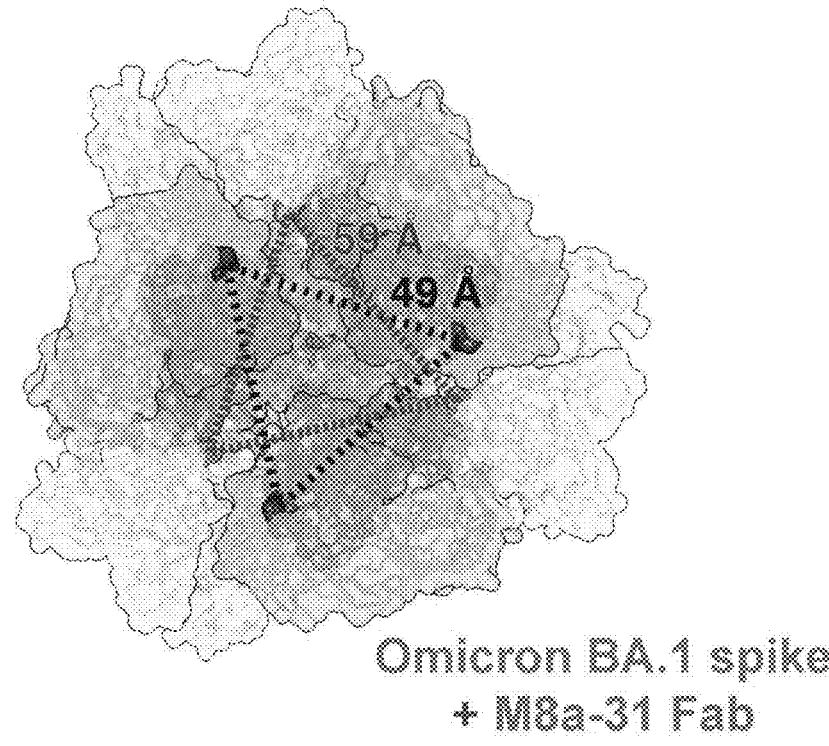
Figure 22G:
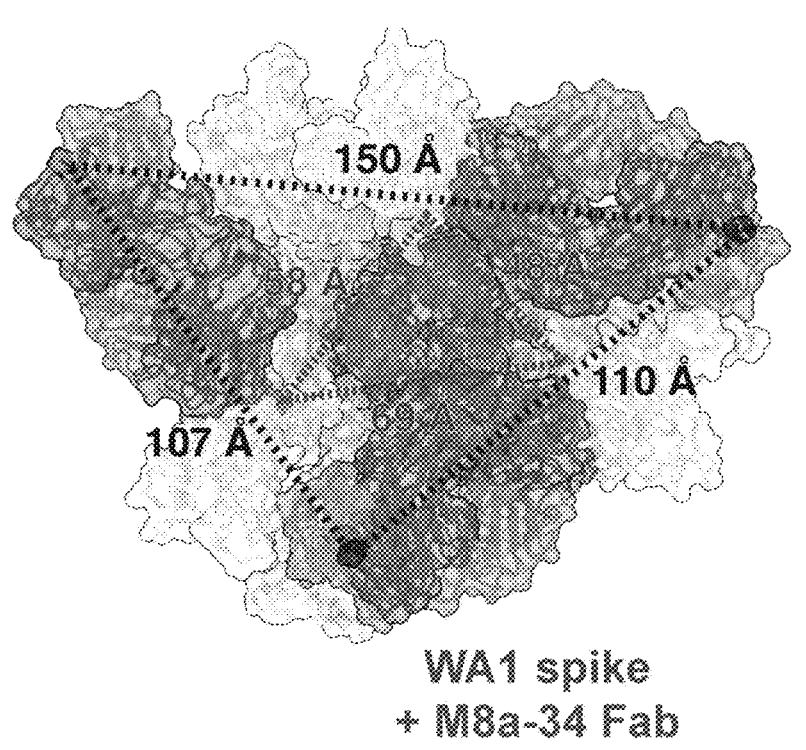
Figure 22H:
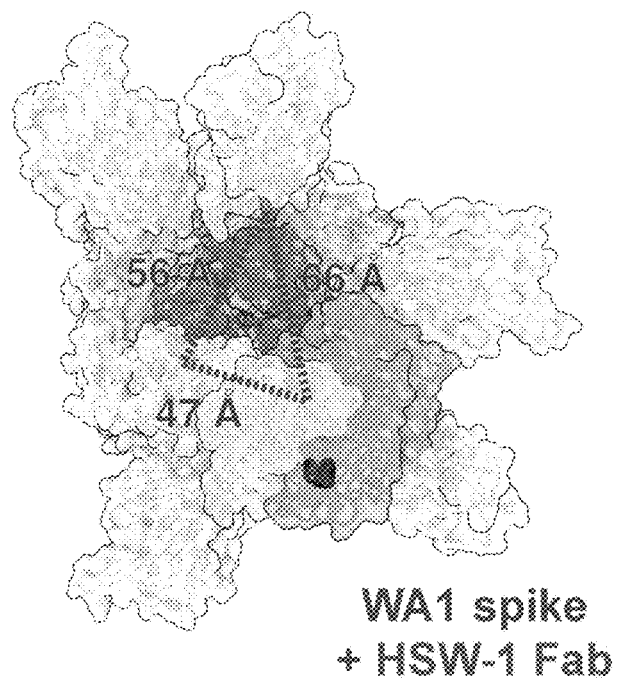
Figure 22I:
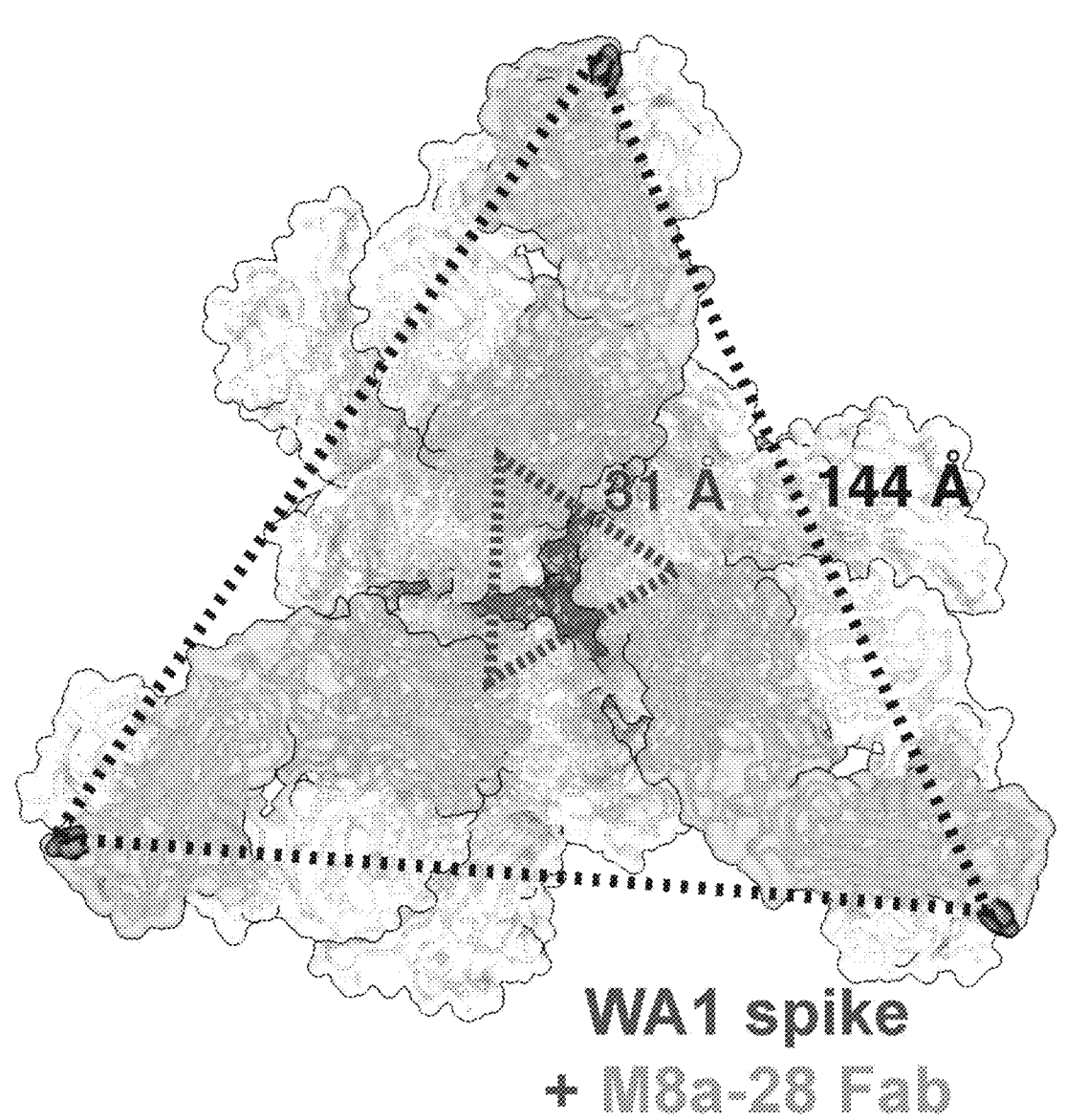

Class ¼ Anti-RBD mAbs Induce Spike Trimer Opening and Exhibit Different Potentials for Intra-Spike Crosslinking and Susceptibility to Mutations To address potential effects of mAb binding on spike trimer conformation, the Fab-bound spike trimer structures reported here were compared to other trimer structures. The distances between the Ca atoms of residue 428 in each of three 'up' RBDs within an intact trimer can be used to assess spike openness, with inter-protomer distances of 39 Å or less indicating a typical prefusion spike trimer conformation (FIG. 22A) (either unliganded, bound to ACE2, or bound to a class 1, 2, or 3 anti-RBD mAb), and binding of class 4 and class ¼ anti-RBD mAbs resulting in increases in the inter-RBD distances. For example, inter-RBD distances for spike trimers bound to C118 or to S2X259 human donor-derived mAbs recognizing class ¼ epitopes, were 53 Å (C118) or 43 Å (S2X259), demonstrating opening of the trimer to accommodate a Fab interacting with the occluded class ¼ region of the RBD (FIG. 22B). Inter-protomer distances ranging from 48-69 Å was found for trimers bound to Fabs from M8a-3 (FIG. 22C), M8a-6 (FIG. 22D), M8a-31 (FIG. 22E-FIG. 22F), M8a-34 (FIG. 22G) and HSW-1 (FIG. 22H), consistent with increased openness of trimers bound to class ¼ and class 4 anti-RBD antibodies. By contrast, the comparable inter-protomer distance was 31 Å in the M8a-28-spike structure with all RBDs in the 'down' conformation (FIG. 22I), consistent with M8a-28 recognition of the non-occluded class 3 RBD epitope.

Figure 5D:
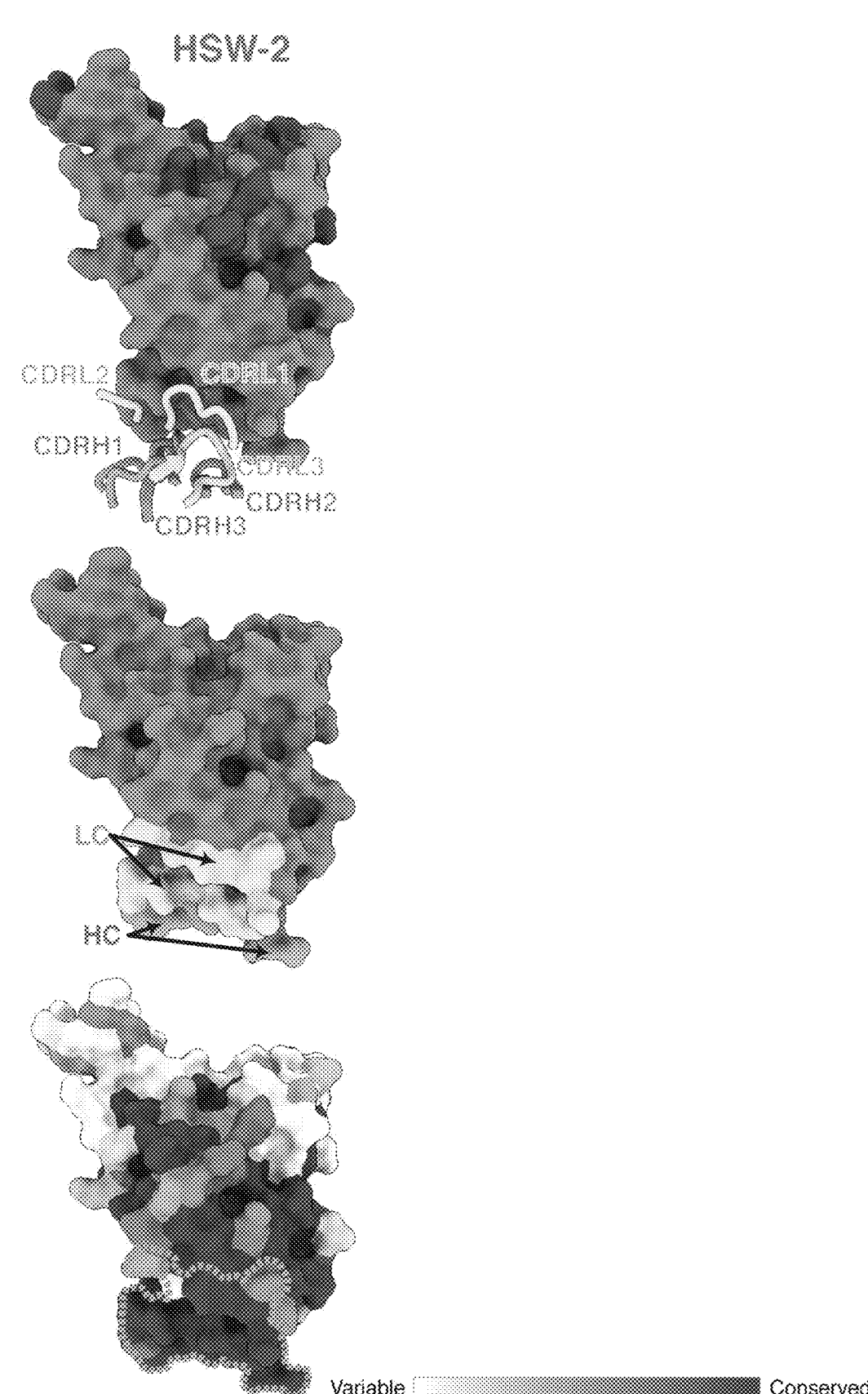
Figure 5E:
Figure 5F:
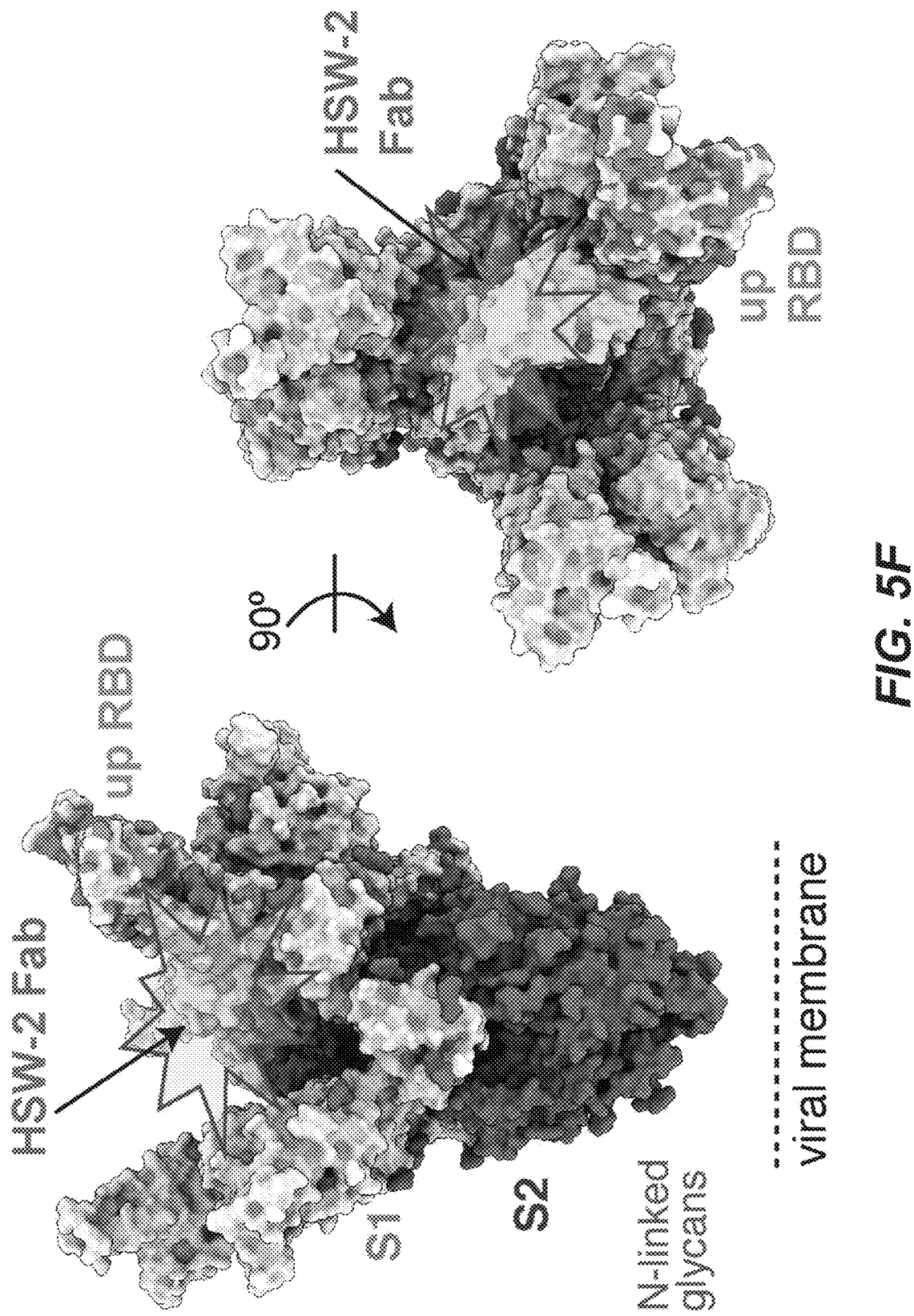
Figure 5G:
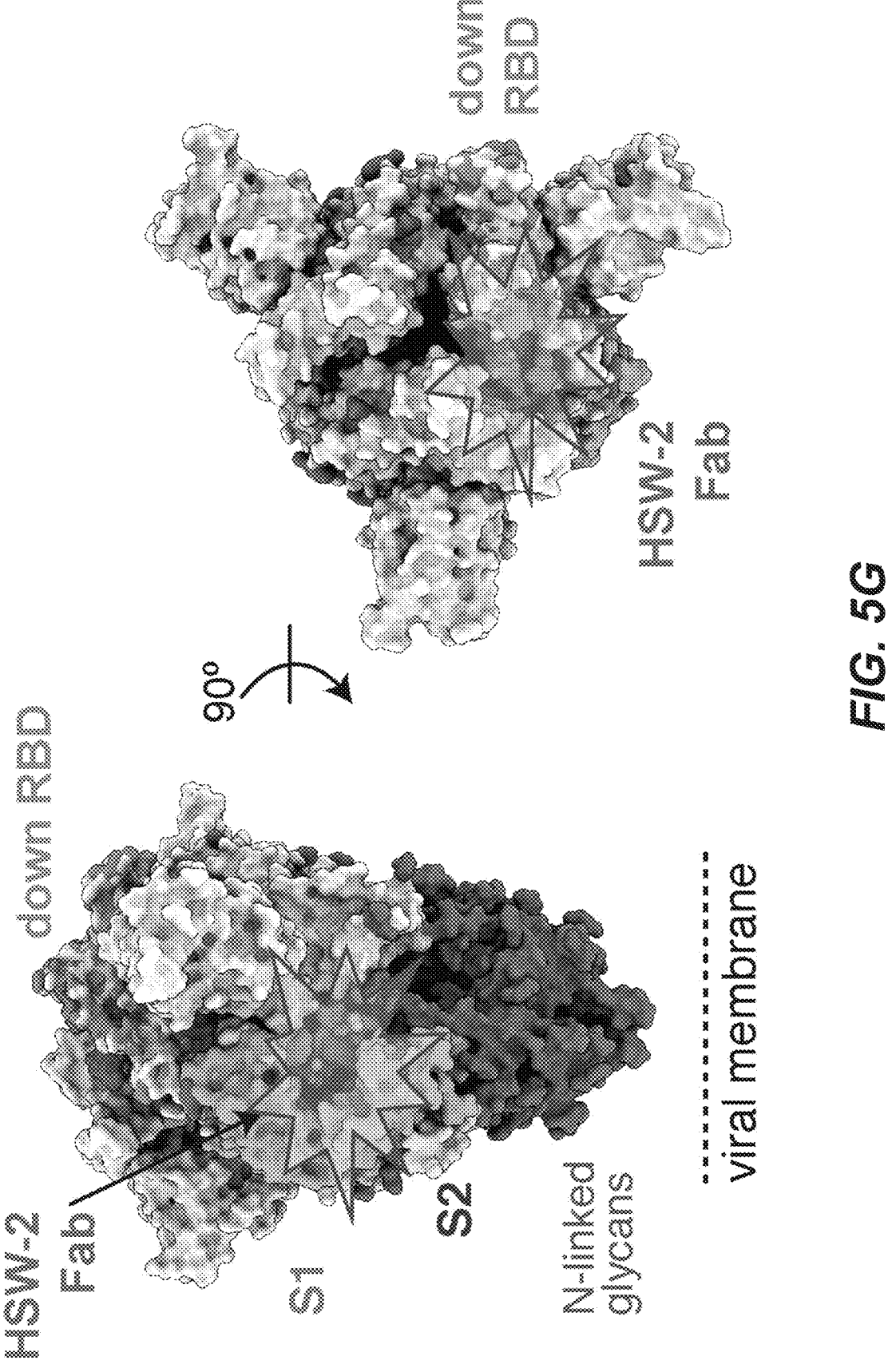
Figure 8A:
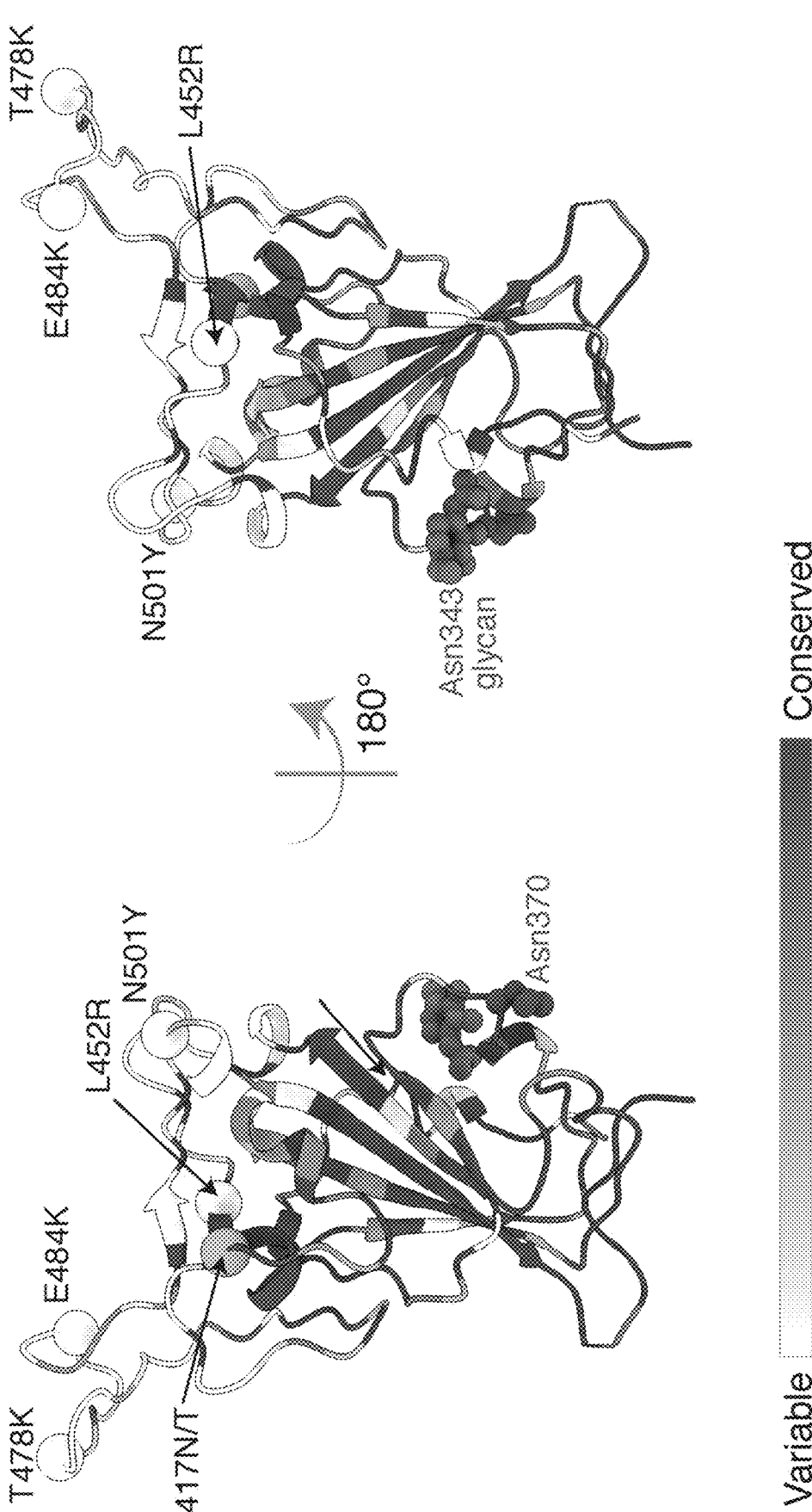
FIG. 8A-FIG. 8C depict RBD VOC and VOI substitutions. Locations of RBD substitutions in VOCs and VOIs are shown as spheres shaded according to a variability gradient (bottom) on the WA1 RBD structure (PDB 7BZ5). The N-linked glycan at position 343 of SARS-CoV-2 RBD is shown as smaller dark spheres, and a potential N-linked glycosylation site at position 370 (SARS-CoV-2 numbering) that is found in sarbecovirus RBDs but not in the SARS-CoV-2 RBD is also shown in spheres.
Figure 8B:
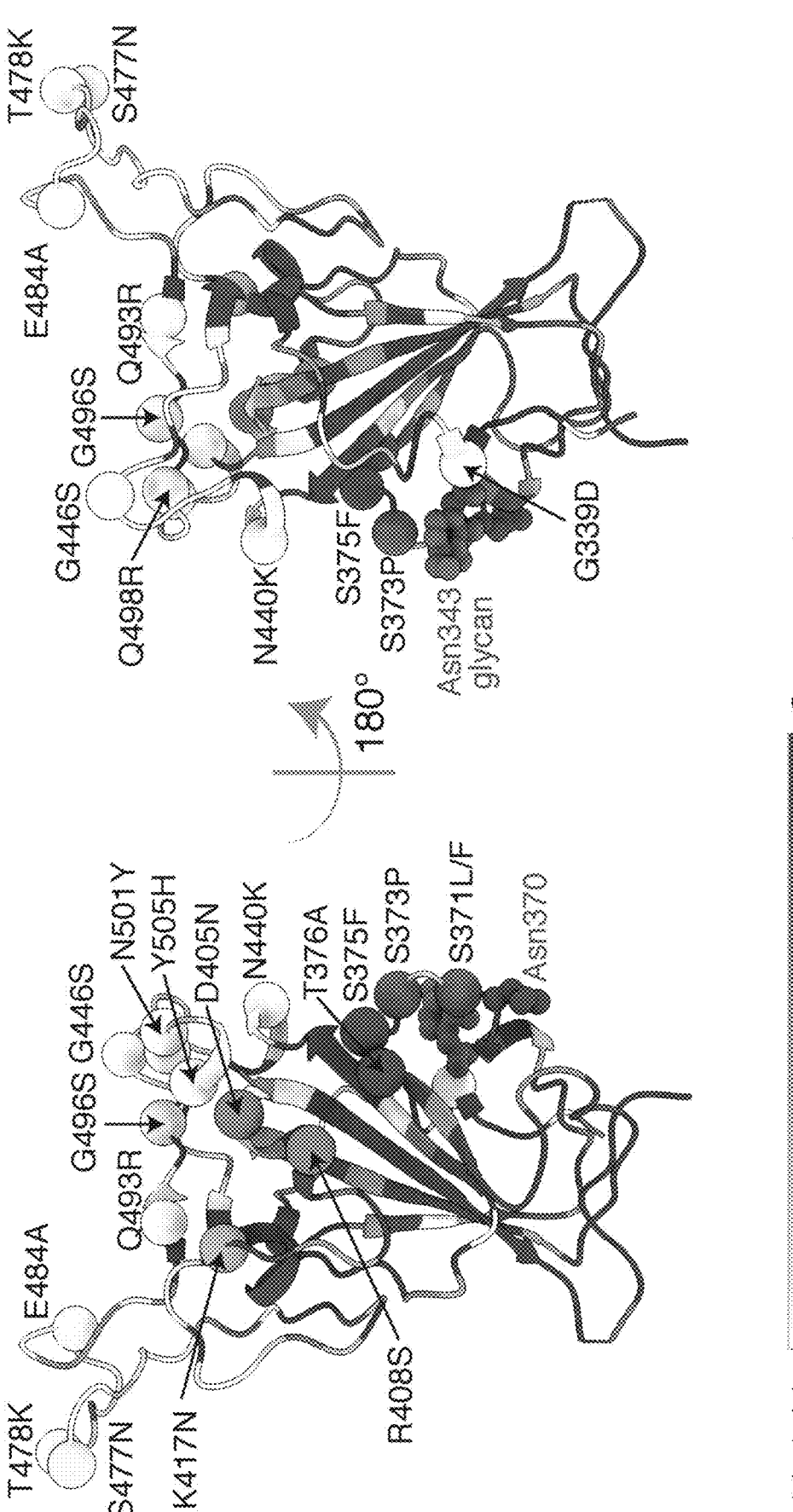
Figure 8C:
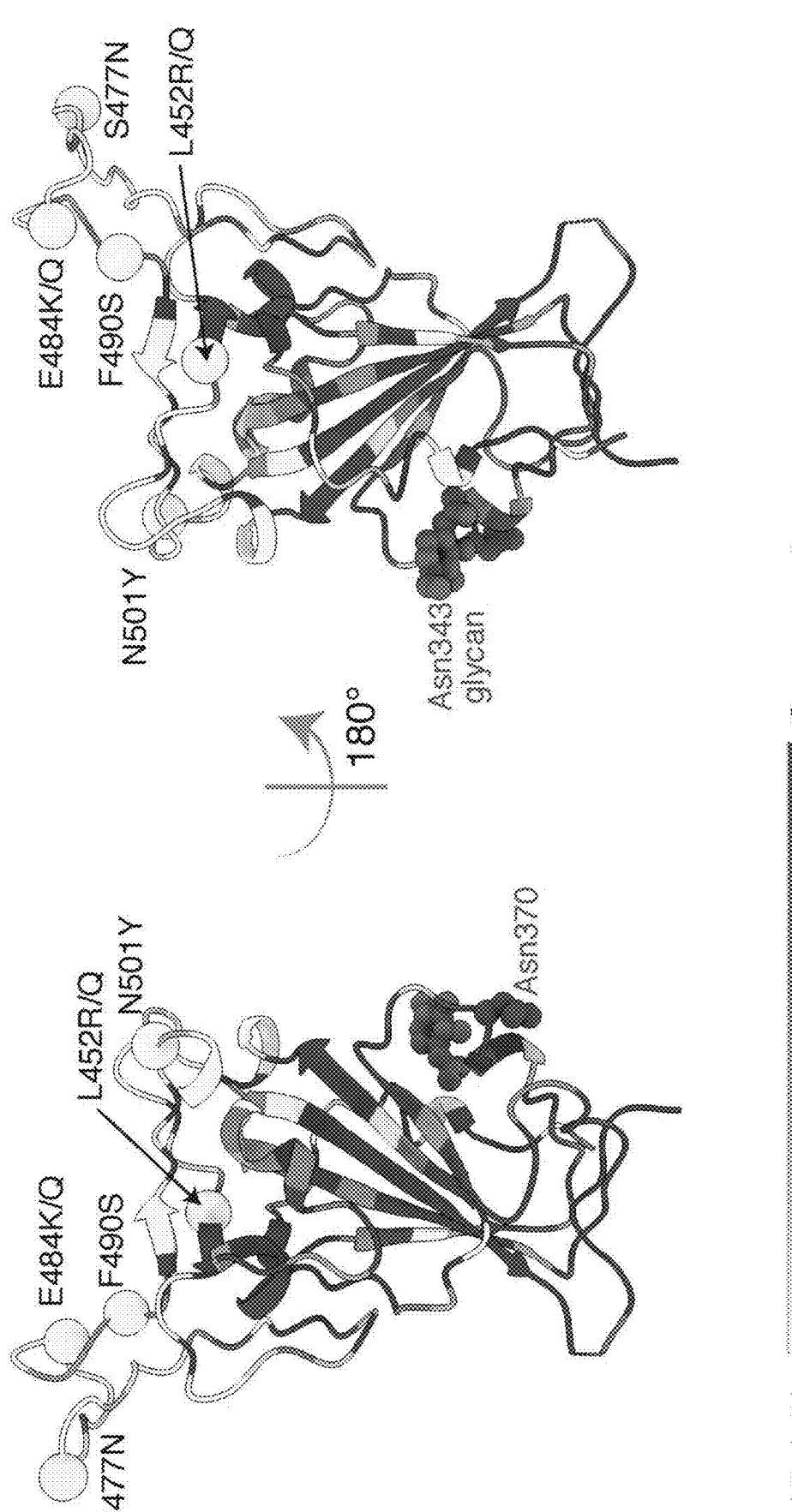

To understand how substitutions in SARS-CoV-2 VOCs might affect binding of the mAbs for which Fab-spike structures were obtained, their binding epitopes compared to the locations of Omicron BA.1 and BA.2 substitutions on the RBD were mapped (FIG. 4B-FIG. 4F, FIG. 5B, FIG. 5D). Most of the Omicron BA.1 an BA.2 substitutions were in the ACE2 binding region (FIG. 4A, FIG. 8B), which includes mainly variable residues (FIG. 1A), with fewer substitutions in conserved regions (FIG. 1A, FIG. 4B-FIG. 4F, FIG. 5B, FIG. 5D, FIG. 8B). The Omicron substitutions were mainly at the peripheries of the RBD epitopes of the m8a mAbs isolated from mosaic-8 nanoparticle-immunized mice (FIG. 4B-FIG. 4F), and there were no Omicron BA.1 or BA.2 substitutions within the binding epitopes of the two HSW mAbs isolated from homotypic SARS-CoV-2 nanoparticle-immunized mice (FIG. 5B, FIG. 5D). Despite the Omicron BA.1 or BA.2 substitutions not greatly affecting RBD binding by the seven mAbs (FIG. 2A), some of the class ¼ M8a mAbs showed somewhat reduced neutralization potencies (FIG. 2B). Evaluation of potent class 1, 2 and 3 anti-RBD human mAbs also revealed that, except for LY-CoV1404 (Bebtelovimab), most showed diminished binding and neutralizing activities against Omicron BA.1. Epitope analysis showed that LY-CoV1404 targets a class 3 RBD epitope adjacent to Omicron BA.1 and BA.2 mutations that is only somewhat conserved with respect to variability within sarbecoviruses, but unlike other EUA-approved class 3 anti-RBD therapeutic mAbs, it was minimally impacted by those substitutions (FIG. 6A-FIG. 6G, Table 4).

Figure 23G:
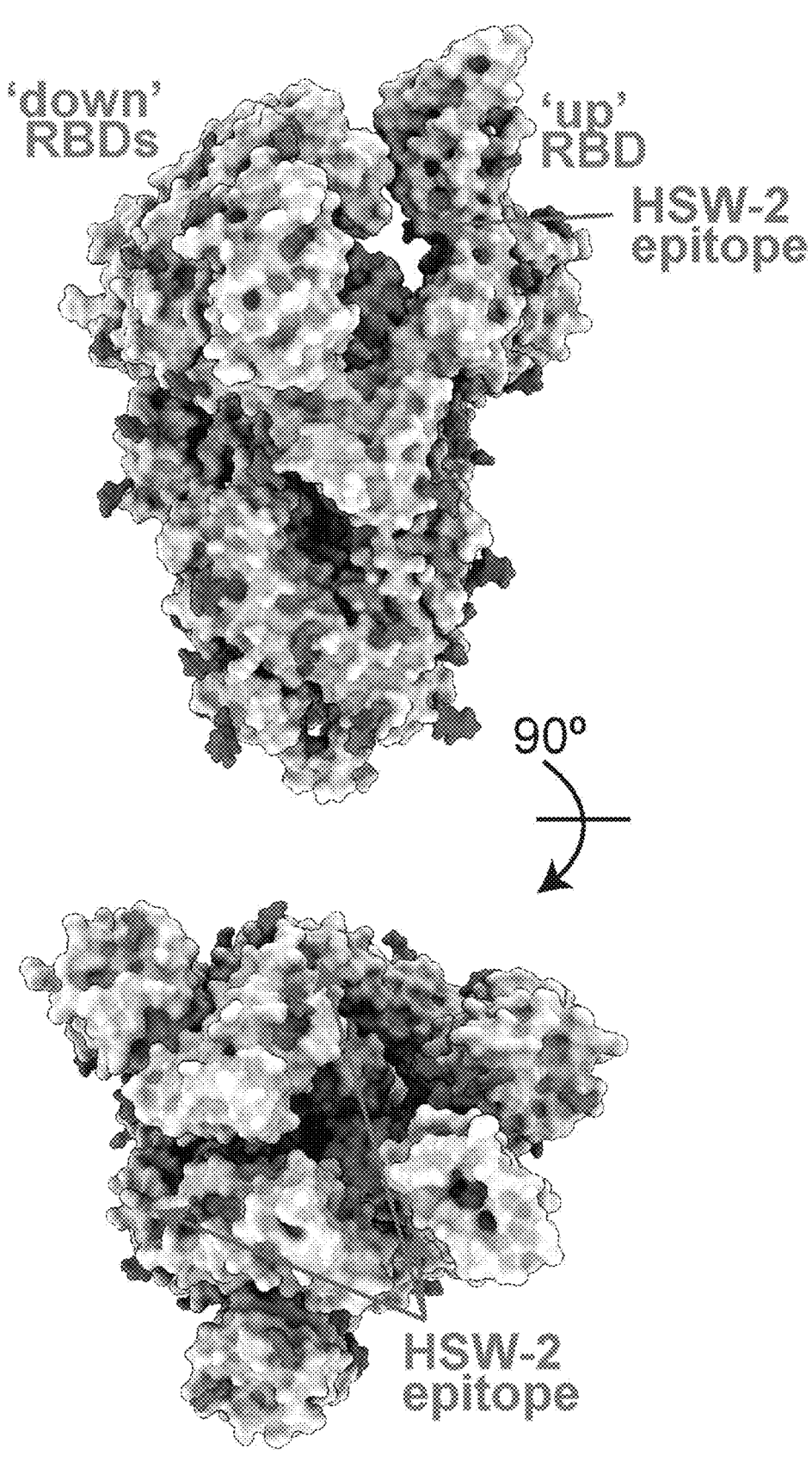
Figure 24G:
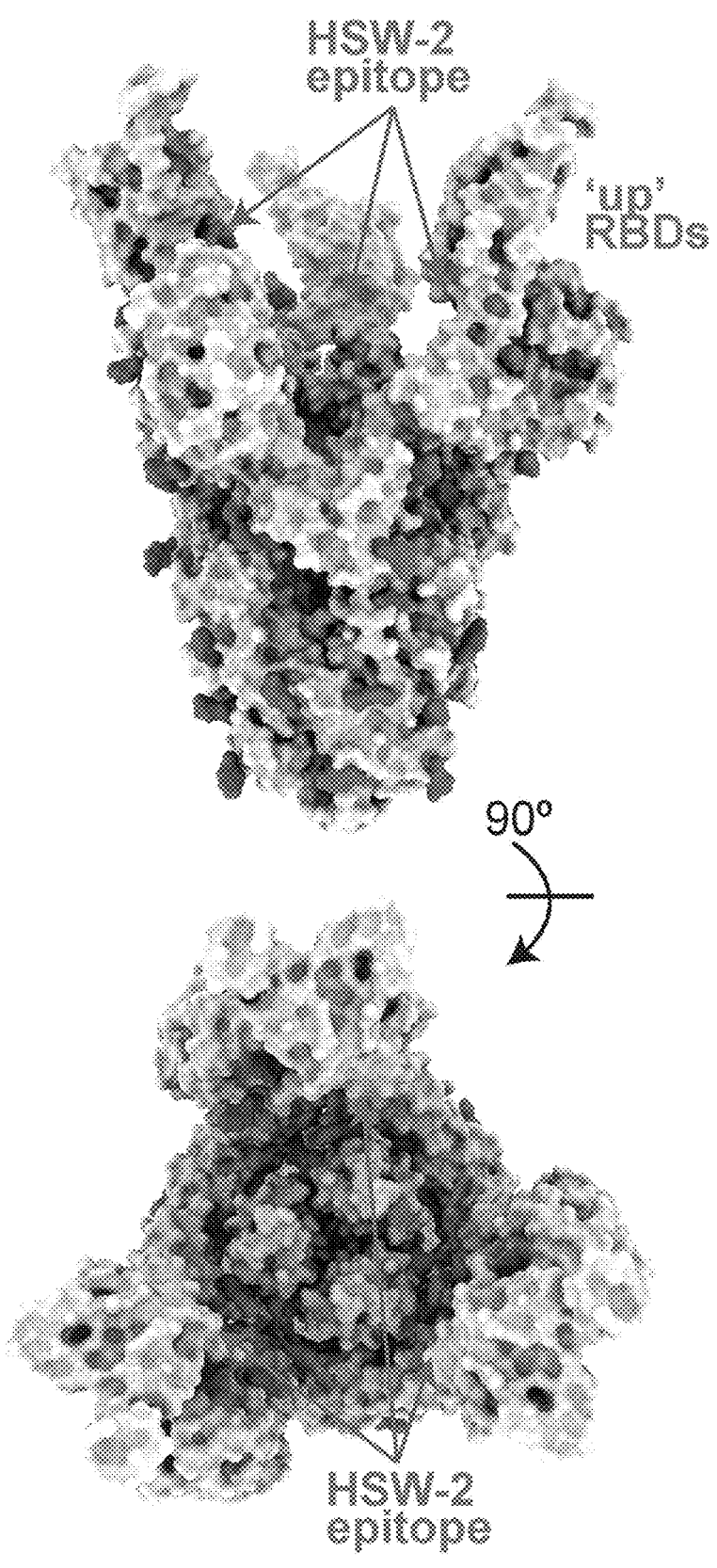
Figure 25A:
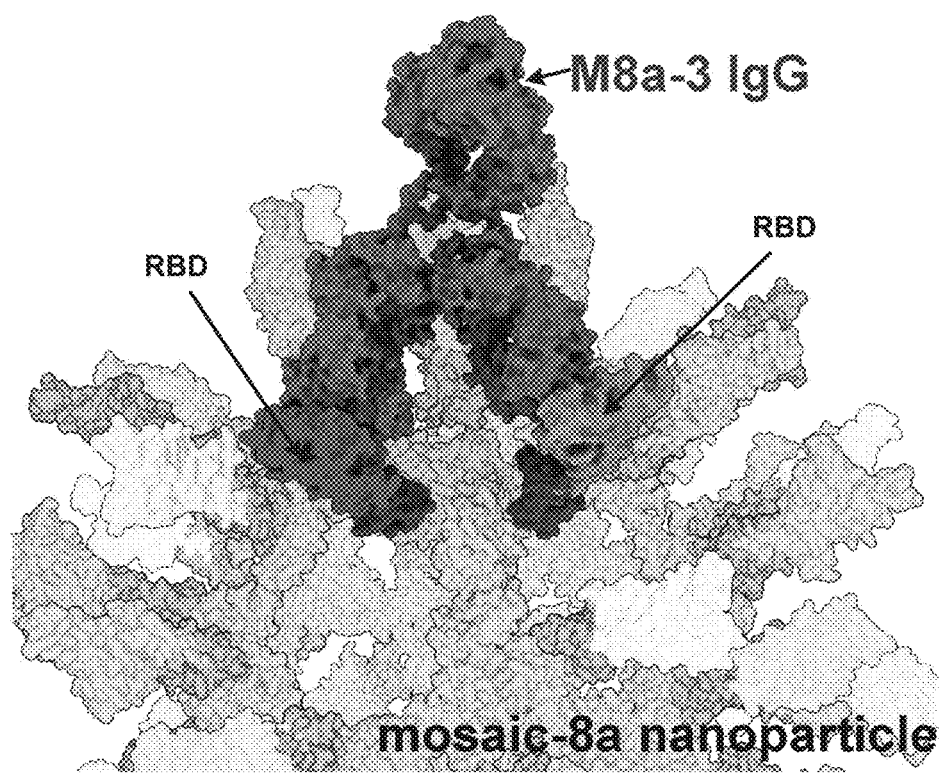
FIG. 25A-FIG. 25G show non-limiting exemplary models of M8a and HSW IgGs binding to adjacent RBDs on SpyCatcher-mi3 nanoparticles. Structural models of RBD-nanoparticles formed by SpyCatcher-mi3 and SpyTagged RBDs were made using coordinates of an RBD (PDB 7SC1) (represented in different shading for mosaic-8 nanoparticles, with two adjacent RBDs indicated by arrows), mi3 (PDB 7B3Y) (gray), and SpyCatcher (PDB 4MLI) (dark blue). IgGs were modeled using the coordinates of each mAb Fab based on an intact IgG crystal structure (PDB 1HZH), and the RBD binding epitope of each Fab in a modeled IgGs was determined based on the Fab-spike structures reported in this study. The two Fabs of each IgGs were positioned with distances between the C-termini of the Fab $C_H1$ domains to be less than 65 Å, as described previously. Both the IgG Fc hinge and the linker region between a SpyTagged RBD and SpyCatcher were assumed to be flexible and adjusted accordingly. Models are shown for (FIG. 25A) M8a-3 IgG interacting with two adjacent RBDs on a mosaic-8 RBD-nanoparticle.
Figure 25B:
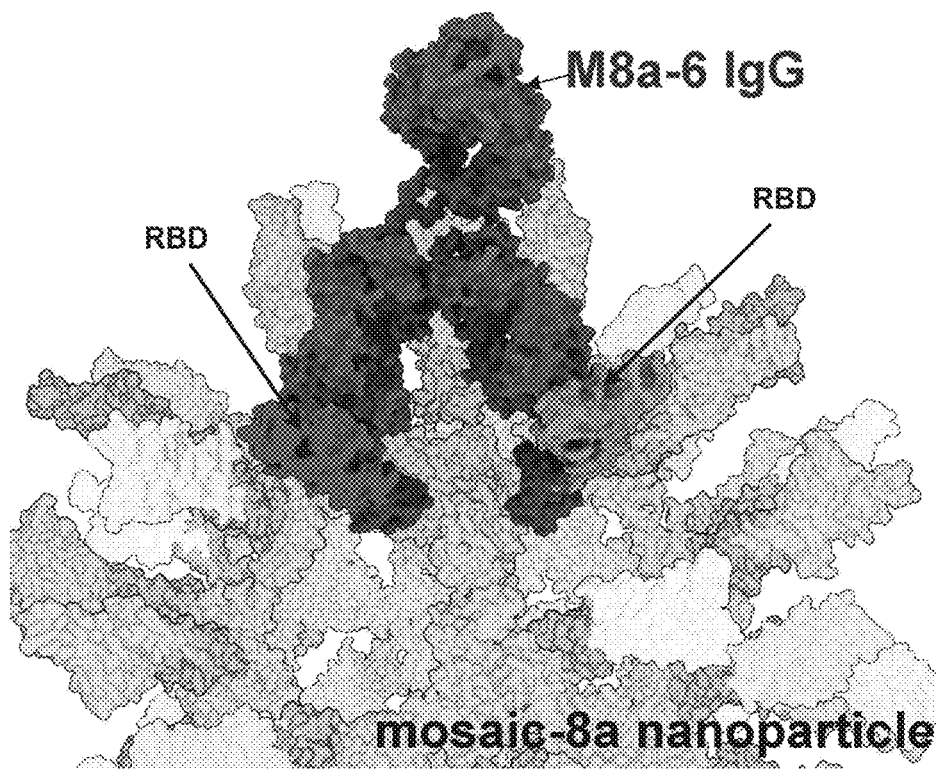
Figure 25C:
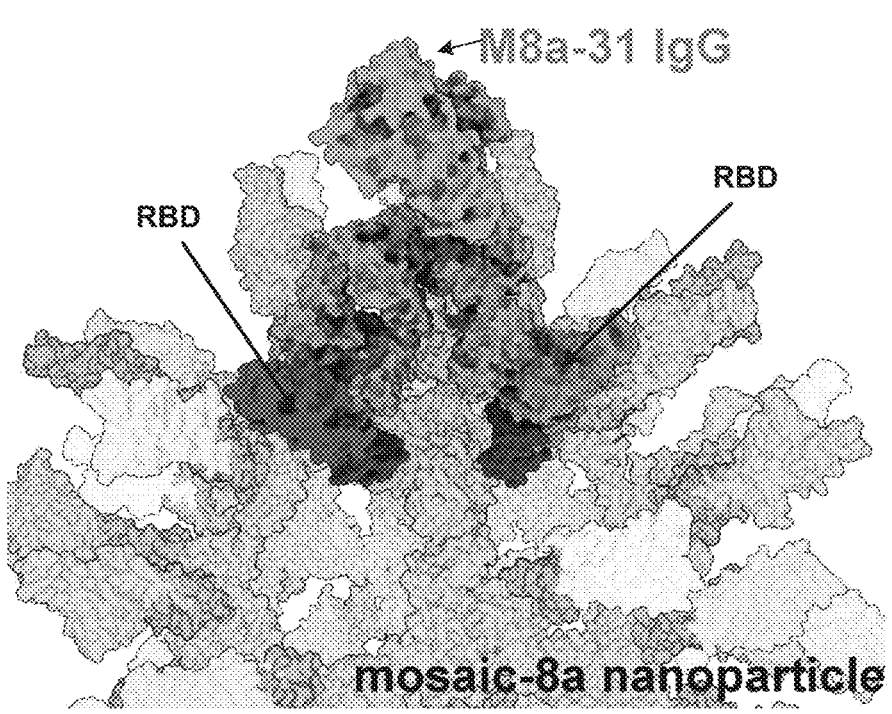
Figure 25D:
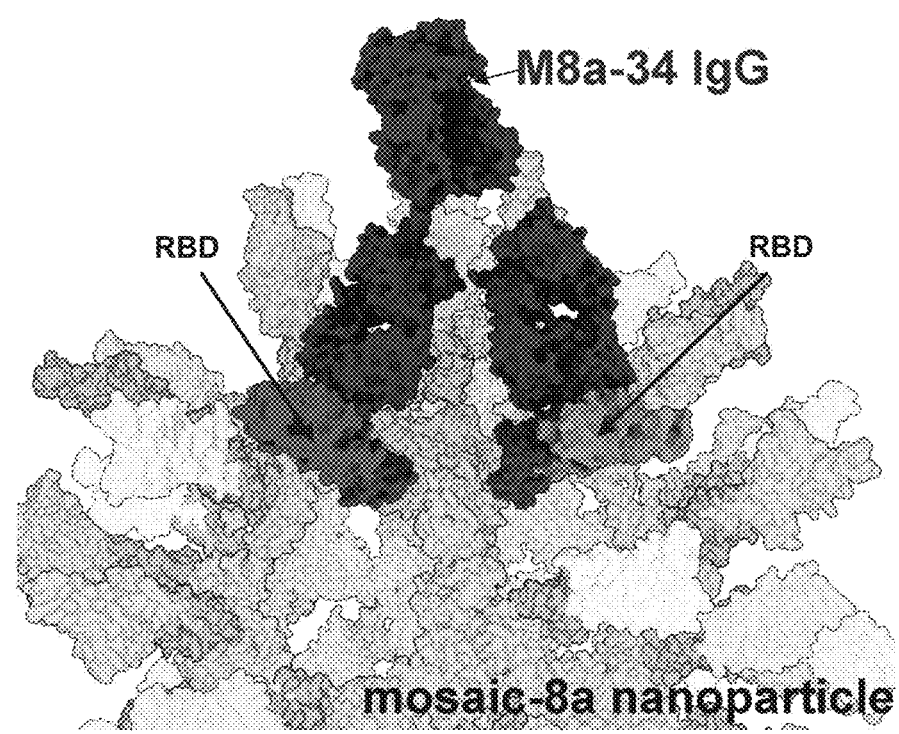
Figure 25E:
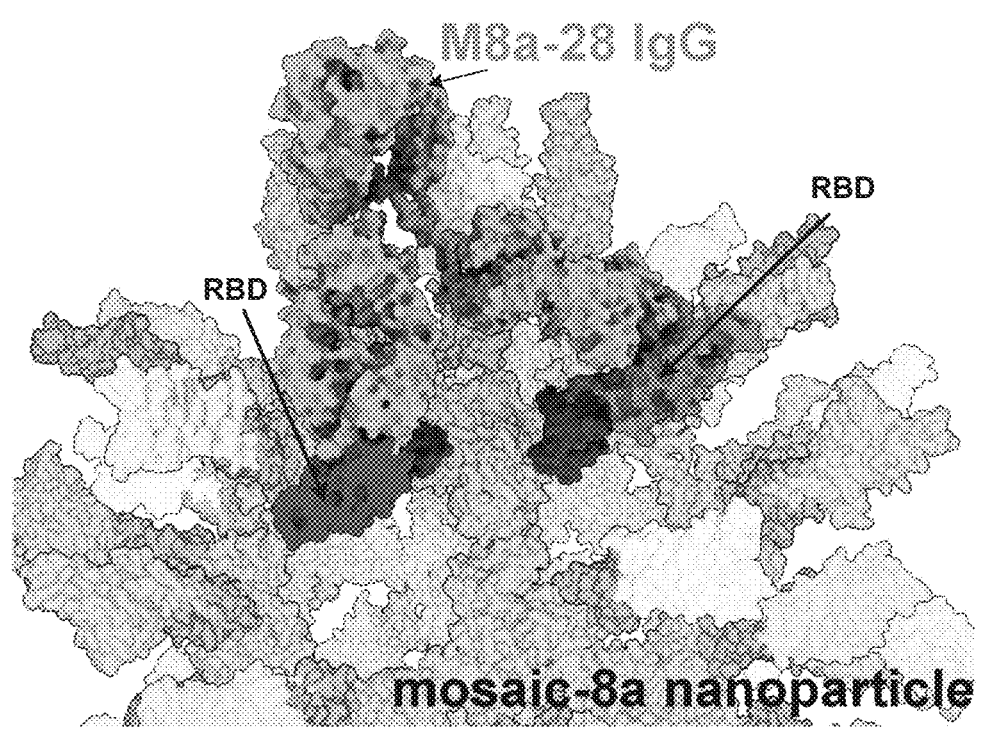
Figure 25F:
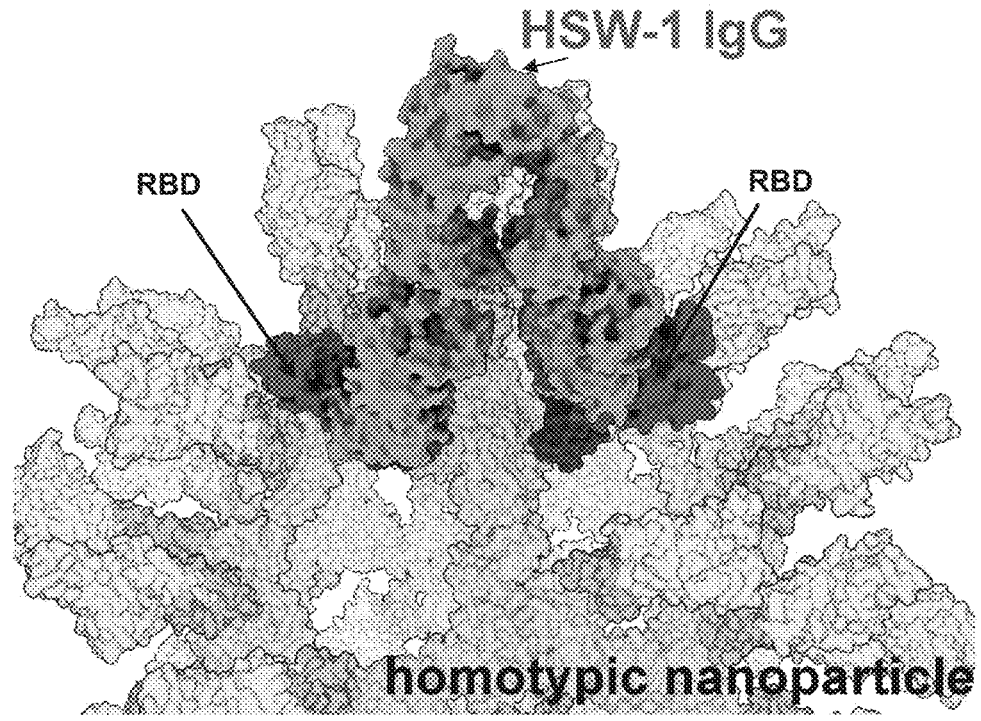
Figure 25G:
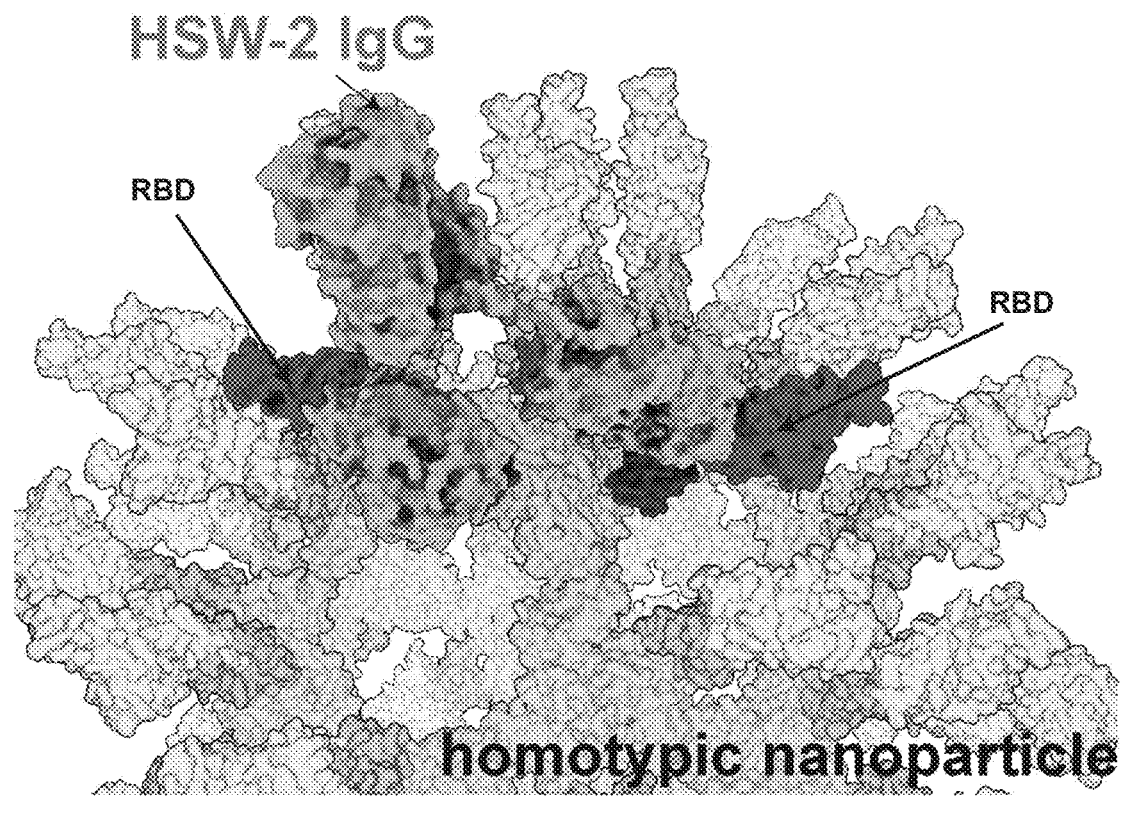

Although, in some embodiments, RBD binding was correlated with neutralization potencies for polyclonal antisera from RBD-nanoparticle immunized animals, this is not always true for mAbs; e.g., mAbs such as CR3022 bind to SARS-CoV-2 RBD, but neutralize only weakly or not at all. Without being bound by any particular theory, one mechanism by which Omicron or other RBD substitutions may indirectly affect neutralization potencies of mAbs (without affecting binding to isolated RBDs) is by changing the dynamics of the conversion between 'up' and 'down' conformations of RBDs on spike trimers. Some classes of anti-RBD mAbs have a strong or absolute preference for binding an 'up' versus a 'down' RBD; for example, most class 1 and class 4 anti-RBD mAbs only recognize 'up' RBDs. To address the ability of the mAbs investigated here to potentially recognize both 'up' and 'down' RBDs, the accessibility of their epitopes on a spike trimer was evaluated by mapping each binding epitope onto an unliganded trimer structure with one 'up' and two 'down' RBDs (PDB 6VYB) (FIG. 23A-FIG. 23G) and a trimer with all 'up' RBDs (PDB 7RKV) (FIG. 24A-FIG. 24G). The class 4 and ¼ epitopes of M8a-3, M8a-6, M8a-31, M8a-34, and HSW-1 were buried when RBDs adopted the 'down' conformation (FIG. 23A-FIG. 23D, FIG. 23F), but fully exposed in the 'up' RBDs (FIG. 24A-FIG. 24D, FIG. 24F). Although the class 4 epitope of HSW-2 was buried in 'down' RBD conformation (FIG. 23G) and can be, in some embodiments, partially exposed in an 'up' RBD conformation (FIG. 24G), structural alignments showed that HSW-2 cannot bind to 'up' or 'down' RBDs in the context of a spike trimer (FIG. 5F-FIG. 5G). By contrast, the class 3 epitope of M8a-28 was exposed in both RBD conformations (FIG. 23E, FIG. 24E). Likely related to these observations, but without being bound by any particular theory, only the M8a-28-bound trimer structure showed an inter-protomer RBD distance of 31 Å (FIG. 22I) that is equivalent to that of an unliganded trimer (28-40 Å) (FIG. 22A). The other class 4 and ¼ mAb Fab-bound trimer structures showed larger inter-protomer RBD distances (up to ~70 Å), corresponding to ~11 to 34 Å more outward displacement of RBDs in comparison to unliganded or class 1- or ACE2-liganded spike trimer structures (FIG. 22B-FIG. 22H). In some embodiments, this outward displacement of RBDs can result in spike trimer destabilization, leading to S1 shedding.

Another property of IgG antibodies that can, in some embodiments, affect their neutralization potencies relates to their ability to utilize bivalency. Since IgG antibodies have two identical Fab arms, they can increase their apparent affinities for binding to tethered viral antigens through avidity effects, which can occur through either inter-spike crosslinking (simultaneous binding of two neighboring spike trimers) or intra-spike crosslinking (simultaneous binding of two neighboring RBDs within the same spike trimer). Inter-spike crosslinking is likely possible for most anti-RBD antibodies based on the numbers and densities of SARS-CoV-2 spikes, and, in some embodiments, intra-spike crosslinking can also occur for some anti-RBD antibodies, depending on their epitopes and binding poses. To evaluate whether the M8a or HSW mAbs can enhance their binding through intra-spike crosslinking, distances between neighboring Fabs in the Fab-spike structures were measured to predict if simultaneous binding of two Fabs within an intact IgG to adjacent RBDs on a trimer would be possible. A distance of 65 Å between the C-termini of the $C_H1$ domains of adjacent RBD-bound Fabs was previously defined as being required to allow the N-termini of the two chains of an IgG hinge to bind each of the C-termini of two bound Fabs. This was compared to the distances measured in a previously characterized class ¼ mAb, C118, in complex with the spike trimer (FIG. 22B). The measured distances in spike trimers complexed with the M8a-3 (126 Å, 130 Å, and 159 Å) (FIG. 22C), M8a-34 (107 Å, 110 Å, and 150 Å) (FIG. 22G), or M8a-28 (144 Å) (FIG. 22I) Fabs were too large to permit intra-spike crosslinking. Although analogous distances in the M8a-6-spike structure could not be measured because only one Fab was bound (FIG. 22D), the similar epitope and pose for M8a-3 and M8a-6 (FIG. 3A-FIG. 3B, FIG. 4B-FIG. 4C) suggest, without being bound by any particular theory, that an IgG version of M8a-6 would also be unable to crosslink adjacent RBDs. Thus, the weak binding of M8a-6 to a spike trimer could not be improved by intra-spike crosslinking avidity effects, again rationalizing its lack of neutralizing activity (FIG. 2B). For spike trimers in complex with M8a-31 Fab (FIG. 22E-FIG. 22F), the distances between the C-termini of adjacent $C_H1$ domains were measured as 52 Å and 49 Å for M8a-31 Fab bound to the WA1 and Omicron BA.1 spikes, respectively, suggestive of potential intra-spike crosslinking. The potential for intra-spike crosslinking for the HSW-1 or HSW-2 mAbs could not be evaluated because either only one Fab was bound per spike (HSW-1) (FIG. 5A) or the reconstructions showed Fab binding to dissociated S1 monomer only (HSW-2) (FIG. 5C).

Modeling was also used to assess how the RBD-nanoparticles used to elicit the mAbs disclosed herein can, in some embodiments, engage with bivalent B cell receptors. To address this issue, it was investigated whether the geometric arrangement of RBDs on mosaic-8 RBD-mi3 nanoparticles would permit bivalent engagement of neighboring RBDs by IgGs, here representing membrane-bound B cell receptors hypothesized to engage adjacent RBDs (FIG. 1D). IgG models of each of the Fabs in the M8a and HSW Fab-spike structures were constructed first (FIG. 3A-FIG. 3F, FIG. 5A-FIG. 5G). Next, it was asked if it was sterically possible for both Fabs of an IgG to interact with the epitope identified from its cryo-EM structure on adjacent RBDs on a modeled RBD-mi3 nanoparticle. For each of the seven mAb epitopes, the RBD-mi3 nanoparticle geometry was predicted to allow simultaneous recognition of adjacent RBDs by both Fabs of an IgG (FIG. 25A-FIG. 25G), thus confirming that the geometric arrangement of RBD attachment sites on Spy-Catcher-mi3 would allow B cell receptor engagement through avidity effects (FIG. 1D).

mAbs Elicited by Mosaic-8 RBD-Nanoparticles Resemble EUA-Approved Therapeutics or a Potent Cross-Reactive Human Class ¼ Anti-RBD Antibody Although the B cell cloning study from mosaic-8 RBD-nanoparticle immunized mice described herein started with <10,000 cells, the five M8a mAbs identified as binding two or more RBDs during screening all target the desired, more conserved epitopes (class 3 and class 14) rather than the class 1 and class 2 RBD epitopes more commonly elicited by vaccination or infection (FIG. 3A-FIG. 3F, FIG. 4A-FIG. 4F). Three of the five mAbs were potently and/or broadly neutralizing (FIG. 2B). By contrast, the only two mAbs isolated from homotypic SARS-CoV-2 RBD-nanoparticle immunized mice that were identified as binding two or more RBDs during screening targeted different epitopes (FIG. 5A-FIG. 5G) and were only weakly- or non-neutralizing (FIG. 2B). This is consistent with mosaic-8 RBD-nanoparticles being superior for eliciting cross-reactive and cross-neutralizing anti-sarbecovirus antibodies against conserved epitopes than homotypic RBD-nanoparticles and argues against use of homotypic RBD-nanoparticles as immunogens to elicit cross-reactive neutralizing antibodies.

Figure 6A:
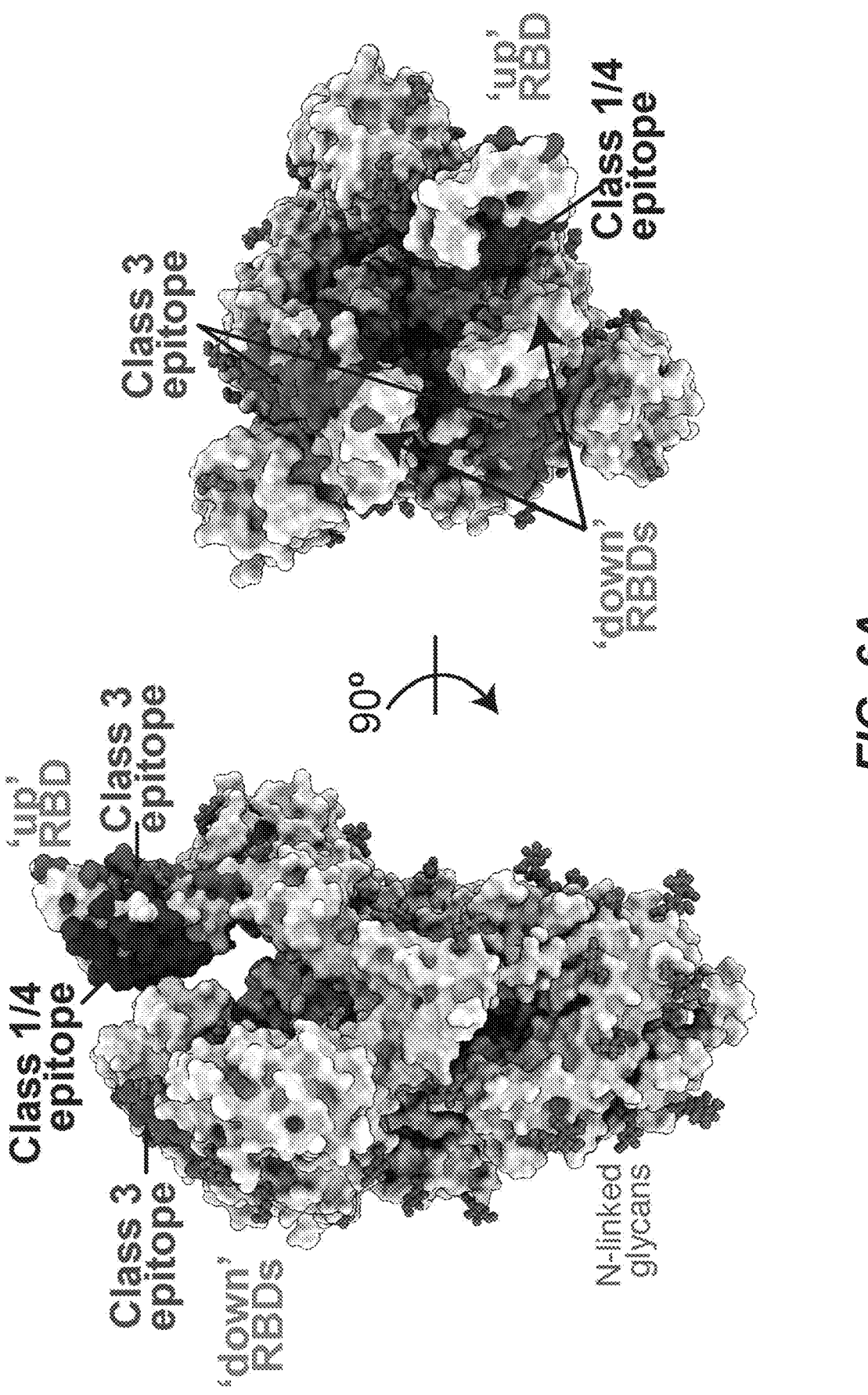
Figure 6D:
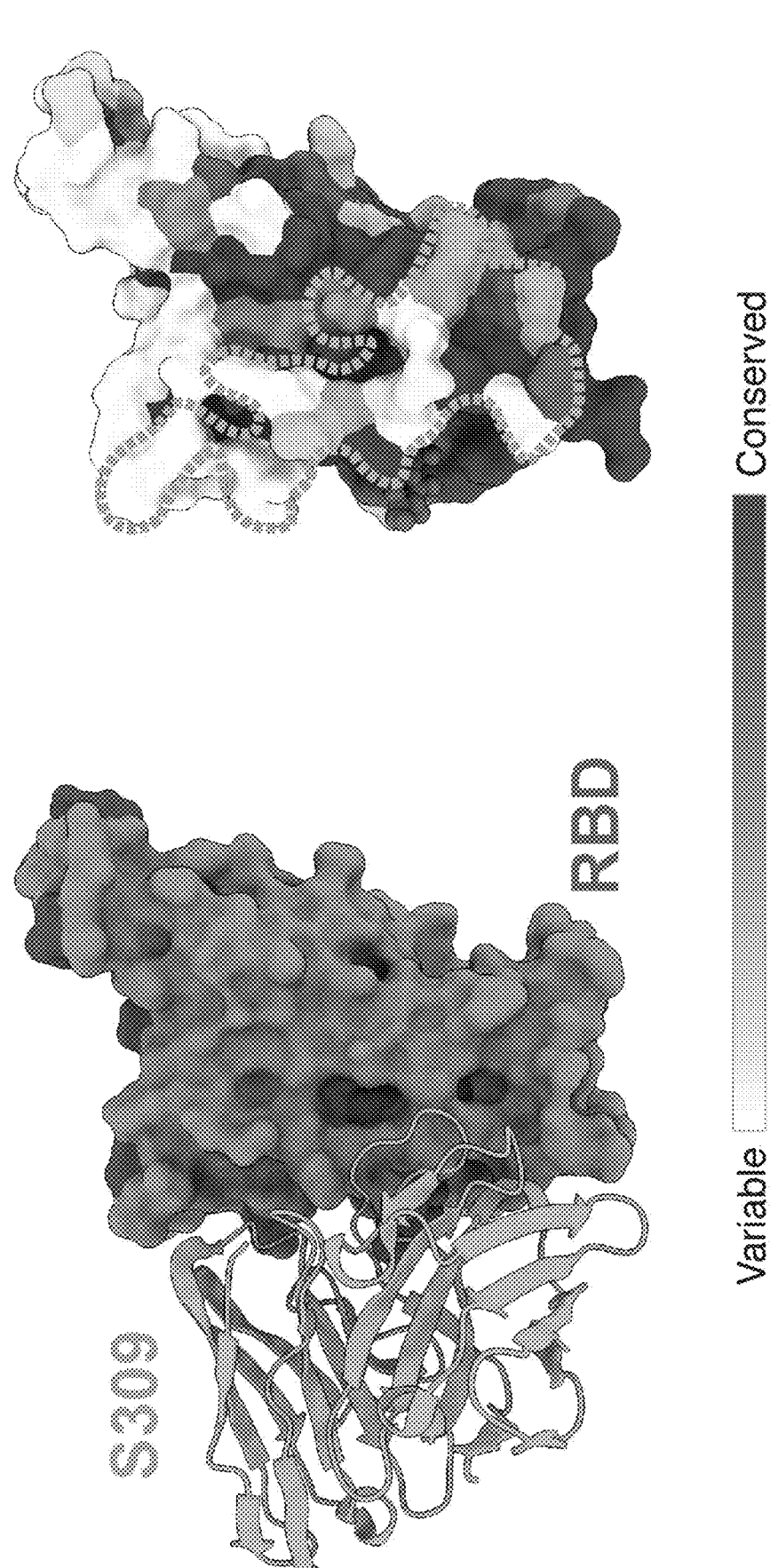
Figure 6G:
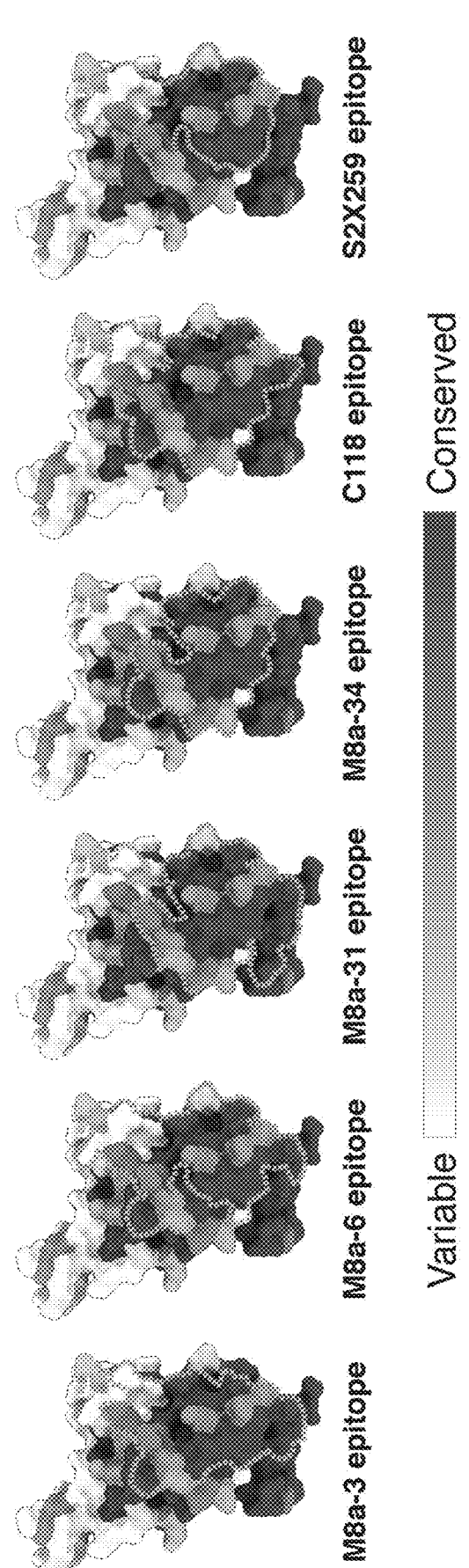

Human mAbs that received Emergency Use Authorization for COVID-19 treatment include class 1 and class 2 anti-RBD mAbs that are not effective against SARS-CoV-2 variants, and class 3 anti-RBD mAbs, two of which, Bebtelovimab and Cilgavimab, retain at least partial efficacy against Omicron variants (FIG. 6A, Table 4).

TABLE 4

CLASS 3 ANTI-RBD MABS THAT HAVE RECEIVED
EMERGENCY USE AUTHORIZATION (EUA) APPROVAL
FOR HUMAN ADMINISTRATION BY THE US
FOOD AND DRUG ADMINISTRATION

| Antibody | Generic Name | PDB ID |
|---|---|---|
| LY-CoV1404 | Bebtelovimab | 7MMO |
| S309 | Sotrovimab | 7JX3 |
| REGN10987 | Imdevimab | 6XDG |
| AZD1061 | Cligavimab/Evusheld | 7L7E |

Of these mAbs, only LY-CoV1404/Bebtelovimab retains full neutralization potency against Omicron BA.1, and the NIH COVID-19 treatment guidelines recommend against use of Bamlanivimab plus Etesevimab, Casirivimab plus Imdevimab, or Sotrovimab for the treatment of COVID-19

The class 3 RBD epitope, although less affected by SARS-CoV-2 VOC substitutions than the immunodominant class 1 and class 2 RBD epitopes, nevertheless encompasses an RBD region that includes variability across sarbecovirus sequences (FIG. 1A-FIG. 1B, FIG. 6B-FIG. 6F). Without being bound by any particular theory, the ability of the class 3 epitope to accumulate substitutions is likely because the class 3 RBD region is accessible on both 'up' and 'down' RBD conformations, thus not being constrained to avoid substitutions because of contacts with other regions of a sarbecovirus spike trimer (FIG. 6A). The epitope identified for M8a-28 (FIG. 6B) resembles, in some embodiments, the more variable epitopes of the class 3 anti-RBD therapeutic mAbs (FIG. 6C-FIG. 6F). The more occluded class ¼ RBD epitope (FIG. 6A), to which bound mAbs can inhibit ACE2 binding, exhibits less variability across sarbecoviruses. In some embodiments, this may be because substitutions that affect its contacts as a 'down' RBD with other spike trimer regions limit its variability between SARS-CoV-2 VOCs and other sarbecoviruses. The fact that four of five mouse mAbs identified as binding to two or more different RBDs during B cell screening after mosaic-8 immunization target the class ¼ epitope, in common with the potent, cross-reactive, and protective S2X259 human mAb (FIG. 6G), supports the potential for using mosaic RBD-nanoparticles as immunogens to efficiently elicit cross-reactive and potent neutralizing mAbs against SARS-CoV-2 variants and animal sarbecoviruses that could spill over to infect humans.

Described herein are mouse mAbs elicited using mosaic RBD-nanoparticles (M8a mAbs) or homotypic RBD-nanoparticles (HSW mAbs). Both structural and functional analyses showed that mosaic RBD-nanoparticles induce potently neutralizing antibodies that cross-react between animal sarbecoviruses and SARS-CoV-2 VOCs (FIG. 2A-FIG. 2B). Amongst the five mAbs that bound to two or more RBDs from mosaic-8 nanoparticle immunized mice that were identified, one mAb (M8a-3) was both cross-reactive and strongly neutralizing, and two others (M8a-31 and M8a-34) were less potently neutralizing but were cross-reactive (FIG. 2A-FIG. 2B), demonstrating the mosaic-8 immunogen can efficiently elicit useful therapeutic antibodies and, that the method described herein can be developed to identify future therapeutic mAbs. Another mAb (M8a-28) potently neutralized SARS-CoV-2 variants and resembled therapeutic antibodies in current use (FIG. 6B-FIG. 6F).

Structural studies of Fab complexes with SARS-CoV-2 spike trimers, including one with Omicron BA.1, demonstrated that four of the five mAbs isolated from mosaic-8 immunized mice recognized conserved epitopes (FIG. 4A-FIG. 4F), as designed in the immunization approach (FIG. 1D) and as shown for polyclonal antisera raised in mice by mosaic-8 RBD-nanoparticle immunization. By contrast, antibodies raised in homotypic SARS-CoV-2 RBD-nanoparticle immunized mice more commonly recognize variable class 1 and class 2 RBD epitopes, explaining, without being bound by any particular theory, why it was more difficult to isolate single B cells from homotypic RBD-nanoparticle immunized mice secreting IgGs that bound two or more labeled RBDs (FIG. 2A, FIG. 9A-FIG. 9B, Table 5-Table 7). The two cross-RBD binding mAbs that were isolated from homotypic RBD-nanoparticle immunized mice showed binding to multiple sarbecovirus RBDs (FIG. 2A) but were only weakly- or non-neutralizing (FIG. 2B). Without being bound by any particular theory, structural studies rationalized the weak neutralization profiles of the HSW mAbs: the HSW-1-spike structure showed only one bound Fab per trimer (FIG. 5A) as compared with three bound Fabs per trimer in the structures of more potently neutralizing mAbs (FIG. 3A-FIG. 3F). Additionally, the HSW-2 Fab epitope (FIG. 5D) was incompatible with binding to its RBD epitope on intact spike trimer (FIG. 5F-FIG. 5G), resulting in a trimer dissociation and a Fab-monomeric S1 subunit structure (FIG. 5C).

The results described herein support the mosaic-8 RBD-nanoparticles as a promising vaccine candidate to protect against SARS-CoV-2, including future variants, and against potential spillover sarbecoviruses from animal reservoirs. In addition, the fact that potent cross-reactive mAbs were identified from relatively few B cells suggest that high-throughput screening of larger samples from animals immunized with mosaic-8 RBD-mi3 using the methods described herein can be used to identify many new therapeutic mAbs, which can then be used to prevent or treat infections of Omicron and future SARS-CoV-2 variants.

Materials and Methods

Preparation of Homotypic and Mosaic-8 RBD-Mi3 Nanoparticles

Mammalian expression vectors encoding RBDs of SARS-CoV-2 and other sarbecoviruses were constructed in two versions: one with a C-terminal 6×-His tag and a SpyTag003 (RGVPHIVMVDAYKRYK, SEQ ID NO: 105) for the 8 RBDs that were coupled to SpyCatcher003-mi3 nanoparticles and other versions with only a 6×-His tag or with a His tag plus an Avi tag for ELISAs. Expression vectors encoding RBDs were constructed similarly for the following sarbecoviruses: BM4831-CoV (GenBank NC014470; spike residues 310-530), BtKY72-CoV (GenBank KY352407; spike residues 309-530), C028 (GenBank AAV98001.1; spike residues 306-523), Khosta2 (GenBank QVN46569.1; spike residues 307-526), LYRa3 (GenBank AHX37569.1; spike residues 310-527), Pangolin17-CoV (GenBank QIA48632; spike residues 317-539), RaTG13-CoV (GenBank QHR63300; spike residues 319-541), Rf1-CoV (GenBank DQ412042; spike residues 310-515), RmYN02-CoV (GISAID EPI_ISL_412977; spike residues 298-503), Rs4081-CoV (GenBank KY417143; spike residues 310-515), RshSTT200 (GISAID EPI_ISL_852605; spike residues 306-519), SARS-CoV (GenBank AAP13441.1; spike residues 318-510), SARS-CoV-2 WA1 (GenBank MT246667.1; spike residues 319-539), SHCO14-CoV (GenBank KC881005; spike residues 307-524), W1V1-CoV (GenBank KF367457; spike residues 307-528), and Yun11-CoV (GenBank JX993988; spike residues 310-515). SARS-CoV-2 variants, including Beta, Delta, Omicron BA.1, and Omicron BA.2 with C-terminal 6×-His tag were also constructed similarly as the SARS-CoV-2 WA1 RBD construct for ELISA. All RBD proteins were expressed by transient transfection of Expi293F cells and purified by Ni-NTA and size exclusion chromatography (SEC) using a HiLoad 16/600 Superdex 200 column (Cytiva, Marlborough, MA). Peak fractions were pooled, concentrated, and stored at 4° C. until use.

SpyCatcher003-mi3 were expressed in *E. coli* BL21 (DE3)-RIPL (Agilent Technology) and purified. Briefly, *E. coli* transduced with a SpyCatcher003-mi3 expression plasmid (Addgene, Watertown, MA) were lysed with a cell disrupter in the presence of 2 mM PMSF. After spinning at 21,000×g for 30 minutes, supernatant containing SpyCatcher003-mi3 particles was passed over a pre-packed Ni-NTA column. The eluent was concentrated and further purified by SEC using a HiLoad 16/600 Superdex 200 column (Cytiva, Marlborough, MA). Peak fractions were pooled and stored at 4° C. until use. SpyCatcher003-mi3 particles were used for SpyTagged RBD conjugation for up to a month after clarification by filtering using a 0.2 μm filter or spinning at 21,000×g for 10 min.

Figure 7B:
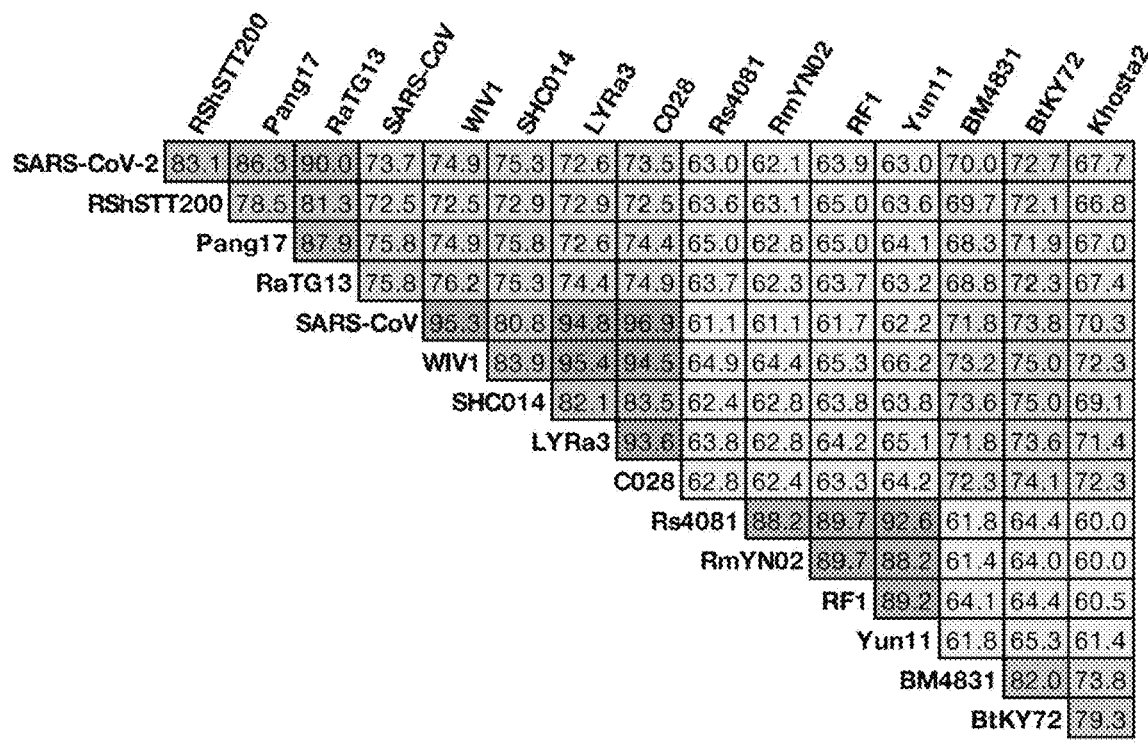
Figure 7C:
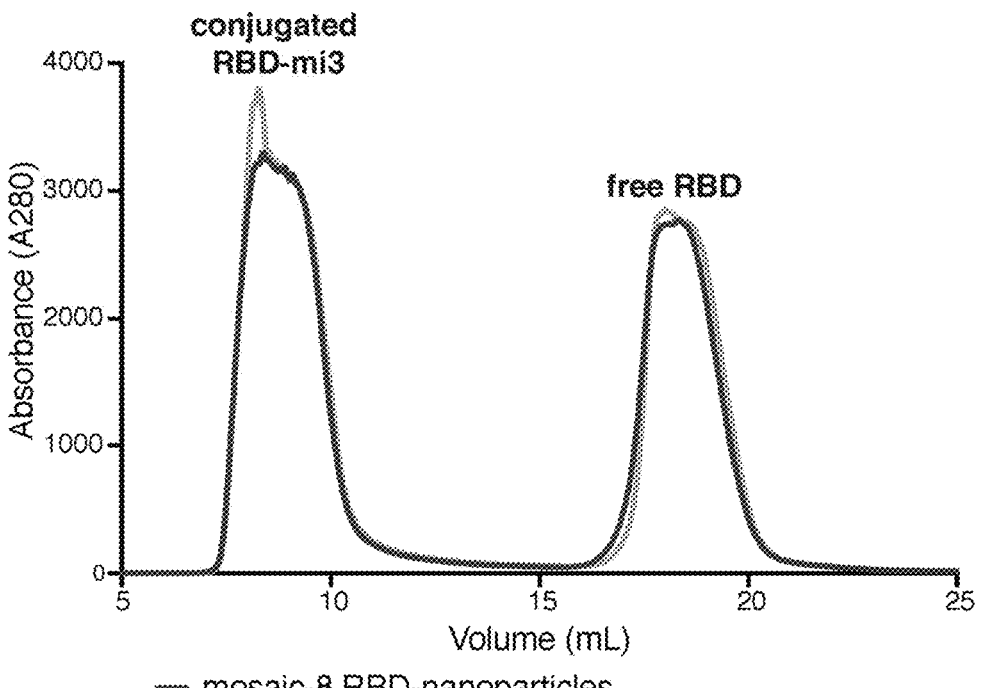
Figure 7D:
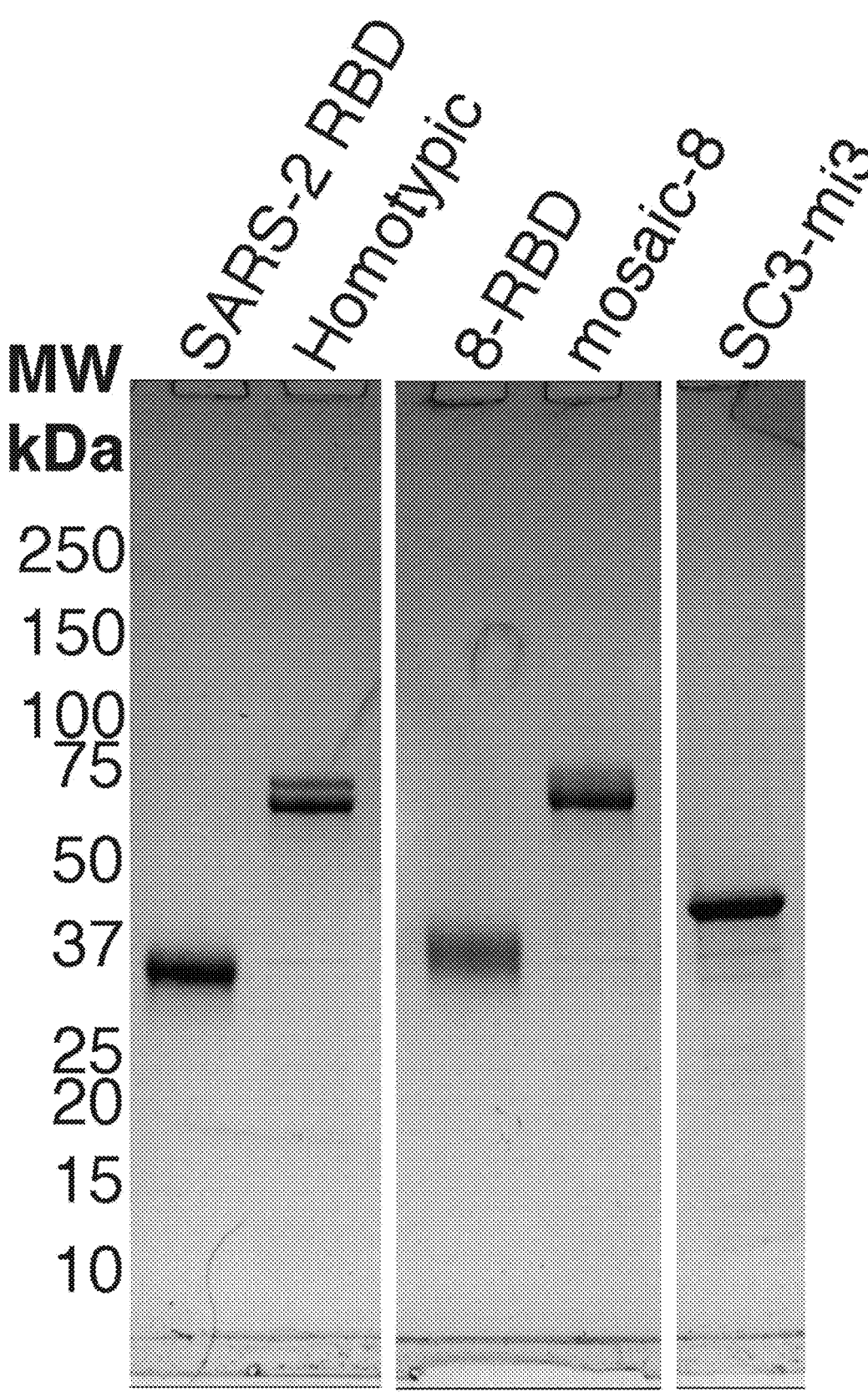
Figure 7E:
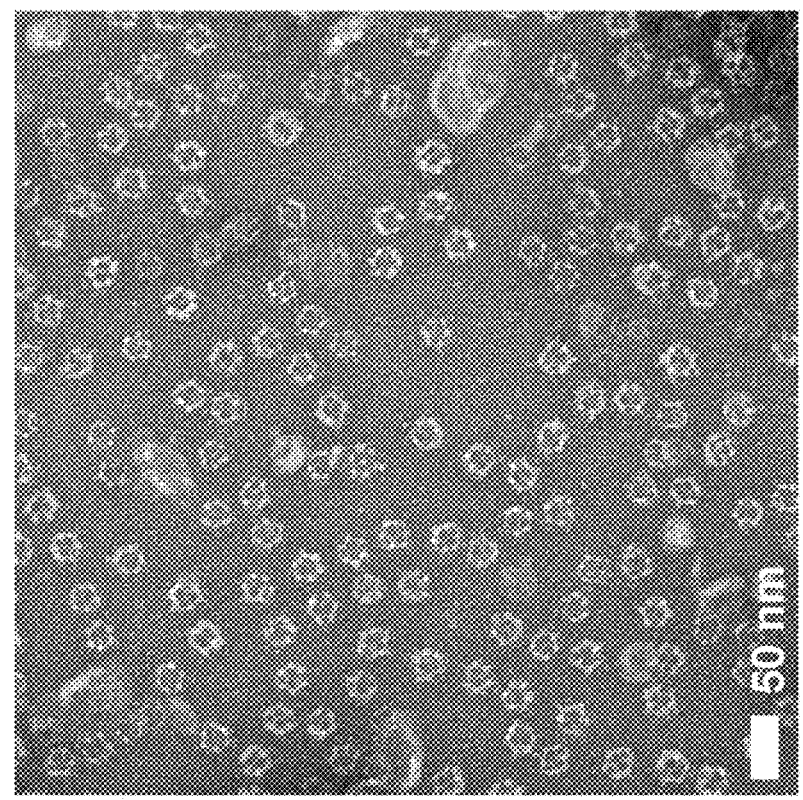
Figure 7E:
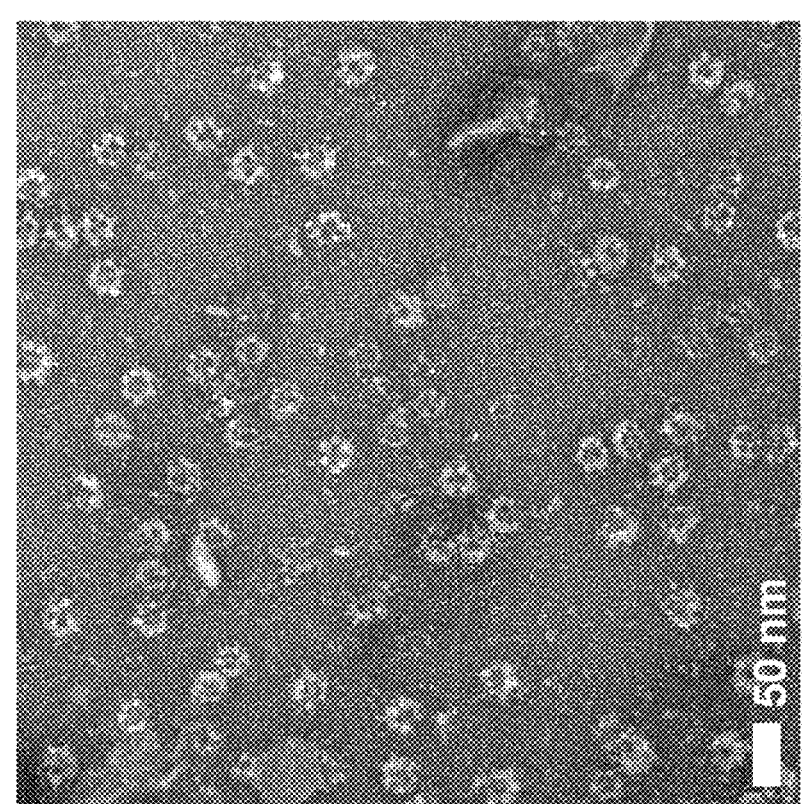

For conjugation, purified SpyCatcher003-mi3 was incubated with purified SpyTagged RBDs (either 8 different RBDs to make mosaic-8 RBD-mi3 or SARS-CoV-2 RBD only to make homotypic RBD-mi3) at a molar ratio of 1:1.2 overnight at room temperature. Conjugation efficiencies of individual RBDs to SpyCatcher003-mi3 were verified. Conjugated mi3-RBD particles were purified by SEC using a Superose 6 10/300 column (Cytiva, Marlborough, MA). Peak fractions were pooled and the concentrations of conjugated mi3 particles were determined using a Bio-Rad Protein Assay (Bio-Rad, Hercules, CA). Conjugated nanoparticles were characterized by electron microscopy imaging and SEC as shown in FIG. 7C-FIG. 7E, and by electron microscopy, SEC and dynamic light scattering.

For negative-stain electron microscopy imaging of mosaic-8 and homotypic SARS-CoV-2 RBD-nanoparticles: ultrathin, holey carbon-coated, 400 mesh Cu grids (Ted Pella, Inc.) were glow discharged (60 s at 15 mA), and a 3 μL aliquot of SEC-purified RBD-nanoparticles was diluted to ~40-100 μg/mL and applied to grids for 60 s. Grids were negatively stained with 2% (w/v) uranyl acetate for 30 s, and images were collected with a 120 keV FEI Tecnai T12 transmission electron microscope at 42,000× magnification.
Immunizations Immunizations were done using protocols, #19023, approved by the City of Hope IACUC committee. Experiments were conducted using 4-6-week-old female C57BL/6 mice (Charles River Laboratories, Wilmington, MA). Immunizations were carried out as previously described using intraperitoneal injections of 5 μg of conjugated RBD-mi3 nanoparticle (calculated as the mass of the RBD, assuming 100% efficiency of conjugation to SpyCatcher003-mi3) in 100 μL of 50% v/v AddaVax™ adjuvant (Invivogen, San Diego, CA). Animals were boosted 4 weeks after the prime with the same quantity of antigen in adjuvant. A final booster was administered intraperitoneally 3 days before mouse spleen harvest.
Beacon Plasma B cells were isolated from immunized animals for characterization on a Berkeley Lights Beacon instrument. Spleens were isolated from two immunized mice per condition and prepared into single cell suspensions as described. Plasma B cells were isolated by CD138$^+$ cell enrichment (Miltenyi Biotec CD138$^+$ plasma cell isolation kit, catalog no. 130-092-530). Enriched plasma B cell samples were loaded onto an OptoSelect 11k chip (Berkeley Lights, Inc., Emeryville, CA) in BLI Mouse Plasma Cell Media (Berkeley Lights, Inc., catalog no. 750-70004). Single cells were then isolated in individual nanoliter-volume compartments (Nanopens) using light-based OptoElectro Positioning (OEP) manipulation with settings optimized for plasma B cells. From Mosaic-8 RBD-nanoparticle immunized animals, 9,695 cells were penned in one chip, of which 7,747 were single cell pens. For homotypic SARS-CoV-2 RBD-nanoparticle immunized animals, 9,130 cells were penned in a second chip, of which 7699 were single cell pens (FIG. 9A). On-chip fluorescence assays were used to identify cells secreting antibodies specific to RBD antigens. Briefly, C-terminally Avi-tagged RBDs were modified with site-specific biotinylation (Avidity, LLC, Aurora, CO) according to the manufacturer's protocol and immobilized on streptavidin-coated beads (Berkeley Lights, Inc. catalog no. 520-00053). Assays were conducted by mixing beads coupled with one of four RBDs used for screening with a fluorescently labeled goat anti-mouse secondary antibody Alexa568 at 1:2500 dilution and importing this assay mixture into the OptoSelect 11k chip. Assays were conducted post 30 minutes incubation after cell penning at 36° C. Images were acquired every 5 minutes for 9 cycles while the beads remained stationary in the main channel above the Nanopens of the OptoSelect chip. Antibodies specific for the immobilized RBD bound the antigen-coupled beads, which sequestered the fluorescent secondary antibody, creating a "bloom" of fluorescent signal immediately above Nanopens containing plasma B cells. Beads were washed out of the chip, and this assay was conducted for each of the four RBDs. After completion of all assays, RBD-specific cells of interest were exported using OEP from individual nanopen chambers to individual wells of a 96-well PCR plate containing lysis buffer.

After running assays and selecting positive blooms with single cells, the OptoSeq BCR Export workflow was run, which performs reverse transcription overnight on the chip and exports cell lysates containing cDNA on capture beads onto a 96 well plate. cDNA amplification and chain-specific PCR were performed the following day and run on an agarose gel to confirm that bands of the correct size were present. PCR products were then purified using AMPure XP magnetic beads and submitted for Sanger sequencing at the City of Hope Sequencing Core.
Cloning Sequences for VH and VL domains were codon optimized using GeneArt (Thermo Fisher Scientific, Waltham, MA) and gene blocks for each domain were purchased from Integrated DNA Technologies (IDT, Coralville, IA). Expression constructs were assembled using Gibson reactions. The heavy chain for IgG expression was constructed by subcloning the $V_H$ gene into a p3BNC expression vector encoding the human IgG $C_H1$, $C_H2$, and $C_H3$ domains, and the heavy chain for Fab expression was constructed by assembling the $V_H$ gene into a p3BNC expression vector encoding a human $C_H1$ and a C-terminal 6×-His tag. The expression plasmid for the light chain was constructed by subcloning the $V_L$ gene into a p3BNC vector that also encoded kappa human $C_L$. The numbering of $V_H$ and $V_L$ protein sequences and the identification of the V gene segments were determined using the ANARCI server.

IG and Spike Trimer Production and Purification

Proteins were expressed in Expi293 cells by transient transfection. IgGs and a previously-described human ACE2-Fc construct were purified from cell supernatants using MabSelect SURE columns (Cytiva, Marlborough, MA), and His-tagged Fabs were isolated from cell supernatants using Ni-NTA columns (Qiagen, Hilden, Germany). IgGs, ACE2-Fc, and Fabs were further purified by SEC using a Superdex 200 16/600 column (Cytiva, Marlborough, MA). Purified proteins were concentrated using a 100 kDa and 30 kDa cutoff concentrator (EMD Millipore, Burlington, MA), respectively, to 10 to 15 mg/mL, and final concentrated proteins were stored at 4° C. until use. 6P versions of soluble SARS-CoV-2 WA1 and SARS-CoV-2 Omicron BA.1 spike trimers were isolated from cell supernatants using a Ni-NTA column (Qiagen, Hilden, Germany). Eluents from Ni-NTA purifications were subjected to SEC using a HiLoad Superdex 200 16/600 column followed by a Superose 6 10/300 (Cytiva, Marlborough, MA) column. Peak fractions were pooled and concentrated to ~6 mg/ml, flash frozen in 50 μL aliquots, and stored at −80° C. until use.

ELISAs

Nunc® MaxiSorp™ 384-well plates (Millipore Sigma, St. Louis, MO) were coated with 10 μg/mL of purified RBD in 0.1 M NaHCO₃ pH 9.8 and stored overnight at 4° C. After blocking with 3% bovine serum albumin (BSA) for an hour at room temperature, plates were washed with Tris-buffered saline including 0.1% Tween 20 (TBST). After removing blocking solution from the plates, 100 μg/mL of purified IgGs were serially diluted by 4-fold using TBST with 3% BSA and incubated with plates at room temperature for 3 hours. Plates were then washed with TBST and incubated with secondary HRP-conjugated goat anti-human IgG (Southern Biotech, Birmingham, AL) at a 1:15,000 dilution for 45 minutes at room temperature. Plates were washed with TBST, developed using SuperSignal ELISA Femto Maximum Sensitivity Substrate (Thermo Fisher Scientific, Waltham, MA), and read at 425 nm. ELISA data were collected in duplicate, and each assay was conducted at least twice for the seven mAbs that were structurally characterized. Curves were plotted and integrated to obtain half-maximal effective concentrations ($EC_{50}$) using Graphpad Prism v9.3.1.

Competition ELISAs were performed using a Tecan Evo liquid handling robot using modifications of a previously described protocol. IgGs were randomly biotinylated at primary amines using EZ-link NHS-PEG4 Biotinylation Kit according to the manufacturer's protocol (Thermo Fisher Scientific, Waltham, MA). SARS-CoV-2 RBD (2.5 μg/mL) was adsorbed overnight at 4° C. to a 384-well Nunc MaxiSorp ELISA plate (Millipore Sigma, St. Louis, MO). The RBD was removed via aspiration and the plate blocked with 3% BSA in TBST for 1 hour at room temperature. The blocking was removed via aspiration and 10 μg/mL unlabeled IgG was added and incubated for 2 hours, followed by addition of 0.25 μg/mL biotinylated IgG. The plate was incubated for 2 hours at room temperature, and bound biotinylated IgG was detected using horseradish peroxidase-conjugated streptavidin (Southern Biotech, Birmingham, AL) (1 hour, room temperature) and developed with Super-Signal ELISA Femto Substrate (Thermo Fisher Scientific, Waltham, MA). Relative light units (RLU) were measured and the signal for each competition pair was normalized to the signal for the biotinylated IgG when unlabeled IgG was not present. Measurements were performed in technical quadruplicates. Data presented are representative of two independent experiments.

Neutralization Assays

SARS-CoV-2, SARS-CoV-2 VOCs, SARS-CoV, WIV1, SHC014, BtKY72 (including mutations allowing human ACE2 binding), Khosta2/SARS-CoV Chimera, and LyRa3/SARS-CoV Chimera pseudoviruses based on HIV lentiviral particles were prepared. Khosta2/SARS-CoV and LyRa3/SARS-CoV Chimeras were constructed by replacing the RBD of SARS-CoV Spike with the RBDs of Khosta2 and LyRa3 Spikes separately. Assays were done using 4-fold dilutions of purified IgGs at a starting concentration of 100 μg/mL by incubating with a pseudovirus at 37° C. for an hour. After incubating with 293TACE2 target cells for 48 hours at 37° C., cells were washed 2 times with phosphate-buffered saline (PBS) and lysed with Luciferase Cell Culture Lysis 5× reagent (Promega, Madison, WI). Using the Nano-Glo Luciferase Assay System (Promega, Madison, WI), the NanoLuc Luciferase activity in lysates was measured. Relative luminescence units (RLUs) were normalized to values derived from cells infected with pseudovirus in the absence of IgG. Data were collected at each IgG concentration in duplicate and reported data come from assays performed at least twice (except for the M8a-28 against Omicron BA.1 assay, which was performed once). Half-maximal inhibitory concentrations ($IC_{50}$ values) were determined using nonlinear regression in AntibodyDatabase.

X-Ray Crystalloraphy

RBD-Fab complexes were formed by incubating SARS-CoV-2 RBD with a 1.1× molar excess of Fab for an hour at room temperature. Complexes were purified by SEC using a Superdex 200 10/300 Increase column (Cytiva, Marlborough, MA). Peak fractions containing RBD-Fab complexes were pooled and concentrated to ~15 mg/ml. Crystallization trials were set up using commercially available screens by mixing 0.2 μL of RBD-Fab complex and 0.2 μL well solution using a TTP LabTech Mosquito instrument via the sitting drop vapor diffusion method at room temperature. Crystals of M8a-6 Fab-RBD complex were obtained from Proplex screen (Molecular Dimensions, Holland, OH), containing 0.1 M sodium citrate pH 5.5 and 15% PEG 6,000. Crystals of M8a-34 Fab-RBD complex were obtained from a PEGion screen (Hampton Research, Aliso Viejo, CA), containing 2% v/v tacsimate pH 4.0, 0.1 M sodium acetate trihydrate pH 4.6, 16% PEG 3,350. Crystals of RBD-HSW-2 complexes were obtained from a Proplex screen (Molecular Dimensions, Holland, OH), containing 0.2 M sodium chloride, 0.1 M sodium/potassium phosphate pH 6.5, 25% PEG 1,000. All crystals were cryoprotected in well solution mixed with 20% glycerol or PEG 400 before freezing in liquid nitrogen.

X-ray diffraction data were collected at the Stanford Synchrotron Radiation Lightsource (SSRL) beamline 12-2 with a Pilatus 6M pixel detector (Dectris, Philadelphia, PA) using the Blu-ice interface (Table 3). All X-ray datasets were indexed and integrated with XDS and scaled with Aimless. The M8a-6 Fab-RBD structure was solved by molecular replacement using a structure of a Fab-RBD complex from a single-particle cryo-EM structure (PDB 7SC1) as the input model for Phaser in Phenix. During the refinement of the M8a-6 Fab-RBD structure, electron density for a second RBD and the variable domains of M8a-6 Fab was observed, but no Fab constant domains were found. Refinement of a model containing the original M8a-6 Fab-RBD complex, a second copy of RBD and the variable domains resulted in no improvements in the refinement statistics. Therefore, the coordinates for the M8a-6 Fab-RBD crystal structure were only partially refined, which were then docked and refined in the cryo-EM M8a-6-spike reconstruction. The M8a-34 Fab-RBD structure was solved by molecular replacement using the partially refined model of M8a-6-RBD complex structure as the input model for Phaser in Phenix. The HSW-2 Fab-RBD structure was solved by molecular replacement using the partially refined model of M8a-34-RBD complex structure as the input model for Phaser in Phenix. Iterative refinement and model-building cycles were carried out with phenix.refine in Phenix and Coot, respectively. The refined models were subsequently used as input models for docking into cryo-EM maps of Fab-spike complexes.

Cryo-EM Sample Preparation

SARS-CoV-2 S-Fab complexes were formed by incubating purified spike trimer and Fabs at a 1.1× molar excess of Fab per spike protomer at room temperature for 30 minutes to a final concentration of ~2 mg/mL. Fluorinated octyl-maltoside solution (Anatrace, Maumee, OH) was added to the spike-Fab complex to a final concentration of 0.02% (w/v) prior to freezing, and 3 μL of the complex/detergent mixture was immediately applied to QuantiFoil 300 mesh 1.2/1.3 grids (Electron Microscopy Sciences, Hatfield, PA) that had been freshly glow discharged with PELCO easiGLOW (Ted Pella, Redding, CA) for 1 min at 20 mA. Grids were blotted for 3 to 4 seconds with 0 blot force using Whatman No. 1 filter paper and 100% humidity at room temperature and vitrified in 100% liquid ethane using a Mark IV Vitrobot (Thermo Fisher Scientific, Waltham, MA).

Cryo-EM Data Collection and Processing

Single-particle cryo-EM datasets for complexes of SARS-CoV-2 WA1 spike 6P with M8a-3 Fab, M8a-6 Fab, M8a-28 Fab, M8a-31 Fab, M8a-34 Fab or HSW-1 Fab and SARS-CoV-2 Omicron BA.1 spike 6P with M8a-31 Fab were collected using SerialEM automated data collection software on a 300 keV Titan Krios (Thermo Fisher Scientific, Waltham, MA) cryo-electron microscope equipped with a K3 direct electron detector camera (Gatan, Pleasanton, CA). For SARS-CoV-2 WA1 spike 6P complexed with HSW-2, a dataset was collected with SerialEM on a 200 keV Talos Arctica cryo-electron microscope (Thermo Fisher Scientific, Waltham, MA) equipped with a K3 camera (Gatan, Pleasanton, CA). Movies were recorded with 40 frames, a defocus range of −1 to −3 μm, and a total dosage of 60 e$^-$/Å$^2$ using a 3×3 beam image shift pattern with 3 exposures per hole in the superresolution mode with a pixel size of 0.416 Å for the collections on the Krios and a single exposure per hole in the super-resolution mode with a pixel size of 0.4345 Å for the collection on the Talos *Arctica*. Detailed data processing workflows for each complex structure are outlined in FIG. 12A-FIG. 19E. All datasets were motion corrected with patch motion correction using a binning factor of 2, and CTF parameters were estimated using Patch CTF in cryoSPARC v3.2. Particle picking was done with blob picker in cryoSPARC using a particle diameter of 100 to 200 Å, and movies and picked particles were inspected before extraction. Particles were extracted and classified using 2D classification in cryoSPARC. After discarding ice and junk particles, the remaining particles were used for ab initio modeling with 4 volumes, which were further refined with heterogeneous refinement in cryoSPARC. Subsequent homogeneous and non-uniform refinements were carried out for final reconstructions in cryoSPARC. Because Fab interactions with 'up' RBDs are generally not well resolved in Fab-spike complex structures, masks were used to locally refine and improve the interfaces of Fabs bound to 'up' RBDs when necessary. For local refinements, masks were generated using UCSF Chimera and refinements were carried out in cryoSPARC.

Cryo-EM Structure Modeling and Refinement

An initial model of the M8a-3 Fab-spike trimer complex was generated by docking a single-particle cryo-EM Fab-SARS-CoV-2 spike 6P complex structure (PDB 7SC1) into the cryo-EM density using UCSF Chimera. The model was refined using real space refinement in Phenix. The Fab amino acid sequence was manually corrected in Coot. The model of the M8a-3 Fab-spike complex was subsequently used for docking and model generation for remaining Fab-spike trimer complexes. For the Fab-spike complexes that RBD-Fab crystal structures were obtained for (M8a-6 Fab-RBD, M8a-34 Fab-RBD and HSW-2 Fab-RBD structures), the spike trimer (PDB 7SC1) was first docked in the EM density map, the RBDs were manually fitted in Coot and the spike trimer was refined using phenix.real_space_refine. The RBD-Fab structures were then aligned to each of the RBDs in the corresponding Fab-spike complexes, and the RBD regions in the EM model were replaced by the RBDs from crystal structures upon structural alignments in Coot. The final model containing the spike trimer and the Fabs were subsequently refined with phenix.real_space_refine. Iterative real space refinement and model building were separately carried out in Phenix and Coot. Single-particle cryo-EM refinement statistics are shown in Table 2.

Structure Analyses

Structure figures were made using UCSF ChimeraX. Distances were measured using PyMol. Interacting residues between a Fab and RBD were analyzed by PDBePISA using the following interaction definitions: potential H bonds were defined as a distance less than 3.9 Å between the donor and acceptor residues when H was present at the acceptor and there was an A-D-H angle between 900 and 270°; potential salt bridges and van der Waals interactions were defined between residues that were less than 4 Å. Sequence alignments were done using Geneious.

To evaluate the potential for intra-spike crosslinking by the two Fabs of a single IgG binding to adjacent RBDs within a single spike trimer, the distances between the Cα atoms of the C-terminal residues of the $C_H1$ domains of adjacent RBD-binding Fabs in the structures of mAb-spike complexes were measured. A cut-off of no more than 65 Å was used to identify IgGs whose binding orientation could allow for both Fabs to bind simultaneously to adjacent RBDs in a single spike trimer. This cut-off was larger than the distance measured between comparable residues of $C_H1$ domains in intact IgG crystal structures (42 Å, PDB 1HZH; 48 Å, PDB 1IGY; 52 Å, PDB 1IGT) to account for potential influences of crystal packing, flexibilities in the elbow bend angle relating the $V_H$-$V_L$ and $C_H1$-$C_L$, and uncertainties in the placements of $C_H1$-$C_L$ domains in cryo-EM structures of the Fab-spike complexes.

TABLE 2

---

SINGLE-PARTICLE CRYO-EM DATA COLLECTION, PROCESSING, AND REFINEMENT

| | WA1 spike in complex with | | | | | | | Omicron BA.1 spike in complex with |
|---|---|---|---|---|---|---|---|---|
| Structures | M8a-3 Fab | M8a-6 Fab | M8a-28 Fab | M8a-31 Fab | M8a-34 Fab | HSW-1 Fab | HSW-2 Fab | M8a-31 Fab |
| Data Collection and processing | | | | | | | | |
| Microscope | Titan Krios | Titan Krios | Titan Krios | Titan Krios | Titan Krios | Titan Krios | Talos Arctica | Titan Krios |
| Camera | Gatan K3 | Gatan K3 | Gatan K3 | Gatan K3 | Gatan K3 | Gatan K3 | Gatan K3 | Gatan K3 |
| Magnification | 105,000 | 105,000 | 105,000 | 105,000 | 105,000 | 105,000 | 45,000 | 105,000 |
| Voltage (keV) | 300 | 300 | 300 | 300 | 300 | 300 | 200 | 300 |
| Exposure (e/$\text{Å}^2$) | 60 | 60 | 60 | 60 | 60 | 60 | 60 | 60 |
| Pixel size (Å) | 0.832 | 0.832 | 0.832 | 0.832 | 0.832 | 0.832 | 0.869 | 0.832 |
| Defocus Range (μm) | −1 to −3 | −1 to −3 | −1 to −3 | −1 to −3 | −1 to −3 | −1 to −3 | −1 to −3 | −1 to −3 |
| Initial Particle Image (no.) | 1,026,209 | 842,602 | 964,614 | 670,746 | 1,186,807 | 1,713,001 | 449,736 | 1,689,653 |
| Final Particle Image (no.) | 272,779 | 159,604 | 332,106 | 295,711 | 421,879 | 336,288 | 43,362 | 142,452 |
| Symmetry Imposed | C1 | C1 | C3 | C3 | C1 | C1 | C1 | C3 |
| Map Resolution (Å) | 3.1 | 3.2 | 2.8 | 2.9 | 3.5 | 3.1 | 4.1 | 3.1 |
| FSC Threshold | 0.143 | 0.143 | 0.143 | 0.143 | 0.143 | 0.143 | 0.143 | 0.143 |
| Map Resolution Range (Å) | 3.0-3.5 | 3.1-3.5 | 2.7 to 3.1 | 2.9-3.2 | 4.1-4.3 | 3.0 to 3.4 | 3.9-4.3 | 2.9-3.3 |
| Refinement | | | | | | | | |
| Initial Model Used | PDB 7SC1 | PDB 7SC1 | PDB 7SC1 | PDB 7SC1 | PDB 7SC1 | PDB 7SC1 | PDB 7SC1 | PDB 7SC1 |
| Model Resolution (Å) | 3.1 | 3.2 | 2.8 | 2.9 | 3.5 | 3.1 | 4.1 | 3.1 |
| FSC Threshold | 0.143 | 0.143 | 0.143 | 0.143 | 0.143 | 0.143 | 0.143 | 0.143 |
| Model composition | | | | | | | | |
| non-hydrogen atoms | 30,762 | 27,051 | 30,942 | 30,552 | 30,669 | 26,992 | 8,392 | 30,075 |
| protein residues | 3,867 | 3,397 | 3,906 | 3,861 | 3,873 | 3,409 | 1,077 | 3,801 |
| ligands | 51 | 48 | 39 | 45 | 42 | 38 | 4 | 33 |
| Average B-factors ($\text{Å}^2$) | | | | | | | | |
| protein | 135.2 | 157.5 | 110.4 | 130.4 | 205.7 | 158.8 | 197.9 | 92.4 |
| ligands | 116.3 | 139.9 | 96.8 | 111.6 | 167.3 | 143.6 | 213.5 | 82.5 |
| R.m.s. deviations | | | | | | | | |
| Bond length (Å) | 0.005 | 0.004 | 0.003 | 0.004 | 0.003 | 0.004 | 0.003 | 0.004 |
| Bond angles (°) | 0.562 | 0.582 | 0.536 | 0.572 | 0.586 | 0.593 | 0.589 | 0.594 |
| Validation | | | | | | | | |
| MolProbity score | 1.85 | 1.63 | 1.74 | 1.72 | 1.75 | 1.83 | 1.9 | 1.77 |
| Clashscore | 10.3 | 9.4 | 9.5 | 9.1 | 11.1 | 12.3 | 14.6 | 10.8 |
| Rotamer outliers | 0.06 | 0.07 | 0.03 | 0 | 0.03 | 0 | 0 | 0.06 |
| Ramachandran plot | | | | | | | | |
| Ramachandran favored (%) | 95.4 | 97.3 | 96.4 | 96.5 | 96.9 | 96.5 | 96.4 | 96.6 |
| Ramachandran allowed (%) | 4.6 | 2.7 | 3.6 | 3.5 | 3.1 | 3.5 | 3.6 | 3.4 |
| Ramachandran outliers (%) | 0 | 0 | 0 | 0 | 0 | 0 | 0 | 0 |
| PDB ID | 7UZ4 | 7UZ5 | 7UZ6 | 7UZ7 | 7UZ9 | 7UZA | 7UZB | 7UZ8 |

TABLE 3

X-RAY CRYSTALLOGRAPHY DATA COLLECTION,
PROCESSING, AND REFINEMENT

| Structures | SARS-CoV-2 RBD + M8a-34 Fab | SARS-CoV-2 RBD + HSW-2 Fab |
|---|---|---|
| Wavelength (Å) | 0.97946 | 0.97946 |
| Resolution range (Å) | 39.23-2.2 (2.279-2.2) | 39.08-3.0 (3.108-3.0) |
| Space group | P2$_1$ | P4$_3$2$_1$2 |
| Unit cell (Å, °) | 54.5 165.2 93.7 90 106.6 90 | 123.6 123.6 145.6 90 90 90 |
| Total reflections (no.) | 553,434 (52,800) | 592,837 (59,309) |
| Unique reflections (no.) | 79,107 (7,859) | 23,174 (2,178) |
| Multiplicity | 7.0 (6.7) | 25.6 (26.2) |
| Completeness (%) | 98.5 (97.9) | 99.5 (96.1) |
| Mean I/sigma(I) | 12.2 (1.24) | 19.6 (2.6) |
| Wilson B-factor (Å$^2$) | 41.4 | 81.1 |
| R-merge | 0.105 (1.378) | 0.147 (1.856) |
| R-meas | 0.113 (1.494) | 0.150 (1.893) |
| R-pim | 0.0425 (0.568) | 0.030 (0.366) |
| CC1/2 | 0.998 (0.642) | 0.999 (0.842) |
| CC* | 1 (0.884) | 1 (0.956) |
| Reflections used in refinement (no.) | 79,082 (7,845) | 23,082 (2,178) |
| Reflections used for R-free (no.) | 1,997 (195) | 1,155 (109) |
| R-work | 0.171 (0.270) | 0.230 (0.360) |
| R-free | 0.243 (0.329) | 0.271 (0.458) |
| CC (work) | 0.971 (0.821) | 0.899 (0.834) |
| CC (free) | 0.962 (0.771) | 0.604 (0.753) |
| Number of non-hydrogen atoms | 10,482 | 4,912 |
| macromolecules | 9,884 | 4,884 |
| ligands | 111 | 28 |
| solvent | 487 | 0 |
| Protein residues (no.) | 1,278 | 633 |
| RMS (bonds) (Å) | 0.008 | 0.009 |
| RMS (angles) (°) | 0.98 | 1.15 |
| Ramachandran favored (%) | 97.5 | 96.3 |
| Ramachandran allowed (%) | 2.5 | 3.7 |
| Ramachandran outliers (%) | 0 | 0 |
| Rotamer outliers (%) | 0.91 | 0 |
| Clashscore | 2.6 | 6.11 |
| Average B-factor (Å$^2$) | 47 | 73.0 |
| macromolecules | 46.7 | 72.7 |
| ligands | 85.0 | 118.3 |
| solvent | 44.3 | — |
| PDB ID | 7UZC | 7UZD |

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An antibody or fragment thereof, wherein the antibody or fragment thereof has specificity to a sarbecovirus spike protein receptor-binding domain (RBD) and comprises:

(a) a heavy chain variable region (VH) CDR1 comprising an amino acid sequence selected from the group consisting of SEQ ID NOs: 49-55;

(b) a VH CDR2 comprising an amino acid sequence selected from the group consisting of SEQ ID NOs: 57-63;

(c) a VH CDR3 comprising an amino acid sequence selected from the group consisting of SEQ ID NOs: 65-71;

(d) a light chain variable region (VL) CDR1 comprising an amino acid sequence selected from the group consisting of SEQ ID NOs: 73-79;

(e) a VL CDR2 comprising an amino acid sequence selected from the group consisting of WAS, YAS, RAS, and RAK; and (f) a VL CDR3 comprising an amino acid sequence selected from the group consisting of SEQ ID NOs: 81-87.

2. The antibody or fragment thereof of claim 1, comprising:

a VH CDR1 of SEQ ID NO: 49;
a VH CDR2 of SEQ ID NO: 57;
a VH CDR3 of SEQ ID NO: 65;
a VL CDR1 of SEQ ID NO: 73;
a VL CDR2 having the amino acid sequence WAS; and
a VL CDR3 of SEQ ID NO: 81.

3. The antibody or fragment thereof of claim 1, comprising:

a VH CDR1 of SEQ ID NO: 51;
a VH CDR2 of SEQ ID NO: 59;
a VH CDR3 of SEQ ID NO: 67;
a VL CDR1 of SEQ ID NO: 75;
a VL CDR2 having the amino acid sequence YAS; and
a VL CDR3 of SEQ ID NO: 83.

4. The antibody or fragment thereof of claim 1, comprising:

a VH CDR1 of SEQ ID NO: 52;
a VH CDR2 of SEQ ID NO: 60;
a VH CDR3 of SEQ ID NO: 68;
a VL CDR1 of SEQ ID NO: 76;
a VL CDR2 having the amino acid sequence WAS; and
a VL CDR3 of SEQ ID NO: 84.

5. The antibody or fragment thereof of claim 1, comprising:

a VH CDR1 of SEQ ID NO: 53;
a VH CDR2 of SEQ ID NO: 61;
a VH CDR3 of SEQ ID NO: 69;
a VL CDR1 of SEQ ID NO: 77;
a VL CDR2 having the amino acid sequence RAS; and
a VL CDR3 of SEQ ID NO: 85.

6. The antibody or fragment thereof of claim 1, comprising a heavy chain variable region comprising (i) an amino acid sequence selected from the group consisting of SEQ ID NOs: 1, 4, 27, 33, 35, 41, and 43, (ii) an amino acid sequence having at least 90% sequence identity to an amino acid sequence selected from the group consisting of SEQ ID NOs: 1, 4, 27, 33, 35, 41, and 43, or (iii) an amino acid sequence having one, two or three mismatches relative to an amino acid sequence selected from the group consisting of SEQ ID NOs: 1, 4, 27, 33, 35, 41, and 43.

7. The antibody or fragment thereof of claim 1, comprising a light chain variable region comprising (i) an amino acid sequence selected from the group consisting of SEQ ID NOs: 2, 5, 28, 34, 36, 42, and 44, (ii) an amino acid sequence having at least 90% sequence identity to an amino acid sequence selected from the group consisting of SEQ ID NOs: 2, 5, 28, 34, 36, 42, and 44, (iii) an amino acid sequence having one, two or three mismatches relative to an amino acid sequence selected from the group consisting of SEQ ID NOs: 2, 5, 28, 34, 36, 42, and 44.

8. The antibody or fragment thereof of claim 1, wherein the antibody or fragment thereof comprises an Fc domain; and/or wherein the antibody or fragment thereof is a single-chain variable fragment (scFv), a single-domain antibody, an immunoglobulin molecule, a monoclonal antibody, a chimeric antibody, a CDR-grafted antibody, a humanized antibody, a Fab fragment, a Fab' fragment, a $F(ab')_2$ fragment, an Fv fragment, a disulfide linked Fv, an scFv, a single domain antibody, a diabody, a multispecific antibody, a dual specific antibody, an anti-idiotypic antibody, a bispecific antibody, or a functionally active epitope-binding fragment thereof.

9. The antibody or fragment thereof of claim 1, wherein the antibody or fragment thereof specifically binds to two or more different sarbecovirus spike protein RBDs.

10. The antibody or fragment thereof of claim 9, wherein the antibody or fragment thereof binds to at least one of the two or more sarbecovirus spike protein RBDs with an EC50 of about 0.001 µg/mL to about 10 µg/mL as assessed by an optofluidic system and/or an ELISA assay.

11. The antibody or fragment thereof of claim 9, wherein at least one of the two or more sarbecovirus spike protein RBDs is selected from the group consisting of SARS-CoV-2 RBD and variants thereof, RsSTT200 RBD and variants thereof, Pang17 RBD and variants thereof, RaTG13 RBD and variants thereof, SARS-CoV RBD and variants thereof, WIV1 RBD and variants thereof, SHC014 RBD and variants thereof, LyRa3 RBD and variants thereof, C028 RBD and variants thereof, Rs4081 RBD and variants thereof, RmYN02 RBD and variants thereof, Rfl RBD and variants thereof, Yun11 RBD and variants thereof, BM4831 RBD and variants thereof, BtKY72 RBD and variants thereof, and Khosta2 RBD and variants thereof.

12. The antibody or fragment thereof of claim 1, wherein the antibody or fragment thereof inhibits infectivity of a virus comprising a sarbecovirus spike protein receptor binding domain (RBD) with an IC50 of about 0.001 µg/mL to about 10 µg/mL.

13. The antibody or fragment thereof of claim 1, wherein the antibody or fragment thereof inhibits infectivity of two or more viruses each comprising a different sarbecovirus spike protein receptor binding domain (RBD).

14. The antibody or fragment thereof of claim 13, wherein the antibody or fragment thereof inhibits infectivity of at least one, at least two, or all of the two or more viruses with an IC50 of about 0.001 µg/mL to about 10 µg/mL.

15. The antibody or fragment thereof of claim 13, wherein the antibody or fragment thereof inhibits infectivity of at least one, at least two, or all of the two or more viruses with an IC50 of about 0.005 µg/mL to about 9 µg/mL.

16. The antibody or fragment thereof of claim 13, wherein the sarbecovirus spike protein RBD is selected from the group consisting of SARS-CoV-2 RBD and variants thereof, SARS-CoV RBD and variants thereof, WIV1 RBD and variants thereof, SHC014 RBD and variants thereof, BtKY72 RBD and variants thereof, Khosta2/SARS-CoV chimera RBD and variants thereof, and LyRa3/SARS-CoV RBD chimera and variants thereof.

17. A composition comprising the antibody or fragment thereof of claim 1 and a pharmaceutically acceptable carrier.

18. A method of treating a coronavirus infection in a patient in need thereof, comprising administering to the patient an effective amount of the antibody or fragment thereof of claim 1, a composition of claim 17, or a combination thereof.

19. The method of claim 18, wherein the coronavirus is a coronavirus in the genus of Alpha-coronavirus, Beta-coronavirus, or both.

20. The method of claim 18, wherein the coronavirus is SARS-CoV-2 and variants thereof, RsSTT200 and variants thereof, Pang17 and variants thereof, RaTG13 and variants thereof, SARS-CoV and variants thereof, WIV1 and variants thereof, SHC014 and variants thereof, LyRa3 and variants thereof, C028 and variants thereof, Rs4081 and variants thereof, RmYN02 and variants thereof, Rfl and variants thereof, Yun11 and variants thereof, BM4831 and variants thereof, BtKY72 and variants thereof, or Khosta2 and variants thereof; or wherein the coronavirus comprises a SARS-CoV-2 variant of concern, variant of interest, or both.

* * * * *